US008987312B2

(12) United States Patent
Boger

(10) Patent No.: US 8,987,312 B2
(45) Date of Patent: Mar. 24, 2015

(54) ALPHA-KETO HETEROCYCLES AS FAAH INHIBITORS

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 434 days.

(21) Appl. No.: 13/002,905

(22) PCT Filed: Jul. 8, 2009

(86) PCT No.: PCT/US2009/004002
§ 371 (c)(1),
(2), (4) Date: Apr. 11, 2011

(87) PCT Pub. No.: WO2010/005572
PCT Pub. Date: Jan. 14, 2010

(65) Prior Publication Data
US 2011/0183947 A1    Jul. 28, 2011

Related U.S. Application Data

(60) Provisional application No. 61/079,271, filed on Jul. 9, 2008.

(51) Int. Cl.
| | | |
|---|---|---|
| *C07D 417/04* | (2006.01) | |
| *A61K 31/13* | (2006.01) | |
| *A61K 9/20* | (2006.01) | |
| *A61K 9/48* | (2006.01) | |
| *A61K 31/18* | (2006.01) | |
| *A61K 31/395* | (2006.01) | |
| *C07D 401/04* | (2006.01) | |
| *C07D 403/04* | (2006.01) | |
| *C07D 413/04* | (2006.01) | |

(52) U.S. Cl.
CPC . *A61K 31/13* (2013.01); *A61K 9/20* (2013.01); *A61K 9/4866* (2013.01); *A61K 31/18* (2013.01); *A61K 31/395* (2013.01); *C07D 401/04* (2013.01); *C07D 403/04* (2013.01); *C07D 413/04* (2013.01); *C07D 417/04* (2013.01)
USPC ......... 514/342; 514/365; 546/270.4; 548/200

(58) Field of Classification Search
USPC ................. 548/200; 514/365, 342; 546/270.4
See application file for complete search history.

(56) References Cited

U.S. PATENT DOCUMENTS

| | | | |
|---|---|---|---|
| 7,662,971 | B2 | 2/2010 | Boger |
| 7,915,270 | B2 | 3/2011 | Boger |
| 2002/0034555 | A1 | 3/2002 | Gelber et al. |
| 2002/0103192 | A1 | 8/2002 | Curtin et al. |
| 2005/0261331 | A1 | 11/2005 | Nielsen et al. |
| 2006/0100212 | A1 | 5/2006 | Boger |
| 2006/0111359 | A1 | 5/2006 | Boger |
| 2007/0203156 | A1 | 8/2007 | Boger |
| 2008/0096931 | A1 | 4/2008 | Boger |
| 2011/0184026 | A1 | 7/2011 | Boger |
| 2012/0302607 | A1 | 11/2012 | Boger |

FOREIGN PATENT DOCUMENTS

| | | |
|---|---|---|
| WO | WO-02/46129 A2 | 6/2002 |
| WO | WO-2004/033652 A2 | 4/2004 |
| WO | WO-2007/061862 A2 | 5/2007 |
| WO | WO-2008/063714 A1 | 5/2008 |
| WO | WO-2009/154785 A2 | 12/2009 |
| WO | WO-2010/005572 A2 | 1/2010 |
| WO | WO-2010/005572 A3 | 1/2010 |
| WO | WO-2009/154785 A3 | 4/2010 |

OTHER PUBLICATIONS

Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Jain et al., "Polymorphism in Pharmacy", Indian Drugs, 1986, 23(6) 315-329.*
U.S. Appl. No. 12/999,442, Non Final Office Action mailed Feb. 2, 2012, 17 pgs.
U.S. Appl. No. 12/999,442, Response filed Jan. 17, 2012 to Restriction Requirement mailed Dec. 27, 2011, 10 pgs.
U.S. Appl. No. 12/999,442, Restriction Requirement mailed Dec. 27, 2011, 9 pgs.
International Application Serial No. PCT/US2009/003680, International Preliminary Report on Patentability mailed Jan. 6, 2011, 7 pgs.
International Application Serial No. PCT/US2009/004002, International Preliminary Report on Patentability dated Jan. 11, 2011, 6 pgs.
International Application No. PCT/US2009/004002, International Search Report and Written Opinion mailed Mar. 12, 2010, (Mar. 12, 2010), 14 pgs.
International Application Serial No. PCT/US2009/004002, Search Report mailed Mar. 12, 2010, 5 pgs.
International Application Serial No. PCT/US2009/004002, Written Opinion mailed Mar. 12, 2010, 5 pgs.
International Application Serial No. PCT/US2009/003680, Search Report mailed Feb. 10, 2010, 12 Pgs.
International Application Serial No. PCT/US2009/003680, Written Opinion mailed Feb. 10, 2010, 12 Pgs.
Boger, D. L., et al., "Discovery of a potent, selective, and efficaciouis class of reversible alpha-ketoheterocycle inhibitors of fatty acid amide hydrolase effective as analgesics", J. Med. Chem., vol. 48, (2005), 1849-1856.
Boger, D. L., et al., "Exceptionally potent inhibitors of fatty acid amide hydrolase: The enzyme responsible for degradation of endogenous oleamide and anandamide", Proceedings of the National Academy of Sciences 97(10), (2000), 5044-5049.
Chang, L., et al., "Inhibition of fatty acid amide hydrolase produces analgesia by multiple mechanisms", British Journal of Pharmacology, 148(1), (2006), 102-113.

(Continued)

*Primary Examiner* — Patricia L Morris
(74) *Attorney, Agent, or Firm* — Schwegman Lundberg & Woessner, P.A.

(57) ABSTRACT

The invention provides a series of -αketoheterocyclic compounds, for example, compounds of formula (I). The compounds can inhibit fatty acid amide hydrolase and can be useful for treatment of malconditions modulated by fatty acid amide hydrolase. The invention further provides methods of making compounds of formula (I), useful intermediates for the preparation of compounds of formula (I), and methods of using compounds of formula (I) and compositions thereof.

6 Claims, 1 Drawing Sheet

(56) References Cited

OTHER PUBLICATIONS

Chiang, K. P., et al., "An enzyme that regulates ether lipid signaling pathways in cancer annotated by multidimensional profiling", Chemistry & Biology, vol. 13, (Oct. 2006), 1041-1050.

Garfunkle, J, et al., "Optimization of the central heterocycle of alpha-ketoheterocycle inhibitors of fatty acid amide hydrolase", Journal of Medicinal Chemistry, vol. 51, (Jul. 16, 2008), pp. 4392-4403.

Hardouin, C., et al., "Structure-activity relationships of alpha-ketooxazole inhibitors of fatty acid amide hydrolase", J. Med. Chem., vol. 50, (Jun. 9, 2007), 3359-3368.

Kimball, F. S., et al., "Optimization of alpha-ketooxazole inhibitors of fatty acid amide hydrolase", J. Med Chem., vol. 51, (Feb. 5, 2008), 937-947.

Leung, D., et al., "Discovery of an exceptionally potent and selective class of fatty acid amide hydrolase inhibitors enlisting proteome-wide selectivity screening: concurrent optimization of enzyme inhibitor potency and selectivity", Bioorganic & Medicinal Chemnistry Letters, vol. 15, (2005), 1423-1428.

Lichtman, A., et al., "Reversible inhibitors of fatty acid amide hydrolase that promote analgesia: Evidence for an unprecedented combination of potency and selectivity", The Journal of Pharmacology and Experimental Therapeutics, vol. 311, No. 2, (2004), 441-448.

Romero, F. A., et al., "Delineation of a fundamental alpha-ketoheterocycle substituent effect for use in the design of enzyme inhibitors", J. Am. Chem. Soc., vol. 128, (Jun. 26, 2006), 14004-14005.

Romero, F. A., et al., "Potent and selective alpha-ketoheterocycle-based inhibitors of the anandamide and oleamide catabolizing enzyme, fatty acid amide hydrolase", J. Med. Chem (50), (2007), 1058-1068.

U.S. Appl. No. 12/999,442, Examiner Interview Summary mailed Aug. 10, 2012, 2 pgs.

U.S. Appl. No. 13/564,863, Response filed Apr. 11, 2013 to Non Final Office Action mailed Jan. 18, 2013, 14 pgs.

U.S. Appl. No. 13/564,863, Final Office Action mailed Jun. 27, 2013, 15 pgs.

U.S. Appl. No. 13/564,863, Non Final Office Action mailed Jan. 18, 2013, 23 pgs.

* cited by examiner

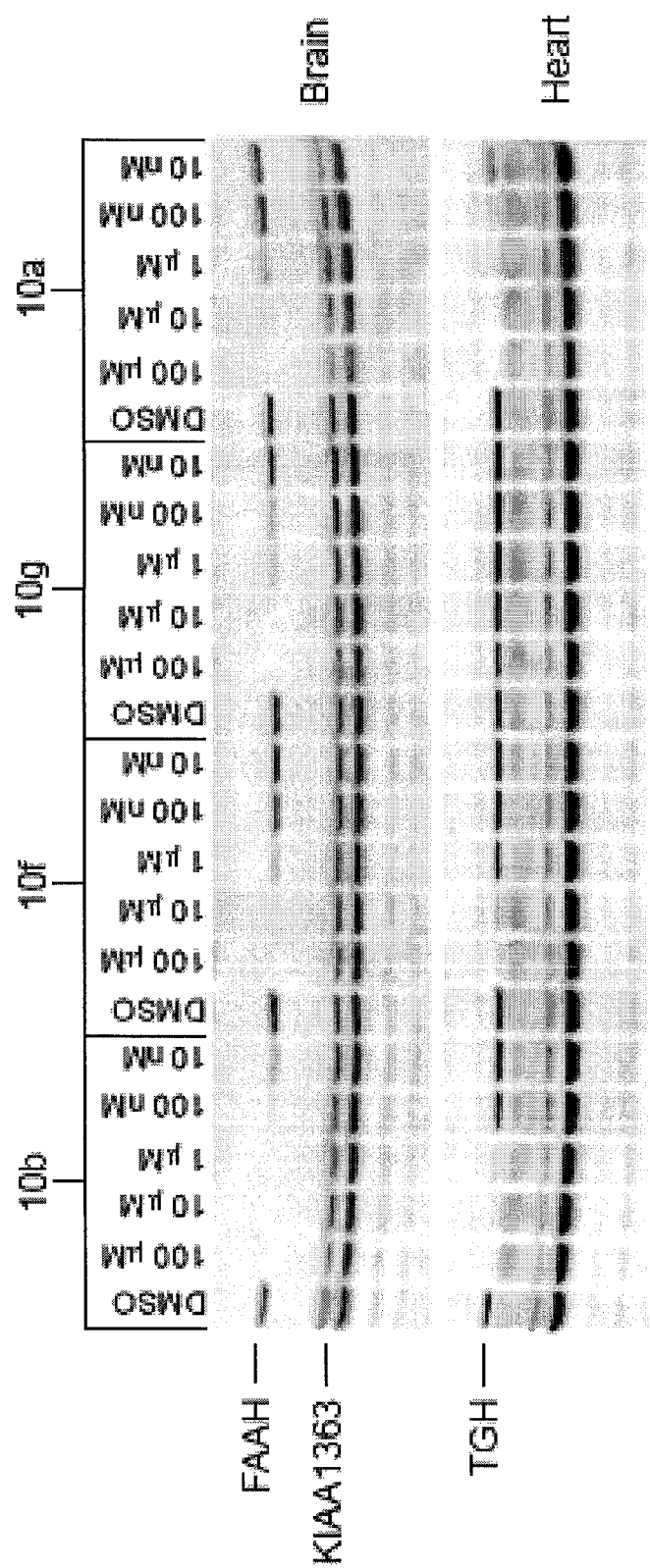

ALPHA-KETO HETEROCYCLES AS FAAH INHIBITORS

RELATED APPLICATIONS

This application is a U.S. National Stage Filing under 35 U.S.C. 371 and claims the benefit of priority under 35 U.S.C. §120 to International Patent Application Serial No. PCT/US2009/004002, filed Jul. 8, 2009, and published on Jan. 14, 2010, as WO 2010/005572 A2, and republished on May 14, 2010, as WO 2010/005572 A3, which claims the benefit of priority under 35 U.S.C. §119(e) of U.S. Provisional Application Ser. No. 61/079,271, filed Jul. 9, 2008, the benefit of priority of each of which is claimed hereby and each of which are incorporated by reference herein in their entirety.

GOVERNMENT SUPPORT

This invention was made with government support under Grant No. DA15648 awarded by the National Institutes of Health. The United States Government has certain rights in the invention.

BACKGROUND OF THE INVENTION

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663). Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

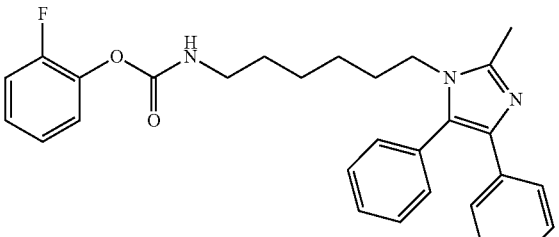

BMS-1

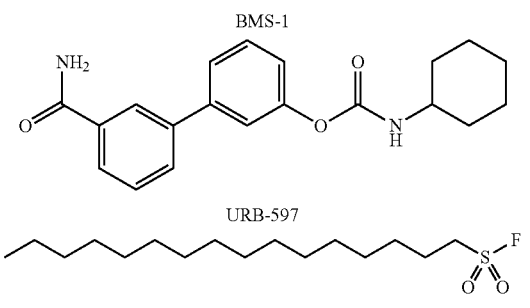

URB-597

AM-374

In addition, the oxazolopyridine ketone OL-135 is reported to be a potent inhibitor of FAAH, and has been reported to have analgesic activity in both the hot plate and tail emersion tests of thermal nociception in rats (WO 04/033652).

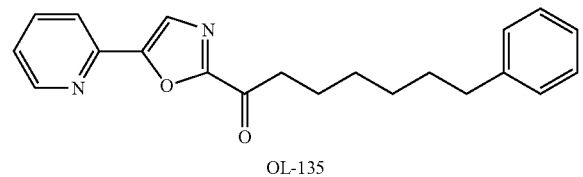 [SMILES: O=C(CCCCCCc1ccccc1)c1ncc(-c2ccccn2)o1]

OL-135

Results of research on the effects of certain exogenous cannabinoids has elucidated that an FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reported to have been initiated in Germany in May 2002.

A number of individuals with multiple sclerosis have claimed a benefit from cannabis for both disease-related pain and spasticity, with support from small controlled trials (Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD).

Reports of small-scale controlled trials have been conducted to investigate other potential commercial uses of cannabinoids have been made. Trials in volunteers have been reported to have confirmed that oral, injected and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH –/– mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of a FAAH inhibitor on AEA and other endo-cannabinoids, inhibitors of FAAH's catabolism of other lipid mediators may be used in treating other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel, et al. *J. Pharmacol. Exp. Ther.* 2006, 317 (1), 251-257) and depression (Gobbi, et al. *Proc. Natl. Acad. Sci. USA* 2005, 102(51), 18620-18625).

Thus, there is evidence that small-molecule FAAH inhibitors may be useful in treating pain of various etiologies, anxiety, multiple sclerosis and other movement disorders, nausea/emesis, eating disorders, epilepsy, glaucoma, inflammation, immunosuppression, neuroprotection, depression, cognition enhancement, and sleep disorders, and potentially with fewer side effects than treatment with an exogenous cannabinoid.

Various small-molecule FAAH modulators have been described, e.g., in U.S. Patent Application Publication No. US 2006/0100212, U.S. patent application Ser. No. 11/708,788 (filed Feb. 20, 2007), and U.S. Provisional Patent Appl. No. 60/843,277 (filed Sep. 8, 2006). However, there remains a need for potent and/or selective FAAH modulators with suitable pharmaceutical properties.

SUMMARY

A series of α-ketooxazoles were discovered that inhibit the serine hydrolase fatty acid amide hydrolase and/or provide FAAH-modulating activity. Accordingly, the invention provides a compound of formula

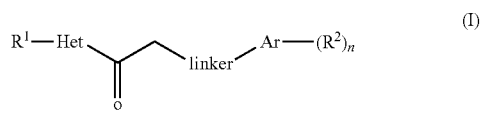

wherein
$R^1$ is aryl, heteroaryl, —$CO_2(C_1$-$C_8)$alkyl, or —$CO_2H$;
Het is a 1,2-diazine, a thiazole, a 1,2,4-oxadiazole, a 1,3,4-thiadiazole, a 1,3,4-triazole, or a tetrazole;
linker is a $(C_1$-$C_{20})$alkyl chain wherein one to five carbons of the chain are optionally be replaced with O or S, or linker is a direct bond;
Ar is $(C_6$-$C_{14})$aryl;
n is 1-4;
each $R^2$ is independently H, —X—$R^3$, or —X-Ph-X—$R^3$;
each X is independently —$CH_2$—, —O—, —$CH_2O$—, —$OCH_2$—, —C(=O)—, —$CO_2$—, —OC(=O)—, —S—, —S(O)—, —S(O)$_2$—, —N($R^a$)—, or a direct bond;
each $R^3$ is independently H, $(C_1$-$C_8)$alkyl, $(C_3$-$C_8)$cycloalkyl, aryl, heteroaryl, —$CF_3$, —CN, —C(O)$(C_1$-$C_8)$alkyl optionally substituted with one, two, or three fluoro substituents, —$CO_2(C_1$-$C_8)$alkyl, —$CO_2H$, —C(O)$NR^aR^b$, —OH, —O$(C_1$-$C_8)$alkyl, -halo, —$NO_2$, —N($R^a$)C(O)$R^b$, —N($R^a$)$SO_2R^b$, —$SO_2NR^aR^b$, —S(O)$_{0-2}R^a$, or —$CH_2NR^cR^d$ wherein $R^c$ and $R^d$ are each independently H or $(C_1$-$C_8)$alkyl, or $R^c$ and $R^d$ taken together with the nitrogen to which they are attached form a monocyclic saturated heterocyclic group;
each $R^a$ and $R^b$ are each independently H, $(C_1$-$C_8)$alkyl, $(C_3$-$C_8)$cycloalkyl, aryl$(C_1$-$C_8)$alkyl, or a nitrogen protecting group; and
the aryl or heteroaryl of $R^1$ is optionally substituted with one, two, or three $R^2$ groups;
or a pharmaceutically acceptable salt, solvate, or hemiketal thereof, and various derivatives thereof.

The invention further provides a composition comprising a compound of formula I and a pharmaceutically acceptable diluent or carrier. The composition can be a pharmaceutical composition, for example, a pharmaceutical composition for treating a disease, disorder, or medical condition mediated by FAAH activity. The composition can include an effective amount of at least one compound of formula I, or a pharmaceutically acceptable salt thereof, a solvate thereof, a hemiketal thereof, a pharmaceutically acceptable prodrug thereof, a pharmaceutically active metabolite thereof, or any combination thereof.

The composition can include an analgesic, such as an opioid or a non-steroidal anti-inflammatory drug. In some embodiments, the composition can include a second active ingredient, for example, aspirin, acetaminophen, opioids, ibuprofen, naproxen, COX-2 inhibitors, gabapentin, pregabalin, or tramadol.

The invention also provides a method for treating a subject suffering from or diagnosed with a disease, disorder, or medical condition mediated by FAAH activity. The method can include administering to a subject in need of such treatment an effective amount of at least one compound of formula I, a pharmaceutically acceptable salt thereof, a pharmaceutically acceptable prodrug thereof, or a pharmaceutically active metabolite thereof, or a composition containing said ingredient.

The disease, disorder, or medical condition can include anxiety, depression, pain, sleep disorders, eating disorders, inflammation, movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, neuroinflammation, or a combination thereof. In certain embodiments, the disease, disorder, or medical condition is anxiety, pain, inflammation, sleep disorders, eating disorders, and movement disorders.

The invention further provides a method of inhibiting fatty acid amide hydrolase activity comprising contacting the fatty acid amide hydrolase (FAAH) with an effective amount of a compound of formula I. The method can include contacting the FAAH either in vivo or in vitro.

Additionally, the invention provides intermediates for the synthesis of compounds of formula I, as well as methods of preparing compounds of formula I. The invention also provides compounds of formula I that are useful as intermediates for the synthesis of other useful compounds. The invention further provides for the use of compounds of formula I for the manufacture of medicaments useful for the treatment conditions in a mammal, such as a human, wherein the conditions are mediated by FAAH.

Additional embodiments, features, aspects, and advantages of the invention will be apparent from the following detailed description and through practice of the invention.

BRIEF DESCRIPTION OF THE DRAWINGS

FIG. 1 illustrates the activity based protein profiling of FAAH inhibitors 10b, 10f, 10g, 10a with FP-Rh in brain and heart membrane proteome, according to an embodiment of the invention; enzyme targets such as FAAH, KIAA1363, and TGH are labeled at the left margin.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference. Reference is herein made to the subject matter recited by certain claims, examples of which are illustrated in the accompanying structures and formulas. While the exemplary subject matter will be described, it will be understood that the exemplary descriptions are not intended to limit the claims. On the contrary, the inventive subject matter is intended to cover all alternatives, modifications, and equivalents, which may be included within the scope of the presently disclosed subject matter as defined by the claims.

References in the specification to "an embodiment" or "one embodiment" indicate that the embodiment described may include a particular feature, structure, or characteristic, but every embodiment may not necessarily include the particular feature, variable, structure, or characteristic. Moreover, such phrases, features, or variables are not necessarily referring to the same embodiment. Further, when a particular feature, structure, or characteristic is described in connection with an embodiment, it is within the knowledge of one skilled in the art to affect such feature, structure, or characteristic in connection with other embodiments whether or not explicitly described in connection with the first feature, structure, or characteristic.

DEFINITIONS

As used herein, certain terms have the following meanings. All other terms and phrases used in this specification have their ordinary meanings as one of skill in the art would understand. Such ordinary meanings may be obtained to their use in the art and by reference to general and technical dictionaries, such as *Hawley's Condensed Chemical Dictionary* $14^{th}$ Edition, by R. J. Lewis, John Wiley & Sons, New York, N.Y., 2001; *Webster's New World Dictionary*, Simon & Schuster, New York, N.Y., 1995; and *The American Heritage Dictionary of the English Language*, Houghton Mifflin, Boston Mass., 1981.

The following explanations of certain terms are meant to be illustrative rather than exhaustive. These terms have their ordinary meanings given by usage in the art and in addition include the following explanations.

The term "and/or" refers to any one of the items, any combination of the items, or all of the items with which this term is associated.

The singular forms "a," "an," and "the" include plural reference unless the context clearly dictates otherwise. For example, a reference to "a compound" includes a plurality of such compounds, so that a compound X includes a plurality of compounds X. Thus, the singular article of speech forms "a," "an," and "the" include plural reference such as, but not limited to, multiples of the element, term, feature, compound, composition, method, and the like, to which the article of speech refers unless the context clearly dictates otherwise.

The term "about" can refer to a variation of ±5%, 10%, or 20% of the value specified. For example, "about 50" percent can in some embodiments carry a variation from 45 to 55 percent. For integer ranges, the term "about" can include one or two integers greater than and less than a recited integer.

As used herein, "contacting" refers to the act of touching, making contact, or of bringing to immediate or close proximity, including at the molecular level, such as in solution, in a tissue, or in a cell, for example, in vitro or in vivo.

As to any of the groups or "substituents" described herein, each can further include one or more (e.g., 1, 2, 3, 4, 5, or 6) substituents. It is understood, of course, that such groups do not contain any substitution or substitution patterns which are sterically impractical and/or synthetically non-feasible.

The terms "comprising", "including", "having", and "composed of" are open-ended terms as used herein.

The term "alkyl" refers to a straight- or branched-chain alkyl group having from 1 to about 20 carbon atoms in the chain. For example, the alkyl group can be a $(C_1-C_{20})$alkyl, a $(C_1-C_{12})$alkyl, $(C_1-C_8)$alkyl, $(C_1-C_6)$alkyl, or $(C_1-C_4)$alkyl. Examples of alkyl groups include methyl (Me, which also may be structurally depicted by a/symbol), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group.

The term "alkenyl" refers to a straight- or branched-chain alkenyl group having from 2 to 20 carbon atoms in the chain. (The double bond of the alkenyl group is formed by two $sp^2$ hybridized carbon atoms.) Illustrative alkenyl groups include $C_1$-$C_{12}$ alkenyl groups, such as prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples. Alkenyl groups can be optionally substituted or unsubstituted.

The term "cycloalkyl" refers to a saturated or partially saturated, monocyclic, fused polycyclic, or Spiro polycyclic carbocycle having from 3 to 12 ring atoms per carbocycle, and can be optionally substituted or unsubstituted. Illustrative examples of cycloalkyl groups include the following entities, in the form of properly bonded moieties:

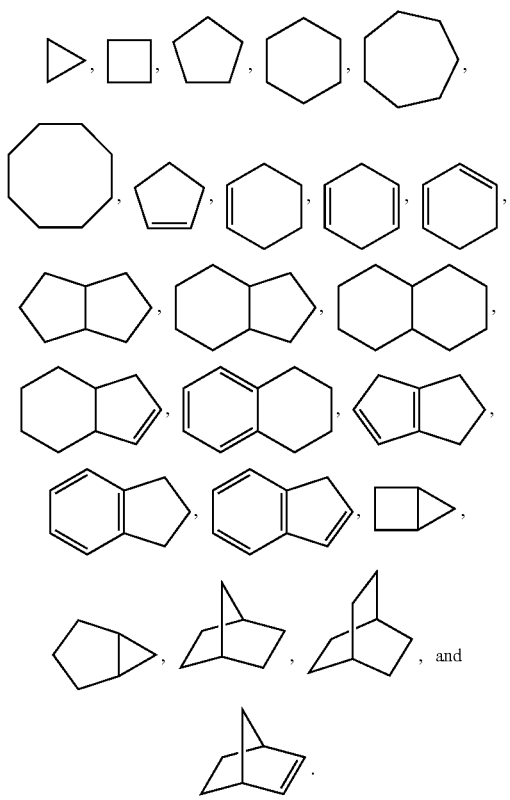

A "heterocycle" or "heterocycloalkyl" group refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members, and can be optionally substituted or unsubstituted. Illustrative examples of heterocycle groups include the following entities, in the form of properly bonded moieties:

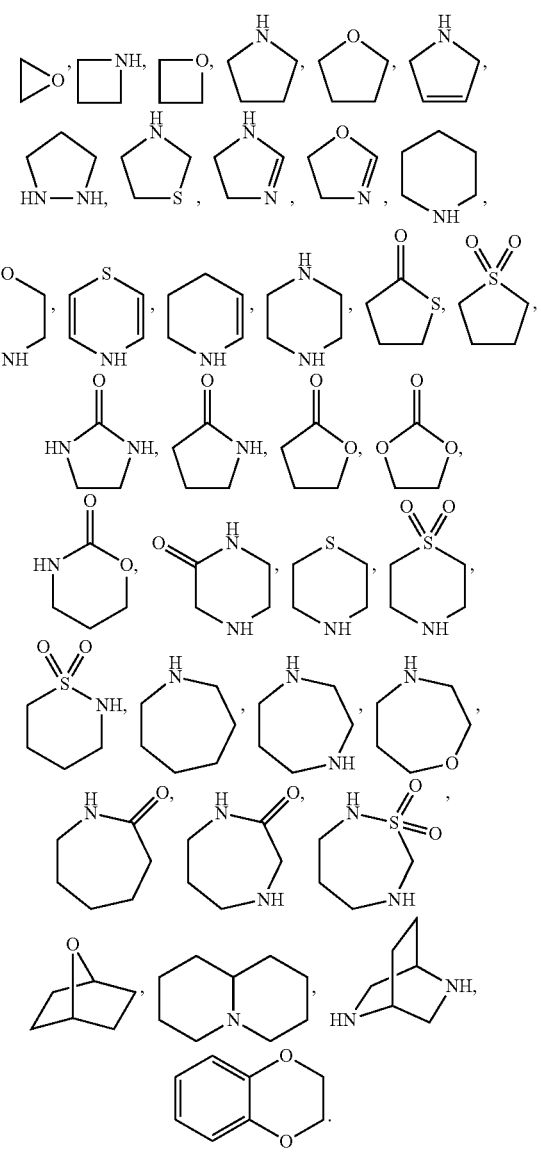

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-14 carbon atoms, about 6-13 carbon atoms, or about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. The heteroaryl can be unsubstituted or optionally substituted. Illustrative examples of heteroaryl groups include the following entities, in the form of properly bonded moieties:

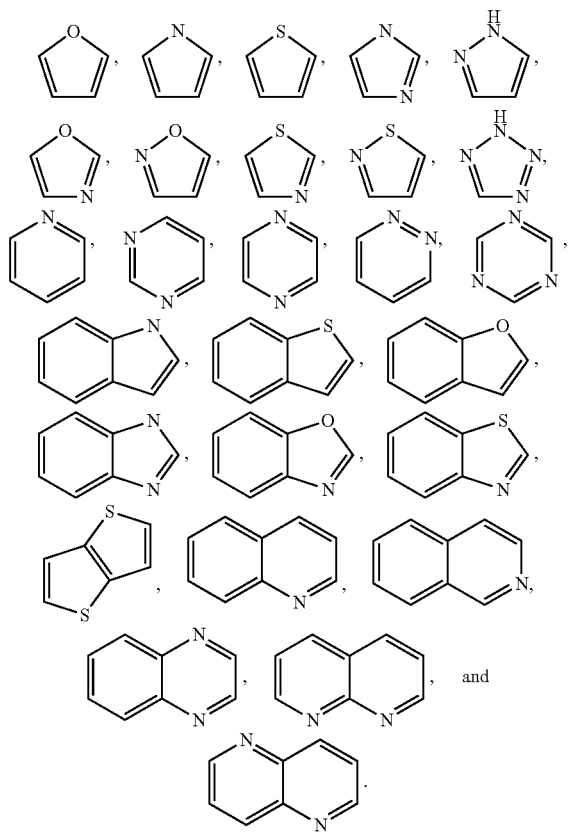

Those skilled in the art will recognize that the species of cycloalkyl, heterocycle, and heteroaryl groups listed or illustrated above are not exhaustive, and that additional species within the scope of these defined terms may also be selected.

As used herein, the term "Het" can refer to oxadiazoles, thiadiazoles, oxazoles, thiazoles, diazines, triazoles, and tetrazoles. In one embodiment, Het specifically refers to 1,3,4-oxadiazoles, 1,2,4-oxadiazoles, the isomeric 1,2,4-oxadiazoles, tetrazoles, 1,3,4-thiadiazoles, oxazoles, 1,2-diazines, thiazoles, and 1,3,4-triazoles. In another specific embodiment, Het specifically refers to 1,2-diazine, a thiazole, a 1,2,4-oxadiazole, a 1,3,4-thiadiazole, a 1,3,4-triazole, or a tetrazole. In yet another embodiment, Het specifically refers to a 1,2,4-oxadiazole, or a 1,3,4-thiadiazole. In other embodiments, Het can refer to a 5-membered heterocyclic ring wherein the ring includes three heteroatoms independently selected from O, S, and N; in some embodiments, at least two of the heteroatoms are N. In yet other embodiments, Het is specifically any 1, 2, 3, 4, 5, 6, 7, or 8 groups selected from 1,3,4-oxadiazoles, 1,2,4-oxadiazoles, the isomeric 1,2,4-oxadiazoles, tetrazoles, 1,3,4-thiadiazoles, oxazoles, 1,2-diazines, thiazoles, and 1,3,4-triazoles.

The term "halogen" represents chlorine, fluorine, bromine or iodine. The term "halo" represents chloro, fluoro, bromo or iodo.

The term "substituted" means that a specified group or moiety can bear one or more (e.g., 1, 2, 3, 4, 5, or 6) substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and/or cyano. In certain embodiments, any one of the above groups can be excluded from a variable or from a group of substituents.

Any formula given herein is intended to represent compounds having structures depicted by the structural formula as well as certain variations or forms. In particular, compounds of any formula given herein may have asymmetric centers and therefore exist in different enantiomeric and/or diastereomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

Such isotopically labeled compounds are useful in metabolic studies (preferably with reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to limit the definition of the moiety for the variable appearing elsewhere. In other words, where a variable appears more than once, the choice of the species from a specified list is independent of the choice of the species for the same variable elsewhere in the formula, or elsewhere in a different formula.

The invention also includes pharmaceutically acceptable salts of the compounds represented by formula I, such as those described above and of the specific compounds exemplified herein, and methods of treatment using such salts.

A "pharmaceutically acceptable salt" is intended to mean a salt of a free acid or base of a compound represented by formula I that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of formula I may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, besylates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of formula I contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of formula I includes an acid moiety, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The term "solvate" refers to a solid compound that has one or more solvent molecules associated with its solid structure. Solvates can form when a compound is crystallized from a solvent, wherein one or more solvent molecules become integral part(s) of the crystal. The compounds of formula I can be solvates, for example, ethanol solvates. Likewise, a "hydrate" refers to a solid compound that has one or more water molecules associated with its solid structure. A hydrate is a subgroup of solvates. Hydrates can form when a compound is crystallized from water, wherein one or more water molecules become integral part(s) of the crystal. The compounds of formula I can be hydrates.

Prodrugs and Metabolites

The invention also relates to pharmaceutically acceptable prodrugs of a compound of formula I, and treatment methods employing such a pharmaceutically acceptable prodrugs. The term "prodrug" refers to a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of formula I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of formula I. Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone, and protected versions thereof.

Additional types of a prodrug may be produced, for instance, by derivatizing free carboxyl groups of structures of formula I as amides or alkyl esters. Examples of amides include those derived from ammonia, primary $C_{1-6}$alkyl amines and secondary di($C_{1-6}$alkyl)amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs.

Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. These prodrug moieties may incorporate groups including ether, amine, and carboxylic acid functionalities.

The present invention also relates to a pharmaceutically active metabolite of a compound of formula I, and use(s) of such a metabolite in the methods of the invention. A "pharmaceutically active metabolite" refers to a pharmacologically active product of metabolism in the body of a compound of formula I or salt thereof. A prodrug or an active metabolite of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

Therapeutic Methods

A compound of formula I and its pharmaceutically acceptable salt, its pharmaceutically acceptable prodrug, and its pharmaceutically active metabolite (collectively, "active agents") of the present invention can be useful as FAAH inhibitors in the methods of the invention. The active agents may be used for the treatment or prevention of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

Compounds and pharmaceutical compositions suitable for use in the present invention include those wherein the active agent is administered in an effective amount to achieve its intended purpose. The phrase "therapeutically effective amount" can refer to an amount effective to treat the disease, disorder, and/or condition, for example, an amount effective to reduce the progression or severity of the condition or symptoms being treated. Determination of a therapeutically effective amount is well within the capacity of persons skilled in the art, especially in light of the detailed disclosure provided herein. The term "effective amount" can include an amount of a compound described herein, or an amount of a combination of compounds described herein, e.g., to treat or prevent a disease or disorder, or to treat the symptoms of the disease or disorder, in a host.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" can include each of medical, therapeutic, and/or prophylactic administration, as appropriate.

Exemplary medical conditions, diseases, and disorders include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm, or combinations thereof.

The active agents may be used to treat subjects (patients) diagnosed with or suffering from a disease, disorder, or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of lessening the severity of, or preventing a disease, disorder, or condition, or one or more symptoms of such disease, disorder or condition mediated through modulation of FAAH activity.

The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

Compounds and Methods of the Invention

The invention provides useful FAAH modulators, for example, inhibitors, including compounds of formula I:

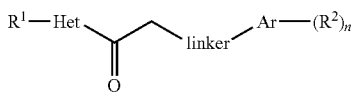

(I)

wherein $R^1$ is aryl, heteroaryl, —$CO_2(C_1$-$C_8)$alkyl, or —$CO_2H$;

Het is a 1,2-diazine, a thiazole, a 1,2,4-oxadiazole, a 1,3,4-thiadiazole, a 1,3,4-triazole, or a tetrazole;

linker is a ($C_1$-$C_{20}$)alkyl chain wherein one to five carbons of the chain are optionally be replaced with O or S, or linker is a direct bond;

Ar is ($C_6$-$C_{14}$)aryl;

n is 1-4;

each $R^2$ is independently H, —X—$R^3$, or —X-Ph-X—$R^3$;

each X is independently —$CH_2$—, —O—, —$CH_2O$—, —$OCH_2$—, —C(=O)—, —$CO_2$—, —OC(=O)—, —S—, —S(O)—, —S(O)$_2$—, —N($R^a$)—, or a direct bond;

each $R^3$ is independently H, ($C_1$-$C_8$)alkyl, ($C_3$-$C_8$)cycloalkyl, aryl, heteroaryl, —$CF_3$, —CN, —C(O)($C_1$-$C_8$)alkyl optionally substituted with one, two, or three fluoro substituents, —$CO_2(C_1$-$C_8)$alkyl, —$CO_2H$, —C(O)$NR^aR^b$, —OH, —O($C_1$-$C_8$)alkyl, -halo, —$NO_2$, —$NR^aR^b$, —N($R^a$)C(O)$R^b$, —N($R^a$)SO$_2R^b$, —SO$_2NR^aR^b$, —S(O)$_{0-2}R^a$, or —$CH_2NR^cR^d$ wherein $R^c$ and $R^d$ are each independently H or ($C_1$-$C_8$)alkyl, or $R^c$ and $R^d$ taken together with the nitrogen to which they are attached form a monocyclic saturated heterocyclic group;

each $R^a$ and $R^b$ are each independently H, ($C_1$-$C_8$)alkyl, ($C_3$-$C_8$)cycloalkyl, aryl($C_1$-$C_8$)alkyl, or a nitrogen protecting group; and the aryl or heteroaryl of $R^1$ is optionally substituted with one, two, or three $R^2$ groups;

or a pharmaceutically acceptable salt, solvate, or hemiketal thereof. In some embodiments, Het can be defined as in the Definitions section above.

In certain embodiments, the compound of formula I can be a compound of formula II:

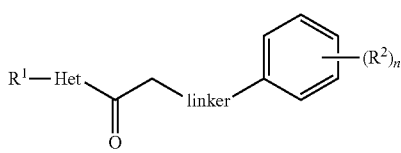

(II)

wherein $R^1$, linker, and $R^2$ are as defined for formula I.

In one embodiment, the compound of formula I can be a compound of formula III:

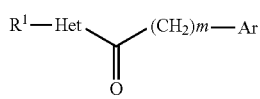

(III)

wherein $R^1$ and Ar are as defined for formula I, Ar is optionally substituted with 1-5 $R^2$ groups, and wherein m is 1 to about 20, for example, about 2 to about 10, wherein one to five carbons of the chain can optionally be replaced with one or more O or S atoms. In certain embodiments, m can be 1, 2, 3, 4, 5, 6, 7, 8, 9, 10, 11, 12, 13, 14, 15, 16, 17, 18, 19, or 20, or any range between any two of the foregoing integers.

In certain embodiments, the compound of formula I can be a compound of formula IV:

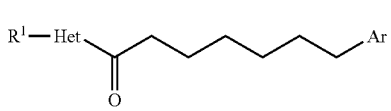

(IV)

wherein $R^1$ and Ar as defined for formula I, and Ar is optionally substituted with 1-5 $R^2$ groups. In some embodiments, Ar can be a phenyl or naphthyl group, optionally substituted with 1, 2, 3, 4, or 5 substituents, as defined herein.

In yet another embodiment, the compound of formula I can be a compound of formula V:

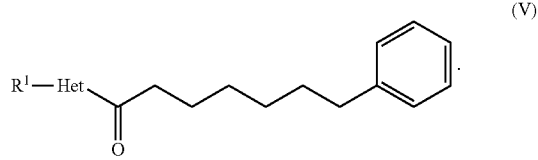

(V)

In yet another embodiment, the compound of the invention includes compounds of formula VI:

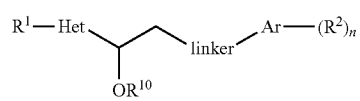

(VI)

wherein $R^1$, $R^2$, n, Het, linker, and Ar are as defined in formula I, and $R^{10}$ is H or an oxygen protecting group, such as a silicon protecting group, for example, TBS, TIPS or TBDPS.

In yet another embodiment, a compound of the invention includes a compound of formula VII:

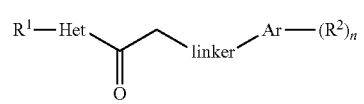

(VII)

wherein linker, Ar, $R^2$, n, are as defined in formula I, Het can be as defined in formula I or as defined in the Definition section above, and $R^1$ is H or optionally any one or more of the $R^1$ groups as defined in formula I.

In one embodiment, Het can be a 1,2,4-oxadiazole, or a 1,3,4-thiadiazole.

In one embodiment, $R^1$ can be 2-pyridyl, 2-furyl, 2-thiophenyl, or phenyl. In another embodiment, $R^1$ is —$CO_2H$ or —$CO_2(C_1$-$C_8)$alkyl, such as methyl, ethyl, or hexyl, wherein the alkyl is optionally substituted. In another embodiment, the aryl or heteroaryl of $R^1$ is optionally substituted with one or two $R^2$ groups.

In one embodiment, linker is a ($C_1$-$C_8$)alkyl or a direct bond. In other embodiments, alkyl chain of the linker has 1, 2, 3, 4, or 5 carbons of the chain independently replaced with O or S, including either of the terminal carbons of the linker.

In one embodiment, Ar is phenyl, biphenyl, or naphthyl.

In one embodiment, $R^2$ is H and n is 1. In another embodiment, $R_2$ can be —X—$R^3$; wherein X is —O—, —S—, or a direct bond; and $R^3$ is optionally substituted phenyl.

In one embodiment, $R^3$ is H, $(C_1$-$C_8)$alkyl, aryl, heteroaryl, —$CF_3$, —CN, —$CO_2H$, —OH, —$O(C_1$-$C_8)$alkyl, -halo, or —$NO_2$. The heteroaryl group can be selected from the following:

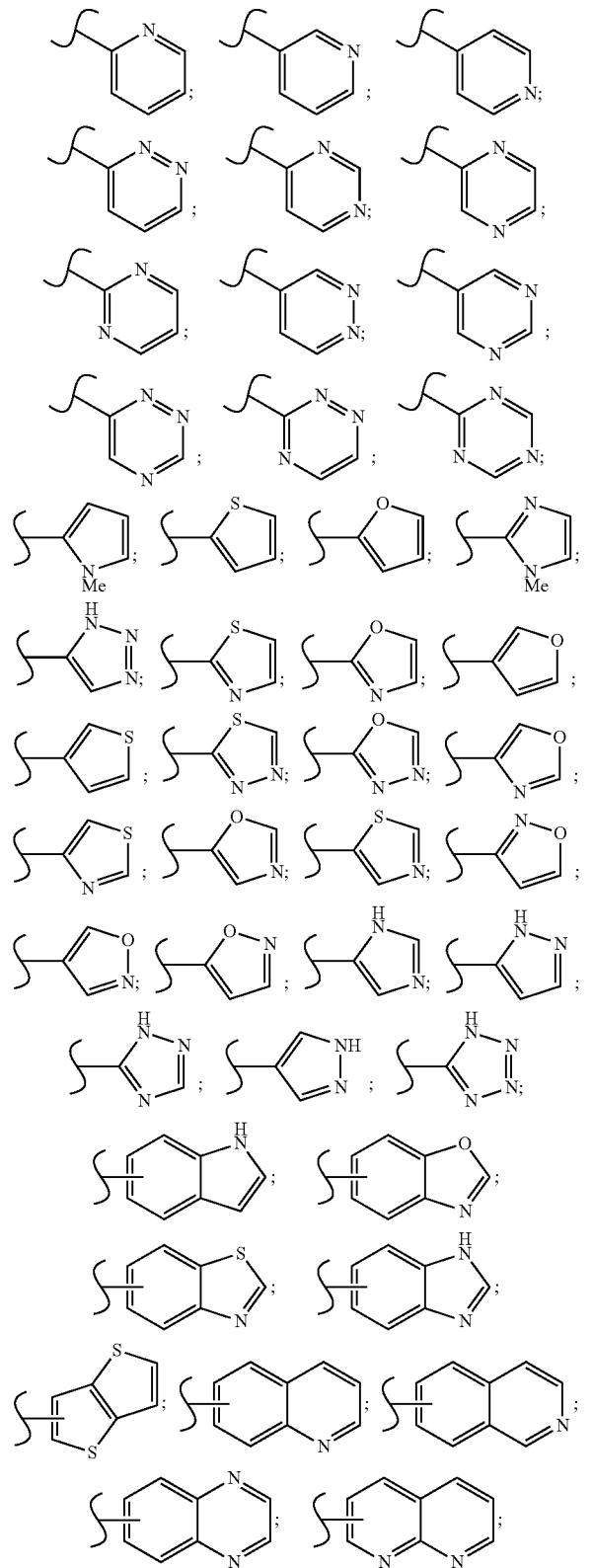

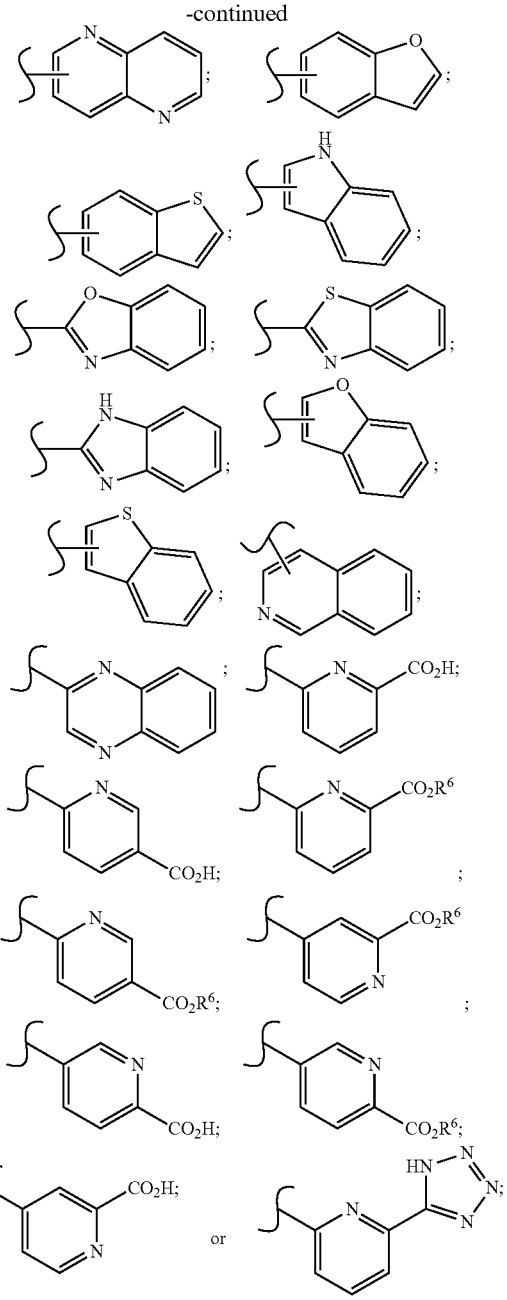

where $R^6$ can be $(C_1$-$C_6)$alkyl. Any aryl or heteroaryl can be optionally substituted with one or more $R^2$ groups, wherein each $R^2$ is independently H, —X—$R^3$, or —X-Ph-X—$R^3$; and X and $R^3$ are as defined above for formula I.

In one embodiment, $R^c$ and $R^d$ are taken together with the nitrogen to which they are attached to form a piperidine, morpholine, thiomorpholine, pyrrolidine, or N-methylpiperazine group.

Accordingly, compounds of the invention include, but are not limited to:

1-(3-(6-Chloropyridin-2-yl)-1,2,4-oxadiazol-5-yl)-7-phenylheptan-1-one (21);
1-(3-(6-Bromopyridin-2-yl)-1,2,4-oxadiazol-5-yl)-7-phenylheptan-1-one (22);
1-(3-(6-Iodopyridin-2-yl)-1,2,4-oxadiazol-5-yl)-7-phenylheptan-1-one (23);

1-(3-(6-Cyanopiridin-2-yl)-1,2,4-oxadiazol-5-yl)-7-phenyl-heptan-1-one (24);
Methyl 6-(5-(7-Phenylheptanoyl)-1,2,4-oxadiazol-3-yl)-picolinate (9f);
6-(5-(7-Phenylheptanoyl)-1,2,4-oxadiazol-3-yl)-picolinic acid (9g);
7-Phenyl-1-(3-(pyridin-2-yl)-1,2,4-oxadiazol-5-yl)-heptan-1-one (9b);
1-(3-(Furan-2-yl)-1,2,4-oxadiazol-5-yl)-7-phenylheptan-1-one (9c);
7-Phenyl-1-(3-(thiophen-2-yl)-1,2,4-oxadiazol-5-yl)-heptan-1-one (9d);
1-(1,2,4-Oxadiazol-5-yl)-7-phenylheptan-1-one (9a);
1-(1,2,4-Oxadiazol-3-yl)-7-phenylheptan-1-one (10a);
7-Phenyl-1-(5-(pyridin-2-yl)-1,2,4-oxadiazol-3-yl)-heptan-1-one (10b);
1-(5-(Furan-2-yl)-1,2,4-oxadiazol-3-yl)-7-phenylheptan-1-one (10c);
7-Phenyl-1-(5-(thiophen-2-yl)-1,2,4-oxadiazol-3-yl)-heptan-1-one (10d);
Methyl 6-(3-(7-Phenylheptanoyl)-1,2,4-oxadiazol-5-yl)-picolinate (10f);
6-(3-(7-Phenylheptanoyl)-1,2,4-oxadiazol-5-yl)-picolinic acid (10g);
Methyl 3-(7-Phenylheptanoyl)-1,2,4-oxadiazole-5-carboxylate (10h);
7-Phenyl-1-(thiazol-2-yl)-heptan-1-one (11a);
7-Phenyl-1-(5-(pyridin-2-yl)-thiazol-2-yl)-heptan-1-one (11b);
1-(5-(Furan-2-yl)-thiazol-2-yl)-7-phenylheptan-1-one (11c);
7-Phenyl-1-(5-(thiophen-2-yl)-thiazol-2-yl)-heptan-1-one (11d);
Methyl 6-(2-(7-Phenylheptanoyl)-thiazol-5-yl)-picolinate (11f);
6-(2-(7-Phenylheptanoyl)thiazol-5-yl)-picolinic Acid (11g);
7-Phenyl-1-(5-(pyridin-2-yl)-1,3,4-thiadiazol-2-yl)-heptan-1-one (12b);
1-(5-(Furan-2-yl)-1,3,4-thiadiazol-2-yl)-7-phenylheptan-1-one (12c);
7-Phenyl-1-(5-(thiophen-2-yl)-1,3,4-thiadiazol-2-yl)-heptan-1-one (12d);
1-(5-(6-Bromopyridin-2-yl)-1,3,4-thiadiazol-2-yl)-7-phenylheptan-1-one (25);
Methyl 6-(5-(7-Phenylheptanoyl)-1,3,4-thiadiazol-2-yl)-picolinate (12f);
6-(5-(7-Phenylheptanoyl)-1,3,4-thiadiazol-2-yl)-picolinic acid (12g);
Methyl 5-(7-Phenylheptanoyl)-1,3,4-thiadiazole-2-carboxylate (12h);
7-Phenyl-1-(1,3,4-thiadiazol-2-yl)-heptan-1-one (12a);
7-Phenyl-1-(6-(pyridin-2-yl)-pyridazin-3-yl)-heptan-1-one (13b);
1-(6-(Furan-2-yl)-pyridazin-3-yl)-7-phenylheptan-1-one (13c);
7-Phenyl-1-(6-(thiophen-2-yl)-pyridazin-3-yl)-heptan-1-one (13d);
6-(6-(7-Phenylheptanoyl)-pyridazin-3-yl)-picolinonitrile (26);
Methyl 6-(6-(7-Phenylheptanoyl)-pyridazin-3-yl)-picolinate (13f);
6-(6-(7-Phenylheptanoyl)-pyridazin-3-yl)-picolinic acid (13g);
7-Phenyl-1-(pyridazin-3-yl)-heptan-1-one (13a);
7-Phenyl-1-(5-(pyridin-2-yl)-4H-1,2,4-triazol-3-yl)-heptan-1-one (14b);
1-(5-(Furan-2-yl)-4H-1,2,4-triazol-3-yl)-7-phenylheptan-1-one (14c);
7-Phenyl-1-(5-(thiophen-2-yl)-4H-1,2,4-triazol-3-yl)-heptan-1-one (14d);
Methyl 5-(7-Phenylheptanoyl)-4H-1,2,4-triazole-3-carboxylate (14h);
7-Phenyl-1-(4H-1,2,4-triazol-3-yl)-heptan-1-one (14a);
1-(1-Methyl-3-(pyridin-2-yl)-1H-1,2,4-triazol-5-yl)-7-phenylheptan-1-one (16);
1-(1-Methyl-5-(pyridin-2-yl)-1H-1,2,4-triazol-3-yl)-7-phenylheptan-1-one (17);
1-(4-Methyl-5-(pyridin-2-yl)-4H-1,2,4-triazol-3-yl)-7-phenylheptan-1-one (18);
7-Phenyl-1-(2H-tetrazol-5-yl)-heptan-1-one (15a);
7-Phenyl-1-(2-(pyridin-2-yl)-2H-tetrazol-5-yl)-heptan-1-one (15b);
1-(2-(Furan-2-yl)-2H-tetrazol-5-yl)-7-phenylheptan-1-one (15c);
7-Phenyl-1-(2-(thiophen-2-yl)-2H-tetrazol-5-yl)-heptan-1-one (15d);
7-Phenyl-1-(2-phenyl-2H-tetrazol-5-yl)-heptan-1-one (15e);
1-(2-Methyl-2H-tetrazol-5-yl)-7-phenylheptan-1-one (19a);
1-(1-Methyl-1H-tetrazol-5-yl)-7-phenylheptan-1-one (19b);
and their salts, solvates, and/or hemiketals. In certain embodiments, these compounds are compounds of one or more of formulas I-V and/or VII. They may be employed in the compositions and methods of the invention described herein.

The invention also provides a composition comprising a compound of any one of formulas I-VII and a pharmaceutically acceptable diluent or carrier. The composition can be a pharmaceutical composition. The pharmaceutical composition can include an analgesic, such as an opioid or a non-steroidal anti-inflammatory drug. Examples of such analgesics include aspirin, acetaminophen, opioids, ibuprofen, naproxen, COX-2 inhibitors, gabapentin, pregabalin, tramadol, or combinations thereof.

Accordingly, the invention also provides a method of treating a subject suffering from or diagnosed with a disease, disorder, or medical condition mediated by FAAH activity, comprising administering to the subject in need of such treatment an effective amount of at least one compound of a formula described herein, a pharmaceutically acceptable salt thereof, a pharmaceutically acceptable prodrug thereof, or a pharmaceutically active metabolite thereof. The disease, disorder, or medical condition can include anxiety, depression, pain, sleep disorders, eating disorders, inflammation, movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, neuroinflammation, or a combination thereof.

The invention further includes a pharmaceutical composition for treating a disease, disorder, or medical condition mediated by FAAH activity, comprising: (a) an effective amount of at least one compound of a formula described herein, or a pharmaceutically acceptable salt, a pharmaceutically acceptable prodrug, or an pharmaceutically active metabolite thereof, or any combination thereof, and a pharmaceutically acceptable excipient. The invention also includes a method of inhibiting fatty acid amide hydrolase activity comprising contacting the fatty acid amide hydrolase with an effective amount of a compound of any one of formulas I-VII. The contacting can be in vivo or in vitro.

Protecting Groups

The term "protecting group" refers to any group that, when bound to a hydroxyl, nitrogen, or other heteroatom prevents undesired reactions from occurring at this group and that can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyldiphenylsilyl (TBDPS), triisopropylsilyl (TIPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Typical nitrogen and oxygen protecting groups described in Greene (pages 14-118) include benzyl ethers, silyl ethers, esters including sulfonic acid esters, carbonates, sulfates, and sulfonates. For example, suitable nitrogen or oxygen protecting groups can include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate);
groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy) ethyl carbonate, 4-(methylthiomethoxy)butyrate,
miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-polybenzoate, α-naphthoate, nitrate, alkyl N,N,N',N'-tetramethyl-phosphorodiamidate, n-phenylcarbamate, borate, 2,4-dinitrophenylsulfenate); and sulfonates (sulfate, methanesulfonate (mesylate), benzylsulfonate, tosylate, triflate).

Delivery Modes and Preparations Therefor

In treatment methods according to the invention, an effective amount of at least one active agent is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

An exemplary dose can be in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent a formula described herein or included with such an agent in a pharmaceutical composition according to the invention. In an example of an embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition may contain one or more additional active ingredients, for example, one or more of opioids, NSAIDs (e.g., ibuprofen, cyclooxygenase-2 (COX-2) inhibitors, and naproxen), gabapentin, pregabalin, tramadol, acetaminophen, and/or aspirin.

The active agents of the invention can be used, alone or in combination with one or more additional active ingredients, to formulate pharmaceutical compositions of the invention. A pharmaceutical composition of the invention can include, for example, (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the methods by a suitable route of delivery, e.g., oral, parenteral, rectal, topical, or ocular routes, or by inhalation. Suitable routes include administration by catheter or by injection (e.g., IV, IM, or SC).

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily. These dosages may be orally administered using any of the foregoing preparations and the administration will be accomplished according to the wisdom and judgment of the patient's attending physician.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days. Administration will be accomplished according to the wisdom and judgment of the patient's attending physician.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered by inhalation, via the nasal or oral routes, e.g., in a spray formulation also containing a suitable carrier.

Compound Preparation and Enzyme Inhibitory Activity

Exemplary chemical entities useful in methods of the invention are described herein by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified or defined, the variables can be defined with reference to formula I above.

Many compounds of the invention can generally be prepared by metallation of a Het group, for example, an acidic hydrogen of a 1,3,4-oxadiazole, 1,2,4-oxadiazole, a tetrazole, a 1,3,4-thiadiazole, an oxazole, a thiazole, or a 1,3,4-triazole, and reaction with a suitable acid chloride (see Ham, N. K. et al., *Tetrahedron Lett.* 1995, 36, 9453-9456). Alternatively, compounds of the invention can be prepared by metallation of a Het group and reaction with suitable aldehydes to form alcohols. Protection of the alcohol functionality with a suitable protecting group, PG (such as a silyl protecting group), provides compounds that can be further metallated at another position to add a second substituent, such as an $R^1$ group. For example, metallation of the 5-position of an appropriate 5-membered Het group and quenching with iodine or tributyltin chloride provides compounds with iodine or —SnBu$_3$ leaving groups. Palladium-mediated coupling with suitable reagents $R^1$-M, where M is —SnBu$_3$, —B(OH)$_2$, I, or Br, followed by deprotection of the alcohol protecting group and oxidation under standard conditions, provides several examples of the compounds of the invention. For suitable and related synthetic techniques, see Boger et al. *J. Med. Chem.* 2005, 48, 1849-1856.

Compounds of formula I may be converted to their corresponding salts using methods described in the art. In particular, an amine-containing compound of the invention may be treated with trifluoroacetic acid, HCl, or citric acid in a solvent such as Et$_2$O, CH$_2$Cl$_2$, THF, and MeOH to provide the corresponding salt form.

Compounds prepared according to the schemes described below may be obtained as single enantiomers, diastereomers, or regioisomers, by enantio-, diastero-, or regiospecific synthesis, or by resolution. Compounds prepared according to the schemes above may alternately be obtained as racemic (1:1) or scalemic (non-racemic) (not 1:1) mixtures or as mixtures of diastereomers or regioisomers. Where racemic and scalemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

Using the synthetic techniques described above, a series of α-ketoheterocycles were prepared and were discovered to be substrates of fatty acid amide hydrolase (FAAH). The nature of the central heterocycle significantly influenced the inhibitor activity. Analysis of the compounds prepared provided certain trends of activity. The trend, in ascending order, was determined to be: 1,3,4-oxadiazoles and 1,2,4-oxadiazoles 9>tetrazoles, the isomeric 1,2,4-oxadiazoles 10, 1,3,4-thiadiazoles>oxazoles>1,2-diazines>thiazoles>1,3,4-triazoles (Scheme A).

Scheme A. Representative compounds according to an embodiment of the invention.

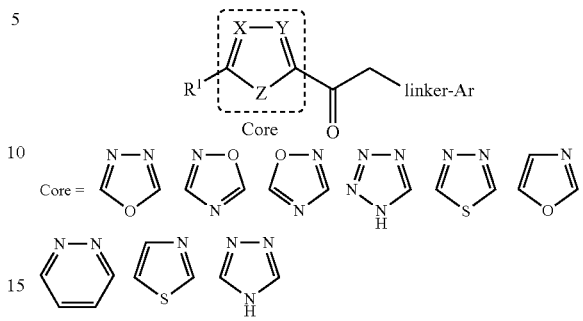

It was surprisingly found that the introduction of an additional heteroatom at position 4 (oxazole numbering, activity=N>O>CH) substantially increases modulation activity. Such newly discovered compounds of the invention may reduce destabilizing steric interaction at the FAAH active site. It was also found that the addition of certain substituents, for example, certain heterocycle substituents, were found to further enhance the inhibitor potency and, more significantly, to enhance the inhibitor selectivity. Accordingly, the invention provides compounds that possess enhanced FAAH activity or selectivity compared to known compounds and compounds that can also disrupt binding affinity for competitive off-target enzymes.

Fatty acid amide hydrolase (FAAH) is the enzyme that serves to hydrolyze endogenous lipid amides including anandamide (1a) and oleamide (1b) (Scheme 1). Its distribution is consistent with its role in degrading and regulating such neuromodulating and signaling fatty acid amides at their sites of action. Although it is a member of the amidase signature family of serine hydrolases, for which there are a number of prokaryotic enzymes, it is currently the only characterized mammalian enzyme bearing the family's unusual Ser-Ser-Lys catalytic triad.

Scheme 1. Substrates of fatty acid amide hydrolase (FAAH)

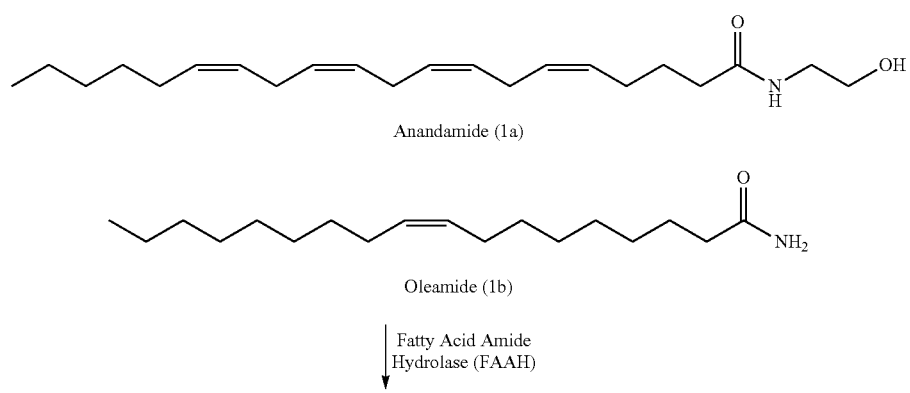

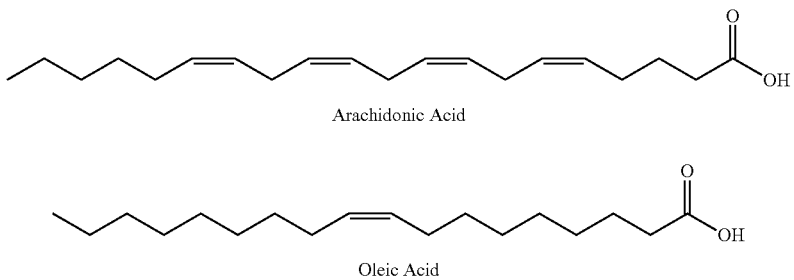

Arachidonic Acid

Oleic Acid

Due to the therapeutic potential of inhibiting FAAH, especially for the treatment of pain, inflammatory, or sleep disorders, there has been an increasing interest in the development of selective and potent inhibitors of the enzyme. Early studies shortly following the initial characterization of the enzyme led to the discovery that the endogenous sleep-inducing molecule 2-octyl α-bromoacetoacetate is an effective FAAH inhibitor. A series of nonselective reversible inhibitors bearing an electrophilic ketone (e.g., trifluoromethyl ketone-based inhibitors) and a set of irreversible inhibitors (e.g., fluorophosphonates and sulfonyl fluorides) were also reported. To date, only two classes of inhibitors have been disclosed that provide opportunities for the development of inhibitors with therapeutic potential.

One class is the reactive aryl carbamates and ureas that irreversibly acylate a FAAH active site serine and that have been shown to exhibit anxiolytic activity and produce analgesic effects. To date and with some exceptions, the selectivity of such inhibitors has often been low, further complicating the development of inhibitors that irreversibly and covalently modify the target enzyme. A second class is the α-keto-heterocycle-based inhibitors that bind to FAAH via reversible hemiketal formation with an active site serine. Many of these inhibitors have been shown to be efficacious analgesics in vivo, and certain oxazoles were found to be inhibitors of FAAH (see Boger et al., *J. Med. Chem.* 2005, 48, 1849-1856). Scheme 2 illustrates a new class of inhibitors, according to various embodiments of the invention.

Scheme 2. Potent FAAH inhibitors.

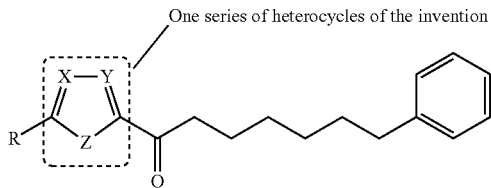

One series of heterocycles of the invention

The compounds of the invention can be potent and selective (≥100-300 fold) FAAH inhibitor that induce analgesia and increases endogenous anandamide levels. The compounds can exhibit analgesic activity in the tail flick assay, hot plate assay, formalin test of noxious chemical pain ($1^{st}$ and $2^{nd}$ phase), the mild thermal injury (MTI) model of peripheral pain, and the spinal nerve ligation (SNL) model of neuropathic pain with efficacies that match or exceed those of morphine (at 1-3 mg/kg in MTI/SNL), ibuprofen (at 100 mg/kg in MTI), or gabapentin (at 500 mg/kg in SNL) and at administered doses (10-20 mg/kg, i.p.) that approach or exceed those of such common pain medications. The compounds can lack significant offsite target activity (Cerep assay profiling), not bind cannabinoid (CB1 or CB2) or vanilloid (TRP) receptors, and not significantly inhibit common P450 metabolism enzymes (3A4, 2C9, 2D6) or the human ether-a-go-go related gene (hERG).

The compounds of the invention can be effective to promote analgesia in FAAH knockout mice. In such instances, the activity would verify that FAAH is the only relevant target responsible for the in vivo analgesic effects of the compound. Moreover, the analgesic effects may take place without the respiratory depression or chronic dosing desensitization characteristic of opioid administration or the increased feeding and decreased mobility and motor control characteristic of a cannabinoid (CB1) agonist administration.

Thus, the compounds for formula I can alter and even increase FAAH activity and selectivity with respect to certain known compounds. During the course of preparing certain compounds of the invention, it was discovered that altering the substituents at the 5-position of the central heterocycle (aryl and nonaromatic substituents) and at the C2 acyl side chain provided extraordinarily potent and selective FAAH inhibitors (Scheme 2 above). The results of these discoveries wherein the central heterocycle of the α-keto-heterocycle is varied, along with results of the proteome-wide selectivity screening of the resulting compounds of the invention are reported herein.

Preparation of Certain Compounds of the Invention.

The preparation of the 1,3,4-thiadiazole (12), 1,3,4-oxadiazole (8), and 1,2,4-oxadiazole (9) inhibitors is illustrated below in Scheme 3. A one pot procedure was utilized to prepare the C-5 aryl substituted 1,3,4-thiadiazole, 1,3,4-oxadiazole, and 1,2,4-oxadiazole methyl esters. In the case of the 1,3,4-thiadiazole and 1,3,4-oxadiazole, the corresponding aryl(R) methyl ester was converted to the hydrazide with hydrazine monohydrate, whereas the aryl(R) nitrile was transformed to the N-hydroxycarbamide with hydroxylamine for the 1,2,4-oxadiazole, all of which were subsequently treated with methyl oxalyl chloride in the presence of $Et_3N$ to give a diacyl hydrazide intermediate.

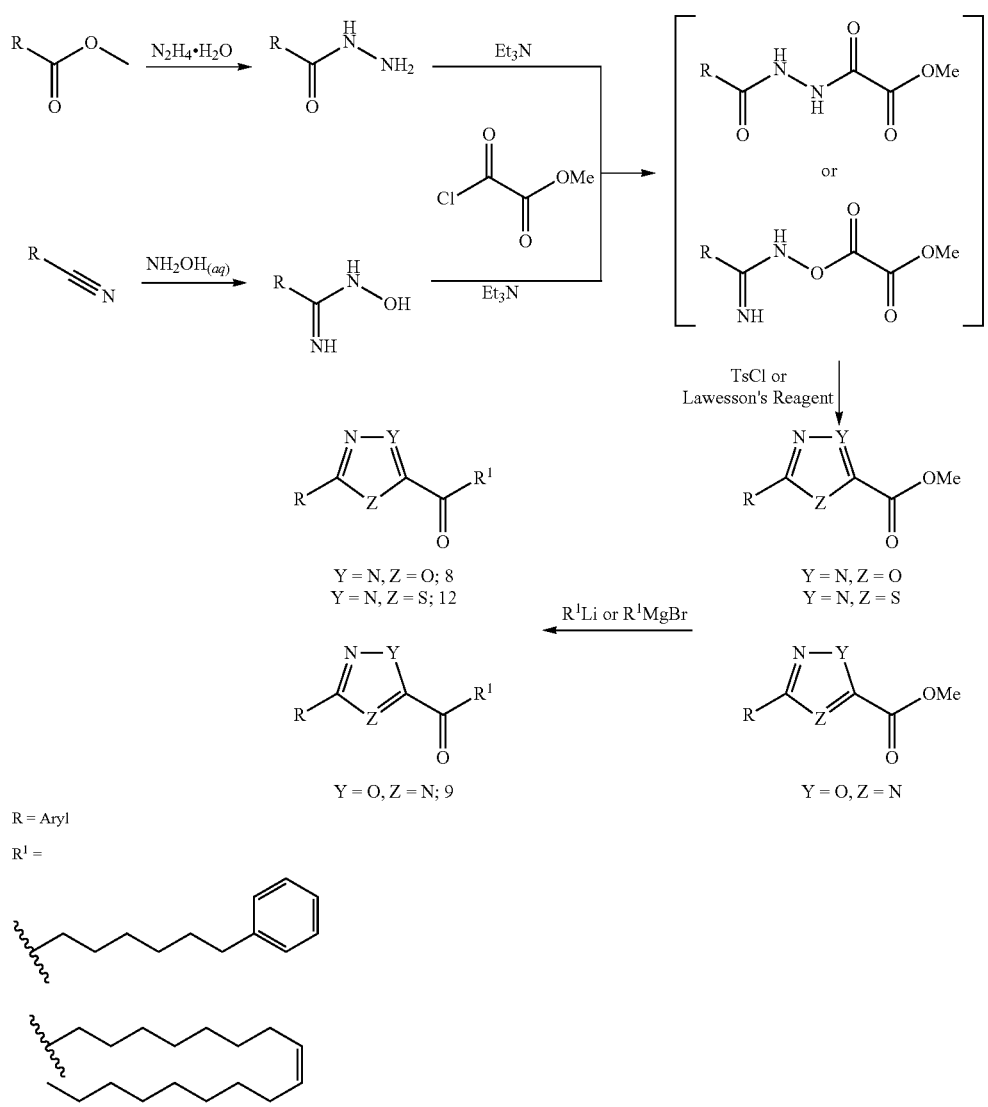

The diacyl hydrazide intermediates cyclized upon treatment with Lawesson's reagent to provide the desired 1,3,4-thiadiazole, or with p-toluenesulfonyl chloride (TsCl) for the 1,3,4-oxadiazole and 1,2,4-oxadiazole. Subsequent addition of the side chain ($R^1$) to the methyl ester was accomplished via a metal-halogen exchange of the corresponding alkylbromide to provide the α-ketooxadiazole or α-ketothiadiazole.

Synthesis of the 1,2,4-triazole series (14) in an analogous fashion was unsuccessful. The side chain nucleophilic addition to the corresponding methyl ester failed to afford product. An alternative approach was developed to obtain the desired 1,2,4-triazoles (Scheme 4).

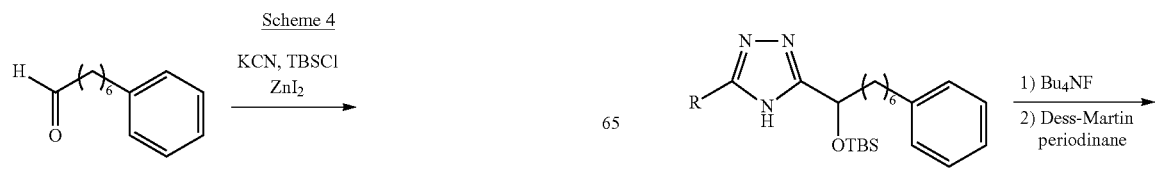

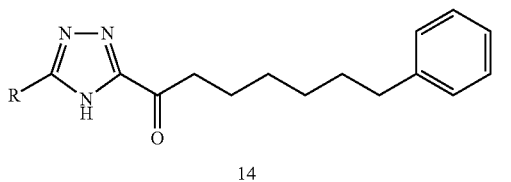

14

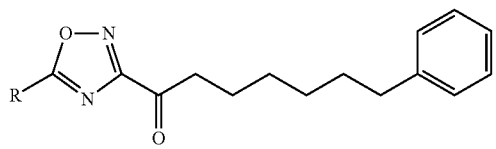

10

7-Phenylheptanal was converted to the silyl-protected cyanohydrin upon treatment with potassium cyanide, TBSCl, and catalytic ZnI$_2$ (Rawal et al., *Tetrahedron Lett.* 1985, 26, 4275-4278). The corresponding amidrazone (see Kauffman, *Angew. Chem. Int. Ed.* 1964, 3, 342-353; Garg at al., *Tetrahedron Lett.* 2005, 46, 1997-2000; and Li at al., *J. Org. Chem.* 1993, 58, 516-519) was formed by in situ generation of sodium hydrazine followed by dropwise addition of the cyanohydrin, which was treated with an aryl(R) acid chloride.

Surprisingly, the cyclization afforded mainly the 1,3,4-oxadiazole product along with a small amount of the desired 1,2,4-triazole product. Although this offered an additional route to the 1,3,4-oxadiazoles, it required modification for 1,2,4-triazole formation. The alternative was a two-step condensation and oxidation pathway via reaction of the amidrazone with aryl(R) aldehydes to provide a stable imine, which undergoes oxidative cyclization to the triazole upon treatment with DDQ (see Walker et al., *Chem. Rev.* 1967, 67, 153-195; and Bruché et al.; *Tetrahedron* 1989, 45, 7427-7432). The desired 1,2,4-triazoles 14 were obtained after TBS deprotection (Bu$_4$NF) and oxidation of the liberated alcohol with Dess-Martin periodinane.

The TBS protected cyanohydrin was also a key intermediate for the preparation of two additional inhibitor series, the isomeric 1,2,4-oxadiazoles (10) and tetrazoles (15). For the 1,2,4-oxadiazoles, the cyanohydrin was converted to the N-hydroxycarbamide upon treatment with hydroxylamine. Its treatment with acid chlorides in the presence of Et$_3$N to give the diacyl hydrazide intermediates followed by dehydration with p-toluenesulfonyl chloride (TsCl) at elevated temperatures gave the desired 1,2,4-oxadiazoles 10 after TBS deprotection (Bu$_4$NF) and oxidation of the liberated alcohol with Dess-Martin periodinane (Scheme 5).

The tetrazoles (15) were obtained by treatment of the cyanohydrin with sodium azide (see Demko and Sharpless, *Org. Lett.* 2002, 4, 2525-2527). Reprotection of the alcohol using TBSCl followed by regioselective N-arylation using a copper-catalyzed Ullmann condensation with iodopyridine or with mixed-aryl hypervalent iodonium salts afforded N2 substituted tetrazoles, which were converted to the corresponding products upon TBS deprotection (Bu$_4$NF) and oxidation of the liberated alcohol with Dess-Martin periodinane (Scheme 6).

Scheme 6

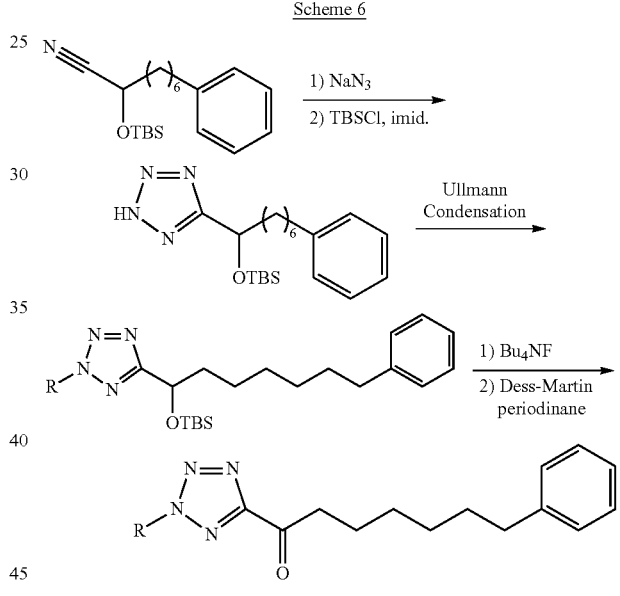

15

The synthesis of the 1,3-thiazole inhibitors (11) entailed a selective C2-lithiation of thiazole followed by condensation with 7-phenylheptanal. TBS protection of the resulting alcohol followed by selective C5-lithiation (t-BuLi) and stannylation or iodination and subsequent Stille coupling produced the substituted thiazoles, which were converted to the corresponding ketones by TBS deprotection (Bu$_4$NF) and oxidation of the liberated alcohol with Dess-Martin periodinane (Scheme 7).

Scheme 5

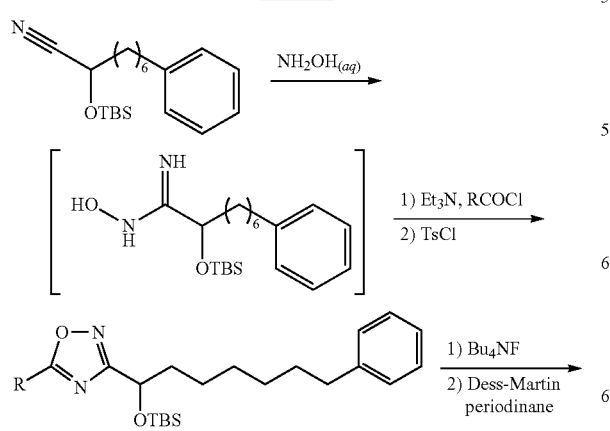

Scheme 7

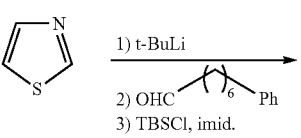

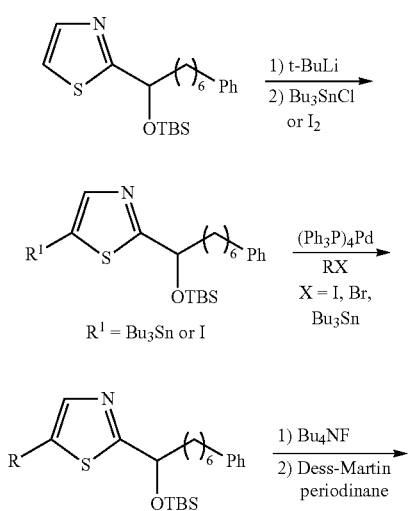

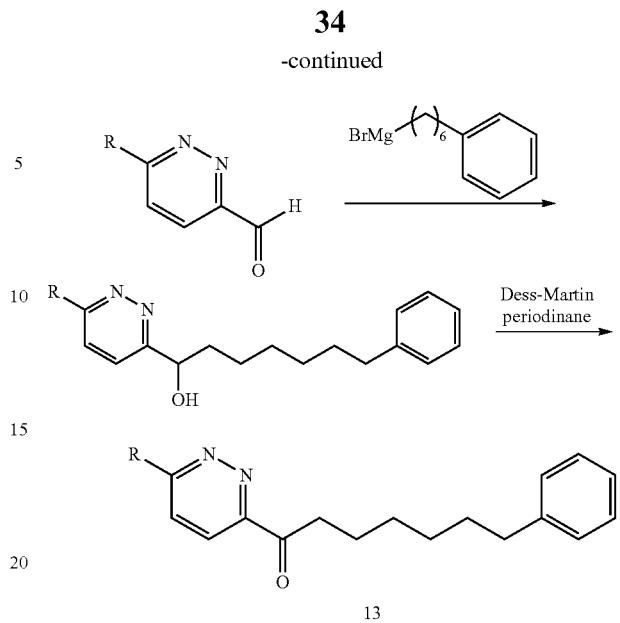

Synthesis of the 1,2-diazine inhibitors (13) began with Stille coupling of a known chloropyridazine (Olsen et al., Bioorg. Med. Chem. Lett. 2004, 14, 1551-1554) and a series of 2-(tributylstannyl)arenes or 2-aryl boronic esters to afford the series of 6-aryl substituted pyridazine-3-carboxylates. The corresponding methyl ester was converted to the aldehyde by a reduction-oxidation process in order to increase the electrophilicity of the intermediate for subsequent side chain addition, which was accomplished via metal-halogen exchange of the corresponding alkylbromide. The alcohol precursor was oxidized with Dess-Martin periodinane to provide the 1,2,-diazines 13 (Scheme 8).

Scheme 8

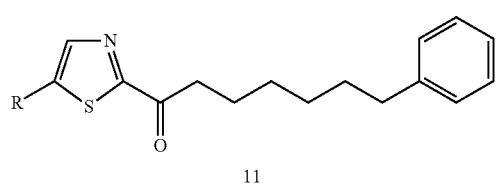

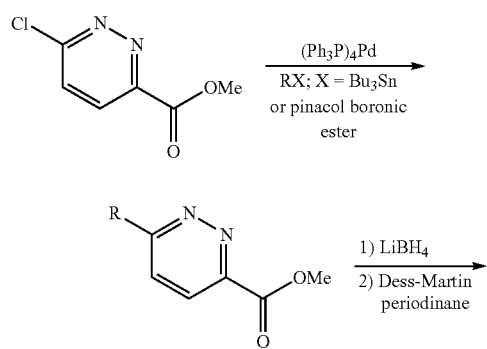

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Discovery of Selective FAAH Inhibitors

Enzyme Assays.

Enzyme assays were performed at 20-23° C. with purified recombinant rat FAAH expressed in *Escherichia coli* (unless indicated otherwise) or with solubilized COS-7 membrane extracts from cells transiently transfected with human FAAH cDNA (where specifically indicated) in a buffer of 125 mM Tris/1 mM EDTA/0.2% glycerol/0.02% Triton X-100/0.4 mM Hepes, pH 9.0. See Patricelli et al., *Biochemistry* 1998, 37, 15177-15187; and Giang et al., *Proc. Natl. Acad. Sci. U.S.A.* 1997, 94, 2238-2242. The initial rates of hydrolysis ($\leq$10-20% reaction) were monitored using enzyme concentrations (typically 1 nM) at least 3 times below the measured $K_i$ by following the breakdown of $^{14}C$-oleamide, and $K_i$ values were established as described (Dixon plot). Lineweaver-Burk analysis previously established reversible, competitive inhibition for 2 and related inhibitors (see Boger et al., *J. Med. Chem.* 2005, 48, 1849-1856).

Results

The central heterocycle of a series of compounds was discovered to provide significant activity and selectivity toward FAAH. Their preparation and evaluation led to the discovery of important features of the heterocycle substituents and the C2-aryl side chain that enhance inhibitor potency or inhibitor selectivity. It was discovered that the active site hydrogen bonding and steric interactions favor a 5-membered versus 6-membered heterocycle. These results and increases in activity and selectivity are reported below.

Phenhexyl-Based Inhibitors.

Oxazole isomer 6 was prepared and evaluated. By switching the location of the oxazole nitrogen atom within 6 (with respect to oxazole 2) resulted in a >4000-fold loss of FAAH inhibition (Scheme 9). It was determined that this result could be based on the reduced electrophilicity of such ketones, therefore additional members of this class were not examined.

Scheme 9. Activity of the isomeric oxazole.

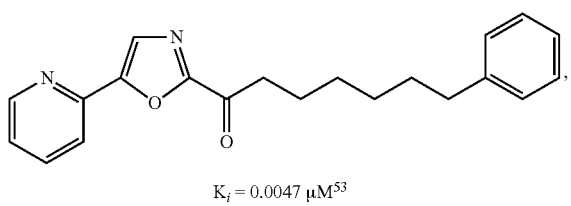

2

$K_i = 0.0047\ \mu M^{53}$

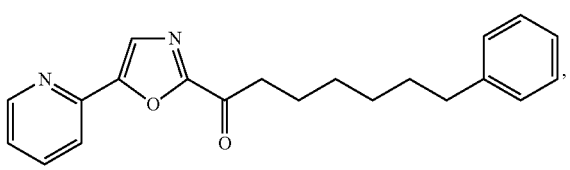

6

$K_i = 22\ \mu M$

Surprising results were obtained by preparing other 5-membered heterocycles bearing two or more heteroatoms. A series of representative C5 substituents was examined. These compounds allowed for an assessment of not only the central heterocycle, but also the substituents. Table 2 illustrates the data obtained from the extensive compound preparation and analysis.

TABLE 2

Inhibitors containing new central heterocycles, $K_i$ (nM).

| heterocycle | H | 2-pyridyl | 2-furyl | 2-thienyl | phenyl | OMe-pyridyl | OH-pyridyl |
|---|---|---|---|---|---|---|---|
| oxazole (R-C5) | 48 (7a) | 4.7 (2) | 12 (7c) | 55 (7d) | 80 (7e) | 8.0 (7f) | 20 (7g)$^a$ |
| 1,3,4-oxadiazole | 1.0 (8a) | 0.29 (8b) | 0.56 (8c) | 0.80 (8d) | 2.2 (8e) | 3.0 (8f) | 14 (8g)$^a$ |
| 1,2,4-oxadiazole | 1.0 (9a) | 0.34 (9b) | 1.0 (9c) | 1.6 (9d) | — | 3.0 (9f) | 13 (9g)$^a$ |
| 1,2,4-oxadiazole isomer | 7.0 (10a) | 1.1 (10b) | 8.5 (10c) | 44 (10d) | — | 7.0 (10f) | 53 (10g)$^a$ |
| thiazole | 800 (11a) | 24 (11b) | 1500 (11c) | 2000 (11d) | — | 500 (11f) | 10,000 (11g)$^a$ |

TABLE 2-continued

Inhibitors containing new central heterocycles, $K_i$ (nM).

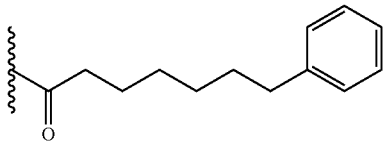 [SMILES: *C(=O)CCCCCCc1ccccc1]

R =

| heterocycle | H | 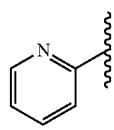 | 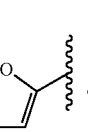 | 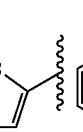 | 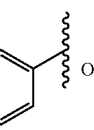 | 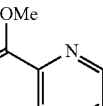 | 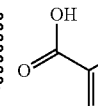 |
|---|---|---|---|---|---|---|---|
| 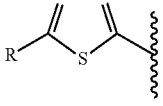 | 1.4 (12a) | 0.80 (12b) | 7.4 (12c) | 27 (12d) | — | 7.7 (12f) | 50 (12g)[a] |
|  | 140 (13a) | 25 (13b) | 40 (13c) | 46 (13d) | — | 110 (13f) | 360 (13g)[a] |
|  | >1000 (14a)[a] | >100000 (14b)[a] | >1000 (14c)[a] | >1000 (14d)[a] | — | — | — |
|  | >1000 (15a)[a] | 1.1 (15b) | 5.0 (15c) | 8.5 (15d) | 16 (15e) | — | — |

[a]Deprotonated under the pH = 9 assay conditions.

Thus, the substituent impact within each heterocycle series was found to follow the potency order of 2-pyr>2-furanyl>2-thienyl>phenyl, reflecting their relative hydrogen bonding ability and for which the 2-pyr derivatives were 10-20 fold more active than the corresponding phenyl derivative. Moreover, the unsubstituted derivative (R═H) was always less potent than the corresponding 2-pyr derivative, but more potent than the corresponding phenyl derivative, displaying a $K_i$ that approached or exceeded those of the 2-furanyl or 2-thienyl derivative. Typically, the 2-pyr-6-$CO_2$Me derivative was less potent than the corresponding 2-pyr derivative and the corresponding 2-pyr-6-$CO_2$H derivative was 2-10 fold less potent than its ester.

However, the results with these latter carboxylic acid derivatives represent $K_i$'s measured at pH 9 under conditions where they are fully ionized, thus destabilizing their active site binding. These $K_i$'s improve when measured at pH 8 and 7.4 (physiological pH). For example oxazole 7 g was examined and displayed an increase in inhibitory potency with decreasing pH (7 g: pH=9, $K_i$=20 nM; pH=8, $K_i$=14.5 nM; pH=7.4, $K_i$=10.3 nM).

The nature of the heterocycles themselves proved even more significant. The thiazole-based inhibitors 11 proved significantly less active than the oxazole-based inhibitors 7, and replacing the position 4 CH of the oxazole or thiazole with a heteroatom uniformly and substantially improved the potency. The most potent of these were the 1,3,4-oxadiazoles 8 and 1,2,4-oxadiazoles 9, which were typically 10-70 fold more active than the corresponding oxazoles, followed closely by the isomeric 1,2,4-oxadiazoles 10.

A surprising change in potency occurred between the thiazole 11 and 1,3,4-thiadiazole 12 series where incorporation of the position 4 nitrogen improved potencies 30-600 fold. As such, the 1,3,4-thiadiazoles 12 typically exceed the potency of the corresponding oxazoles 7, approaching the activity of the 1,2,4-oxadiazoles 10, albeit still being less potent than the isomeric 1,2,4-oxadiazoles 9 or 1,3,4-oxadiazoles 8. This position 4 heteroatom effect (N>O>CH) is consistent with its role in reducing a destabilizing steric interaction at the active site as well as lowering the torsional energy penalty for coplanar binding of the heterocycle and its aryl C5 substituent.

Given that this latter effect is not contributing to the differences observed with the heterocycles when R═H, the result suggests that it is the former steric effect or an as yet unrecognized effect that dominates the differences in binding affinity. Such unrecognized effects could include the introduction of a stabilizing hydrogen bond acceptor site (N>O>>CH), heteroatom effects leading to increases in the heterocycle $pK_b$ and intrinsic hydrogen bonding capabilities, or even simply productive increases in the intrinsic electron-withdrawing character of the central heterocycle.

Interestingly, the isosteric replacement of sulfur in the 1,3,4-thiadiazoles 12 with CH═CH, providing the corresponding 1,2-diazines 13, afforded effective but significantly less potent inhibitors (typically 5-50 fold). Nonetheless, such inhibitors were still more effective than the corresponding triazoles 14. The 1,2,4-triazoles 14 proved inactive, but this behavior represents the destabilizing binding of the deprotonated acidic heterocycle under the pH 9 assay conditions resulting from the C2 acyl substitution. (Scheme 10).

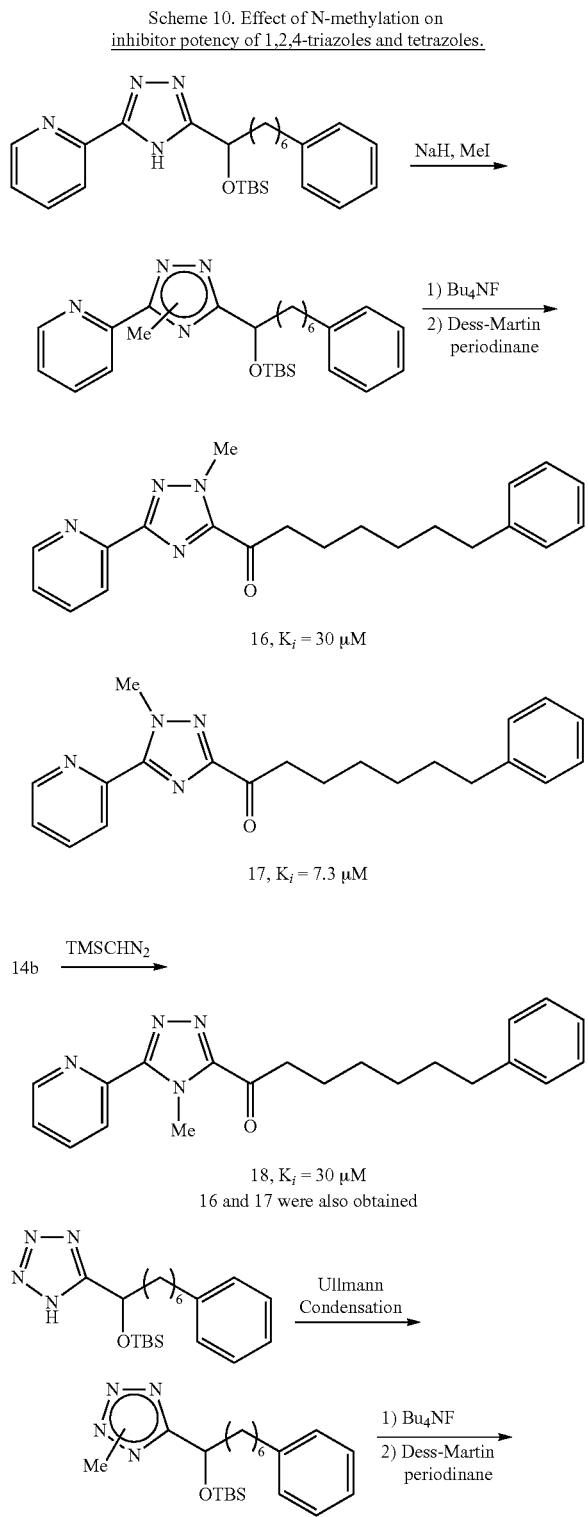

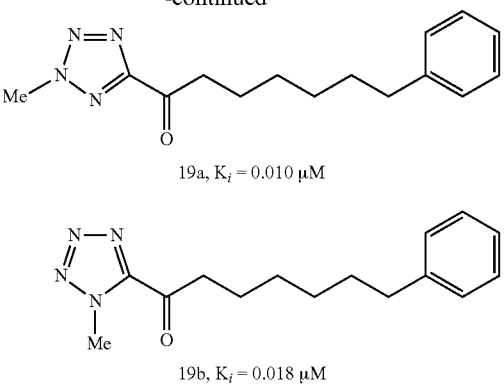

Surprising results were further obtained from preparing and examining the tetrazoles 15. In addition to being the most electron-deficient of the heterocycles examined, position 4 (oxazole numbering) incorporates a N(N>O>CH), and all three accessible sites on the heterocycle constitute potential hydrogen bond acceptor sites (N). The tetrazoles 15 proved substantially more active than the oxazoles 7, comparable in potency with the 1,2,4-oxadiazoles 10, albeit not quite as potent as the isomeric 1,2,4-oxadiazoles 9 or 1,3,4-oxadiazoles 8. There are clearly subtle and unrecognized effects that account for the small differences in binding affinity between the most potent classes of heterocycles (8, 9>10, 12, 15) as well as the less active heterocycles (13>11>14).

Analysis of the tetrazoles seems to suggest that the most potent activity within the 5-membered heterocycles is observed with those that incorporate a hydrogen bonding acceptor N and O (vs N and N) bracketing the electrophilic carbonyl attachment site. This may account for the subtly more potent activity of the 1,3,4-oxadiazoles 8 and 1,2,4-oxadiazoles 9 (N and O) relative to the isomeric 1,2,4-oxadiazoles 10 and the comparable tetrazoles 15 (N and N). Each incorporate a heteroatom at the oxazole position 4 that enhance their activity relative to the oxazole series. The results with the tetrazole series 15 suggest the subtle differences in the 7-15 series have more to do with the location of the oxygen atom than a preference for an added nitrogen versus oxygen at the oxazole position 4.

The exception to the behavior in the tetrazole series 15 is the unsubstituted derivative 15a. This unsubstituted and acidic central heterocycle, like the 1,2,4-triazole series 14, is deprotonated under the pH 9 assay conditions destabilizing active site binding or its activation of the reversible hemiketal formation with the otherwise electrophilic carbonyl. However, methylation of 15a rendered the isomeric 2- and 1-methyltetrazole derivatives 19a and 19b, respectively, incapable of this deprotonation and which now displayed FAAH inhibition at levels consistent with related compounds (Scheme 10). The isomer assignments for 16-19 were made by HMBC (long range proton-carbon correlation) NMR analysis.

A methyl ester substituent was placed directly on certain heterocycle and these compounds were further analyzed (Scheme 11). Certain FAAH inhibitors display activity reflecting the strength of the conjugated electron-withdrawing substituent, but lack the intrinsic enzyme selectivity observed with oxazole 2 and related inhibitors. With the exception of the acidic triazole 14h, which was inactive presumably because of its deprotonation under the assay conditions, this substitution with 8h, 10h, and 12h provided potent FAAH inhibitors ($K_i$<10 nM). However and unlike the behavior of the corresponding oxazole, in each case the activity approached, but did not exceed that of the unsubstituted heterocycles (8a, 10a, and 12a).

Scheme 11. Methyl ester substituted α-ketoheterocycle inhibitors of FAAH.

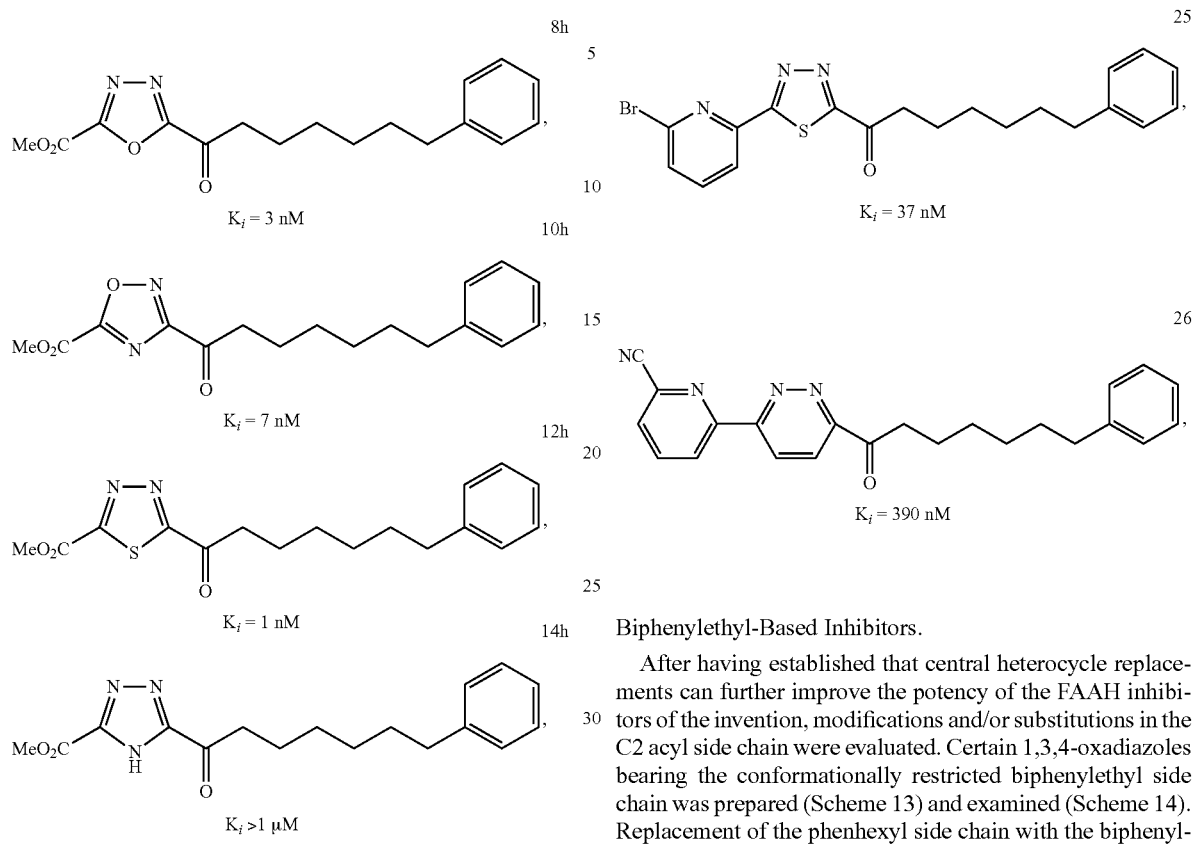

Inhibitors compounds of the invention incorporating a substituted pyridine substituent on the central heterocycle were examined and constituted potential synthetic intermediates en route to 8f-13f (Scheme 12). Each displayed activity that approached the unsubstituted pyridine derivative (b series in Table 2) or, in the case of 24 and 26, the corresponding methyl esters 9f and 13f.

Scheme 12. Additional C6 substituted 2-pyridyl substituents.

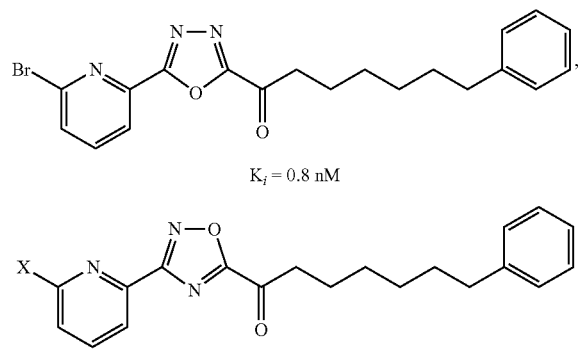

Biphenylethyl-Based Inhibitors.

After having established that central heterocycle replacements can further improve the potency of the FAAH inhibitors of the invention, modifications and/or substitutions in the C2 acyl side chain were evaluated. Certain 1,3,4-oxadiazoles bearing the conformationally restricted biphenylethyl side chain was prepared (Scheme 13) and examined (Scheme 14). Replacement of the phenhexyl side chain with the biphenylethyl side chain maintained or further enhanced the extraordinary potency of the inhibitor compounds of the invention (e.g., $K_i$ of 27=300 pM).

Scheme 13

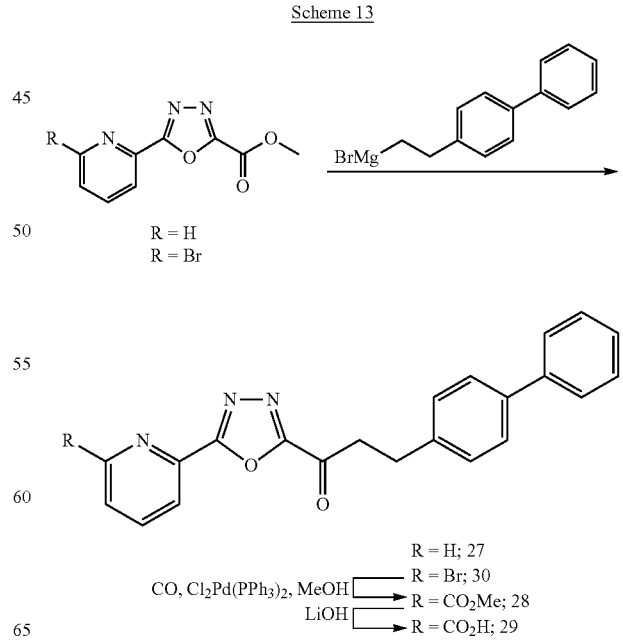

Scheme 14. Biphenylethyl-based inhibitors.

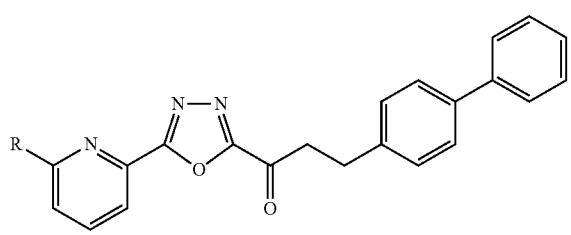

27, R = H, $K_i$ = 0.3 nM (300pM)
28, R = CO$_2$Me, $K_i$ = 1.6 nM
29, R = CO$_2$H, $K_i$ = 48 nM
30, R = Br, $K_i$ = 3.6 nM

The Electrophilic Carbonyl.

Compounds of the invention that bear a secondary alcohol or a methylene in place of the ketone were also examined. The former were often prepared en route to the α-ketoheterocycles. The 1,3,4-oxadiazole inhibitors bearing a methylene were prepared by simple dehydrative ring closure of the corresponding diacylhydrazide as the key step (Scheme 15).

Scheme 15

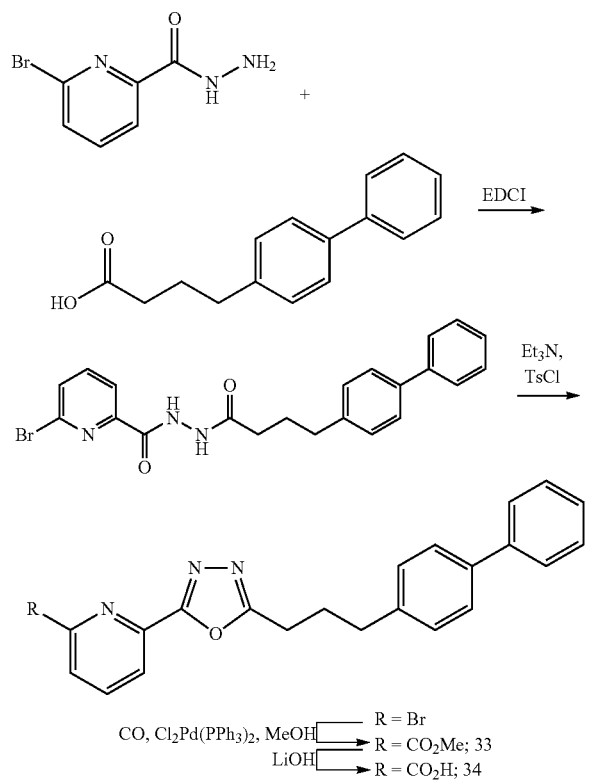

Consistent with a mechanism of reversible Ser addition to the electrophilic carbonyl forming a hemiketal at the enzyme active site, the corresponding alcohol and methylene inhibitors were found to be ≥10000-fold less active than the corresponding ketone; Scheme 16. This level of reduced inhibition (0.01% activity) could be attributable to contaminant ketone in the samples of the alcohol and methylene compounds that can arise from air oxidation upon storage or even while undergoing the assay. According to certain embodiments of the invention, the ketone is significantly important to the potent activity of the inhibitors and the reduction to an alcohol or removal altogether leads to ≥10$^4$ reductions in activity.

Scheme 16. Effect of the electrophilic carbonyl.

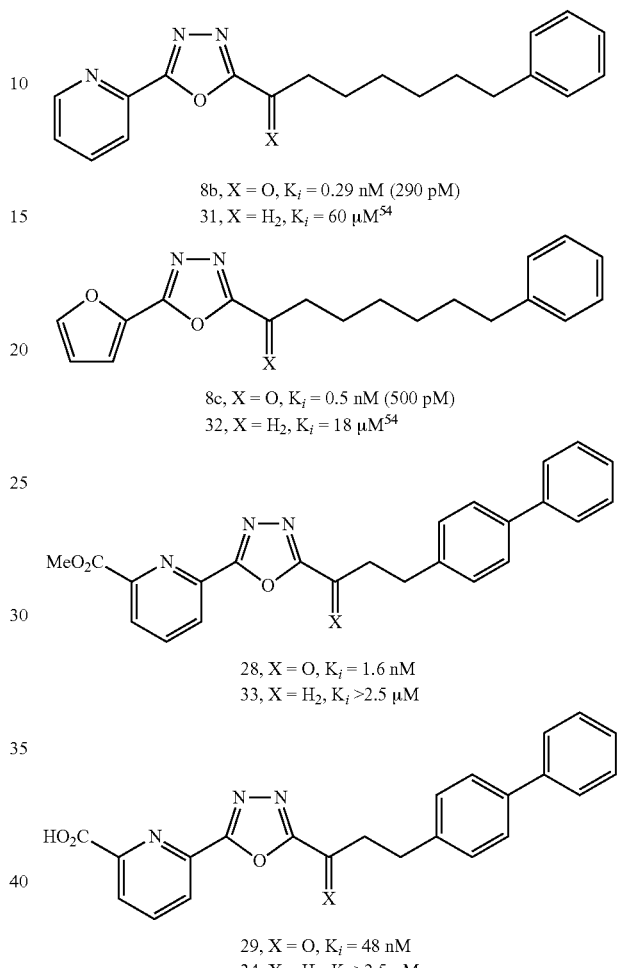

8b, X = O, $K_i$ = 0.29 nM (290 pM)
31, X = H$_2$, $K_i$ = 60 μM[54]

8c, X = O, $K_i$ = 0.5 nM (500 pM)
32, X = H$_2$, $K_i$ = 18 μM[54]

28, X = O, $K_i$ = 1.6 nM
33, X = H$_2$, $K_i$ >2.5 μM

29, X = O, $K_i$ = 48 nM
34, X = H$_2$, $K_i$ >2.5 μM

Several additional and unique compounds of the invention were prepared (Scheme 17) and analyzed (Scheme 18). These constitute ketone inhibitors with a methylene inserted between the reactive carbonyl and heterocycle. These compounds were prepared and analyzed to establish whether the inductive electron-withdrawing properties of the electron-deficient heterocycle would be sufficient to activate the carbonyl for active site hemiketal formation. Unlike the potent activity of the α-keto-heterocycles, these β-ketoheterocycles and their corresponding alcohols were found to be inactive against FAAH.

Scheme 17

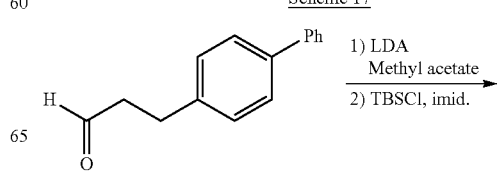

1) LDA
   Methyl acetate
2) TBSCl, imid.

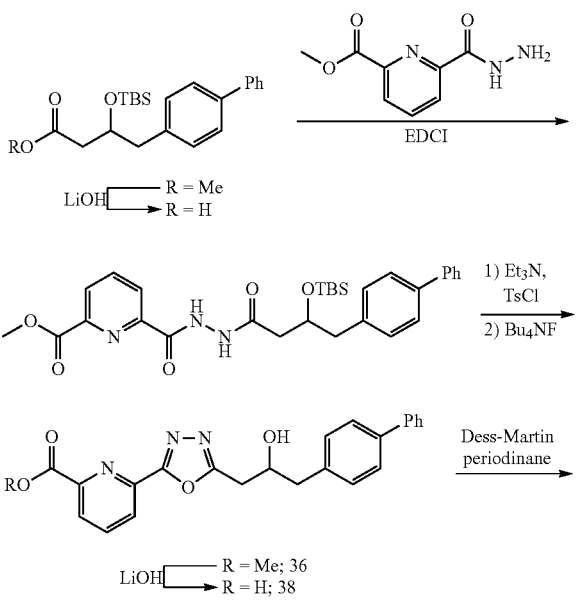

Scheme 18. β-keto-1,3,4-oxadiazoles.

35, X = O, $K_i$ >2.5 μM
36, X = H, OH, $K_i$ >2.5 μM

37, X = O, $K_i$ >2.5 μM
38, X = H, OH, $K_i$ >2.5 μM

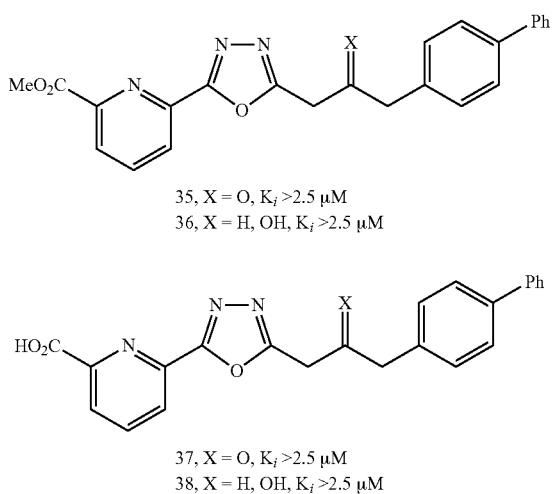

Inhibition of Recombinant Human FAAH.

Rat and human FAAH are very homologous (82% sequence identity), exhibit near identical substrate selectivity and inhibitor sensitivity, and embody an identical amidase signature sequence, suggesting the observations made with rat FAAH would be analogous to those made with the human enzyme. Consequently, various inhibitors of the invention were examined against the human enzyme and were found to exhibit the same relative and absolute potencies consistent with previous observations (Table 3).

TABLE 3

Inhibition of recombinant human fatty acid amide hydrolase.

| compd | $K_i$, μM (human) | $K_i$, μM (rat) |
|---|---|---|
| 7b | 0.0090 | 0.0047 |
| 7g | 0.026 | 0.020 |
| 8b | 0.0012 | 0.00029 |
| 8g | 0.037 | 0.014 |
| 9b | 0.00092 | 0.00034 |
| 10b | 0.016 | 0.0011 |
| 10g | 0.110 | 0.053 |
| 12b | 0.003 | 0.0008 |
| 15b | 0.0055 | 0.0011 |

Selectivity.

Early assessments of certain α-ketoheterocycle inhibitors of FAAH against possible competitive enzymes (e.g., phospholipase A2, ceramidase) revealed no inhibition. Consequently, a method for proteome-wide screening capable of globally profiling all mammalian serine hydrolases was developed, and studies have shown that certain α-ketoheterocycle inhibitors can be highly selective for FAAH. However, two enzymes did emerge as potential competitive targets: triacylglycerol hydrolase (TGH) and a previously uncharacterized membrane-associated hydrolase that lacked known substrates or function (KIAA1363). In this screen, $IC_{50}$ values are typically higher than the measured $K_i$ values, but the relative potency, the magnitude of binding affinity differences, and the rank order binding determined in the assay parallel those established by standard substrate assays.

Summarized in Table 4 are the results of the selectivity screening of selected inhibitor compounds of the invention. In general, the inhibitors were selective for FAAH over TGH and KIAA1363. The inhibitors bearing the unsubstituted heterocycles (7-13a) were selective for FAAH over KIAA1363, but were typically more selective for TGH over FAAH (1-125-fold). The potent inhibitors incorporating even the small methyl ester substituent (7-12h series) on the heterocycle were found to be selective for FAAH versus KIAA1363 (>100-fold), and now modestly selective for FAAH versus TGH (2-200-fold).

The addition of a 2-pyridyl substituent (7-15b series) increased not only the FAAH potency, but also FAAH selectivity such that the most potent inhibitors failed to inhibit KIAA1363 (>$10^4$-fold selective) and are now typically 4-300-fold selective for FAAH versus TGH. Addition of a C6-carboxylic acid to the 2-pyridyl substituent (7-15g series) further enhanced this intrinsic selectivity such that the resulting inhibitors are typically no longer viable competitive inhibitors of KIAA1363 or TGH (Table 4 and FIG. 1). FIG. 1 illustrates the activity based protein profiling of FAAH inhibitors 10b, 10f, 10g, 10a with FP-Rh in brain and heart membrane proteome. Enzyme targets such as FAAH, KIAA1363, and TGH are labeled at the left margin.

TABLE 4

Activity based protein profiling of FAAH α-ketoheterocycles.

| | | FAAH $K_i$, μM | FAAH $IC_{50}$, μM | KIAA1363 $IC_{50}$, μM | TGH $IC_{50}$, μM |
|---|---|---|---|---|---|
| *Oxazole series* | | | | | |
| 7a | R = H | 0.048 | 2.5 | 20 (8) | 0.02 (0.008) |
| 2 | R = 2-pyr | 0.0047 | 0.002 | >100 (>50000) | 0.6 (300) |
| 7c | R = 2-furanyl | 0.012 | 0.08 | >100 (>1250) | 0.3 (4) |
| 7d | R = 2-thiophenyl | 0.055 | 0.8 | >100 (>125) | 0.2 (0.25) |
| 7e | R = Ph | 0.08 | 0.9 | >100 (>110) | 0.7 (0.8) |
| 7f | R = 2-pyr-6-CO$_2$Me | 0.008 | 0.17 | 40 (240) | 1.0 (6) |
| 7g | R = 2-pyr-6-CO$_2$H | 0.02 | 0.1 | >100 (>1000) | >100 (>1000) |
| 7h | R = CO$_2$Me | 0.0009 | 0.03 | >100 (>3300) | 0.3 (10) |
| *1,3,4-Oxadiazole series* | | | | | |
| 8a | R = H | 0.001 | 0.016 | >100 (>6250) | 0.025 (1.5) |
| 8b | R = 2-pyr | 0.00029 | 0.001 | 90 (90000) | 0.14 (140) |
| 8c | R = 2-furanyl | 0.00056 | 0.001 | >100 (>10$^5$) | 0.08 (80) |
| 8e | R = Ph | 0.0022 | 0.025 | >100 (>4000) | 0.25 (10) |
| 8f | R = 2-pyr-6-CO$_2$Me | 0.003 | 0.008 | >100 (>12500) | 0.04 (5) |
| 8g | R = 2-pyr-6-CO$_2$H | 0.014 | 0.1 | >100 (>1000) | 40 (400) |
| 8h | R = CO$_2$Me | 0.001 | 1.0 | >100 (>100) | 2.0 (2) |
| *1,2,4-Oxadiazole series 9* | | | | | |
| 9a | R = H | 0.001 | 0.004 | 25 (6250) | 0.0007 (0.18) |
| 9b | R = 2-pyr | 0.00034 | 0.003 | 30 (10000) | 0.03 (10) |
| 9f | R = 2-pyr-6-CO$_2$Me | 0.003 | 0.003 | 40 (13000) | 0.15 (50) |
| 9g | R = 2-pyr-6-CO$_2$H | 0.013 | 0.04 | >100 (>2500) | 40 (1000) |
| *1,2,4-Oxadiazole series 10* | | | | | |
| 10a | R = H | 0.007 | 0.5 | >100 (>200) | 0.01 (0.02) |
| 10b | R = 2-pyr | 0.0011 | 0.007 | >100 (>14000) | 0.4 (60) |
| 10f | R = 2-pyr-6-CO$_2$Me | 0.007 | 0.3 | >100 (>330) | 3.0 (10) |
| 10g | R = 2-pyr-6-CO$_2$H | 0.053 | 0.07 | >100 (>1400) | >100 (>1400) |
| 10h | R = CO$_2$Me | 0.007 | 0.01 | >100 (>10000) | 0.2 (20) |
| *Thiazole series* | | | | | |
| 11a | R = H | 0.8 | >100 | >100 (1) | 2 (<0.02) |
| 11b | R = 2-pyr | 0.024 | 2 | >100 (>50) | 8 (4) |
| 11f | R = 2-pyr-6-CO$_2$Me | 0.5 | >100 | >100 (1) | 40 (<0.4) |
| 11g | R = 2-pyr-6-CO$_2$H | 10 | 8 | >100 (>12) | 30 (4) |
| *1,3,4-Thiadiazole series* | | | | | |
| 12a | R = H | 0.0014 | 0.3 | >100 (>330) | 0.1 (1) |
| 12b | R = 2-pyr | 0.0008 | 0.03 | >100 (>3300) | 4.5 (150) |
| 12f | R = 2-pyr-6-CO$_2$Me | 0.0077 | 0.8 | >100 (>125) | 0.8 (1) |
| 12g | R = 2-pyr-6-CO$_2$H | 0.050 | 3 | >100 (>33) | >100 (>33) |
| 12h | R = CO$_2$Me | 0.001 | 0.06 | >100 (>1700) | 11 (180) |
| *1,2-Diazine series* | | | | | |
| 13a | R = H | 0.14 | 3 | >100 (>30) | 5 (1) |
| 13b | R = 2-pyr | 0.025 | 6 | >100 (>20) | >100 (>20) |
| 13f | R = 2-pyr-6-CO$_2$Me | 0.110 | 10 | >100 (>10) | >100 (>10) |
| 13g | R = 2-pyr-6-CO$_2$H | 0.360 | 20 | >100 (>5) | >100 (>5) |
| 13h | R = 2-pyr-6-CN | 0.390 | 13 | >100 (>8) | 12 (1) |

TABLE 4-continued

Activity based protein profiling of FAAH α-ketoheterocycles.

| | | FAAH $K_i$, μM | FAAH $IC_{50}$, μM | KIAA1363 $IC_{50}$, μM | TGH $IC_{50}$, μM | |
|---|---|---|---|---|---|---|
| | | | | Tetrazole series | | |
| 15a | R = Me | 0.010 | 0.6 | 60 (100) | 0.08 (0.13) | |
| 15b | R = 2-pyr | 0.0011 | 0.003 | >100 (>30000) | 0.12 (40) | |

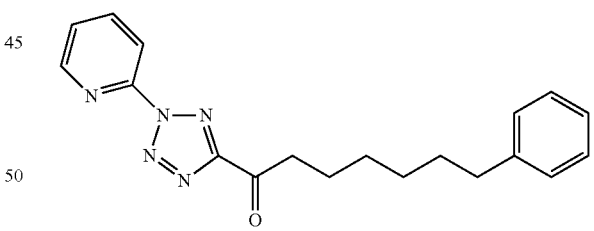

Many of the central heterocycle features and added substituents that were found to increase FAAH were also found to enhance FAAH selectivity by simultaneously disrupting KIAA1363 and TGH affinity.

CONCLUSIONS

The synthesis and evaluation of a series of α-ketoheterocycles incorporating changes in the central heterocycle that provided extraordinarily potent ($K_i$=300 pM) inhibitors of fatty acid amide hydrolase are reported herein. The nature of the central heterocycle significantly influenced the inhibitor activity that can be defined as 1,3,4-oxadiazoles (50) and 1,2,4-oxadiazoles 9 (50)>tetrazoles (5), the isomeric 1,2,4-oxadiazoles 10 (7), 1,3,4-thiadiazoles (2-30)>oxazoles including 2 (rel. activity=1)>1,2-diazines (0.3)>thiazoles (0.06)>1,3,4-triazoles (–). One of the most surprising discoveries is that the introduction of an additional position 4 heteroatom (oxazole numbering) substantially increases the activity (N>O>CH). Although not a limitation of this disclosure, the additional heteroatom may reduce destabilizing steric interaction at the FAAH active site. Additionally the position 1 and 3 heteroatoms exhibit a N,O>N,N>N,S trend in terms of activity.

On each heterocyclic core, additional aryl substituents (e.g., 2-pyr or 2-pyr-6-$CO_2H$) placed on the central heterocycle increase FAAH potency, and significantly modify physical properties (e.g., solubility) in a manner that can impact PK and PD behavior of the inhibitors. Just as significantly, the nature of the substituent substantially impacts the selectivity of the FAAH inhibitors. This is especially evident with the TGH selectivity for the unsubstituted heterocycles (7-13a series, 1-100-fold selective for TGH vs FAAH), which can be improved by the independent choice of the C2 side chain, as well as the heterocycle substituent (compare 7-13a vs 7-15b and 7-15g). A combination of these independent features, which simultaneously improve FAAH potency and disrupt TGH or KIAA1363 binding, provide highly selective and potent FAAH inhibitors.

FAAH Inhibition.

$^{14}$C-labeled oleamide was prepared from $^{14}$C-labeled oleic acid as described in the literature (Cravatt et al., *Science* 1995, 268, 1506-1509). The truncated rat FAAH (rFAAH) was expressed in *E. coli* and purified as described (Patricelli et al., *Biochemistry* 1998, 37, 15177-15187). The purified recombinant rFAAH was used in the inhibition assays unless otherwise indicated. The full-length human FAAH (hFAAH) was expressed in COS-7 cells as described (Giang et al., *Proc. Natl. Acad. Sci. U.S.A.* 1997, 94, 2238-2242), and the lysate of hFAAH-transfected COS-7 cells was used in the inhibition assays where explicitly indicated.

The inhibition assays were performed as described (Cravatt et al., *Science* 1995, 268, 1506-1509). In brief, the enzyme reaction was initiated by mixing 1 nM of rFAAH (800, 500, or 200 pM rFAAH for inhibitors with $K_i$≤1-2 nM) with 10 μM of $^{14}$C-labeled oleamide in 500 μL of reaction buffer (125 mM TrisCl, 1 mM EDTA, 0.2% glycerol, 0.02% Triton X-100, 0.4 mM Hepes, pH 9.0) at room temperature in the presence of three different concentrations of inhibitor. The enzyme reaction was terminated by transferring 20 μL of the reaction mixture to 500 μL of 0.1 N HCl at three different time points. The $^{14}$C-labeled oleamide (substrate) and oleic acid (product) were extracted with EtOAc and analyzed by TLC. The $K_i$ of the inhibitor was calculated using a Dixon plot as described (standard deviations are provided in Table 4 above). Lineweaver-Burk analysis was performed as described confirming competitive, reversible inhibition (Boger et al., *J. Med. Chem.* 2005, 48, 1849-1856).

Selectivity Screening.

The selectivity screening was conducted as detailed in the literature (Leung et al., *Nature Biotech.* 2003, 21, 687-691).

Example 2

Preparation of 7-Phenyl-1-(2-(pyridin-2-yl)-2H-tetrazol-5-yl)-heptan-1-one (15b)

A solution of 7-phenylheptanal (1.93 g, 0.01 mol) in MeCN (64 mL) was treated with KCN (2.65 g, 0.04 mol), $ZnI_2$ (77.7 mg, 0.0002 mol), and TBSCl (3.06 g, 0.02 mol) under Ar at room temperature. The reaction mixture was stirred vigorously and the progress monitored by TLC ($SiO_2$, 5% EtOAc-hexanes). After 72 h, the solvent was removed in vacuo and the residue resuspended in $Et_2O$. The salts were removed by filtration and rinsed thoroughly with $Et_2O$. The filtrate was washed with water, dried over $Na_2SO_4$, and concentrated in vacuo to give a yellow oil that was purified by flash chromatography ($SiO_2$, 4×25 cm, 1% EtOAc-hexanes) to afford 2-(tert-butyldimethylsilyloxy)-8-phenyloctamide (2.6 g, 80%) as a colorless oil: $^1$H NMR ($CDCl_3$, 500 MHz) δ 7.30 (m, 2H), 7.20 (m, 3H), 4.43 (t, 1H, J=6.4 Hz), 2.63 (t, 2H, J=7.7 Hz), 1.80 (m, 2H), 1.65 (m, 2H), 1.49 (m, 2H), 1.39 (m, 4H), 0.94 (s, 9H), 0.21 (s, 3H), 0.16 (s, 3H); $^{13}$C NMR (CDCl$_3$, 125 MHz) δ 142.7, 128.5, 128.4, 125.7, 120.2, 62.0, 36.4, 36.0, 31.4, 29.1, 28.9, 25.6, 24.6, 18.2 (3C), −5.0, −5.2; HRMS-ESI-TOF m/z 354.2221 ([M+Na]$^+$, C$_{20}$H$_{33}$NOSi requires 354.2223).

A sample of 2-(tert-butyldimethylsilyloxy)-8-phenyloctamide (335 mg, 1.01 mmol) was dissolved in a mixture of 2-propanol (1.4 mL): water (2.9 mL). NaN$_3$ (197 mg, 3.04 mmol) and ZnBr (250 mg, 1.11 mmol) were added to the reaction mixture as solids, which was subsequently warmed at 100° C. for 90 h. Upon disappearance of starting material, the solution was cooled to room temperature and diluted with EtOAc. 2 N HCl was added to the reaction mixture, which was stirred until all solids dissolved. The organic layer was isolated and the aqueous layer was washed several times with EtOAc. The combined organic phases were dried over Na$_2$SO$_4$ and the solvent was removed under reduced pressure to afford 7-phenyl-1-(2H-tetrazol-5-yl)-heptan-1-ol as a colorless oil that was used without further purification (270 mg, quant.): $^1$H NMR (CDCl$_3$, 600 MHz) δ 7.25 (m, 2H), 7.15 (m, 3H), 5.26 (m, 1H), 2.57 (t, 2H, J=7.7 Hz), 2.02 (m, 1H), 1.90 (m, 1H), 1.59 (m, 2H), 1.44 (m, 2H), 1.34 (m, 4H); HRMS-ESI-TOF m/z 261.1707 ([M+H]$^+$, C$_{14}$H$_{20}$N$_4$O requires 261.1710).

A solution of 7-phenyl-1-(2H-tetrazol-5-yl)-heptan-1-ol (36 mg, 0.14 mmol), TBSCl (63 mg, 0.42 mmol) and imidazole (28 mg, 0.42 mmol) in DMF (0.7 mL) was stirred at room temperature for 72 h before it was diluted with EtOAc, and washed with H$_2$O and saturated aqueous NaCl. The organic layer was dried over Na$_2$SO$_4$ and the solvent was removed under reduced pressure to afford the crude material that was purified by flash chromatography (SiO$_2$, 1.5×15 cm, 10% acetone-hexanes) to afford 5-(1-(tert-butyldimethylsilyloxy)-7-phenylheptyl)-2H-tetrazole (39 mg, 75%) as a colorless oil: $^1$H NMR (CDCl$_3$, 400 MHz) δ 7.26 (dd, 2H, J=6.3, 8.4 Hz), 7.16 (m, 3H), 5.25 (t, 1H, J=5.8 Hz), 2.57 (t, 2H, J=7.7 Hz), 1.85 (m, 2H), 1.58 (m, 2H), 1.31 (m, 6H), 0.90 (s, 9H), 0.13 (s, 3H), 0.01 (s, 3H).

In a gas tight vessel, a solution of 5-(1-(tert-butyldimethylsilyloxy)-7-phenylheptyl)-2H-tetrazole (16 mg, 0.043 mmol), 2-iodopyridine (7 μL, 0.064 mmol), CuI (1 mg, 0.004 mmol), K$_2$CO$_3$ (12 mg, 0.085 mmol), and N,N-dimethylethylene diamine (1 μL, 0.006 mmol) in DMF (200 μL) was purged with Ar and sealed. The reaction mixture was warmed at 100° C. for 18 h before it was cooled to room temperature, diluted with EtOAc, and washed with H$_2$O, 9:1 NH$_4$OH: saturated aqueous NH$_4$Cl, and saturated aqueous NaCl. The organic layer was dried over Na$_2$SO$_4$ and the solvent was removed under reduced pressure to afford the crude material that was purified by flash chromatography (SiO$_2$, 1.5×15 cm, 5-10% acetone-hexanes) to afford 2-(5-(1-(tert-butyldimethylsilyloxy)-7-phenylheptyl)-2H-tetrazol-2-yl)-pyridine (4.0 mg, 21%) as a colorless oil: $^1$H NMR (CDCl$_3$, 400 MHz) δ 8.69 (dd, 1H, J=0.9, 4.8 Hz), 8.16 (d, 1H, J=7.5 Hz), 7.98 (dt, 1H, J=1.8, 7.9 Hz), 7.48 (m, 1H), 7.26 (m, 2H), 7.16 (m, 3H), 5.16 (dd, 1H, J=5.9, 7.4 Hz), 2.58 (t, 2H, J=7.7 Hz), 1.99 (m, 2H), 1.60 (m, 2H), 1.34 (m, 6H), 0.88 (s, 9H), 0.10 (s, 3H), −0.02 (s, 3H); $^{13}$C NMR (CDCl$_3$, 150 MHz) δ 169.7, 149.6, 149.0, 142.9, 139.5, 128.5, 128.4, 125.7, 125.0, 115.2, 67.4, 37.5, 36.1, 31.5, 29.3, 25.9 (3C), 25.4, 18.4, −4.1, −4.8; HRMS-ESI-TOF m/z 452.2823 ([M+H]$^+$, C$_{25}$H$_{37}$N$_5$OSi requires 452.2840).

2-(5-(1-(tert-Butyldimethylsilyloxy)-7-phenylheptyl)-2H-tetrazol-2-yl)-pyridine (4.4 mg, 0.009 mmol) was dissolved in THF (122 μL), treated with Bu$_4$NF (1 M in THF, 0.013 mL, 0.013 mmol) and stirred at room temperature for 2 h under Ar. The reaction mixture was diluted with EtOAc, washed with saturated aqueous NaCl and dried over Na$_2$SO$_4$. Evaporation in vacuo yielded the crude alcohol that was purified by flash chromatography (SiO$_2$, 0.5×4 cm, 20-50% EtOAc-hexanes) to afford 7-phenyl-1-(2-(pyridin-2-yl)-2H-tetrazol-5-yl)-heptan-1-ol (2.7 mg, 79%) as a white solid: $^1$H NMR (CDCl$_3$, 600 MHz) δ 8.69 (dd, 1H, J=1.1, 4.7 Hz), 8.18 (d, 1H, J=8.1 Hz), 8.00 (m, 1H), 7.50 (ddd, 1H, J=0.7, 4.8, 7.4 Hz), 7.26 (m, 2H), 7.16 (m, 3H), 5.16 (m, 1H), 2.59 (t, 2H, J=7.7 Hz), 2.48 (d, 1H(—OH), J=6.1 Hz), 2.07 (m, 2H), 1.61 (m, 2H), 1.52 (m, 2H), 1.40 (m, 4H); $^{13}$C NMR (CDCl$_3$, 150 MHz) δ 169.5, 149.6, 148.8, 142.9, 139.6, 128.5, 128.4, 125.7, 125.3, 115.3, 67.0, 36.7, 36.1, 31.5, 29.3 (2C), 25.2; HRMS-ESI-TOF m/z 338.1966 ([M+H]$^+$, C$_{19}$H$_{23}$N$_5$O requires 338.1975).

7-Phenyl-1-(2-(pyridin-2-yl)-2H-tetrazol-5-yl)-heptan-1-ol (2.7 mg, 0.007 mmol) was dissolved in CH$_2$Cl$_2$ (0.24 mL) and Dess-Martin periodinane (4.5 mg, 0.011 mmol) was added. The mixture was stirred at room temperature for 2 h before the reaction mixture was reduced to half volume and this mixture was directly loaded onto silica gel and purified by flash chromatography (SiO$_2$, 0.5×4 cm, 10-30% EtOAc-hexanes) to afford 7-phenyl-1-(2-(pyridin-2-yl)-2H-tetrazol-5-yl)-heptan-1-one (15b, 2.7 mg, 99%) as a white solid: $^1$H NMR (CDCl$_3$, 600 MHz) δ 8.74 (m, 1H), 8.23 (m, 1H), 8.05 (dt, 1H, J=1.6, 7.9 Hz), 7.57 (dd, 1H, J=4.8, 7.5 Hz), 7.27 (t, 2H, J=7.6 Hz), 7.17 (m, 3H), 3.26 (t, 2H, J=7.4 Hz), 2.61 (t, 2H, J=7.7 Hz), 1.83 (m, 2H), 1.64 (m, 2H), 1.43 (m, 4H); $^{13}$C NMR (CDCl$_3$, 150 MHz) δ 191.5, 162.5, 149.9, 148.6, 142.8, 139.8, 128.5, 128.4, 126.0, 125.8, 115.9, 41.0, 36.0, 31.4, 29.1, 29.0, 23.5; HRMS-ESI-TOF m/z 336.1813 ([M+H]$^+$, C$_{19}$H$_{21}$N$_5$O requires 336.1819). Purity 99%.

Example 3

Preparatory Procedures

Oxazole (6):

2-(Pyridin-2-yl)-oxazole (S1)

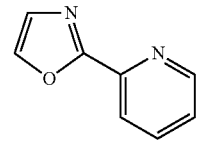 [SMILES: c1ccc(-c2ncco2)nc1]

2-(Tributylstannyl)oxazole (1.00 g, 2.79 mmol), (Ph$_3$P)$_4$Pd (0.1 equiv), and 2-bromopyridine (2 equiv) were dissolved in anhydrous 1,4-dioxane (15 mL) and the mixture was warmed at reflux for 24 h under Ar. The mixture was diluted with EtOAc, washed with saturated aqueous NaCl and dried over Na$_2$SO$_4$. Evaporation in vacuo yielded the crude product that was purified by flash chromatography (SiO$_2$, 10-60% EtOAc-hexanes) to yield the title compound (275 mg, 67%) as a light yellow oil: $^1$H NMR (CDCl$_3$, 500 MHz) δ 8.63 (m, 1H), 8.04 (d, 1H, J=7.5 Hz), 7.73-7.70 (m, 2H), 7.26-7.22 (m, 2H); $^{13}$C NMR (CDCl$_3$, 125 MHz) δ 161.0, 150.2, 146.4, 140.1, 137.3, 129.1, 125.0, 122.3.

7-Phenyl-1-(2-(pyridin-2-yl)oxazol-5-yl)-heptan-1-ol (S2)

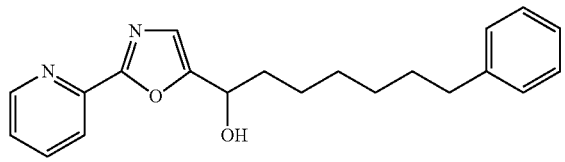 [SMILES: OC(CCCCCCc1ccccc1)c1cnc(-c2ccccn2)o1]

A solution of 2-(pyridin-2-yl)-oxazole (S1, 54 mg, 0.369 mmol) in THF (2 mL) was cooled to −78° C. before it was treated dropwise with 2.5 M n-BuLi (0.177 mL, 0.443 mmol). The reaction mixture was stirred at −78° C. for 20 min before 7-phenylheptanal (77 mg, 0.405 mmol) in THF (1 mL) was added dropwise. The solution was stirred for an additional 10 min at −78° C. before being warmed to room temperature. The reaction mixture was quenched with the addition of saturated aqueous NaHCO$_3$, diluted with EtOAc and the aqueous layer was extracted with EtOAc. The combined organic extracts were washed with saturated aqueous NaCl, dried over Na$_2$SO$_4$ and the solvent was removed under reduced pressure. Flash chromatography (SiO$_2$, 20-70% EtOAc-hexanes) yielded the title compound (35 mg, 28%) as a colorless oil: $^1$H NMR (CDCl$_3$, 500 MHz) δ 8.77 (s, 1H), 8.17 (d, 1H, J=8.0 Hz), 7.86 (t, 1H, J=8.0 Hz), 7.41 (m, 1H), 7.35-7.32 (m, 2H), 7.23 (m, 3H), 7.18 (s, 1H), 4.93 (t, 1H, J=6.5 Hz), 3.22 (br s, 1H), 2.65 (t, 2H, J=6.5 Hz), 2.01-1.98 (m, 2H), 1.68-1.66 (m, 2H), 1.44-1.42 (m, 5H); $^{13}$C NMR (CDCl$_3$, 125 MHz) δ 160.3, 156.1, 150.2, 146.4, 143.1, 137.5, 128.8, 128.6, 126.0, 125.1, 124.9, 122.5, 66.5, 36.3, 35.8, 31.8, 29.6 (2C), 25.8.

7-Phenyl-1-(2-(pyridin-2-yl)oxazol-5-yl)-heptan-1-one (6)

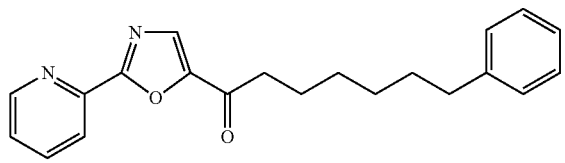 [SMILES: O=C(CCCCCCc1ccccc1)c1cnc(-c2ccccn2)o1]

7-Phenyl-1-(2-(pyridin-2-yl)oxazol-5-yl)-heptan-1-ol (S2, 20 mg, 0.059) was dissolved in CH$_2$Cl$_2$ (4 mL) and Dess-Martin periodinane (1.5 equiv) was added. The mixture was stirred at room temperature for 2 h before silica gel was added and the reaction mixture was evaporated in vacuo to afford the crude ketone absorbed on silica gel. This mixture was subsequently purified by flash chromatography (SiO$_2$, 10-50% EtOAc-hexanes) to yield the title compound (18 mg, 90%) as a white solid: $^1$H NMR (CDCl$_3$, 500 MHz) δ 8.89 (s, 1H), 8.31 (d, 1H, J=8.0 Hz), 7.99-7.94 (m, 2H), 7.55-7.52 (m, 1H), 7.36-7.33 (m, 2H), 7.26-7.23 (m, 3H), 3.00 (t, 2H, J=7.5 Hz), 2.69 (t, 2H, J=7.5 Hz), 1.87-1.81 (m, 2H), 1.75-1.69 (m, 2H), 1.51-1.47 (m, 4H); $^{13}$C NMR (CDCl$_3$, 125 MHz) δ 189.4, 162.6, 150.8, 150.7, 145.6, 143.1, 137.6, 134.7, 128.8, 128.7, 126.2, 126.0, 123.8, 39.7, 36.3, 31.7, 29.4 (2C), 24.1; HRMS-ESI-TOF m/z 335.1750 ([M+H]$^+$, C$_{21}$H$_{22}$N$_2$O$_2$ requires 335.1754).

1,3,4-Oxadiazoles (4a-4-d, 8a-8h, 20, 27-30) and 1,2,4-Oxadiazoles (9a-9g, 21-24):

General Procedure A.

The ester (1 equiv) was dissolved in a mixture of 3:2 THF/H$_2$O and LiOH (2.5 equiv) was added at 0° C. The reaction mixture was stirred for 1 h while slowly warming to room temperature before the mixture was made acidic with the addition of aqueous 0.1 N KHSO$_4$. The solution was diluted with EtOAc and the organic layer was separated from the aqueous layer. The aqueous layer was extracted with EtOAc (3×). The combined organic extracts were washed with saturated aqueous NaCl and dried over Na$_2$SO$_4$. Evaporation in vacuo yielded the crude carboxylic acid which was purified by chromatography (SiO$_2$).

General Procedure B.

The alcohol (1 equiv) was dissolved in CH$_2$Cl$_2$ (0.03 M) and Dess-Martin periodinane (1.5 equiv) was added. The mixture was stirred at room temperature for 2 h before the reaction mixture was reduced to half volume and this mixture was directly loaded onto silica gel and purified by flash chromatography (SiO$_2$) yielding the pure α-ketoheterocycle.

6-Bromopicolinyl Hydrazide (S3)

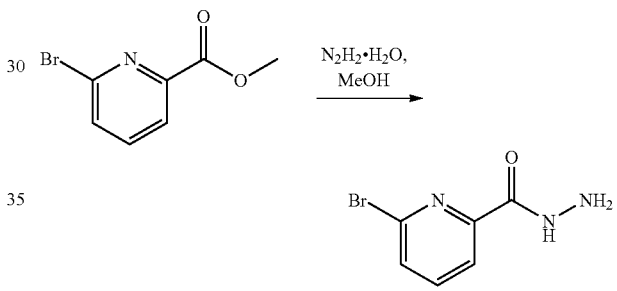

Methyl 6-bromopicolinate (208 mg, 0.963 mmol) was dissolved in MeOH (6.5 mL) and treated dropwise with hydrazine monohydrate (467 µL, 9.63 mmol) at room temperature. After 1 h, the solvent was removed in vacuo to afford a white solid that was used without further purification (207 mg, quant.): $^1$H NMR (CDCl$_3$, 600 MHz) δ 8.82 (br s, 1H), 8.12 (d, 1H, J=7.5 Hz), 7.72 (t, 1H, J=7.7 Hz), 7.63 (d, 1H, J=7.9 Hz), 4.06 (br s, 2H); $^{13}$C NMR (CDCl$_3$, 150 MHz) δ 163.3, 150.1, 140.9, 139.8, 131.2, 121.4.

N-Hydroxyfuran-2-carboximidamide (S4)

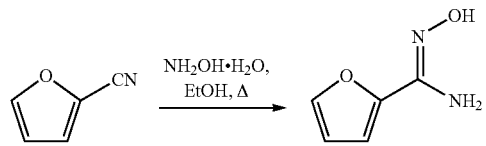 [SMILES: N#Cc1ccco1 ; N/C(=N\O)c1ccco1]

2-Cyanofuran (150 mg, 1.61 mmol) was dissolved in EtOH (1.61 mL) and treated dropwise with aq. hydroxylamine (50% w/w, 296 µL, 4.83 mmol) at room temperature. The mixture was warmed at 80° C. for 1.5 h. Upon completion, the solvent was removed to afford a colorless oil that was used without purification (203 mg, quant.): $^1$H NMR (CDCl$_3$, 500

MHz) δ 9.34 (br s, 1H), 7.42 (d, 1H, J=1.1 Hz), 6.79 (d, 1H, J=3.3 Hz), 6.42 (dd, 1H, J=1.8, 3.4 Hz), 5.09 (br s, 2H).

6-Chloro-N-hydroxypicolinimidamide (S5)

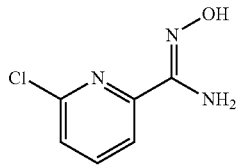

The title compound was prepared from 6-chloro-2-cyanopyridine (150 mg, 1.08 mmol) by using a procedure similar to that detailed for S4, providing the product (180 mg, 98%) as a white solid: $^1$H NMR (acetone-$d_6$, 400 MHz) δ 9.32 (br s, 1H), 7.90 (dd, 1H, J=1.0, 7.8 Hz), 7.84 (t, 1H, J=7.8 Hz), 7.46 (dd, 1H, J=1.0, 7.7 Hz), 5.70 (br s, 2H).

6-Bromo-N-hydroxypicolinimidamide (S6)

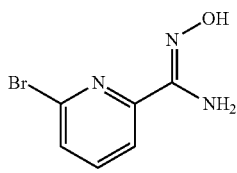 [SMILES: N/C(=N\O)c1cccc(Cl)n1]

The title compound was prepared from 6-bromo-2-cyanopyridine (200 mg, 1.09 mmol) by using a procedure similar to that detailed for S4, providing the product (232 mg, 99%) as a white solid: $^1$H NMR (acetone-$d_6$, 500 MHz) δ 9.30 (s, 1H), 7.93 (dd, 1H, J=0.8, 7.8 Hz), 7.73 (t, 1H, J=7.8 Hz), 7.61 (dd, 1H, J=0.8, 7.8 Hz), 5.69 (br s, 2H).

Methyl 5-(Pyridin-2-yl)-1,3,4-oxadiazole-2-carboxylate (S7)

(General Procedure C)

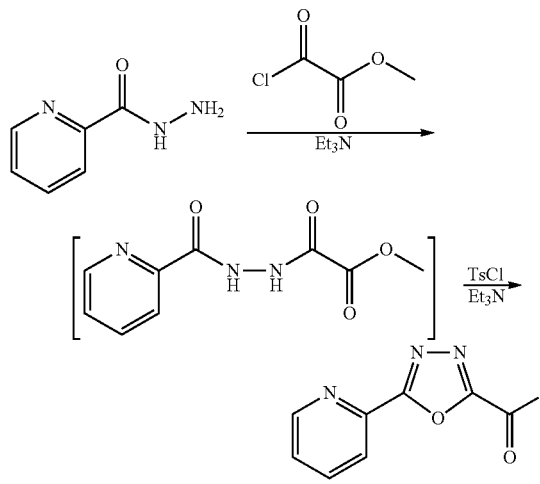

2-Picolinyl hydrazide (1.37 g, 10 mmol) and Et$_3$N (4.15 mL, 30 mmol) were dissolved in CH$_2$Cl$_2$ (50 mL) and treated dropwise with methyl oxalyl chloride (0.95 mL, 10 mmol) at 0° C. The reaction mixture was warmed slowly to room temperature and stirred for 6 h before it was treated with TsCl (1.91 g, 10 mmol) and stirred overnight. The reaction mixture was diluted with CH$_2$Cl$_2$ and washed with water, saturated aqueous NaHCO$_3$ and saturated aqueous NaCl. The organic layer was collected and evaporated. Flash chromatography (SiO$_2$, 3×15 cm, 40% EtOAc-hexanes) afforded the title compound (1.87 g, 91%) as a white solid: $^1$H NMR (CDCl$_3$, 400 MHz) δ 8.80 (dd, 1H, J=4.2, 1.2 Hz), 8.29 (d, 1H, J=7.9 Hz), 7.92 (td, 1H, J=7.8, 1.8 Hz), 7.52 (ddd, 1H, J=7.8, 4.9, 1.2 Hz), 4.07 (s, 3H); $^{13}$C NMR (CDCl$_3$, 100 MHz) δ 165.2, 156.8, 154.4, 150.6, 142.3, 137.3, 126.7, 123.8, 53.8; IR (film) $v_{max}$ 1737, 1530, 1447, 1376, 1312, 1208, 1176, 1104, 941, 819, 797, 739, 713, 645 cm$^{-1}$.

Methyl 5-(Furan-2-yl)-1,3,4-oxadiazole-2-carboxylate (S8)

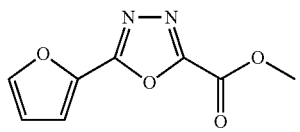

The title compound was prepared from commercially available furan-2-carbohydrazide (1.26 g, 10 mmol) by using general procedure C providing the product (1.63 g, 84%) as a white solid: $^1$H NMR (CDCl$_3$, 400 MHz) δ 7.69 (dd, 1H, J=1.8, 0.9 Hz), 7.33 (dd, 1H, J=3.5, 0.6 Hz), 6.63 (dd, 1H, J=3.8, 1.8 Hz), 4.06 (s, 3H); $^{13}$C NMR (CDCl$_3$, 100 MHz) δ 158.9, 155.3, 154.4, 146.9, 138.2, 116.4, 112.5, 53.8; IR (film) $v_{max}$ 3129, 1744, 1631, 1519, 1439, 1297, 1161, 1106, 984, 902, 814, 773, 726 cm$^{-1}$.

Methyl 5-(6-Bromopyridin-2-yl)-1,3,4-oxadiazole-2-carboxylate (S9)

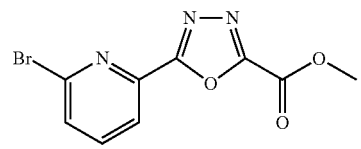 [SMILES: COC(=O)c1nnc(-c2cccc(Br)n2)o1]

The title compound was prepared from 6-bromopicolinyl hydrazide (S3, 350 mg, 1.62 mmol) following general procedure C. Recrystallization from EtOAc yielded the title compound (330 mg, 72%) as a white solid: $^1$H NMR (CDCl$_3$, 500 MHz) δ 8.28 (dd, 1H, J=0.9, 7.5 Hz), 7.78 (t, 1H, J=7.8 Hz), 7.72 (dd, 1H, J=0.9, 8.0 Hz), 4.10 (s, 3H); HRMS-ESI-TOF m/z 283.9670 ([M+H]$^+$, C$_9$H$_6$BrN$_3$O$_3$ requires 283.9665).

Methyl 3-(Pyridin-2-yl)-1,2,4-oxadiazole-5-carboxylate (S10)

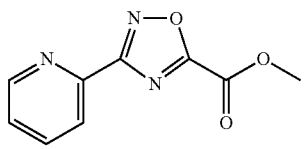

The title compound was prepared from commercially available N-hydroxypyridine-2-carboximidamide (150 mg, 1.09 mmol) by using general procedure C. Flash chromatography (SiO$_2$, 2.5×17 cm, 10-30% EtOAc-hexanes) afforded the title compound (40 mg, 18%) as a white solid: $^1$H NMR (CDCl$_3$, 400 MHz) δ 8.82 (ddd, 1H, J=0.9, 1.6, 4.7 Hz), 8.20 (td, 1H, J=0.9, 8.1 Hz), 7.89 (dt, 1H, J=1.6, 7.8 Hz), 7.48 (ddd, 1H, J=1.0, 4.8, 7.6 Hz), 4.11 (s, 3H); $^{13}$C NMR (CDCl$_3$, 150 MHz) δ 169.2, 166.9, 154.4, 149.8, 145.3, 138.2, 127.1, 122.8, 55.0; HRMS-ESI-TOF m/z 206.0568 ([M+H]$^+$, C$_9$H$_7$N$_3$O$_3$ requires 206.0560).

Methyl 3-(Furan-2-yl)-1,2,4-oxadiazole-5-carboxylate (S11)

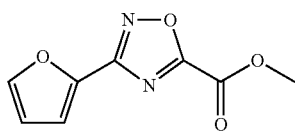

The title compound was prepared from N-hydroxyfuran-2-carboximidamide (S4, 203 mg, 1.61 mmol) by using general procedure C. Flash chromatography (SiO$_2$, 2.5×20 cm, 7-20% EtOAc-hexanes) afforded the title compound (134 mg, 43%) as a white solid: $^1$H NMR (CDCl$_3$, 500 MHz) δ 7.63 (d, 1H, J=1.4 Hz), 7.24 (d, 1H, J=3.5 Hz), 6.58 (dd, 1H, J=1.8, 3.4 Hz), 4.08 (s, 3H); $^{13}$C NMR (CDCl$_3$, 150 MHz) δ 166.3, 162.3, 154.4, 146.1, 141.2, 115.5, 112.3, 54.4; HRMS-ESI-TOF m/z 195.0391 ([M+H]$^+$, C$_8$H$_6$N$_2$O$_4$ requires 195.0400).

Methyl 3-(Thiophen-2-yl)-1,2,4-oxadiazole-5-carboxylate (S12)

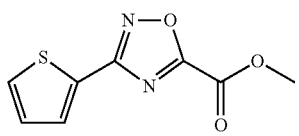

The title compound was prepared from commercially available N-hydroxythiophene-2-carboximidamide (155 mg, 1.09 mmol) by using general procedure C. Flash chromatography (SiO$_2$, 2.5×18 cm, 0-5% EtOAc-hexanes) afforded the title compound (63 mg, 27%) as a white solid: $^1$H NMR (CDCl$_3$, 500 MHz) δ 7.88 (dd, 1H, J=1.3, 3.7 Hz), 7.55 (dd, 1H, J=1.2, 5.0 Hz), 7.16 (dd, 1H, J=3.7, 5.0 Hz), 4.09 (s, 3H); $^{13}$C NMR (CDCl$_3$, 150 MHz) δ 166.3, 165.7, 154.5, 130.9, 130.5, 128.3, 127.0, 54.4; HRMS-ESI-TOF m/z 211.01703 ([M+H]$^+$, C$_8$H$_6$N$_2$O$_3$S requires 211.0172).

Methyl 3-(6-Chloropyridin-2-yl)-1,2,4-oxadiazole-5-carboxylate (S13)

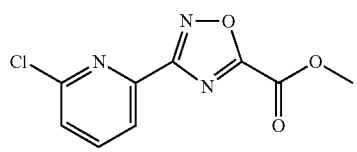 [SMILES: COC(=O)c1nc(-c2cccc(Cl)n2)no1]

The title compound was prepared from 6-chloro-N-hydroxypicolinimidamide (S5, 175 mg, 1.02 mmol) by using general procedure C. Flash chromatography (SiO$_2$, 2.5×15 cm, 20% acetone-hexanes) afforded the title compound (128 mg, 52%) as a white solid: $^1$H NMR (CDCl$_3$, 500 MHz) δ 8.12 (dd, 1H, J=0.8, 7.6 Hz), 7.85 (t, 1H, J=7.8 Hz), 7.52 (dd, 1H, J=0.7, 8.1 Hz), 4.12 (s, 3H); $^{13}$C NMR (CDCl$_3$, 150 MHz) δ 168.2, 167.2, 154.4, 152.6, 145.7, 139.9, 127.4, 122.3, 54.4; HRMS-ESI-TOF m/z 240.0167 ([M+H]$^+$, C$_9$H$_6$ClN$_3$O$_3$ requires 240.017).

Methyl 3-(6-Bromopyridin-2-yl)-1,2,4-oxadiazole-5-carboxylate (S14)

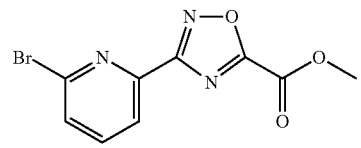

The title compound was prepared from 6-bromo-N-hydroxypicolinimidamide (S6, 230 mg, 1.06 mmol) by using general procedure C. Flash chromatography (SiO$_2$, 3×16 cm, 20-25% EtOAc-hexanes) afforded the title compound (98 mg, 31%) as a white solid: $^1$H NMR (CDCl$_3$, 600 MHz) δ 8.14 (d, 1H, J=7.7 Hz), 7.75 (t, 1H, J=7.7 Hz), 7.67 (dd, 1H, J=0.8, 8.0 Hz), 4.10 (s, 3H); $^{13}$C NMR (CDCl$_3$, 150 MHz) δ 168.0, 167.0, 154.3, 145.9, 143.0, 139.5, 131.1, 122.6, 54.5; HRMS-ESI-TOF m/z 283.9674 ([M+H]$^+$, C$_9$H$_6$BrN$_3$O$_3$ requires 283.9665).

Methyl 3-(6-Iodopyridin-2-yl)-1,2,4-oxadiazole-5-carboxylate (S15)

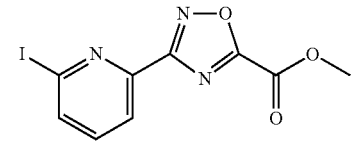 [SMILES: COC(=O)c1nc(-c2cccc(I)n2)no1]

The title compound was prepared from N-hydroxy-6-iodopicolinimidamide (55 mg, 0.21 mmol) by using general procedure C. Flash chromatography (SiO$_2$, 1.5×15 cm, 10-20% EtOAc-hexanes) afforded the title compound (10.0 mg, 14%) as a white solid: $^1$H NMR (CDCl$_3$, 500 MHz) δ 8.15 (dd, 1H, J=0.6, 7.7 Hz), 7.91 (dd, 1H, J=0.7, 7.9 Hz), 7.51 (t, 1H, J=7.8 Hz), 4.11 (s, 3H); $^{13}$C NMR (CDCl$_3$, 150 MHz) δ 168.1, 167.1, 154.4, 146.5, 138.4, 137.8, 123.0, 118.6, 54.4.

7-Phenyl-1-(5-(pyridin-2-yl)-1,3,4-oxadiazol-2-yl)-heptan-1-one (8b)

(General Procedure D)

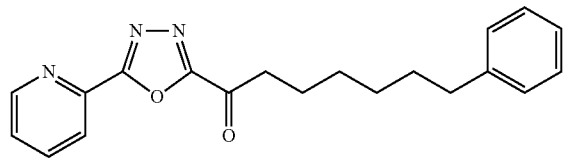

A dry vial was charged with freshly activated Mg turnings (115 mg, 5 mmol), 100 µL of anhydrous THF and a drop of 1,2-dibromoethane under Ar. This mixture was treated dropwise with a solution of 6-bromohexylbenzene (240 mg, 1 mmol) in THF (1 mL) at 23° C. The mixture was warmed and sonicated repeatedly until Grignard formation occurred. The gray solution of the Grignard reagent was added to a solution of methyl 5-(pyridin-2-yl)-1,3,4-oxadiazole-2-carboxylate (S7, 40 mg, 0.17 mmol) in THF (2 mL) at −40° C. Stirring was continued for 2 h before the reaction was quenched by the addition of MeOH at −40° C. The mixture was extracted with EtOAc and washed with water, saturated $NaHCO_3$ and saturated aqueous NaCl followed by separation and evaporation. Flash chromatography ($SiO_2$, 1×4 cm, 40% EtOAc-hexanes) afforded the title compound (30 mg, 51%) as a white solid: $^1$H NMR ($CDCl_3$, 400 MHz) δ 8.85 (d, 1H, J=4.7 Hz), 8.30 (d, 1H, J=7.9 Hz), 7.93 (td, 1H, J=1.5, 7.8 Hz), 7.54 (ddd, 1H, J=0.9 4.7, 7.6 Hz), 7.26-7.30 (m, 2H), 7.16-7.19 (m, 3H), 3.31 (t, 2H, J=7.3 Hz), 2.62 (t, 2H, J=7.6 Hz), 1.82 (quintet, 2H, J=7.3 Hz), 1.66 (quintet, 2H, J=7.5 Hz), 1.43 (m, 4H); $^{13}$C NMR ($CDCl_3$, 100 MHz) δ 187.1, 165.0, 161.2, 150.8, 142.6 (2C), 137.3, 128.3, 128.2, 126.7, 125.6, 124.0, 40.0, 35.8, 31.2, 28.9, 28.8, 23.5; IR (film) $v_{max}$ 2927, 2856, 1709, 1589, 1442, 1398, 1038, 986, 798, 754, 710 cm$^{-1}$; HRMS-ESI-TOF m/z 336.1717 ([M+H]$^+$, $C_{20}H_{21}N_3O_2$ requires 336.1706).

1-(5-(Furan-2-yl)-1,3,4-oxadiazol-2-yl)-heptan-1-one (8c)

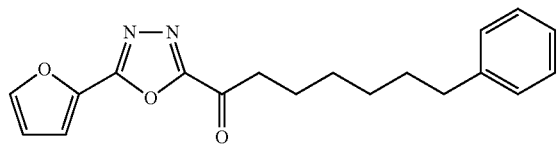 [SMILES: O=C(CCCCCCc1ccccc1)c1nnc(-c2ccco2)o1]

The title compound was prepared from S8 (50 mg, 0.25 mmol) by using general procedure D. Flash chromatography ($SiO_2$, 1×4 cm, 40% EtOAc-hexanes) afforded the title compound (47 mg, 57%) as a white solid: $^1$H NMR ($CDCl_3$, 400 MHz) δ 7.72 (dd, 1H, J=0.9, 1.8 Hz), 7.36 (dd, 1H, J=0.9, 3.8 Hz), 7.26-7.30 (m, 2H), 7.18-7.19 (m, 3H), 6.66 (ddd, 1H, J=0.9, 1.8, 3.5 Hz), 3.18 (t, 2H, J=7.3 Hz), 2.62 (t, 2H, J=7.6 Hz), 1.81 (quintet, 2H, J=7.3 Hz), 1.65 (quintet, 2H, J=7.3 Hz), 1.43 (m, 4H); $^{13}$C NMR ($CDCl_3$, 100 MHz) δ 187.1, 159.9, 158.7, 147.0, 142.5, 138.5, 128.3, 128.2, 125.6, 116.6, 112.6, 39.9, 35.6, 31.2, 28.9, 28.8, 23.6; IR (film) $v_{max}$ 3133, 2918, 2854, 1713, 1632, 1511, 1468, 1441, 1401, 1274, 1247, 1108, 1019, 987, 902, 772 cm$^{-1}$; HRMS-ESI-TOF m/z 325.1548 ([M+H]$^+$, $C_{19}H_{20}N_2O_3$ requires 325.1547).

7-Phenyl-1-(5-(thien-2-yl)-1,3,4-oxadiazol-2-yl)-heptan-1-one (8d)

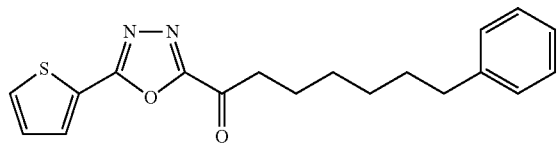

The title compound was prepared from methyl 5-(furan-2-yl)-1,3,4-oxadiazole-2-carboxylate (12 mg, 0.036 mmol) by using general procedure D. Flash chromatography ($SiO_2$, 1×5 cm, 10% EtOAc-hexanes) afforded the title compound (9 mg, 57%) as a white solid: $^1$H NMR ($CDCl_3$, 400 MHz) δ 7.92 (dd, 1H, J=1.1, 3.8 Hz), 7.66 (dd, 1H, J=1.1, 5.0 Hz), 7.27 (dd, 2H, J=4.9, 9.9 Hz), 7.22 (dd, 1H, J=3.8, 5.0 Hz), 7.17 (m, 3H), 3.17 (t, 2H, J=7.4 Hz), 2.61 (t, 2H, J=7.6 Hz), 1.80 (m, 2H), 1.64 (m, 2H), 1.42 (m, 4H); $^{13}$C NMR ($CDCl_3$, 150 MHz) δ 187.4, 162.7, 160.4, 142.7, 132.3, 131.9, 128.7, 128.5, 128.4, 125.8, 124.1, 40.0, 36.0, 31.4, 29.1, 29.0, 23.8; HRMS-ESI-TOF m/z 341.1309 ([M+H]$^+$, $C_{19}H_{20}N_2O_2S$ requires 341.1318).

1-(5-(6-Bromopyridin-2-yl)-1,3,4-oxadiazol-2-yl)-7-phenylheptan-1-one (20)

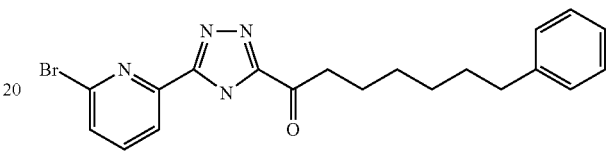

The title compound was prepared from S9 (97 mg, 3.9 mmol) by using general procedure D. Flash chromatography ($SiO_2$, 1.5×11 cm, 5-15% EtOAc-hexanes) afforded the title compound (12 mg, 18%) as a white solid: $^1$H NMR ($CDCl_3$, 500 MHz) δ 8.25 (dd, 1H, J=0.9, 7.5 Hz), 7.77 (t, 1H, J=7.8 Hz), 7.71 (dd, 1H, J=1.0, 8.0 Hz), 7.27 (m, 2H), 7.17 (m, 3H), 3.20 (t, 2H, J=7.4 Hz), 2.61 (t, 2H, J=7.7 Hz), 1.81 (m, 2H), 1.64 (m, 2H), 1.42 (m, 4H); $^{13}$C NMR ($CDCl_3$, 150 MHz) δ 187.2, 164.1, 161.5, 143.3, 143.2, 142.7, 139.5, 131.7, 128.5, 128.4, 125.8, 123.0, 40.3, 36.0, 31.4, 29.0 (2C), 23.7; HRMS-ESI-TOF m/z 414.0819 ([M+H]$^+$, $C_{20}H_{20}BrN_3O_2$ requires 414.0812).

Methyl 6-(5-(7-Phenylheptanoyl)-1,3,4-oxadiazol-2-yl)-picolinate (8f)

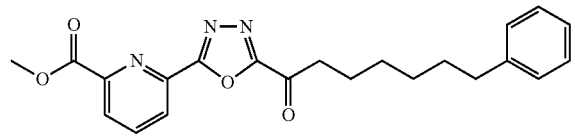 [SMILES: COC(=O)c1cccc(-c2nnc(C(=O)CCCCCCc3ccccc3)o2)n1]

In a gas tight vessel, compound 20 (59 mg, 0.14 mmol) was dissolved in 8:2 toluene-MeOH (2 mL), then $Cl_2Pd(PPh_3)_2$ (20 mg, 0.028 mmol) and $Et_3N$ (60 μL, 0.427 mmol) were added. CO(g) was bubbled through the reaction mixture for 30 min, before the reaction vessel was sealed and warmed at 90° C. for 36 h. The reaction mixture was diluted with EtOAc, washed with water and saturated aqueous NaCl, and dried over $Na_2SO_4$. Evaporation in vacuo yielded the crude ester which was purified by flash chromatography ($SiO_2$, 20-30% EtOAc-hexanes) to provide the title compound (41 mg, 73%) as a white solid: $^1$H NMR ($CDCl_3$, 600 MHz) δ 8.47 (dd, 1H, J=1.0, 7.8 Hz), 8.34 (dd, 1H, J=0.7, 7.9 Hz), 8.10 (t, 1H, J=7.9 Hz), 7.27 (m, 2H), 7.17 (m, 3H), 4.06 (s, 3H), 3.21 (t, 2H, J=7.3 Hz), 2.61 (t, 2H, J=7.7 Hz), 1.81 (m, 2H), 1.64 (m, 2H), 1.42 (m, 4H); $^{13}$C NMR ($CDCl_3$, 150 MHz) δ 187.1, 164.6 (2C), 161.6, 149.3, 143.0, 142.7, 138.8, 128.5, 128.4, 127.8, 127.1, 125.8, 53.4, 40.3, 36.0, 31.4, 29.1, 29.0, 23.7; HRMS-ESI-TOF m/z 394.1766 ([M+H]+, C22H23N3O4 requires 394.1761).

6-(5-(7-Phenylheptanoyl-1,3,4-oxadiazol-2-yl)-picolinic Acid (8g)

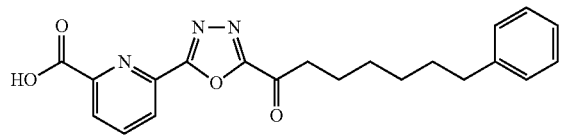

The title compound was prepared from 8f (11.8 mg, 0.029 mmol) following general procedure A. Flash chromatography (SiO2, 0.5×6 cm, 0-2% AcOH-EtOAc) afforded the title compound (11.4 mg, 100%) as a white solid: $^1$H NMR (acetone-$d_6$+0.1% TFA, 500 MHz) δ 8.77 (d, 1H, J=7.4 Hz), 8.61 (d, 1H, J=7.8 Hz), 8.56 (t, 1H, J=7.7 Hz), 7.46 (t, 2H, J=7.4 Hz), 7.41 (d, 2H, J=6.9 Hz), 7.35 (m, 1H), 3.44 (t, 2H, J=7.3 Hz), 2.83 (t, 2H, J=7.7 Hz), 2.01 (m, 2H), 1.86 (m, 2H), 1.66 (m, 4H); $^{13}$C NMR (acetone-$d_6$+0.1% TFA, 150 MHz) δ 189.0, 188.9, 166.1, 163.6, 150.7, 144.6, 144.5, 141.5, 130.2, 130.0, 129.1, 129.0, 127.4, 41.4, 37.4, 33.2, 31.3, 25.1, 25.0; HRMS-ESI-TOF m/z 380.1606 ([M+H]+, C21H21N3O4 requires 380.1605).

1-(3-(6-Chloropyridin-2-yl)-1,2,4-oxadiazol-5-yl)-7-phenylheptan-1-one (21)

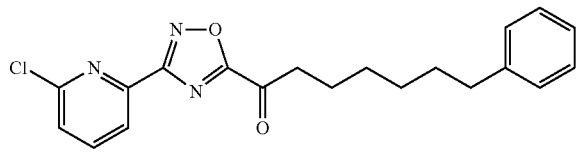 [SMILES: O=C(CCCCCCc1ccccc1)c1nc(-c2cccc(Cl)n2)no1]

The title compound was prepared from S13 (24 mg, 0.10 mmol) by using general procedure D. Flash chromatography (SiO2, 1.5×11 cm, 10-20% EtOAc-hexanes) afforded the title compound (13 mg, 37%) as a white solid: $^1$H NMR (CDCl3, 600 MHz) δ 8.12 (d, 1H, J=7.6 Hz), 7.86 (t, 1H, J=7.8 Hz), 7.53 (d, 1H, J=8.0 Hz), 7.27 (m, 2H), 7.17 (m, 3H), 3.21 (t, 2H, J=7.3 Hz), 2.62 (t, 2H, J=7.7 Hz), 1.80 (m, 2H), 1.65 (m, 2H), 1.42 (m, 4H); $^{13}$C NMR (CDCl3, 150 MHz) δ 187.3, 170.6, 168.0, 152.6, 145.9, 142.7, 139.9, 128.5, 128.4, 127.2, 125.8, 122.2, 40.9, 36.0, 31.3, 29.0, 28.9, 23.2; HRMS-ESI-TOF m/z 370.1308 ([M+H]+, C20H20N3O2Cl requires 370.1317).

1-(3-(6-Bromopyridin-2-yl)-1,2,4-oxadiazol-5-yl)-7-phenylhentan-1-one (22)

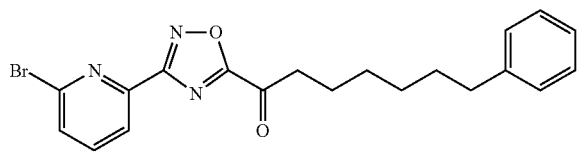 [SMILES: O=C(CCCCCCc1ccccc1)c1nc(-c2cccc(Br)n2)no1]

The title compound was prepared from S14 (51 mg, 0.18 mmol) by using general procedure D. Flash chromatography (SiO2, 1.5×21 cm, 10-20% EtOAc-hexanes) afforded the title compound (41 mg, 55%) as a white solid: $^1$H NMR (CDCl3, 600 MHz) δ 8.14 (d, 1H, J=7.5 Hz), 7.75 (t, 1H, J=7.7 Hz), 7.68 (d, 1H, J=8.0 Hz), 7.28 (d, 2H, J=7.7 Hz), 7.17 (m, 3H), 3.21 (t, 2H, J=7.3 Hz), 2.62 (t, 2H, J=7.7 Hz), 1.80 (m, 2H), 1.65 (m, 2H), 1.42 (m, 4H); $^{13}$C NMR (CDCl3, 150 MHz) δ 187.3, 170.6, 167.9, 146.4, 143.1, 142.7, 139.5, 131.0, 128.5, 128.4, 125.8, 122.6, 40.9, 36.0, 31.3, 29.0, 28.9, 23.2; HRMS-ESI-TOF m/z 414.0806 ([M+H]+, C20H20N3O2Br requires 414.0812).

1-(3-(6-Iodopyridin-2-yl)-1,2,4-oxadiazol-5-yl)-7-phenylheptan-1-one (23)

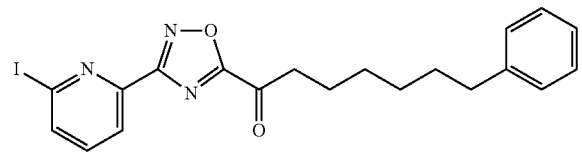 [SMILES: O=C(CCCCCCc1ccccc1)c1nc(-c2cccc(I)n2)no1]

The title compound was prepared from S15 (10 mg, 0.03 mmol) by using general procedure D. Flash chromatography (SiO2, 1×10 cm, 10-20% EtOAc-hexanes) afforded the title compound (3.5 mg, 25%) as a white solid: $^1$H NMR (CDCl3, 600 MHz) δ 8.14 (dd, 1H, J=0.7, 7.8 Hz), 7.92 (dd, 1H, J=0.7, 7.9 Hz), 7.51 (t, 1H, J=7.7 Hz), 7.27 (m, 2H), 7.17 (m, 3H), 3.20 (t, 2H, J=7.3 Hz), 2.62 (t, 2H, J=7.7 Hz), 1.80 (m, 2H), 1.64 (td, 2H, J=6.9, 7.5 Hz), 1.42 (m, 4H); $^{13}$C NMR (CDCl3, 150 MHz) δ 187.3, 170.5, 167.9, 146.8, 142.7, 138.4, 137.7, 128.5, 128.4, 125.8, 122.9, 118.6, 40.9, 36.0, 31.3, 29.0, 28.9, 23.2; HRMS-ESI-TOF m/z 462.0664 ([M+H]+, C20H20N3O2I requires 462.0673).

1-(3-(6-Bromopyridin-2-yl)-1,2,4-oxadiazol-5-yl)-7-phenylheptan-1-ol (S16)

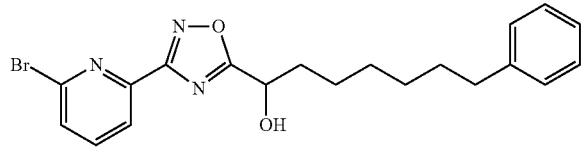 [SMILES: OC(CCCCCCc1ccccc1)c1nc(-c2cccc(Br)n2)no1]

A sample of 22 (28 mg, 0.068 mmol) was dissolved in a 2:1 mixture of MeOH-THF (0.8 mL) and cooled to 0° C. LiBH4 was added portionwise to the cooled solution and the mixture was allowed to slowly warm to 23° C. After 1 h, the reaction was quenched with the addition of 5% AcOH in EtOH (1 mL) and the mixture was stirred overnight. The solution was diluted with EtOAc, washed with water and saturated aqueous NaCl, and dried over Na2SO4. Evaporation yielded the crude alcohol that was purified by flash chromatography (SiO2, 1×12 cm, 25-50% EtOAc-hexanes) to afford the alcohol (17.0 mg, 62%) as a colorless oil: $^1$H NMR (CDCl3, 500 MHz) δ 8.08 (dd, 1H, J=0.9, 7.5 Hz), 7.70 (t, 1H, J=7.9 Hz), 7.63 (dd, 1H, J=0.8, 8.0 Hz), 7.26 (t, 2H, J=7.6 Hz), 7.16 (m, 3H), 5.06 (dd, 1H, J=5.4, 7.7 Hz), 2.59 (t, 2H, J=7.7 Hz), 1.99 (m, 2H), 1.61 (m, 2H), 1.48 (m, 2H), 1.36 (m, 4H).

1-(3-(6-Cyanopyridin-2-yl)-1,2,4-oxadiazol-5-yl)-7-phenylheptan-1-ol (S17)

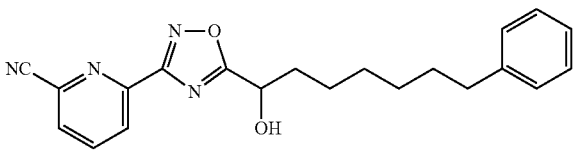 [SMILES: N#Cc1cccc(-c2noc(C(O)CCCCCCc3ccccc3)n2)n1]

Alcohol S16 (19 mg, 0/046 mmol) was dissolved in DMF. Zn(CN)$_2$ and (Ph$_3$P)$_4$Pd were added sequentially and the resulting mixture was warmed at 80° C. until the disappearance of starting material (2.5 h). The reaction mixture was cooled and diluted with EtOAc. The slurry was filtered through a pad of Celite and concentrated to give the crude product which was purified by flash chromatography (SiO$_2$, 1×5 cm, 50% EtOAc-hexanes) to afford the title compound (12.0 mg, 72%) as a colorless oil: $^1$H NMR (CDCl$_3$, 500 MHz) δ 8.36 (dd, 1H, J=0.9, 8.1 Hz), 8.03 (t, 1H, J=7.9 Hz), 7.85 (dd, 1H, J=0.9, 7.6 Hz), 7.26 (m, 2H), 7.17 (m, 3H), 5.07 (dd, 1H, J=5.4, 7.5 Hz), 2.62 (t, 2H, J=7.7 Hz), 2.60 (br s, 1H (—OH)), 2.01 (m, 2H), 1.62 (m, 4H), 1.48 (m, 2H), 1.37 (m, 2H).

1-(3-(6-Cyanopiridin-2-yl)-1,2,4-oxadiazol-5-yl)-7-phenylheptan-1-one (24)

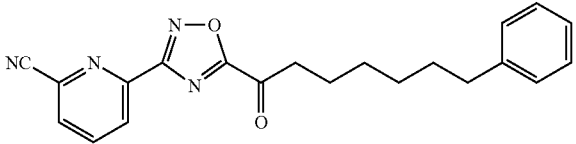 [SMILES: N#Cc1cccc(-c2noc(C(=O)CCCCCCc3ccccc3)n2)n1]

The title compound was prepared from S17 (5.0 mg, 0.014 mmol) following general procedure B. Flash chromatography (SiO$_2$, 1×10 cm, 20-25% EtOAc-hexanes) afforded the title compound (3.0 mg, 60%) as a white solid: $^1$H NMR (CDCl$_3$, 600 MHz) δ 8.41 (d, 1H, J=8.0 Hz), 8.08 (t, 1H, J=7.9 Hz), 7.89 (dd, 1H, J=0.8, 7.8 Hz), 7.26 (m, 2H), 7.17 (m, 3H), 3.22 (t, 2H, J=7.3 Hz), 2.62 (t, 2H, J=7.7 Hz), 1.81 (m, 2H), 1.65 (m, 2H), 1.42 (m, 4H); $^{13}$C NMR (CDCl$_3$, 150 MHz) δ 187.1, 170.9, 167.7, 147.4, 142.7, 138.8, 135.0, 130.6, 128.5, 128.4, 126.6, 125.8, 116.4, 41.0, 36.0, 31.3, 29.0, 28.9, 23.2; HRMS-ESI-TOF m/z 361.1673 ([M+H]$^+$, C$_{21}$H$_{20}$N$_4$O$_2$ requires 361.1659).

Methyl 6-(5-(1-Hydroxy-7-phenylheptyl)-1,2,4-oxadiazol-3-yl)-picolinate (S18)

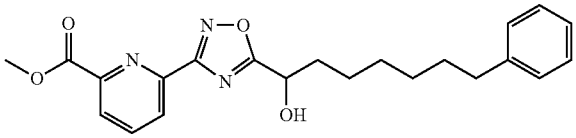 [SMILES: COC(=O)c1cccc(-c2noc(C(O)CCCCCCc3ccccc3)n2)n1]

A sample of S17 (5.0 mg, 0.01 mmol) was dissolved in MeOH (0.05M) and concentrated HCl (15 µL) was added. The solution was warmed at 80° C. for 4 h. Upon completion, the solution was cooled to 23° C., diluted with EtOAc, washed with saturated aqueous NaHCO$_3$ and saturated aqueous NaCl, and dried over Na$_2$SO$_4$. Evaporation in vacuo yielded the crude ester that was purified by preparative thin layer chromatography (SiO$_2$, 50% EtOAc-hexanes) to afford the title compound (3.0 mg, 73%) as a white solid: $^1$H NMR (CDCl$_3$, 600 MHz) δ 8.29 (m, 2H), 8.03 (t, 1H, J=7.8 Hz), 7.25 (m, 2H), 7.16 (m, 3H), 5.04 (dd, 1H, J=5.3, 7.5 Hz), 4.02 (s, 3H), 2.59 (t, 2H, J=7.7 Hz), 2.00 (m, 2H), 1.61 (m, 2H), 1.48 (m, 2H), 1.36 (m, 4H); $^{13}$C NMR (CDCl$_3$, 150 MHz) δ 181.8, 167.4, 165.3, 149.0, 146.4, 142.8, 138.5, 128.5, 128.3, 126.9, 126.5, 125.7, 67.3, 53.3, 36.0, 35.7, 31.4, 29.8, 29.1, 24.8.

Methyl 6-(5-(7-Phenylheptanoyl)-1,2,4-oxadiazol-3-yl)-picolinate (9f)

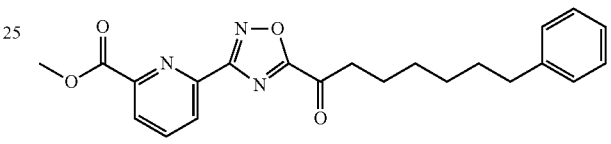

The title compound was prepared from S18 (8.0 mg, 0.02 mmol) following general procedure B. Flash chromatography (SiO$_2$, 1×10 cm, 20-30% EtOAc-hexanes) afforded the title compound (5.0 mg, 64%) as a white solid: $^1$H NMR (CDCl$_3$, 600 MHz) δ 8.36 (dd, 1H, J=1.0, 7.8 Hz), 8.32 (dd, 1H, J=1.1, 7.8 Hz), 8.07 (t, 1H, J=7.9 Hz), 7.27 (m, 2H), 7.17 (m, 3H), 4.05 (s, 3H), 3.24 (t, 2H, J=7.3 Hz), 2.62 (t, 2H, J=7.7 Hz), 1.80 (m, 2H), 1.65 (m, 2H), 1.42 (m, 4H); $^{13}$C NMR (CDCl$_3$, 150 MHz) δ 187.4, 170.7, 168.4, 165.2, 149.2, 145.8, 142.7, 138.7, 128.5, 128.4, 127.3, 126.7, 125.8, 53.4, 40.9, 36.0, 31.4, 29.0, 28.9, 23.1; HRMS-ESI-TOF m/z 394.1760 ([M+H]$^+$, C$_{22}$H$_{23}$N$_3$O$_4$ requires 394.1761).

6-(5-(7-Phenylheptanoyl)-1,2,4-oxadiazol-3-yl)-picolinic Acid (9g)

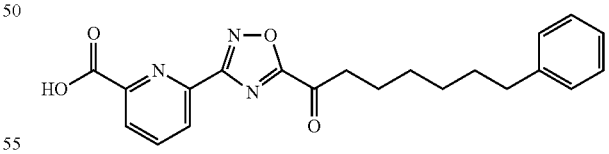

The title compound was prepared from 9f (4.0 mg, 0.01 mmol) following general procedure A. Tritration with hexanes and Et$_2$O afforded the title compound (1.0 mg, 25%) as a white solid: $^1$H NMR (acetone-d$_6$, 600 MHz) δ 8.45 (dd, 1H, J=1.2, 7.7 Hz), 8.37 (dd, 1H, J=1.2, 7.8 Hz), 8.33 (t, 1H, J=7.7 Hz), 7.26 (t, 2H, J=7.5 Hz), 7.21 (d, 2H, J=6.9 Hz), 7.15 (t, 1H, J=7.3 Hz), 3.29 (t, 2H, J=7.2 Hz), 2.63 (t, 2H, J=7.7 Hz), 1.80 (m, 2H), 1.66 (m, 2H), 1.50 (m, 2H), 1.43 (m, 2H); $^{13}$C NMR (acetone-d$_6$, 150 MHz) δ 188.9, 172.7, 169.9, 166.3, 150.5, 147.3, 144.5, 141.5, 130.2, 130.1, 128.7, 128.4, 127.4, 42.0, 37.4, 33.2, 31.3, 30.4, 24.6; HRMS-ESI-TOF m/z 380.1608 ([M+H]$^+$, $C_{21}H_{21}N_3O_4$ requires 380.1605).

3-(Biphenyl-4-yl)-1-(5-(pyridin-2-yl)-1,3,4-oxadiazol-2-yl)-propan-1-one (27)

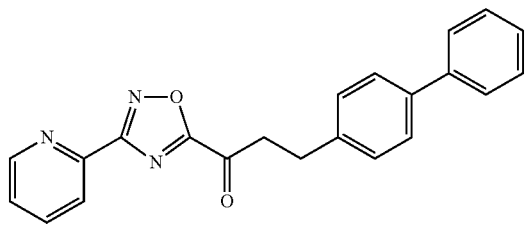 [SMILES: O=C(CCc1ccc(-c2ccccc2)cc1)c1nc(-c2ccccn2)no1]

4-Biphenylethanol (see Kawasaki et al., *Tetrahedron: Asymmetry* 2001, 12, 585-596) (1.47 g, 7.41 mmol) and CBr$_4$ (1.12 equiv) were dissolved in CH$_2$Cl$_2$ (25 mL), the mixture was cooled to 0° C. and triphenylphosphine (1.1 equiv) was added in small portions. The reaction mixture was warmed at room temperature and stirred for 1 h before the solvent was removed in vacuo. Flash chromatography (0-5% EtOAc-hexanes) yielded 4-(2-bromoethyl)biphenyl (1.59 g, 82%). The title compound was prepared from S7 (55 mg, 0.27 mmol) and 4-(2-bromoethyl)biphenyl (280 mg, 1.07 mmol) by using general procedure D. Flash chromatography (SiO$_2$, 1.5×18 cm, 50-100% EtOAc-hexanes) afforded the title compound (38 mg, 40%) as a white solid: $^1$H NMR (CDCl$_3$, 500 MHz) δ 8.84 (dd, 1H, J=0.7, 4.7 Hz), 8.29 (d, 1H, J=7.9 Hz), 7.92 (dt, 1H, J=1.7, 7.8 Hz), 7.57 (m, 2H), 7.53 (m, 3H), 7.42 (t, 2H, J=7.7 Hz), 7.33 (m, 3H), 3.60 (t, 2H, J=7.5 Hz), 3.19 (t, 2H, J=7.5 Hz); $^{13}$C NMR (CDCl$_3$, 150 MHz) δ 186.2, 165.3, 161.3, 150.9, 142.7, 141.0, 139.6, 139.0, 137.5, 129.0, 128.9, 127.5, 127.3, 127.2, 126.9, 124.2, 41.7, 29.1; HRMS-ESI-TOF m/z 356.1392 ([M+H]$^+$, $C_{22}H_{17}N_3O_2$ requires 356.1393).

3-(Biphenyl-4-yl)-1-(5-(6-bromopyridin-2-yl)-1,3,4-oxadiazol-2-yl)-propan-1-one (30)

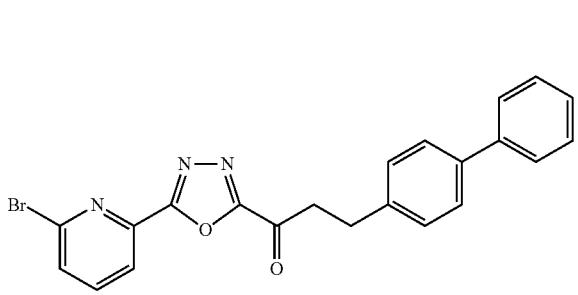 [SMILES: O=C(CCc1ccc(-c2ccccc2)cc1)c1nnc(-c2cccc(Br)n2)o1]

The title compound was prepared from S9 (122 mg, 0.429 mmol) and 4-(2-bromoethyl)biphenyl (450 mg, 1.72 mmol) by using general procedure D. Flash chromatography (SiO$_2$, 3×16 cm, 50-100% EtOAc-hexanes) afforded the title compound (70 mg, 38%) as a white solid: $^1$H NMR (CDCl$_3$, 600 MHz) δ 8.25 (d, 1H, J=7.6 Hz), 7.77 (t, 1H, J=7.8 Hz), 7.71 (d, 1H, J=7.9 Hz), 7.55 (m, 4H), 7.43 (t, 2H, J=7.7 Hz), 7.33 (m, 3H), 3.60 (t, 2H, J=7.5 Hz), 3.19 (t, 2H, J=7.5 Hz); $^{13}$C NMR (CDCl$_3$, 150 MHz) δ 186.1, 164.1, 161.4, 143.2 (2C), 141.0, 139.7, 139.5, 138.9, 131.7, 129.0, 128.9, 127.5, 127.3, 127.2, 123.0, 41.8, 29.1; HRMS-ESI-TOF m/z 434.0488 ([M+H]$^+$, $C_{22}H_{16}BrN_3O_2$ requires 434.0499).

Methyl 6-(5-(3-(Biphenyl-4-yl)propanoyl)-1,3,4-oxadiazol-2-yl)-picolinate (28)

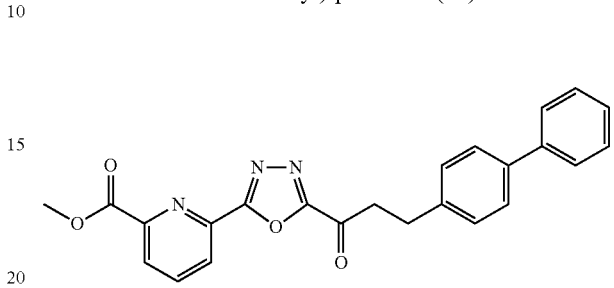

The title compound was prepared from 30 (70 mg, 0.16 mmol) by using a procedure similar to that detailed for 8f. Flash chromatography (SiO$_2$, 2.5×15 cm, 0-1% MeOH—CH$_2$Cl$_2$) afforded the title compound (32 mg, 48%) as a white solid: $^1$H NMR (CDCl$_3$, 600 MHz) δ 8.47 (d, 1H, J=7.8 Hz), 8.34 (d, 1H, J=7.8 Hz), 8.10 (t, 1H, J=7.8 Hz), 7.57 (d, 2H, J=7.2 Hz), 7.53 (d, 2H, J=8.1 Hz), 7.43 (t, 2H, J=7.7 Hz), 7.33 (m, 3H), 4.06 (s, 3H), 3.61 (t, 2H, J=7.5 Hz), 3.19 (t, 2H, J=7.5 Hz); $^{13}$C NMR (CDCl$_3$, 150 MHz) δ 186.1, 164.9, 164.6, 161.5, 149.3, 142.9, 141.0, 139.7, 138.9, 138.8, 129.0, 128.9, 127.9, 127.5, 127.3, 127.2, 127.1, 53.4, 41.8, 29.1; HRMS-ESI-TOF m/z 414.1451 ([M+H]$^+$, $C_{24}H_{19}N_3O_4$ requires 414.1448).

6-(5-(3-(Biphenyl-4-yl)propanoyl)-1,3,4-oxadiazol-2-yl)-picolinic Acid (29)

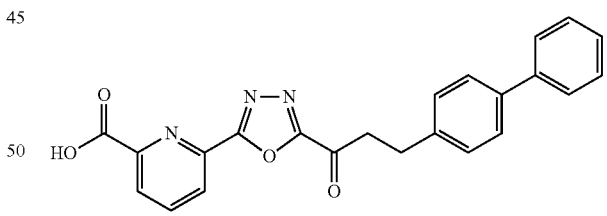

The title compound was prepared from 28 (8.7 mg, 0.021 mmol) following general procedure A. Preparative thin layer chromatography (SiO$_2$, 0-4% AcOH-EtOAc) afforded the title compound (8.4 mg, 100%) as a white solid: $^1$H NMR (DMSO-d$_6$+0.1% TFA, 600 MHz) δ 8.32 (d, 1H, J=7.7 Hz), 8.17 (d, 1H, J=7.8 Hz), 8.01 (t, 1H, J=7.9 Hz), 7.85 (br s, 1H), 7.48 (d, 2H, J=7.4 Hz), 7.45 (d, 2H, J=8.1 Hz), 7.28 (t, 2H, J=7.7 Hz), 7.25 (d, 2H, J=8.1 Hz), 7.18 (t, 1H, J=7.3 Hz), 3.45 (t, 2H, J=7.4 Hz), 3.01 (t, 2H, J=7.4 Hz); $^{13}$C NMR (DMSO-d$_6$+0.1% TFA, 150 MHz) δ 188.0, 167.0, 166.1, 165.0, 163.0, 151.1, 144.2, 142.1, 141.2, 140.5, 140.4, 130.6, 130.4, 129.2, 128.8, 128.5, 128.2, 44.7, 29.9; HRMS-ESI-TOF m/z 400.1288 ([M+H]$^+$, $C_{23}H_{17}N_3O_4$ requires 400.1292).

Z)-1-(5-(Pyridin-2-yl)-1,3,4-oxadiazol-2-yl)-octadec-9-en-1-one (4b (General Procedure E)

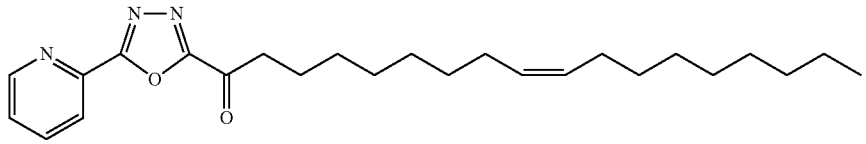

A solution of cis-1-bromoheptadec-8-ene (60 mg, 0.2 mmol) in THF (1 mL) was treated dropwise with 1.5 M t-BuLi (270 µL, 0.4 mmol) at −78° C. After stirring for 15 min, the resulting alkyllithium reagent was added to a cooled solution of methyl 5-(pyridin-2-yl)-1,3,4-oxadiazole-2-carboxylate (S7, 20 mg, 0.1 mmol) in THF (2 mL) at −78° C. The reaction mixture was stirred for 3 h before it was quenched with the addition of MeOH. The mixture was extracted with EtOAc, washed with water, saturated aqueous NaHCO$_3$ and saturated aqueous NaCl, and dried over Na$_2$SO$_4$. Evaporation in vacuo yielded the crude product which was purified by flash chromatography (SiO$_2$, 1×3 cm, 30% EtOAc-hexanes) to provide the title compound (8.5 mg, 23%) as a white solid: $^1$H NMR (400 MHz, CDCl$_3$) δ 8.85 (dd, 1H, J=1.2, 5.0 Hz), 8.30 (dd, 1H, J=1.2, 7.9 Hz), 7.94 (td, 1H, J=1.5, 7.6 Hz), 7.54 (ddd, 1H, J=1.2, 4.7, 7.6 Hz), 5.34-5.37 (m, 2H), 3.22 (t, 2H, J=7.3 Hz), 2.02 (m, 4H), 1.82 (m, 2H), 1.27-1.41 (m, 20H), 0.88 (t, 3H, J=6.4 Hz); $^{13}$C NMR (CDCl$_3$, 100 MHz) δ 187.2, 165.1, 161.2, 150.8, 142.6, 137.3, 130.0, 129.7, 126.7, 124.0, 40.1, 31.9, 29.8, 29.7, 29.5, 29.3, 29.2, 29.1, 29.0, 27.2, 27.1, 23.6, 22.7, 14.1; IR (film) ν$_{max}$ 2922, 2853, 1712, 1543, 1456, 1394, 1097, 1044, 994 cm$^{-1}$; HRMALDI-FTMS m/z 412.2955 ([M+H]$^+$, C$_{25}$H$_{37}$N$_3$O$_2$ requires 412.2958).

7-Phenyl-1-(3-(pyridin-2-yl)-1,2,4-oxadiazol-5-yl)-heptan-1-one (9b)

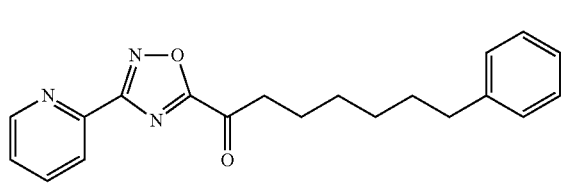 [SMILES: O=C(CCCCCCc1ccccc1)c1nc(-c2ccccn2)no1]

The title compound was prepared from S10 (26 mg, 0.13 mmol) and 6-bromohexylbenzene (68 mg, 0.26 mmol) by using general procedure E. Flash chromatography (SiO$_2$, 1×10 cm, 20% acetone-hexanes) afforded the title compound (0.8 mg, 2%) as a white solid: $^1$H NMR (CDCl$_3$, 600 MHz) δ 8.85 (d, 1H, J=4.4 Hz), 8.21 (d, 1H, J=7.8 Hz), 7.90 (dt, 1H, J=1.6, 7.8 Hz), 7.49 (dd, 1H, J=5.1, 7.2 Hz), 7.27 (m, 2H), 7.16 (m, 3H), 3.24 (t, 2H, J=7.3 Hz), 2.61 (t, 2H, J=7.7 Hz), 1.80 (m, 2H), 1.64 (m, 2H), 1.42 (m, 4H); $^{13}$C NMR (CDCl$_3$, 150 MHz) δ 188.3, 171.2, 169.7, 151.5, 143.4, 138.2, 129.2, 129.1 (2C), 126.9, 126.5, 124.4, 41.6, 36.7, 32.1, 29.8, 29.6, 23.9; HRMS-ESI-TOF m/z 336.1709 ([M+H]$^+$, C$_{20}$H$_{21}$N$_3$O$_2$ requires 336.1706).

1-(3-(Furan-2-yl)-1,2,4-oxadiazol-5-yl)-7-phenyl-heptan-1-one (9c)

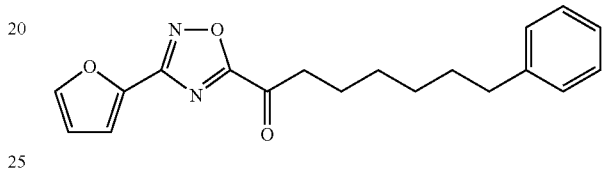

The title compound was prepared from S11 (30 mg, 0.15 mmol) and 6-bromohexylbenzene (72 mg, 0.3 mmol) by using general procedure E. Flash chromatography (SiO$_2$, 1×10 cm, 20% acetone-hexanes) afforded the title compound (10 mg, 20%) as a white solid: $^1$H NMR (CDCl$_3$, 600 MHz) δ 7.66 (m, 1H), 7.27 (m, 2H), 7.24 (d, 1H, J=3.5 Hz), 7.17 (m, 3H), 6.61 (dd, 1H, J=1.8, 3.5 Hz), 3.16 (t, 2H, J=7.3 Hz), 2.62 (t, 2H, J=7.7 Hz), 1.79 (m, 2H), 1.65 (m, 2H), 1.42 (m, 4H); $^{13}$C NMR (CDCl$_3$, 150 MHz) δ 187.3, 169.7, 162.0, 146.0, 142.7, 141.5, 128.5, 128.4, 125.8, 115.0, 112.2, 40.9, 36.0, 31.3, 29.0, 28.9, 23.2; HRMS-ESI-TOF m/z 325.1535 ([M+H]$^+$, C$_{19}$H$_{20}$N$_2$O$_3$ requires 325.1547).

7-Phenyl-1-(3-(thiophen-2-yl)-1,2,4-oxadiazol-5-yl)-heptan-1-one (9d)

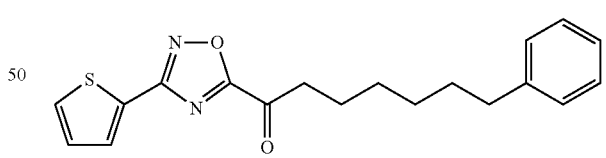

The title compound was prepared from S12 (31 mg, 0.15 mmol) and 6-bromohexylbenzene (72 mg, 0.3 mmol) by using general procedure E. Flash chromatography (SiO$_2$, 1×10 cm, 10% acetone-hexanes) afforded the title compound (7.0 mg, 14%) as a white solid: $^1$H NMR (CDCl$_3$, 600 MHz) δ 7.88 (dd, 1H, J=1.1, 3.7 Hz), 7.56 (dd, 1H, J=1.0, 5.0 Hz), 7.27 (m, 2H), 7.19 (m, 1H), 7.17 (m, 3H), 3.15 (t, 2H, J=7.3 Hz), 2.62 (t, 2H, J=7.7 Hz), 1.79 (m, 2H), 1.65 (m, 2H), 1.42 (m, 4H); $^{13}$C NMR (CDCl$_3$, 150 MHz) δ 187.5, 169.7, 165.4, 142.7, 130.6, 130.3, 128.5, 128.4, 128.3, 127.4, 125.8, 40.9, 36.0, 31.3, 29.0, 28.9, 23.3; HRMS-ESI-TOF m/z 341.1302 ([M+H]$^+$, C$_{19}$H$_{20}$N$_2$O$_2$S requires 341.1318).

2-(tert-Butyldimethylsilyloxy)-8-phenyloctanitrile (S19)

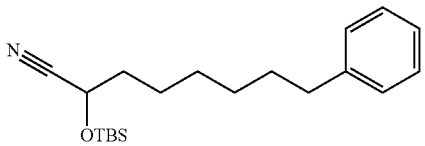 [SMILES: CC(C)(C)[Si](C)(C)OC(C#N)CCCCCCc1ccccc1]

A solution of 7-phenylheptanal (1.93 g, 0.01 mol) in MeCN (64 mL) was treated with KCN (2.65 g, 0.04 mol), ZnI$_2$ (77.7 mg, 0.0002 mol), and TBSCl (3.06 g, 0.02 mol) under Ar at room temperature. The reaction mixture was stirred vigorously and the progress monitored by TLC (SiO$_2$, 5% EtOAc-hexanes). After 72 h, the solvent was removed in vacuo and the residue resuspended in Et$_2$O. The salts were removed by filtration and rinsed thoroughly with Et$_2$O. The filtrate was washed with water, dried over Na$_2$SO$_4$, and concentrated in vacuo to give a yellow oil that was purified by flash chromatography (SiO$_2$, 4×25 cm, 1% EtOAc-hexanes) to afford the title compound (2.6 g, 80%) as a colorless oil: $^1$H NMR (CDCl$_3$, 500 MHz) δ 7.30 (m, 2H), 7.20 (m, 3H), 4.43 (t, 1H, J=6.4 Hz), 2.63 (t, 2H, J=7.7 Hz), 1.80 (m, 2H), 1.65 (m, 2H), 1.49 (m, 2H), 1.39 (m, 4H), 0.94 (s, 9H), 0.21 (s, 3H), 0.16 (s, 3H); $^{13}$C NMR (CDCl$_3$, 125 MHz) δ 142.7, 128.5, 128.4, 125.7, 120.2, 62.0, 36.4, 36.0, 31.4, 29.1, 28.9, 25.6, 24.6, 18.2 (3C), −5.0, −5.2; HRMS-ESI-TOF m/z 354.2221 ([M+Na]$^+$, C$_{20}$H$_{33}$NOSi requires 354.2223).

Methyl 5-(1-Hydroxy-7-phenylheptyl)-1,3,4-oxadiazole-2-carboxylate (S20)

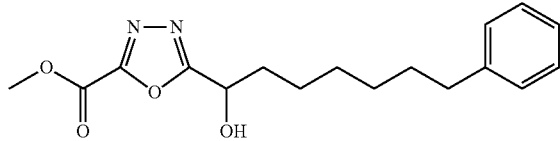

NaH (146 mg, 3.81 mmol) was added to anhydrous THF (3 mL) and cooled to 0° C. Anhydrous N$_2$H$_4$ (119 µl) was added to the reaction mixture behind a blast shield. After 0.5 h, a solution of 2-(tert-butyldimethylsilyloxy)-8-phenyloctanitrile (S19, 460 mg, 1.27 mmol) in THF (5 mL) was added to the slurry over 0.5 h by syringe pump turning the solution light yellow. Upon formation of the amidrazone (2 h), the reaction mixture was quenched with the addition of ice water (3 mL), diluted with Et$_2$O, washed with saturated aqueous NaCl, and dried over Na$_2$SO$_4$. Evaporation in vacuo yielded the crude amidrazone (461 mg, 100%) which was used without further purification. The amidrazone was dissolved in xylenes (1.8 mL) and treated with methyl oxalyl chloride (0.175 mL, 1.90 mmol). The reaction mixture was warmed at 150° C. for 0.75 h. Upon completion of the reaction, the mixture was diluted with EtOAc, washed with water, saturated aqueous NaHCO$_3$ and saturated aqueous NaCl, and dried over Na$_2$SO$_4$. Evaporation in vacuo yielded the crude alcohol which was purified by flash chromatography (SiO$_2$, 2.5×12 cm, 25-50% EtOAc-hexanes) to afford the title compound (26 mg, 6.5%) as a white solid: $^1$H NMR (CDCl$_3$, 600 MHz) δ 7.27 (m, 2H), 7.16 (m, 3H), 5.02 (t, 1H, J=6.4 Hz), 4.05 (s, 3H), 2.60 (t, 2H, J=7.7 Hz), 1.98 (m, 2H), 1.61 (m, 2H), 1.38 (m, 6H).

Methyl 5-(7-Phenylheptanoyl)-1,3,4-oxadiazole-2-carboxylate (8h)

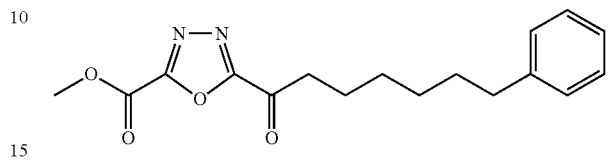

The title compound was prepared from S20 (16 mg, 0.05 mmol) following general procedure B. Flash chromatography (SiO$_2$, 1.5×7 cm, 15% EtOAc-hexanes) afforded the title compound (8.8 mg, 56%) as a white solid: $^1$H NMR (CDCl$_3$, 400 MHz) δ 7.27 (dd, 2H, J=5.1, 9.9 Hz), 7.17 (m, 3H), 4.09 (s, 3H), 3.18 (t, 2H, J=7.3 Hz), 2.61 (t, 2H, J=7.7 Hz), 1.79 (m, 2H), 1.63 (m, 2H), 1.40 (m, 4H); $^{13}$C NMR (CDCl$_3$, 150 MHz) δ 186.8, 161.2, 157.2, 154.2, 142.7, 128.5, 128.4, 125.8, 54.4, 40.5, 36.0, 31.3, 29.0, 28.9, 23.4; HRMS-ESI-TOF m/z 315.1362 ([M−H]$^−$, C$_{17}$H$_{20}$N$_2$O$_4$ requires 315.1350).

1-(1,3,4-Oxadiazol-2-yl)-7-phenylheptan-1-ol (S21)

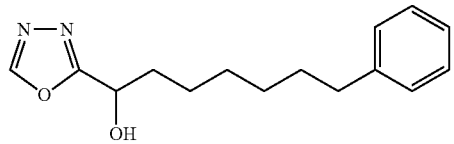 [SMILES: OC(CCCCCCc1ccccc1)c1nnco1]

The title compound was prepared by methyl ester hydrolysis and spontaneous decarboxylation from alcohol S20 (5.4 mg, 0.017 mmol) following general procedure A. Flash chromatography (SiO$_2$, 0.5×6 cm, 20-50% EtOAc-hexanes) afforded the title compound (2.6 mg, 59%) as a colorless oil: $^1$H NMR (CDCl$_3$, 600 MHz) δ 8.39 (s, 1H), 7.27 (m, 2H), 7.17 (m, 3H), 4.99 (dd, 1H, J=6.1, 7.3 Hz), 2.59 (t, 2H, J=7.7 Hz), 1.95 (m, 2H), 1.61 (m, 2H), 1.38 (m, 6H); $^{13}$C NMR (CDCl$_3$, 150 MHz) δ 167.8, 153.2, 142.7, 128.5, 128.4, 125.7, 66.1, 36.0, 35.2, 31.4, 29.2, 29.1, 24.9.

1-(1,3,4-Oxadiazol-2-yl)-7-phenylheptan-1-one (8a)

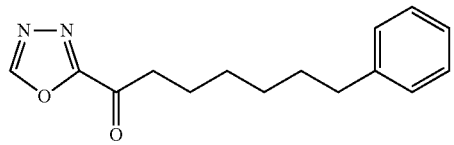 [SMILES: O=C(CCCCCCc1ccccc1)c1nnco1]

The title compound was prepared from S21 (2.6 mg, 0.01 mmol) following general procedure B. Flash chromatography (SiO$_2$, 0.5×5 cm, 10-15% EtOAc-hexanes) afforded the title compound (2.6 mg, 100%) as a white solid: $^1$H NMR (CDCl$_3$, 600 MHz) δ 8.55 (s, 1H), 7.28 (d, 2H, J=7.8 Hz), 7.17 (m, 3H), 3.17 (t, 2H, J=7.4 Hz), 2.61 (t, 2H, J=7.7 Hz), 1.79 (m, 2H), 1.64 (m, 2H), 1.41 (m, 4H); $^{13}$C NMR (CDCl$_3$, 150 MHz) δ 187.3, 160.9, 154.3, 142.7, 128.5, 128.4, 125.8, 40.3, 36.0, 31.4, 29.0 (2C), 23.6; HRMS-ESI-TOF m/z-([M+H]$^+$, C$_{15}$H$_{18}$N$_2$O$_2$ requires 259.1441) (HRMS was not possible on unsubstituted oxadiazole analogues due to ring opening during the ionization process).

5-(1-(tert-Butyldimethylsilyloxy)-7-phenylheptyl)-1,2,4-oxadiazole (S22)

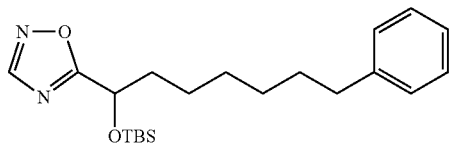 [SMILES: CC(C)(C)[Si](C)(C)OC(CCCCCCc1ccccc1)c1ncno1]

A sample of 2-(tert-butyldimethylsilyloxy)-8-phenyloctamide (S19, 30 mg, 0.086 mmol) was dissolved in Me$_2$NCH(OMe)$_2$ (100 μL) and warmed at 110° C. for 2 h. The excess reagent was removed in vacuo and the residue was dissolved in a mixture of 1,4-dioxane (170 μL) and AcOH (170 μL). NH$_2$OH—HCl (8 mg, 0.11 mmol) and NaOAc (9 mg, 0.11 mmol) were added as solids to the reaction mixture which was warmed at 80° C. for 4 h. Upon completion of the reaction, the mixture was diluted with EtOAc, washed with water and saturated aqueous NaCl, and dried over Na$_2$SO$_4$. Evaporation in vacuo yielded the crude product which was purified by flash chromatography (SiO$_2$, 1.5×12 cm, 0-10% EtOAc-hexanes) to afford the title compound (5.1 mg, 16%) as a colorless oil: $^1$H NMR (CDCl$_3$, 400 MHz) δ 8.37 (s, 1H), 7.27 (m 2H), 7.17 (m, 3H), 4.98 (dd, 1H, J=5.7, 7.1 Hz), 2.59 (t, 2H, J=7.7 Hz), 1.89 (m, 2H), 1.59 (m, 4H), 1.36 (m, 4H), 0.89 (s, 9H), 0.08 (s, 3H), 0.01 (s, 3H).

1-(1,2,4-Oxadiazol-5-yl)-7-phenylheptan-1-ol (S23)

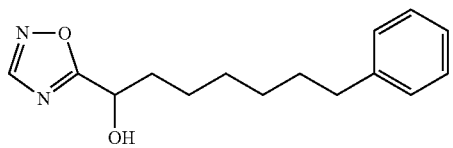 [SMILES: OC(CCCCCCc1ccccc1)c1ncno1]

A sample of S22 (3.0 mg, 0.008 mmol) was dissolved in THF (105 μL) in a plastic centrifuge tube and pyridine (21 μL) was added at 0° C. The solution was treated with HF-pyridine (9 μL) and allowed to warm to 23° C. and shaken for 24 h. The progress was monitored by TLC (SiO$_2$, 50% EtOAc-hexanes) and upon completion, a 1:1 solution of EtOAc:saturated aqueous NaHCO$_3$ (1 mL) was added. The reaction mixture was diluted with EtOAc and the aqueous layer was washed several times with EtOAc. The combined organic phases were washed with saturated aqueous NaCl and dried over Na$_2$SO$_4$. Evaporation in vacuo yielded the alcohol (2.0 mg, 100%) as a colorless oil that required no further purification: $^1$H NMR (CDCl$_3$, 500 MHz) δ 8.39 (s, 1H), 7.27 (m, 2H), 7.17 (m, 3H), 4.99 (dd, 1H, J=5.4, 7.5 Hz), 2.60 (t, 2H, J=7.7 Hz), 1.93 (m, 2H), 1.62 (m, 2H), 1.44 (m, 2H), 1.36 (m, 4H).

1-(1,2,4-Oxadiazol-5-yl)-7-phenylheptan-1-one (9a)

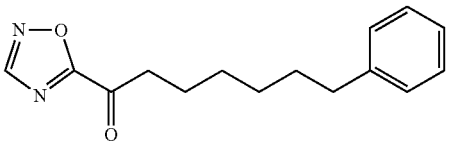 [SMILES: O=C(CCCCCCc1ccccc1)c1ncno1]

The title compound was prepared from 1-(1,2,4-oxadiazol-5-yl)-7-phenylheptan-1-ol (S23, 3 mg, 0.01 mmol) following general procedure B. Flash chromatography (SiO$_2$, 0.5×6 cm, 10% EtOAc-hexanes) afforded the title compound (1.3 mg, 34%) as a colorless oil: $^1$H NMR (CDCl$_3$, 600 MHz) δ 8.59 (s, 1H), 7.28 (dd, 2H, J=1.5, 6.7 Hz), 7.17 (m, 3H), 3.11 (t, 2H, J=7.3 Hz), 2.61 (t, 2H, J=7.7 Hz), 1.77 (m, 2H), 1.64 (m, 2H), 1.40 (m, 4H); $^{13}$C NMR (CDCl$_3$, 150 MHz) δ 187.2, 169.7, 157.9, 142.7, 128.5, 128.4, 125.8, 40.8, 36.0, 31.3, 29.0, 28.9, 23.3; HRMS-ESI-TOF m/z-([M+H]$^+$, C$_{15}$H$_{18}$N$_2$O$_2$ requires 259.1441) (HRMS was not possible on unsubstituted oxadiazole analogues due to ring opening during the ionization process).

Isomeric 1,2,4-Oxadiazoles (10a-10h):

General Procedure F.

The 2-(tert-butyldimethylsilyloxy)-8-phenyloctanitrile (S19, 1 equiv) was dissolved in EtOH (1.0 M) and hydroxylamine (aq.) (50% w/w, 3 equiv) was added at room temperature under Ar. The mixture was warmed at reflux for 1 h, cooled and the solvents were removed under reduced pressure. The residue was dissolved in CH$_2$Cl$_2$, dried over MgSO$_4$, filtered and concentrated to afford a colorless oil that was used without further purification. The N-hydroxycarbamide (1 equiv) and Et$_3$N (3 equiv) were dissolved in 1,2-dichloroethane (0.2 M) and treated with an aryl acid chloride (1.1 equiv) at 0° C. The reaction mixture was slowly warmed to room temperature and stirred for 6 h before it was treated with TsCl (1.1 equiv) and the mixture was warmed at 80° C. for 16 h under Ar. The reaction mixture was diluted with CH$_2$Cl$_2$ and washed with water, saturated aqueous NaHCO$_3$ and saturated aqueous NaCl. The organic layer was collected and evaporated to yield the crude TBS ether that was purified by flash chromatography (SiO$_2$).

General Procedure G.

The TBS ether (1 equiv) was dissolved in THF (0.08 M), treated with Bu$_4$NF (1 M in THF, 1.3 equiv) and stirred at room temperature for 2 h under Ar. The reaction mixture was diluted with EtOAc, washed with saturated aqueous NaCl and dried over Na$_2$SO$_4$. Evaporation in vacuo yielded the crude alcohol that was purified by flash chromatography (SiO$_2$).

3-(1-(tert-Butyldimethylsilyloxy)-7-phenylheptyl)-1,2,4-oxadiazole (S24)

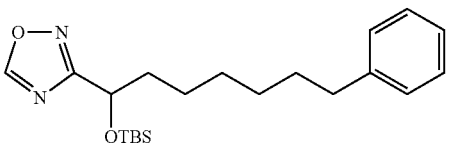 [SMILES: CC(C)(C)[Si](C)(C)OC(CCCCCCc1ccccc1)c1ncon1]

The 2-(tert-butyldimethylsilyloxy)-8-phenyloctanitrile (S19, 50 mg, 0.151 mmol) was dissolved in EtOH (150 μL) and hydroxylamine (aq.) (50% w/w, 28 μL, 0.453 mmol) was added under Ar. The mixture was warmed at reflux for 1 h, cooled and the solvents were removed under reduced pressure. The residue was dissolved in $CH_2Cl_2$, dried over $MgSO_4$, filtered and concentrated to afford a colorless oil that was used without further purification. The N-hydroxycarbamimide (45 mg, 0.123 mmol) was dissolved in freshly distilled triethyl orthoformate (250 μL, 0.5 M) and warmed at reflux for 3 h. The reaction mixture was cooled and the solvent was removed in vacuo to afford a yellow oil. Flash chromatography ($SiO_2$, 1.5×13 cm, 0-20% EtOAc-hexanes) afforded the title compound (7.5 mg, 16%) as a colorless oil: $^1H$ NMR ($CDCl_3$, 400 MHz) δ 8.65 (s, 1H), 7.27 (t, 2H, J=7.5 Hz), 7.17 (m, 3H), 4.93 (t, 1H, J=6.6 Hz), 2.59 (t, 2H, J=7.8 Hz), 1.84 (m, 2H), 1.60 (m, 2H), 1.33 (m, 6H), 0.88 (s, 9H), 0.09 (s, 3H), −0.01 (s, 3H); HRMS-ESI-TOF m/z 375.2465 ([M+H]+, $C_{21}H_{34}N_2O_2Si$ requires 375.2462).

1-(1,2,4-Oxadiazol-3-yl)-7-phenylheptan-1-ol (S25)

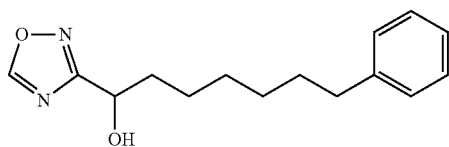 [SMILES: OC(CCCCCCc1ccccc1)c1ncon1]

A solution of S24 (5.9 mg, 0.015 mmol) was dissolved in THF (175 L) in a plastic centrifuge tube and pyridine (35 μL) was added at 0° C. The solution was treated with HF-pyridine (16 μL) and allowed to warm to 25° C. and shaken for 24 h. The progress was monitored by TLC ($SiO_2$, 50% EtOAc-hexanes) and upon completion, a 1:1 solution of EtOAc:saturated aqueous $NaHCO_3$ (1 mL) was added. The reaction mixture was diluted with EtOAc and the aqueous layer was washed with EtOAc (3×). The combined organic phases were washed with saturated aqueous NaCl and dried over $Na_2SO_4$. Evaporation in vacuo yielded the alcohol (4.3 mg, 100%) as a colorless oil that required no further purification: $^1H$ NMR ($CDCl_3$, 500 MHz) δ 8.69 (s, 1H), 7.27 (t, 2H, J=7.6 Hz), 7.17 (m, 3H), 4.93 (t, 1H, J=6.6 Hz), 2.59 (t, 2H, J=7.8 Hz), 1.91 (m, 2H), 1.61 (m, 2H), 1.36 (m, 6H).

1-(1,2,4-Oxadiazol-3-yl)-7-phenylheptan-1-one (10a)

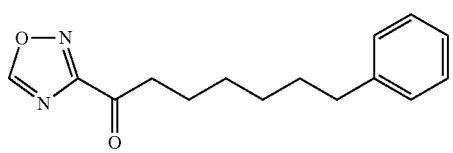 [SMILES: O=C(CCCCCCc1ccccc1)c1ncon1]

The title compound was prepared from S25 (4.3 mg, 0.015 mmol) following general procedure B. Flash chromatography ($SiO_2$, 0.5×6 cm, 10-15% EtOAc-hexanes) afforded the title compound (3.2 mg, 83%) as a colorless oil: $^1H$ NMR ($CDCl_3$, 600 MHz) δ 8.83 (s, 1H), 7.27 (m, 2H), 7.17 (m, 3H), 3.09 (t, 2H, J=7.4 Hz), 2.61 (t, 2H, J=7.7 Hz), 1.78 (m, 2H), 1.63 (m, 2H), 1.41 (m, 4H); $^{13}C$ NMR ($CDCl_3$, 150 MHz) δ 191.0, 165.9, 164.9, 142.8, 128.5, 128.4, 125.8, 41.1, 36.0, 31.4, 29.1, 29.0, 23.5; HRMS-ESI-TOF m/z-([M+H]+, $C_{15}H_{18}N_2O_2$ requires 259.1441)[2].

7-Phenyl-1-(5-(pyridin-2-yl)-1,2,4-oxadiazol-3-yl)-heptan-1-ol (S26)

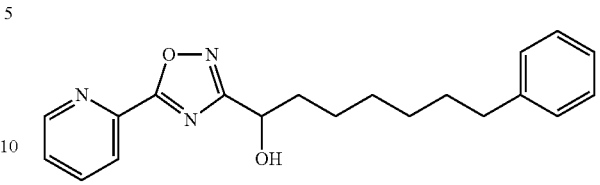

The title compound (deprotected) was prepared from S19 (55 mg, 0.166 mmol) and picolinyl chloride (39 mg, 0.22 mmol) following general procedure F. Flash chromatography ($SiO_2$, 2×15 cm, 0-50% EtOAc-hexanes) afforded the title compound (10.8 mg, 16%) as a white solid: $^1H$ NMR ($CDCl_3$, 600 MHz) δ 8.85 (d, 1H, J=4.7 Hz), 8.23 (dd, 1H, J=0.7, 7.9 Hz), 7.92 (dt, 1H, J=1.5, 7.7 Hz), 7.53 (dd, 1H, J=4.7, 7.6 Hz), 7.26 (dd, 2H, J=5.2, 9.5 Hz), 7.16 (m, 3H), 4.95 (d, 1H, J=5.9 Hz), 2.59 (t, 2H, J=7.7 Hz), 2.55 (d, 1H (—OH), J=5.7 Hz), 1.98 (m, 2H), 1.61 (m, 2H), 1.38 (m, 6H); $^{13}C$ NMR ($CDCl_3$, 150 MHz) δ 174.7, 173.1, 150.9, 143.5, 142.9, 137.5, 128.5, 128.4, 127.0, 125.7, 124.4, 67.0, 36.0, 35.9, 31.5, 29.3 (2C), 25.1; HRMS-ESI-TOF m/z 338.1861 ([M+H]+, $C_{20}H_{23}N_3O_2$ requires 338.1863).

7-Phenyl-1-(5-(pyridin-2-yl)-1,2,4-oxadiazol-3-yl)-heptan-1-one (10b)

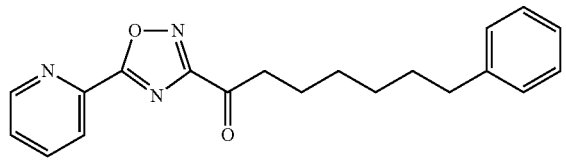 [SMILES: O=C(CCCCCCc1ccccc1)c1noc(-c2ccccn2)n1]

The title compound was prepared from S26 (11 mg, 0.032 mmol) following general procedure B. Flash chromatography ($SiO_2$, 0.5×6 cm, 10-20% EtOAc-hexanes) afforded the title compound (9.9 mg, 92%) as a white solid: $^1H$ NMR ($CDCl_3$, 600 MHz) δ 8.86 (dd, 1H, J=0.7, 5.5 Hz), 8.36 (d, 1H, J=7.9 Hz), 7.95 (dt, 1H, J=1.5, 7.7 Hz), 7.56 (dd, 1H, J=4.8, 7.6 Hz), 7.27 (dd, 2H, J=5.2, 9.9 Hz), 7.17 (m, 3H), 3.15 (t, 2H, J=7.3 Hz), 2.61 (t, 2H, J=7.7 Hz), 1.80 (m, 2H), 1.64 (m, 2H), 1.42 (m, 4H); $^{13}C$ NMR ($CDCl_3$, 150 MHz) δ 191.7, 175.7, 166.3, 150.9, 143.2, 142.8, 137.7, 128.5, 128.4, 127.4, 125.8, 124.9, 41.0, 36.0, 31.4, 29.1, 29.0, 23.5; HRMS-ESI-TOF m/z 336.1714 ([M+H]+, $C_{20}H_{21}N_3O_2$ requires 336.1706).

3-(1-(tert-Butyldimethylsilyloxy)-7-phenylheptyl)-5-(furan-2-yl)-1,2,4-oxadiazole (S27)

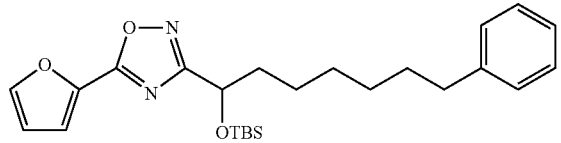 [SMILES: CC(C)(C)[Si](C)(C)OC(CCCCCCc1ccccc1)c1noc(-c2ccco2)n1]

The title compound was prepared from S19 (53 mg, 0.162 mmol) and 2-furoyl chloride (18 μL, 0.178 mmol) following general procedure F. Flash chromatography (SiO$_2$, 1.5×16 cm, 10% EtOAc-hexanes) afforded the title compound (17 mg, 23%) as a colorless oil: $^1$H NMR (CDCl$_3$, 600 MHz) δ 7.68 (m, 1H), 7.33 (dd, 1H, J=0.7, 3.5 Hz), 7.26 (t, 2H, J=7.6 Hz), 7.16 (m, 3H), 6.62 (m, 1H), 4.90 (dd, 1H, J=5.8, 7.4 Hz), 2.58 (t, 2H, J=7.8 Hz), 1.90 (m, 2H), 1.60 (m, 3H), 1.43 (m, 1H), 1.34 (m, 4H), 0.89 (s, 9H), 0.10 (m, 3H), 0.02 (s, 3H); $^{13}$C NMR (CDCl$_3$, 150 MHz) δ 172.7, 167.6, 146.7, 142.9, 140.4, 128.5, 128.4, 125.7, 116.7, 112.6, 67.4, 36.6, 36.1, 31.5, 29.3, 25.9, 25.2, 18.4 (3C), −4.7, −4.9; HRMS-ESI-TOF m/z 441.2571 ([M+H]$^+$, C$_{25}$H$_{36}$N$_2$O$_3$Si requires 441.2568).

1-(5-(Furan-2-yl)-1,2,4-oxadiazol-3-yl)-7-phenyl-heptan-1-ol (S28)

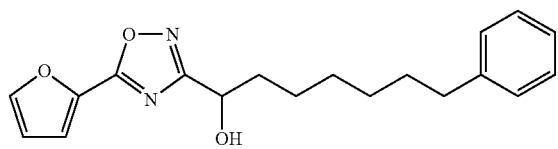

The title compound was prepared from S27 (11 mg, 0.025 mmol) following general procedure G. Flash chromatography (SiO$_2$, 0.5×6 cm, 10-25% EtOAc-hexanes) afforded the title compound (7.7 mg, 94%) as a white solid: $^1$H NMR (CDCl$_3$, 600 MHz) δ 7.69 (m, 1H), 7.34 (d, 1H, J=3.5 Hz), 7.26 (t, 2H, J=7.3 Hz), 7.16 (m, 3H), 6.64 (m, 1H), 4.90 (m, 1H), 2.59 (t, 2H, J=7.7 Hz), 2.43 (d, 1H(—OH), J=6.5 Hz), 1.95 (m, 2H), 1.61 (m, 3H), 1.50 (m, 1H), 1.38 (m, 4H); $^{13}$C NMR (CDCl$_3$, 150 MHz) δ 172.5, 167.9, 147.0, 142.9, 140.1, 128.5, 128.4, 125.7, 117.1, 112.7, 66.9, 36.1, 35.8, 31.5, 29.9, 29.3, 25.1; HRMS-ESI-TOF m/z 327.1705 ([M+H]$^+$, C$_{19}$H$_{22}$N$_2$O$_3$ requires 327.1703).

1-(5-(Furan-2-yl)-1,2,4-oxadiazol-3-yl)-7-phenyl-heptan-1-one (10c)

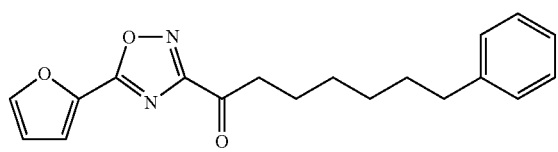 [SMILES: O=C(CCCCCCc1ccccc1)c1noc(-c2ccco2)n1]

The title compound was prepared from S28 (7.7 mg, 0.024 mmol) following general procedure B. Flash chromatography (SiO$_2$, 0.5×6 cm, 10-15% EtOAc-hexanes) afforded the title compound (7.7 mg, 100%) as a white solid: $^1$H NMR (CDCl$_3$, 600 MHz) δ 7.73 (d, 1H, J=1.6 Hz), 7.46 (d, 1H, J=3.5 Hz), 7.27 (m, 2H), 7.17 (m, 3H), 6.66 (dd, 1H, J=1.7, 3.6 Hz), 3.10 (t, 2H, J=7.4 Hz), 2.61 (t, 2H, J=7.7 Hz), 1.79 (m, 2H), 1.64 (m, 2H), 1.41 (m, 4H); $^{13}$C NMR (CDCl$_3$, 150 MHz) δ 191.5, 168.8, 165.9, 147.6, 142.8, 139.6, 128.5, 128.4, 125.8, 118.1, 112.9, 41.0, 36.0, 31.4, 29.1, 29.0, 23.6; HRMS-ESI-TOF m/z 325.1545 ([M+H]$^+$, C$_{19}$H$_{20}$N$_2$O$_3$ requires 325.1547).

3-(1-(tert-Butyldimethylsilyloxy)-7-phenylheptyl)-5-(thiophen-2-yl)-1,2,4-oxadiazole (S29)

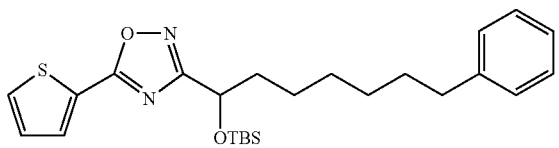

The title compound was prepared from S19 (50 mg, 0.15 mmol) and 2-thiophenecarbonyl chloride (19 μL, 0.54 mmol) following general procedure F. Flash chromatography (SiO$_2$, 2×15 cm, 5% EtOAc-hexanes) afforded the title compound (11.5 mg, 39%) as a colorless oil: $^1$H NMR (CDCl$_3$, 400 MHz) δ 7.91 (dd, 1H, J=1.2, 3.8 Hz), 7.63 (dd, 1H, J=1.2, 5.0 Hz), 7.26 (m 2H), 7.19 (dd, 1H, J=3.8, 5.0 Hz), 7.16 (m, 3H), 4.89 (dd, 1H, J=5.8, 7.5 Hz), 2.59 (t, 2H, J=7.7 Hz), 1.89 (m, 2H), 1.61 (m, 2H), 1.35 (m, 6H), 0.90 (s, 9H), 0.10 (s, 3H), 0.04 (s, 3H); $^{13}$C NMR (CDCl$_3$, 150 MHz) δ 173.0, 171.4, 142.9, 132.0, 128.6, 128.5, 128.4 (2C), 126.1, 125.7, 67.5, 36.6, 36.1, 31.5, 29.3, 25.9, 25.2, 18.4 (3C), −4.7, −4.9; HRMS-ESI-TOF m/z 457.2336 ([M+H]$^+$, C$_{25}$H$_{36}$N$_2$O$_2$SSi requires 457.2339).

7-Phenyl-1-(5-(thiophen-2-yl)-1,2,4-oxadiazol-3-yl)-heptan-1-ol (S30)

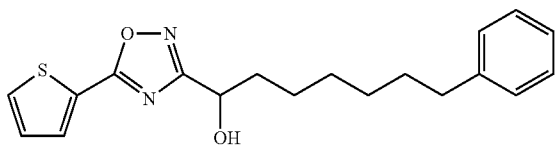 [SMILES: OC(CCCCCCc1ccccc1)c1noc(-c2cccs2)n1]

The title compound was prepared from S29 (9 mg, 0.02 mmol) following general procedure G. Flash chromatography (SiO$_2$, 0.5×6 cm, 10-20% EtOAc-hexanes) afforded the title compound (5.8 mg, 89%) as a white solid: $^1$H NMR (CDCl$_3$, 600 MHz) δ 7.91 (dd, 1H, J=1.2, 3.8 Hz), 7.65 (dd, 1H, J=1.1, 5.0 Hz), 7.26 (t, 2H, J=7.6 Hz), 7.20 (dd, 1H, J=3.9, 4.9 Hz), 7.17 (m, 3H), 4.89 (m, 1H), 2.59 (t, 2H, J=7.7 Hz), 2.34 (d, 1H(—OH), J=6.1 Hz), 1.94 (m, 2H), 1.61 (m, 2H), 1.39 (m, 6H); $^{13}$C NMR (CDCl$_3$, 150 MHz) δ 172.7, 171.7, 142.9, 132.3 (2C), 128.7, 128.5 (2C), 128.4, 125.7, 67.0, 36.1, 35.9, 31.5, 29.9, 29.3, 25.1; HRMS-ESI-TOF m/z 343.1475 ([M+H]$^+$, C$_{19}$H$_{22}$N$_2$O$_2$S requires 343.1475).

7-Phenyl-1-(5-(thiophen-2-yl)-1,2,4-oxadiazol-3-yl)-heptan-1-one (10d)

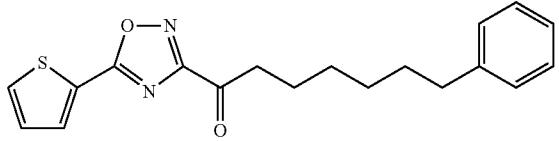

The title compound was prepared from S30 (11 mg, 0.033 mmol) following general procedure B. Flash chromatography (SiO$_2$, 0.5×6 cm, 10% EtOAc-hexanes) afforded the title compound (10.3 mg, 92%) as a white solid: $^1$H NMR (CDCl$_3$, 600 MHz) δ 8.01 (d, 1H, J=3.8 Hz), 7.71 (d, 1H, J=4.9 Hz), 7.27 (m, 2H), 7.17 (m, 1H), 7.23 (m, 3H), 3.09 (t, 2H, J=7.4 Hz), 2.61 (t, 2H, J=7.7 Hz), 1.79 (m, 2H), 1.64 (m, 2H), 1.41 (m, 4H); $^{13}$C NMR (CDCl$_3$, 150 MHz) δ 191.8, 172.9, 166.1, 142.8, 133.3, 133.2, 128.8, 128.5, 128.4, 125.8, 124.9, 40.9, 36.0, 31.4, 29.9, 29.0, 23.6; HRMS-ESI-TOF m/z 341.1315 ([M+H]$^+$, C$_{19}$H$_{20}$N$_2$O$_2$S requires 341.1318).

Methyl 6-(3-(1-(tert-Butyldimethylsilyloxy)-7-phenylheptyl)-1,2,4-oxadiazol-5-yl)-picolinate (S31)

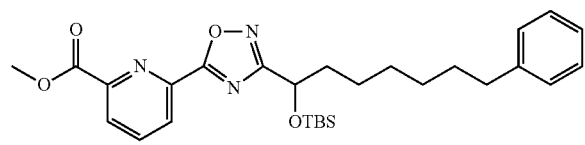 [SMILES: COC(=O)c1cccc(-c2nc(C(CCCCCCc3ccccc3)O[Si](C)(C)C(C)(C)C)no2)n1]

The title compound was prepared from S19 (55 mg, 0.166 mmol) and methyl 6-(chlorocarbonyl)picolinate$^3$ (see Hull et al., *Tetrahedron* 1997, 53, 12405-12414) (37 mg, 0.183 mmol) following general procedure F. Flash chromatography (SiO$_2$, 2×12 cm, 0-50% EtOAc-hexanes) afforded the title compound (10 mg, 12%) as a colorless oil: $^1$H NMR (CDCl$_3$, 500 MHz) δ 8.43 (dd, 1H, J=1.0, 7.9 Hz), 8.33 (dd, 1H, J=1.0, 7.9 Hz), 8.07 (t, 1H, J=7.9 Hz), 7.26 (t, 2H, J=7.5 Hz), 7.16 (m, 3H), 4.97 (dd, 1H, J=5.8, 7.5 Hz), 4.06 (s, 3H), 2.59 (t, 2H, J=7.7 Hz), 1.92 (m, 2H), 1.59 (m, 2H), 1.35 (m, 6H), 0.89 (s, 9H), 0.11 (s, 3H), 0.03 (s, 3H); $^{13}$C NMR (CDCl$_3$, 150 MHz) δ 173.6, 173.3, 165.0, 149.1, 144.1, 142.9, 138.8, 128.5, 128.4, 127.8, 127.3, 125.7, 67.5, 53.4, 36.6, 36.0, 31.5, 29.3, 25.9, 25.2, 18.4 (3C), −4.7, −4.9; HRMS-ESI-TOF m/z 510.2787 ([M+H]$^+$, C$_{28}$H$_{39}$N$_3$O$_4$Si requires 510.2782).

Methyl 6-(3-(1-Hydroxy-7-phenylheptyl)-1,2,4-oxadiazol-5-yl)-picolinate (S32)

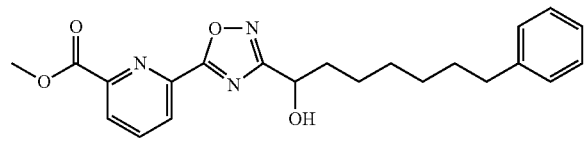 [SMILES: COC(=O)c1cccc(-c2nc(C(O)CCCCCCc3ccccc3)no2)n1]

The title compound was prepared from S31 (10 mg, 0.020 mmol) following general procedure G. Flash chromatography (SiO$_2$, 0.5×6 cm, 10-50% EtOAc-hexanes) afforded the title compound (6.6 mg, 85%) as a white solid: $^1$H NMR (CDCl$_3$, 600 MHz) δ 8.40 (dd, 1H, J=0.7, 7.8 Hz), 8.35 (d, 1H, J=7.8 Hz), 8.09 (t, 1H, J=7.9 Hz), 7.26 (m, 2H), 7.16 (m, 3H), 4.97 (t, 1H, J=6.0 Hz), 4.06 (s, 3H), 2.59 (t, 2H, J=7.7 Hz), 2.45 (br s, 1H), 1.98 (m, 2H), 1.61 (m, 2H), 1.39 (m, 6H); $^{13}$C NMR (CDCl$_3$, 150 MHz) δ 174.0, 173.3, 165.1, 149.3, 143.8, 143.0, 139.0, 128.6, 128.5, 128.1, 127.4, 125.8, 67.1, 53.6, 36.1, 35.9, 31.6, 29.4 (2C), 25.2; HRMS-ESI-TOF m/z 396.1924 ([M+H]$^+$, C$_{22}$H$_{25}$N$_3$O$_4$ requires 396.1918).

Methyl 6-(3-(7-Phenylheptanoyl)-1,2,4-oxadiazol-5-yl)-picolinate (10f)

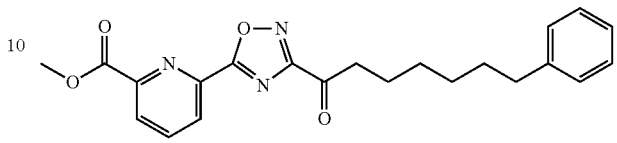

The title compound was prepared from S32 (6.6 mg, 0.017 mmol) following general procedure B. Flash chromatography (SiO$_2$, 0.5×6 cm, 10-30% EtOAc-hexanes) afforded the title compound (5.8 mg, 86%) as a white solid: $^1$H NMR (CDCl$_3$, 400 MHz) δ 8.52 (dd, 1H, J=0.8, 7.9 Hz), 8:3-7 (dd, 1H, J=0.8, 7.9 Hz), 8.12 (t, 1H, J=7.9 Hz), 7.27 (m, 2H), 7.17 (m, 3H), 4.07 (s, 3H), 3.15 (t, 2H, J=7.4 Hz), 2.61 (t, 2H, J=7.7 Hz), 1.80 (m, 2H), 1.64 (m, 2H), 1.42 (m, 4H); $^{13}$C NMR (CDCl$_3$, 125 MHz) δ 191.6, 174.9, 166.3, 164.8, 149.2, 143.3, 142.8, 139.0, 128.5, 128.4 (2C), 127.7, 125.8, 53.5, 41.0, 36.0, 31.4, 29.1, 29.0, 23.5; HRMS-ESI-TOF m/z 394.1758 ([M+H]$^+$, C$_{22}$H$_{23}$N$_3$O$_4$ requires 394.1761).

6-(3-(7-Phenylheptanoyl)-1,2,4-oxadiazol-5-yl)-picolinic Acid (10g)

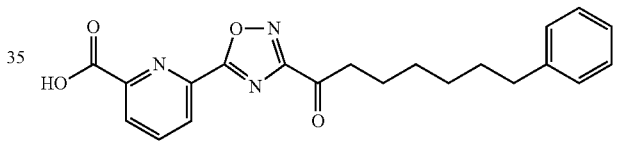

The title compound was prepared from 10f (5.2 mg, 0.008 mmol) following general procedure A. Flash chromatography (SiO$_2$, 0.5×6 cm, 0-2% AcOH-EtOAc) afforded the title compound (3 mg, 99%) as a white solid: NMR (acetone-d$_6$+0.1% TFA, 500 MHz) δ 8.58 (dd, 1H, J=1.0, 7.7 Hz), 8.44 (dd, 1H, J=1.1, 7.8 Hz), 8.38 (t, 1H, J=7.7 Hz), 7.25 (t, 2H, J=7.5 Hz), 7.20 (d, 2H, J=6.9 Hz), 7.14 (t, 1H, J=7.2 Hz), 3.18 (t, 2H, J=7.3 Hz), 2.63 (t, 2H, J=7.7 Hz), 1.78 (m, 2H), 1.65 (m, 2H), 1.44 (m, 4H); $^{13}$C NMR (acetone-d$_6$+0.1% TFA, 150 MHz) δ 192.7, 176.7, 168.3, 166.2, 150.7, 144.7, 144.6, 141.8, 130.2, 130.1, 129.7, 129.6, 127.4, 42.4, 37.5, 33.2, 31.3, 30.5, 24.9; HRMS-ESI-TOF m/z 380.1601 ([M+H]$^+$, C$_{21}$H$_{21}$N$_3$O$_4$ requires 380.1605).

Methyl 3-(1-(tert-Butyldimethylsilyloxy)-7-phenylheptyl)-1,2,4-oxadiazole-5-carboxylate (S33)

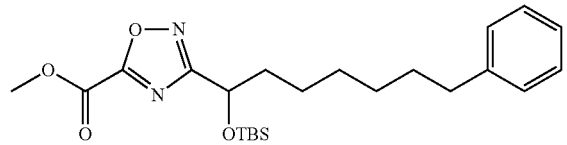 [SMILES: COC(=O)c1nc(C(CCCCCCc2ccccc2)O[Si](C)(C)C(C)(C)C)no1]

The title compound was prepared from S19 (100 mg, 0.302 mmol) and methyl oxalyl chloride (42 μL, 0.45 mmol) following general procedure F. Flash chromatography (SiO₂, 2×22 cm, 0-5% EtOAc-hexanes) afforded the title compound (50 mg, 38%) as a colorless oil: ¹H NMR (CDCl₃, 500 MHz) δ 7.26 (m, 2H), 7.17 (m, 3H), 4.94 (dd, 1H, J=5.8, 7.3 Hz), 4.07 (s, 3H), 2.59 (t, 2H, J=7.7 Hz), 1.87 (m, 2H), 1.60 (m, 2H), 1.33 (m, 6H), 0.88 (s, 9H), 0.09 (s, 3H), -0.003 (s, 3H); ¹³C NMR (CDCl₃, 125 MHz) δ 173.6, 166.4, 154.7, 142.9, 128.5, 128.4, 125.7, 67.4, 54.2, 36.4, 36.0, 31.5, 29.2, 25.8, 25.0, 18.3 (3C), -4.8, -4.9; HRMS-ESI-TOF m/z 433.2509 ([M+H]⁺, C₂₃H₃₆N₂O₄Si requires 433.2517).

Methyl 3-(1-Hydroxy-7-phenylheptyl)-1,2,4-oxadiazole-5-carboxylate (S34)

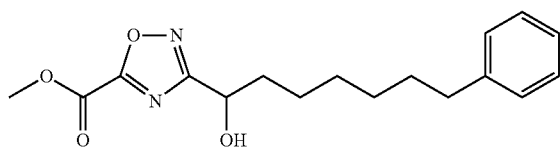 [SMILES: COC(=O)c1nc(C(O)CCCCCCc2ccccc2)no1]

A solution of S33 (15 mg, 0.035 mmol) was dissolved in THF (350 μL) in a plastic centrifuge tube and pyridine (140 μL) was added at 0° C. The solution was treated with HF-pyridine (35 μL) and allowed to warm to 25° C. and shaken for 24 h. The progress was monitored by TLC (SiO₂, 50% EtOAc-hexanes) and upon completion, a 1:1 solution of EtOAc: saturated aqueous NaHCO₃ (1 mL) was added. The reaction mixture was diluted with EtOAc and the aqueous layer was washed with EtOAc (3×). The combined organic phases were washed with saturated aqueous NaCl and dried over Na₂SO₄. Evaporation in vacuo yielded the alcohol (11 mg, 100%) as a colorless oil that required no further purification: ¹H NMR (CDCl₃, 600 MHz) δ 7.27 (m, 2H), 7.17 (m, 3H), 4.94 (dd, 1H, J=6.7, 13.5 Hz), 4.08 (s, 3H), 2.59 (t, 2H, J=7.7 Hz), 2.28 (d, 1H (—OH), J=6.9 Hz), 1.93 (m, 2H), 1.61 (m, 2H), 1.47 (m, 2H), 1.37 (m, 4H); ¹³C NMR (CDCl₃, 150 MHz) δ 173.4, 166.6, 154.5, 142.8, 128.5, 128.4, 125.8, 66.9, 54.4, 36.0, 35.7, 31.5, 29.9, 29.2, 25.0; HRMS-ESI-TOF m/z 319.1645 ([M+H]⁺, C₁₇H₂₂N₂O₄ requires 319.1652).

Methyl 3-(7-Phenylheptanoyl)-1,2,4-oxadiazole-5-carboxylate (10h)

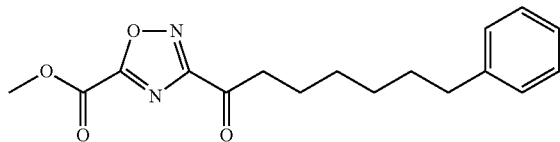 [SMILES: COC(=O)c1nc(C(=O)CCCCCCc2ccccc2)no1]

The title compound was prepared from S34 (13 mg, 0.041 mmol) following general procedure B. Flash chromatography (SiO₂, 0.5×6 cm, 10-25% EtOAc-hexanes) afforded the title compound (9 mg, 69%) as a colorless oil: ¹H NMR (CDCl₃, 600 MHz) δ 7.27 (m, 2H), 7.17 (m, 3H), 4.10 (s, 3H), 3.10 (t, 2H, J=7.3 Hz), 2.60 (t, 2H, J=7.7 Hz), 1.78 (m, 2H), 1.63 (m, 2H), 1.40 (m, 4H); ¹³C NMR (CDCl₃, 150 MHz) δ 190.3, 167.5, 166.1, 154.1, 142.7, 128.5, 128.4, 125.8, 54.5, 41.1, 36.0, 31.3, 29.0, 28.9, 23.3; HRMS-ESI-TOF m/z 317.1496 ([M+H]⁺, C₁₇H₂₀N₂O₄ requires 317.1496).

Thiazoles (11a-11g):

7-Phenyl-1-(thiazol-2-yl)-heptan-1-ol (S35)

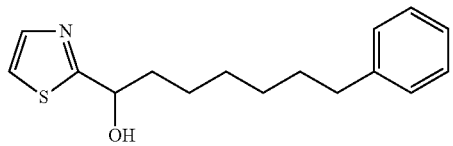 [SMILES: OC(CCCCCCc1ccccc1)c1nccs1]

Thiazole (21 μL, 0.29 mmol) in anhydrous THF (1.9 mL) was cooled to -78° C. and treated dropwise with 1.4 M t-BuLi (273 μL, 0.38 mmol). The reaction mixture was stirred at -78° C. for 0.5 h before a solution of 7-phenylheptanal (73 mg, 0.38 mmol) in THF (1.3 mL) was added. The reaction mixture was stirred at -78° C. for 0.5 h before being warmed to room temperature. The reaction mixture was diluted with EtOAc, and washed with H₂O, saturated aqueous NaHCO₃ and saturated aqueous NaCl before the organic layer was dried over Na₂SO₄ and the solvent was removed under reduced pressure. Flash chromatography (SiO₂, 1.5×6.5 cm, 15-25% EtOAc-hexanes) afforded the title compound (50 mg, 62%) as a colorless oil: ¹H NMR (CDCl₃, 400 MHz) δ 7.68 (d, 1H, J=3.2 Hz), 7.24 (m, 3H), 7.14 (m, 3H), 4.96 (dd, 1H, J=4.8, 7.6 Hz), 3.09 (br s, 1H), 2.56 (t, 2H, J=7.8 Hz), 1.87 (m, 2H), 1.58 (m, 2H), 1.44 (m, 6H).

2-(1-(tert-Butyldimethylsilyloxy)-7-phenylheptyl)-thiazole (S36)

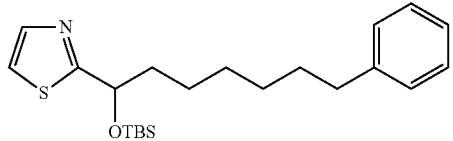 [SMILES: CC(C)(C)[Si](C)(C)OC(CCCCCCc1ccccc1)c1nccs1]

A solution of S35 (177 mg, 0.64 mmol), TBSCl (150 mg, 0.98 mmol) and imidazole (67 mg, 0.98 mmol) in DMF (4.3 mL) was stirred at room temperature for 72 h before it was diluted with EtOAc, and washed with H₂O and saturated aqueous NaCl. The organic phase was dried over Na₂SO₄ and the solvent was removed under reduced pressure to afford a colorless oil that was used without further purification (235 mg, 94%): ¹H NMR (CDCl₃, 500 MHz) δ 7.69 (d, 1H, J=3.3 Hz), 7.26 (m, 2H), 7.23 (d, 1H, J=3.3 Hz), 7.17 (m, 3H), 5.04 (dd, 1H, J=5.0, 6.3 Hz), 2.58 (t, 2H, J=7.8 Hz), 1.84 (m, 2H), 1.58 (m, 2H), 1.35 (m, 6H), 0.94 (s, 9H), 0.10 (s, 3H), 0.00 (s, 3H).

2-(1-(tert-Butyldimethylsilyloxy)-7-phenylheptyl)-5-(tributylstannyl)-thiazole (S37)

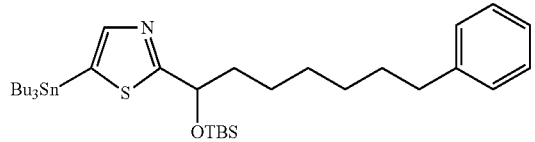

A solution of S36 (47 mg, 0.12 mmol) in THF (1.2 mL) was cooled to -78° C. before it was treated dropwise with 1.6 M t-BuLi (102 μL, 0.16 mmol). The reaction mixture was stirred at −40° C. for 2 h, cooled to −78° C. and treated with a solution of Bu₃SnCl (66 μL, 0.24 mmol) (or I₂) in THF (0.3 mL). After 15 min, the solution was diluted with EtOAc and washed with saturated aqueous NaCl. The organic layer was dried over Na₂SO₄ and the solvent was removed under reduced pressure. Flash chromatography (SiO₂, 1.5×10 cm, 5% EtOAc-hexanes) yielded the title compound (70 mg, 85%) as a thick colorless oil: ¹H NMR (CDCl₃, 500 MHz) δ 7.61 (s, 1H), 7.26 (m, 2H), 7.16 (m, 3H), 5.08 (dd, 1H, J=5.0, 6.6 Hz), 2.58 (t, 2H, J=7.8 Hz), 1.55 (m, 2H), 1.85 (m, 8H), 1.34 (m, 12H), 1.12 (m, 6H), 0.93 (s, 9H), 0.89 (m, 9H), 0.09 (s, 3H), −0.01 (s, 3H).

General Procedure H.

2-(1-(tert-Butyldimethylsilyloxy)-7-phenylheptyl)-5-(tributyl stannyl)-thiazole (S37, 1 equiv), (Ph₃P)₄Pd (0.1 equiv), and aryl halide (1.5 equiv) (or aryl stannane) were dissolved in anhydrous 1,4-dioxane (0.04 M) and the mixture was warmed at reflux for 16 h under Ar. The solution was cooled to room temperature, diluted with EtOAc, washed with saturated aqueous NaCl and dried over Na₂SO₄. Evaporation in vacuo yielded the crude product that was purified by flash chromatography (SiO₂). The TBS ether (1 equiv) was dissolved in THF (0.08 M), treated with Bu₄NF (1 M in THF, 1.3 equiv) and stirred at room temperature for 2 h under Ar. The reaction mixture was diluted with EtOAc, washed with saturated aqueous NaCl and dried over Na₂SO₄. Evaporation in vacuo yielded the crude alcohol that was purified by flash chromatography (SiO₂).

7-Phenyl-1-(thiazol-2-yl)-heptan-1-one (11a)

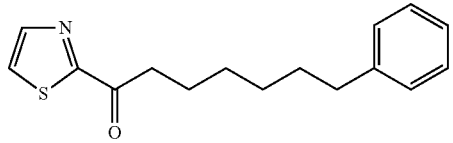 [SMILES: O=C(CCCCCCc1ccccc1)c1nccs1]

The title compound was prepared from 7-phenyl-1-(thiazol-2-yl)-heptan-1-ol (S35, 16 mg, 0.060 mmol) following general procedure B. Flash chromatography (SiO₂, 0.5×6 cm, 4% EtOAc-hexanes) afforded the title compound (14 mg, 84%) as a clear oil: ¹H NMR (CDCl₃, 600 MHz) δ 7.99 (d, 1H, J=3.0 Hz), 7.65 (d, 1H, J=2.9 Hz), 7.26 (dd, 2H, J=5.1, 9.9 Hz), 7.16 (m, 3H), 3.14 (t, 2H, J=7.5 Hz), 2.60 (t, 2H, J=7.8 Hz), 1.76 (m, 2H), 1.63 (m, 2H), 1.41 (m, 4H); ¹³C NMR (CDCl₃, 150 MHz) δ 194.2, 167.5, 144.8, 142.8, 128.5, 128.4, 126.2, 125.7, 38.6, 36.0, 31.4, 29.22, 29.17, 24.1; HRMS-ESI-TOF m/z 274.1252 ([M+H]⁺, C₁₆H₁₉NOS requires 274.1260).

7-Phenyl-1-(5-(pyridin-2-yl)-thiazol-2-yl)-heptan-1-ol (S38)

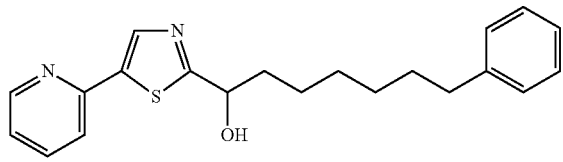 [SMILES: OC(CCCCCCc1ccccc1)c1ncc(-c2ccccn2)s1]

The title compound was prepared from S37 (32 mg, 0.047 mmol) and 2-iodopyridine (7.6 μL, 0.071 mmol) following general procedure H. Flash chromatography (SiO₂, 0.5×6 cm, 30% EtOAc-hexanes) afforded the title compound (11.5 mg, 39%) as a white solid: ¹H NMR (CDCl₃, 400 MHz) δ 8.58 (d, 1H, J=4.9 Hz), 8.12 (s, 1H), 7.71 (dt, 1H, J=1.7, 7.6 Hz), 7.64 (d, 1H, J=7.9 Hz), 7.26 (dd, 2H, J=4.8, 10.2 Hz), 7.20 (m, 1H), 7.16 (m, 3H), 4.99 (dd, 1H, J=3.8, 6.9 Hz), 3.09 (d, 1H(—OH), J=3.5 Hz), 2.59 (t, 2H, J=7.7 Hz), 1.99-1.87 (m, 2H), 1.64-1.59 (m, 4H), 1.48-1.35 (m, 4H); ¹³C NMR (CDCl₃, 150 MHz) δ 176.8, 150.8, 150.0, 142.9, 140.3, 139.1, 136.9, 128.5, 128.4, 125.7, 122.7, 119.7, 72.2, 38.3, 36.1, 31.5, 29.4, 29.3, 25.1; HRMS-ESI-TOF m/z 353.1677 ([M+H]⁺, C₂₁H₂₄N₂OS requires 353.1682).

7-Phenyl-1-(5-(pyridin-2-yl)-thiazol-2-yl)-heptan-1-one (11b)

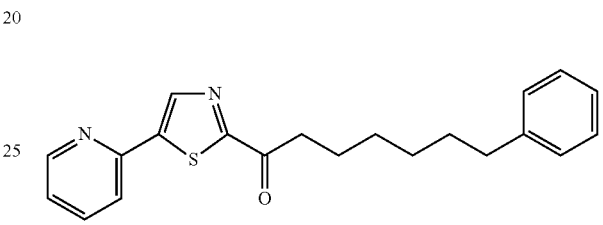

The title compound was prepared from S38 (11 mg, 0.031 mmol) following general procedure B. Flash chromatography (SiO₂, 0.5×6 cm, 20% EtOAc-hexanes) afforded the title compound (9.2 mg, 85%) as a white solid: ¹H NMR (CDCl₃, 600 MHz) δ 8.64 (d, 1H, J=4.6 Hz), 8.38 (s, 1H), 7.76 (dt, 1H, J=1.5, 7.7 Hz), 7.72 (m, 1H), 7.26 (m, 3H), 7.16 (t, 3H, J=7.6 Hz), 3.14 (t, 2H, J=7.4 Hz), 2.60 (t, 2H, J=7.7 Hz), 1.77 (m, 2H), 1.63 (m, 2H), 1.42 (m, 4H); ¹³C NMR (CDCl₃, 150 MHz) δ 194.5, 167.5, 150.4, 149.9, 147.0, 142.9, 141.3, 137.1, 128.5, 128.4, 125.7, 123.8, 120.6, 38.3, 36.0, 31.5, 29.24, 29.20, 24.1; HRMS-ESI-TOF m/z 351.1531 ([M+H]⁺, C₂₁H₂₂N₂OS requires 351.1526).

1-(5-(Furan-2-yl)-thiazol-2-yl)-7-phenylheptan-1-ol (S39)

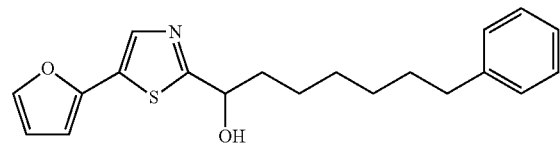

The title compound was prepared from S37-iodo (48 mg, 0.093 mmol) and 2-(tributylstannyl)furan (44 μL, 0.14 mmol) following general procedure H. Flash chromatography (SiO₂, 1×7 cm, 30% EtOAc-hexanes) afforded the title compound (13 mg, 41%) as a white solid: ¹H NMR (CDCl₃, 600 MHz) δ 7.82 (s, 1H), 7.44 (d, 1H, J=0.8 Hz), 7.26 (m, 2H), 7.16 (m, 3H), 6.52 (d, 1H, J=3.4 Hz), 6.46 (m, 1H), 4.96 (br s, 1H), 2.92 (br s, 1H), 2.59 (t, 2H, J=7.7 Hz), 1.96 (m, 1H), 1.86 (m, 1H), 1.61 (m, 2H), 1.47 (m, 2H), 1.36 (m, 4H); ¹³C NMR (CDCl₃, 150 MHz) δ 173.8, 146.5, 142.9, 142.7, 137.4, 129.0, 128.5, 128.4, 125.7, 111.9, 107.3, 72.1, 38.3, 36.1, 31.5, 29.4, 29.3, 25.1; HRMS-ESI-TOF m/z 342.1524 ([M+H]$^+$, C$_{20}$H$_{23}$NO$_2$S requires 342.1522).

1-(5-(Furan-2-yl)-thiazol-2-yl)-7-phenylheptan-1-one (11c)

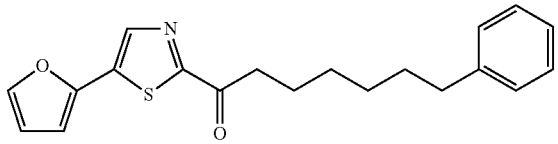

The title compound was prepared from S39 (13 mg, 0.038 mmol) following general procedure B. Flash chromatography (SiO$_2$, 1×9 cm, 4% EtOAc-hexanes) afforded the title compound (12 mg, 95%) as a white solid: $^1$H NMR (CDCl$_3$, 600 MHz) δ 8.08 (s, 1H), 7.52 (d, 1H, J=1.7 Hz), 7.27 (dd, 2H, J=5.5, 9.7 Hz), 7.16 (m, 3H), 6.73 (d, 1H, J=3.4 Hz), 6.52 (dd, 1H, J=1.8, 3.4 Hz), 3.12 (t, 2H, J=7.5 Hz), 2.61 (t, 2H, J=7.7 Hz), 1.77 (m, 2H), 1.64 (m, 2H), 1.42 (m, 4H); $^{13}$C NMR (CDCl$_3$, 150 MHz) δ 194.2, 164.7, 146.0, 143.9, 142.9, 139.5, 135.9, 128.5, 128.4, 125.7, 112.4, 109.8, 38.3, 36.0, 31.4, 29.24, 29.21, 24.3; HRMS-ESI-TOF m/z 340.1372 ([M+H]$^+$, C$_{20}$H$_{21}$NO$_2$S requires 340.1366).

7-Phenyl-1-(5-(thiophen-2-yl)-thiazol-2-yl)-heptan-1-ol (S40)

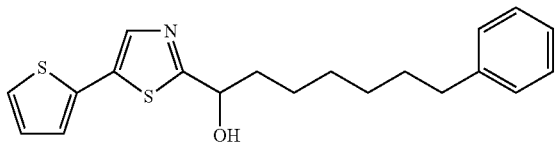 [SMILES: OC(CCCCCCc1ccccc1)c1ncc(-c2ccco2)s1]

The title compound was prepared from S37-iodo (33 mg, 0.064 mmol) and 2-(tributylstannyl)thiophene (30 μL, 0.096 mmol) following general procedure H. Flash chromatography (SiO$_2$, 0.5×6 cm, 20% EtOAc-hexanes) afforded the title compound (10 mg, 45%) as a white solid: $^1$H NMR (CDCl$_3$, 600 MHz) δ 7.74 (s, 1H), 7.28 (dd, 1H, J=1.2, 3.9 Hz), 7.26 (t, 2H, J=3.8 Hz), 7.17 (m, 3H), 7.16 (m, 1H), 7.04 (dd, 1H, J=3.7, 5.0 Hz), 4.95 (m, 1H), 2.86 (d, 1H(—OH), J=3.0 Hz), 2.59 (t, 2H, J=7.7 Hz), 1.97 (m, 1H), 1.87 (m, 1H), 1.62 (m, 2H), 1.48 (m, 2H), 1.37 (m, 4H); $^{13}$C NMR (CDCl$_3$, 150 MHz) δ 173.9, 142.9, 138.0, 133.3, 132.7, 128.5, 128.4, 128.1, 125.8, 125.7, 125.6, 72.2, 38.3, 36.1, 31.5, 29.4, 29.3, 25.2; HRMS-ESI-TOF m/z 358.1304 ([M+H]$^+$, C$_{20}$H$_{23}$NOS$_2$ requires 358.1294).

7-Phenyl-1-(5-(thiophen-2-yl)-thiazol-2-yl)-heptan-1-one (11d)

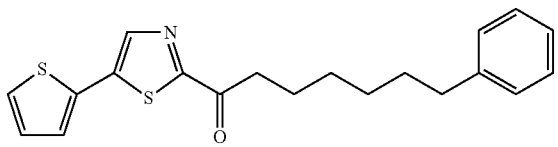 [SMILES: O=C(CCCCCCc1ccccc1)c1ncc(-c2ccco2)s1]

The title compound was prepared from S40 (10 mg, 0.028 mmol) following general procedure B. Flash chromatography (SiO$_2$, 1×8 cm, 4% EtOAc-hexanes) afforded the title compound (8.8 mg, 87%) as a white solid: $^1$H NMR (CDCl$_3$, 500 MHz) δ 8.00 (s, 1H), 7.39 (dd, 1H, J=1.1, 5.1 Hz), 7.33 (dd, 1H, J=1.1, 3.6 Hz), 7.27 (m, 2H), 7.17 (m, 3H), 7.09 (dd, 1H, J=3.7, 5.1 Hz), 3.12 (t, 2H, J=7.4 Hz), 2.61 (t, 2H, J=7.7 Hz), 1.77 (m, 2H), 1.64 (m, 2H), 1.42 (m, 4H); $^{13}$C NMR (CDCl$_3$, 125 MHz) δ 194.2, 164.9, 142.9, 140.2, 140.1, 132.6, 128.5 (2C), 128.4, 127.4 (2C), 125.7, 38.3, 36.0, 31.5, 29.25, 29.19, 24.3; HRMS-ESI-TOF m/z 356.1154 ([M+H]$^+$, C$_{20}$H$_{21}$NOS$_2$ requires 356.1137).

Methyl 6-(2-(1-Hydroxy-7-phenylheptyl)-thiazol-5-yl)-picolinate (S41)

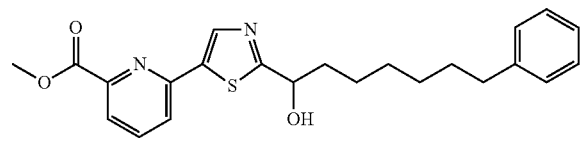 [SMILES: COC(=O)c1cccc(-c2cnc(C(O)CCCCCCc3ccccc3)s2)n1]

The title compound was prepared from S37 (23 mg, 0.034 mmol) and methyl 6-bromopicolinate (11 mg, 0.051 mmol) following general procedure H. Flash chromatography (SiO$_2$, 0.5×6 cm, 30% EtOAc-hexanes) afforded the title compound (7.5 mg, 59%) as a white solid: $^1$H NMR (CDCl$_3$, 600 MHz) δ 8.19 (s, 1H), 8.01 (d, 1H, J=7.6 Hz), 7.86 (t, 1H, J=7.8 Hz), 7.79 (d, 1H, J=7.9 Hz), 7.26 (t, 2H, J=7.5 Hz), 7.16 (m, 3H), 5.00 (dd, 1H, J=4.9, 7.3 Hz), 4.01 (s, 3H), 2.95 (br s, 1H), 2.59 (t, 2H, J=7.7 Hz), 1.99 (m, 1H), 1.88 (m, 1H), 1.61 (m, 2H), 1.47 (m, 2H), 1.37 (m, 4H); $^{13}$C NMR (CDCl$_3$, 150 MHz) δ 177.6, 165.5, 151.1, 148.4, 142.9, 140.1, 139.4, 138.0, 128.5, 128.4, 125.7, 123.9, 122.9, 72.3, 53.1, 38.3, 36.1, 31.5, 29.4, 29.3, 25.1; HRMS-ESI-TOF m/z 411.1737 ([M+H]$^+$, C$_{17}$H$_{20}$N$_2$O$_4$ requires 411.1737).

Methyl 6-(2-(7-Phenylheptanoyl)-thiazol-5-yl)-picolinate (11f)

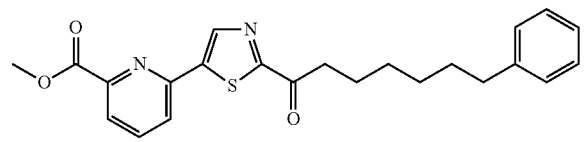 [SMILES: COC(=O)c1cccc(-c2cnc(C(=O)CCCCCCc3ccccc3)s2)n1]

The title compound was prepared from S41 (8 mg, 0.02 mmol) following general procedure B. Flash chromatography (SiO$_2$, 0.5×6 cm, 20% EtOAc-hexanes) afforded the title compound (8.0 mg, 100%) as a white solid: $^1$H NMR (CDCl$_3$, 600 MHz) δ 8.45 (s, 1H), 8.09 (d, 1H, J=7.6 Hz), 7.93 (t, 1H, J=7.8 Hz), 7.87 (d, 1H, J=7.8 Hz), 7.27 (dd, 2H, J=5.5, 9.7 Hz), 7.17 (m, 3H), 4.03 (s, 3H), 3.15 (t, 2H, J=7.4 Hz), 2.61 (t, 2H, J=7.7 Hz), 1.78 (m, 2H), 1.64 (m, 2H), 1.42 (m, 4H); $^{13}$C NMR (CDCl$_3$, 150 MHz) δ 194.4, 168.1, 165.3, 150.1, 148.8, 145.8, 142.9, 142.2, 138.3, 128.5, 128.4, 125.7, 124.9, 123.7, 53.2, 38.4, 36.0, 31.4, 29.22, 29.19, 24.1; HRMS-ESI-TOF m/z 409.1585 ([M+H]$^+$, $C_{22}H_{24}N_2O_3S$ requires 409.1580).

6-(2-(7-Phenylheptanoyl)thiazol-5-yl)-picolinic Acid (11g)

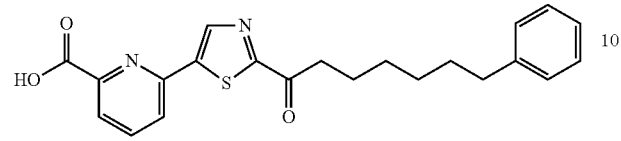

The title compound was prepared from 11f (6.8 mg, 0.016 mmol) following general procedure A. Flash chromatography (SiO$_2$, 0.5×6 cm, 0-2% AcOH-EtOAc) afforded the title compound (5.4 mg, 86%) as a white solid: $^1$H NMR (CDCl$_3$, 400 MHz) δ 10.51 (s, 1H(—OH)), 8.46 (s, 1H), 8.23 (dd, 1H, J=0.9, 7.6 Hz), 8.07 (t, 1H, J=7.8 Hz), 8.00 (dd, 1H, J=0.9, 7.9 Hz), 7.27 (m, 2H), 7.17 (m, 3H), 3.16 (t, 2H, J=7.4 Hz), 2.61 (t, 2H, J=7.7 Hz), 1.79 (m, 2H), 1.65 (m, 2H), 1.42 (m, 4H); $^{13}$C NMR (CDCl$_3$, 150 MHz) δ 194.3, 175.8, 168.6, 149.0, 146.7, 144.1, 142.8, 142.6, 139.9, 128.5, 128.4, 125.8, 124.7, 123.8, 38.4, 36.0, 31.4, 29.23, 29.17, 24.1; HRMS-ESI-TOF m/z 395.1436 ([M+H]$^+$, $C_{22}H_{22}N_2O_3S$ requires 395.1424). 1,3,4-Thiadiazoles (5a-5c, 12a-12, 25):

Methyl 5-(Thiophen-2-yl)-1,3,4-thiadiazole-2-carboxylate (S42)

(General Procedure I)

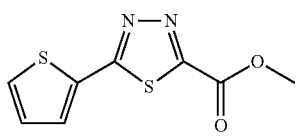

2-Thiophenecarboxylic acid hydrazide (200 mg, 1.4 mmol) and Et$_3$N (392 μL, 2.8 mmol) were dissolved in CH$_2$Cl$_2$ (7 mL) and treated with methyl oxalyl chloride (130 μL, 1.4 mmol) dropwise at 0° C. The reaction mixture was warmed slowly to room temperature and stirred for 16 h before the solvent was removed in vacuo. The residue was dissolved in toluene (13 mL) and treated with recrystallized Lawesson's reagent (1.14 g, 2.1 mmol), and warmed at 110° C. for 6 h. Upon completion, the reaction mixture was diluted with EtOAc and washed with water, saturated aqueous NaHCO$_3$ and saturated aqueous NaCl. The organic layer was dried over Na$_2$SO$_4$ and the solvent was removed under reduced pressure. Flash chromatography (SiO$_2$, 3×18 cm, 25% EtOAc-hexanes) afforded the title compound (106 mg, 33%) as a yellow solid: $^1$H NMR (CDCl$_3$, 500 MHz) δ 7.66 (dd, 1H, J=0.9, 3.7 Hz), 7.58 (dd, 1H, J=0.9, 5.1 Hz), 7.16 (dd, 1H, J=3.9, 4.8 Hz), 4.05 (s, 3H); $^{13}$C NMR (CDCl$_3$, 150 MHz) δ 166.5, 159.2, 158.4, 131.5, 131.2, 131.17, 128.5, 53.9; HRMS-ESI-TOF m/z 226.9943 ([M+H]$^+$, $C_8H_6N_2O_2S_2$ requires 226.9943).

Methyl 5-(Pyridin-2-yl)-1,3,4-thiadiazole-2-carboxylate (S43)

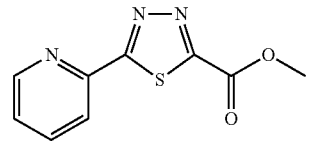

The title compound was prepared from 2-picolinyl hydrazide (100 mg, 0.73 mmol) by using general procedure I providing the product (45 mg, 20%) as a yellow solid: $^1$H NMR (CDCl$_3$, 500 MHz) δ 8.69 (d, 1H, J=4.9 Hz), 8.43 (d, 1H, J=7.9 Hz), 7.90 (dt, 1H, J=1.8, 7.8 Hz), 7.46 (m, 1H), 4.08 (s, 3H); $^{13}$C NMR (CDCl$_3$, 125 MHz) δ 174.4, 161.0, 159.4, 150.2, 148.3, 137.4, 126.3, 121.6, 53.8; HRMS-ESI-TOF m/z 222.0330 ([M+H]$^+$, $C_9H_7N_3O_2S$ requires 222.0332).

Methyl 5-(6-Bromopyridin-2-yl)-1,3,4-thiadiazole-2-carboxylate (S44)

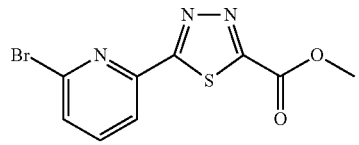

The title compound was prepared from S3 (415 mg, 1.92 mmol) by using general procedure I providing the product (417 mg, 73%) as a white solid: $^1$H NMR (CDCl$_3$, 600 MHz) δ 8.38 (d, 1H, J=8.0 Hz), 7.75 (t, 1H, J=7.8 Hz), 7.63 (d, 1H, J=7.8 Hz), 4.08 (s, 3H); $^{13}$C NMR (CDCl$_3$, 150 MHz) δ 172.7, 161.5, 159.3, 149.2, 142.2, 139.7, 130.8, 120.5, 55.0; HRMS-ESI-TOF m/z 299.9438 ([M+H]$^+$, $C_9H_6BrN_3O_2S$ requires 299.9437).

Methyl 5-(Furan-2-yl)-1,3,4-thiadiazole-2-carboxylate (S45)

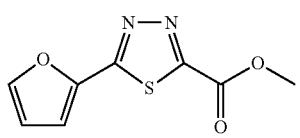

The title compound was prepared from furan-2-carbohydrazide (150 mg, 1.19 mmol) by using general procedure I providing the product (76 mg, 31%) as an off-white solid: $^1$H NMR (CDCl$_3$, 500 MHz) δ 7.66 (dd, 1H, I=0.6, 1.5 Hz), 7.36 (dd, 1H, J=0.6, 3.4 Hz), 6.64 (dd, 1H, J=1.8, 3.6 Hz), 4.07 (s, 3H); $^{13}$C NMR (CDCl$_3$, 125 MHz) δ 162.5, 159.2, 158.2, 146.2, 145.1, 113.6, 113.0, 53.8; HRMS-ESI-TOF m/z 211.0172 ([M+H]$^+$, $C_8H_6N_2O_3S$ requires 211.0172).

7-Phenyl-1-(5-(pyridin-2-yl)-1,3,4-thiadiazol-2-yl)-heptan-1-one (12b)

(General Procedure J)

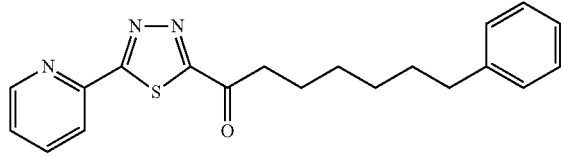 [SMILES: O=C(CCCCCCc1ccccc1)c1nnc(-c2ccccn2)s1]

A solution of 6-bromohexylbenzene (31 pt, 0.2 mmol) in THF (1 mL) was treated dropwise with 1.7 M t-BuLi (235 µL, 0.4 mmol) at −78° C. After stirring for 30 min, the resulting alkyllithium reagent was added to a cooled solution of methyl 5-(pyridin-2-yl)-1,3,4-thiadiazole-2-carboxylate (S43, 44 mg, 0.2 mmol) in THF (0.5 mL) at −78° C. The reaction mixture was stirred for 3 h at −78° C. before it was quenched with the addition of MeOH. The mixture was extracted with EtOAc, washed with water, saturated aqueous $NaHCO_3$ and saturated aqueous NaCl, and dried over $Na_2SO_4$. Evaporation in vacuo yielded the crude product which was purified by flash chromatography ($SiO_2$, 3×14 cm, 15% EtOAc-hexanes) to provide the title compound (5.1 mg, 7%) as white solid: $^1$H NMR ($CDCl_3$, 600 MHz) δ 8.69 (m, 1H), 8.41 (dd, 1H, J=0.8, 7.9 Hz), 7.89 (m, 1H), 7.45 (m, 1H), 7.27 (m, 2H), 7.17 (m, 3H), 3.27 (t, 2H, J=7.4 Hz) 2.61 (t, 2H, J=7.7 Hz), 1.81 (m, 2H), 1.65 (m, 2H), 1.45 (m, 4H); $^{13}$C NMR ($CDCl_3$, 150 MHz) δ 194.1, 174.9, 169.6, 150.3, 148.6, 142.8, 137.5, 128.5, 128.4, 126.3, 125.7, 121.7, 39.4, 36.0, 31.4, 29.9, 29.1, 24.0; IR (film) $v_{max}$ 2927, 2854, 1734, 1685, 1647, 1584, 1406, 1009, 785, 742, 698 cm$^{-1}$; HRMS-ESI-TOF m/z 352.1474 ([M+H]$^+$, $C_{20}H_{21}N_3OS$ requires 352.1478).

1-(5-(Furan-2-yl)-1,3,4-thiadiazol-2-yl)-7-phenyl-heptan-1-one (12c)

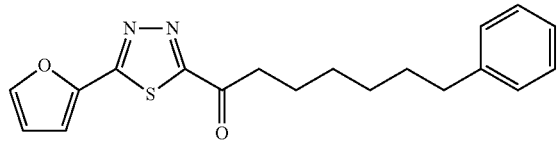

The title compound was prepared from S45 (52 mg, 0.25 mmol) by using general procedure J providing the product (3 mg, 4%) as a white solid: $^1$H NMR ($CDCl_3$, 600 MHz) 7.66 (br s, 1H), 7.34 (d, 1H, J=3.5 Hz), 7.27 (d, 2H, J=7.9 Hz), 7.17 (m, 3H), 6.63 (dd, 1H, J=1.6, 3.4 Hz), 3.24 (t, 2H, J=7.4 Hz), 2.61 (t, 2H, J=7.7 Hz), 1.80 (m, 2H), 1.64 (m, 3H), 1.42 (m, 3H); $^{13}$C NMR ($CDCl_3$, 125 MHz) δ 193.7, 167.0, 163.0, 146.3, 145.5, 142.8, 128.5, 128.4, 125.7, 113.7, 113.1, 39.5, 36.0, 31.4, 31.1, 29.1, 24.0; IR (film) $v_{max}$ 2928, 1700, 1684, 1653, 1507, 1457, 890, 668 cm$^{-1}$; HRMS-ESI-TOF m/z 341.1317 ([M+H]$^+$, $C_{19}H_{20}N_2O_2S$ requires 340.1245).

Z)-1-(1,3,4-Thiadiazol-2-yl)-octadec-9-en-1-one (5a

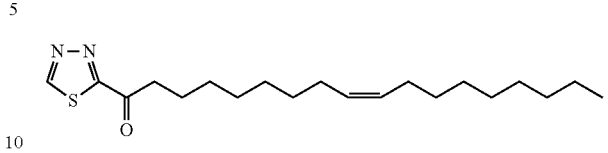

A suspension of the Dess-Martin periodinane (1.2 equiv, 0.013 mmol, 14 mg) in anhydrous $CH_2Cl_2$ (0.5 mL) was treated with a solution of (Z)-1-(1,3,4-thiadiazol-2-yl)-octadec-9-en-1-ol (4 mg, 0.011 mmol) in anhydrous $CH_2Cl_2$ (0.5 mL) at room temperature under $N_2$. After 10 h the suspension was diluted with $Et_2O$ (10 mL), and poured into a solution of $Na_2S_2O_3$ (40 mg) in saturated aqueous $NaHCO_3$ (3.4 mL). The mixture was stirred at room temperature for 1 h and the layers were separated. The ethereal layer was washed with saturated aqueous $NaHCO_3$ and $H_2O$, dried over $MgSO_4$, filtered and condensed. Flash chromatography ($SiO_2$, 1.5 cm×15 cm, 2% MeOH—$CH_2Cl_2$) afforded the title compound (3 mg, 70% yield) as a dark yellow oil: $^1$H NMR ($CDCl_3$, 250 MHz) δ 9.29 (s, 1H), 5.41-5.27 (m, 2H), 3.10 (t, 2H, J=7.4 Hz), 2.12-1.88 (m, 4H), 1.84-1.75 (m, 2H), 1.47-1.19 (m, 20H), 0.87 (br t, 3H, J=6.6 Hz); IR ($CDCl_3$) $v_{max}$ 2936, 2855, 1710, 1610, 1562, 1516, 1426, 1372 cm$^{-1}$; MALDI-FTMS (DHB) m/z 351.2464 ([M+H]$^+$, $C_{20}H_{34}N_2OS$ requires 351.2470).

Z)-1-(5-(Pyridin-2-yl)-1,3,4-thiadiazol-2-yl)-octadec-9-en-1-one (5b

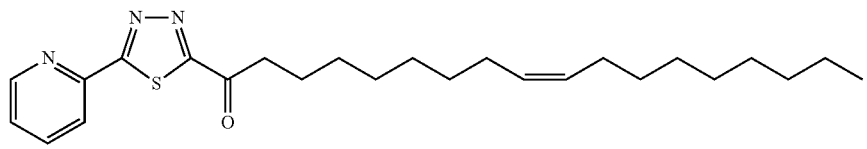

The title compound was prepared from S43 (36 mg, 0.16 mmol) and cis-1-bromoheptadec-8-ene (99 mg, 0.33 mmol) by using general procedure J providing the product (3 mg, 4%) as a white solid: $^1$H NMR ($CDCl_3$, 500 MHz) δ 8.68 (ddd, 1H, J=1.0, 1.6, 4.8 Hz), 8.41 (td, 1H, J=0.9, 8.0 Hz), 7.89 (dt, 1H, J=1.7, 7.8 Hz), 7.45 (ddd, 1H, J=1.1, 4.8, 7.6 Hz), 5.34 (m, 2H), 3.27 (t, 2H, J=7.4 Hz), 2.01 (m, 4H), 1.81 (m, 2H), 1.35 (m, 20H), 0.87 (t, 3H, J=7.0 Hz); $^{13}$C NMR ($CDCl_3$, 125 MHz) δ 194.1, 174.9, 169.6, 150.3, 148.6, 137.4, 130.2, 129.9, 126.3, 121.6, 39.5, 32.1, 29.9, 29.8, 29.7, 29.5 (2C), 29.4, 29.3 (2C), 27.4, 27.3, 24.1, 22.8, 14.3; IR (film) $v_{max}$ 2924, 2853, 1700, 1696, 1653, 1406, 1009, 784, 668 cm$^{-1}$; HRMS-ESI-TOF m/z 428.2732 ([M+H]$^+$, $C_{25}H_{37}N_3OS$ requires 427.2657).

Z)-1-(5-(Furan-2-yl)-1,3,4-thiadiazol-2-yl)-octadec-9-en-1-one (5c

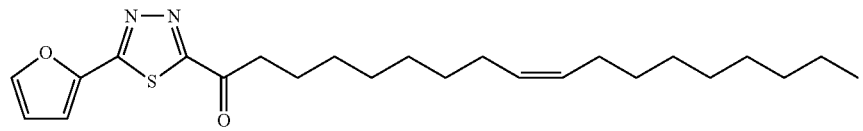 [SMILES: CCCCCCCC/C=C\CCCCCCCC(=O)c1nnc(-c2ccco2)s1]

The title compound was prepared from S45 (40 mg, 0.19 mmol) and cis-1-bromoheptadec-8-ene (114 mg, 0.38 mmol) by using general procedure J providing the product (10 mg, 13%) as a white solid: $^1$H NMR (CDCl$_3$, 500 MHz) δ 7.66 (dd, 1H, J=0.6, 1.8 Hz), 7.33 (dd, 1H, J=0.6, 3.6 Hz), 6.63 (dd, 1H, J=1.7, 3.5 Hz), 5.35 (m, 2H), 3.24 (t, 2H, J=7.4 Hz), 2.01 (m, 4H), 1.80 (m, 2H), 1.28 (m, 20H), 0.88 (t, 3H, J=7.0 Hz); $^{13}$C NMR (CDCl$_3$, 125 MHz) δ 193.6, 166.9, 162.8, 146.1, 145.4, 130.0, 129.7, 113.5, 112.9, 39.4, 31.9, 29.8, 29.7, 29.5 (2C), 29.2 (2C), 29.1 (2C), 27.2 (2C), 24.0, 22.7, 14.1; IR (film) ν$_{max}$ 3076, 2917, 2849, 1700, 1696, 1685, 1653, 1380, 1074, 997, 895, 741, 669; HRMS-ESI-TOF m/z 417.2574 ([M+H]$^+$, C$_{24}$H$_{36}$N$_2$O$_2$S requires 417.257).

7-Phenyl-1-(5-(thiophen-2-yl)-1,3,4-thiadiazol-2-yl)-heptan-1-one (12d)

(General Procedure K)

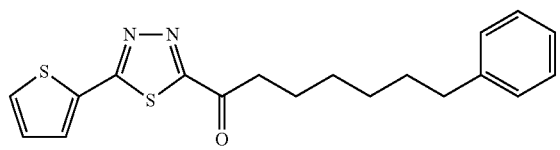 [SMILES: O=C(CCCCCCc1ccccc1)c1nnc(-c2cccs2)s1]

A dry vial was charged with freshly activated Mg turnings (94 mg, 3.9 mmol), 100 μL of anhydrous THF and a drop of 1,2-dibromoethane under Ar. This mixture was treated dropwise with a solution of 6-bromohexylbenzene (121 μL, 0.7 mmol) in THF (1 mL) at 23° C. The mixture was warmed and sonicated repeatedly until Grignard formation occurred. The gray solution of the Grignard reagent was added to a solution of S42 (35 mg, 0.16 mmol) in THF (1 mL) at −40° C. Stirring was continued for 2 h before the reaction was quenched by the addition of MeOH at −40° C. The mixture was extracted with EtOAc and washed with water, saturated NaHCO$_3$ and saturated aqueous NaCl followed by separation and evaporation. Flash chromatography (SiO$_2$, 1×4 cm, 40% EtOAc-hexanes) afforded the title compound (7 mg, 13%) as a white solid: $^1$H NMR (CDCl$_3$, 600 MHz) δ 7.67 (d, 1H, J=3.6 Hz), 7.59 (d, 1H, J=5.0 Hz), 7.27 (m, 2H), 7.17 (m, 4H), 3.23 (t, 2H, J=7.4 Hz), 2.61 (t, 2H, J=7.7 Hz), 1.80 (m, 2H), 1.64 (m, 2H), 1.42 (m, 4H); $^{13}$C NMR (CDCl$_3$, 150 MHz) δ 193.7, 167.2, 166.9, 142.8, 132.0, 131.3 (2C), 128.6, 128.5, 128.4, 125.8, 39.5, 36.0, 31.4, 29.1 (2C), 24.1; HRMS-ESI-TOF m/z 357.1090 ([M+H]$^+$, C$_{19}$H$_{20}$N$_2$OS$_2$ requires 357.1090).

1-(5-(6-Bromopyridin-2-1/1)-1,3,4-thiadiazol-2-yl)-7-phenylhentan-1-one (25)

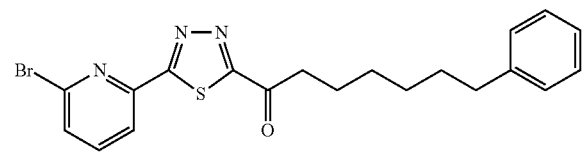

The title compound was prepared from S44 (292 mg, 12 mmol) by using general procedure K providing the product (64 mg, 31%) as a white solid: $^1$H NMR (CDCl$_3$, 500 MHz) δ 8.37 (d, 1H, J=7.7 Hz), 7.74 (t, 1H, J=7.8 Hz), 7.63 (d, 1H, J=7.8 Hz), 7.27 (m, 2H), 7.17 (m, 3H), 3.26 (t, 2H, J=7.4 Hz), 2.61 (t, 2H, J=7.7 Hz), 1.81 (m, 2H), 1.65 (m, 2H), 1.43 (m, 4H); $^{13}$C NMR (CDCl$_3$, 125 MHz) δ 193.8, 173.1, 169.9, 149.4, 142.8, 142.2, 139.6, 130.8, 128.5, 128.4, 125.8, 120.4, 39.5, 36.0, 31.4, 29.1 (2C), 23.9; HRMS-ESI-TOF m/z 430.0585 ([M+H]$^+$, C$_{20}$H$_{20}$BrN$_3$OS requires 430.0583).

Methyl 6-(5-(7-Phenylheptanoyl)-1,3,4-thiadiazol-2-yl)-picolinate (12f)

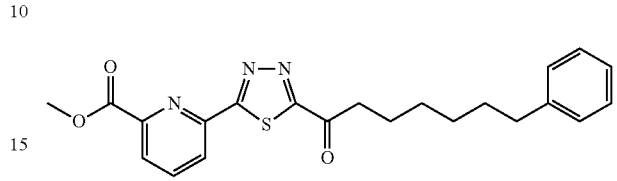

In a gas tight vessel, compound 25 (45 mg, 0.11 mmol) was dissolved in 8:2 toluene-MeOH (2 mL), then Cl$_2$Pd(PPh$_3$)$_2$ (15 mg, 0.02 mmol) and Et$_3$N (44 μL, 0.32 mmol) were added. CO(g) was bubbled through the reaction mixture for 30 min, before the reaction vessel was sealed and warmed at 90° C. for 36 h. The reaction mixture was diluted with EtOAc, washed with water and saturated aqueous NaCl, and dried over Na$_2$SO$_4$. Evaporation in vacuo yielded the crude ester which was purified by flash chromatography (SiO$_2$, 20-25% EtOAc-hexanes) to provide the title compound (26 mg, 61%) as a white solid: $^1$H NMR (CDCl$_3$, 500 MHz) δ 8.57 (dd, 1H, J=1.0, 7.9 Hz), 8.24 (dd, 1H, J=1.0, 7.8 Hz), 8.05 (t, 1H, J=7.8 Hz), 7.27 (m, 2H), 7.16 (m, 3H), 4.03 (s, 3H), 3.27 (t, 2H, J=7.4 Hz), 2.61 (t, 2H, J=7.7 Hz), 1.82 (m, 2H), 1.65 (m, 2H), 1.44 (m, 4H); $^{13}$C NMR (CDCl$_3$, 150 MHz) δ 193.9, 173.9, 167.0, 164.9, 148.8, 148.7, 142.8, 138.7, 128.5, 128.4, 127.3, 125.8, 124.6, 53.2, 39.5, 36.0, 31.4, 29.1 (2C), 23.9; HRMS-ESI-TOF m/z 410.1535 ([M+H]$^+$, C$_{22}$H$_{23}$N$_3$O$_3$S requires 410.1533).

6-(5-(7-Phenylheptanoyl)-1,3,4-thiadiazol-2-yl)-picolinic Acid (12g)

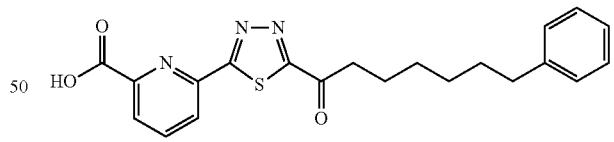

The title compound was prepared from 12f (8.7 mg, 0.021 mmol) following general procedure A. Preparative thin layer chromatography (SiO$_2$, 0-2% AcOH-EtOAc) afforded the title compound (8.4 mg, 100%) as a white solid: $^1$H NMR (acetone-d$_6$+0.1% TFA, 500 MHz) δ 8.64 (dd, 1H, J=1.8, 7.2 Hz), 8.34 (m, 2H), 7.25 (m, 2H), 7.20 (dd, 2H, J=3.0, 5.1 Hz), 7.14 (t, 1H, J=7.2 Hz), 3.28 (t, 2H, J=7.3 Hz), 2.62 (t, 2H, J=7.7 Hz), 1.80 (m, 2H), 1.65 (m, 2H), 1.45 (m, 4H); $^{13}$C NMR (acetone-d$_6$+0.1% TFA, 150 MHz) δ 195.2, 174.9, 171.9, 166.1, 150.4, 150.1, 144.5, 141.6, 130.2, 130.1, 128.9, 127.4, 126.4, 40.7, 37.4, 33.2, 31.3, 30.6, 25.4; HRMS-ESI-TOF m/z 396.1380 ([M+H]$^+$, C$_{21}$H$_{21}$N$_3$O$_3$S requires 396.1376).

Methyl 5-(1-Hydroxy-7-phenylheptyl)-1,3,4-thiadiazole-2-carboxylate (S46)

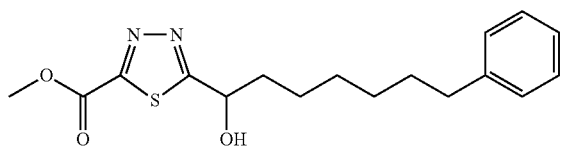

2-(tert-Butyldimethylsilyloxy)-8-phenyloctahydrazide (100 mg, 0.27 mmol) and Et$_3$N (76 µL, 0.55 mmol) were dissolved in CH$_2$Cl$_2$ (1.4 mL) and treated dropwise with methyl oxalyl chloride (25 µL, 0.27 mmol) at 0° C. The reaction mixture was warmed slowly to room temperature and stirred for 16 h before the solvent was removed in vacuo. The residue was dissolved in toluene (1.7 mL) and treated with recrystallized Lawesson's reagent (222 mg, 0.55 mmol) and warmed at 110° C. for 6 h. Upon completion, the reaction mixture was diluted with EtOAc and washed with water, saturated aqueous NaHCO$_3$ and saturated aqueous NaCl. The organic layer was dried over Na$_2$SO$_4$ and the solvent was removed under reduced pressure. Flash chromatography (SiO$_2$, 2×12 cm, 20% EtOAc-hexanes) afforded the title compound (82g, 67%) as a colorless oil: $^1$H NMR (CDCl$_3$, 500 MHz) δ 7.26 (m, 2H), 7.16 (m, 3H), 5.20 (dd, 1H, J=4.8, 7.9 Hz), 4.03 (s, 3H), 3.26 (br s, 1H), 2.59 (t, 2H, J=7.7 Hz), 1.94 (m, 2H), 1.60 (m, 2H), 1.39 (m, 6H); $^{13}$C NMR (CDCl$_3$, 125 MHz) δ 180.7, 160.4, 159.4, 142.8, 128.5, 128.4, 125.7, 70.4, 53.9, 38.4, 36.0, 31.4, 29.2 (2C), 24.9; HRMS-ESI-TOF m/z 335.1430 ([M+H]$^+$, C$_{17}$H$_{22}$N$_2$O$_3$S requires 335.1424).

Methyl 5-(7-Phenylheptanoyl)-1,3,4-thiadiazole-2-carboxylate (12h)

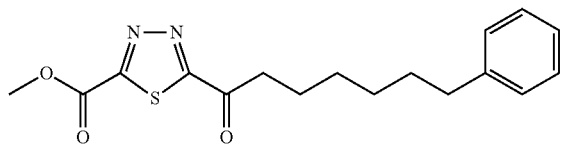 [SMILES: COC(=O)c1nnc(C(=O)CCCCCCc2ccccc2)s1]

The title compound was prepared from S46 (22 mg, 0.07 mmol) following general procedure B. Flash chromatography (SiO$_2$, 1.5×7 cm, 10% EtOAc-hexanes) afforded the title compound (18 mg, 84%) as a white solid: $^1$H NMR (CDCl$_3$, 500 MHz) δ 7.27 (m, 2H), 7.17 (m, 3H), 4.08 (s, 3H), 3.27 (t, 2H, J=7.4 Hz), 2.61 (t, 2H, J=7.7 Hz), 1.79 (m, 2H), 1.64 (m, 2H), 1.44 (m, 4H); $^{13}$C NMR (CDCl$_3$, 125 MHz) δ 193.5, 171.4, 163.6, 158.8, 142.7, 128.5, 128.4, 125.8, 54.2, 39.7, 36.0, 31.4, 29.1, 29.0, 23.7; HRMS-ESI-TOF m/z 333.1251 ([M+H]$^+$, C$_{17}$H$_{20}$N$_2$O$_3$S requires 333.1267).

7-Phenyl-1-(1,3,4-thiadiazol-2-yl)-heptan-1-one (12a)

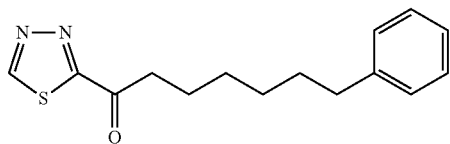 [SMILES: O=C(CCCCCCc1ccccc1)c1nncs1]

The title compound was prepared by methyl ester hydrolysis and spontaneous decarboxylation from ketone 12h (9.2 mg, 0.027 mmol) following general procedure A. Flash chromatography (SiO$_2$, 0.5×6 cm, 20-30% EtOAc-hexanes) afforded the title compound (6.7 mg, 89%) as a colorless oil: $^1$H NMR (CDCl$_3$, 500 MHz) δ 9.30 (s, 1H), 7.27 (m, 2H), 7.17 (m, 3H), 3.27 (t, 2H, J=7.4 Hz), 2.61 (t, 2H, J=7.7 Hz), 1.80 (m, 2H), 1.64 (m, 2H), 1.42 (m, 4H); $^{13}$C NMR (CDCl$_3$, 125 MHz) δ 193.5, 168.4, 156.1, 142.8, 128.5, 128.4, 125.8, 39.9, 36.0, 31.4, 29.1 (2C), 23.9; HRMS-ESI-TOF m/z 275.1214 ([M+H]$^+$, C$_{15}$H$_{18}$N$_2$OS requires 275.1213).

Pyridazines (13a-13f, 26):

Methyl 6-Oxo-1,4,5,6-tetrahydropyridazine-3-carboxylate (S47)

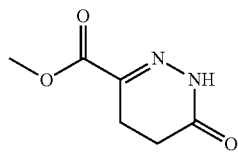

Dimethyl 2-oxoglutarate (1.5 g, 8.98 mmol) was dissolved in MeOH (62 mL). Hydrazine monohydrate (500 mg, 9.88 mmol) and AcOH (540 mg, 8.98 mmol) were added to the solution sequentially. The reaction mixture was warmed at 70° C. for 18 h. The solution was cooled and reduced to a residue which was subsequently redissolved in toluene and evaporated to afford an off-white solid. The solid was tritrated with hexanes and needed no further purification (1.2 g, 100%): $^1$H NMR (CDCl$_3$, 600 MHz) δ 8.75 (s, 1H), 3.90 (s, 3H), 2.93 (t, 2H, J=8.5 Hz), 2.58 (t, 2H, J=8.5 Hz).

Methyl 6-Oxo-1,6-dihydropyridazine-3-carboxylate (S48)

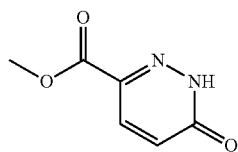

Manganese dioxide (3.12 g, 35.9 mmol) was suspended as a slurry in toluene (10 mL) and pyridine (720 µL). A sample of S47 (280 mg, 1.8 mmol) was added portionwise to the stirring solution and the resulting mixture was warmed at 65° C. until the disappearance of all starting material (6 h). The warm solution was filtered through a pad of Celite that was washed with several hundred milliliters of hot EtOAc and THF. The organic wash was evaporated to afford a yellowish solid which was used without further purification (160 mg, 58%): $^1$H NMR (CDCl$_3$, 300 MHz) δ 7.92 (d, 1H, J=9.9 Hz), 7.02 (d, 1H, J=9.8 Hz), 3.99 (s, 3H); HRMS-ESI-TOF m/z 155.0450 ([M+H]$^+$, C$_6$H$_6$N$_2$O$_3$ requires 155.0451).

Methyl 6-Chloropyridazine-3-carboxylate (S49)

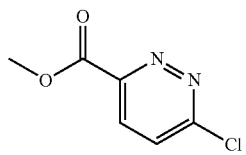

A sample of S48 (333 mg, 2.16 mmol) was dissolved in POCl$_3$ (3.2 mL) and warmed at 110° C. for 5 h. Upon disappearance of starting material, the solution was cooled to room temperature and diluted with EtOAc. The organic layer was poured onto ice and extracted. The organic layer was subsequently washed with saturated aqueous NaCl. The aqueous layer was back extracted with EtOAc and the combined organic phase was dried over Na$_2$SO$_4$ and filtered. The solution was evaporated and the residue was purified by flash chromatography (50% EtOAc-hexanes) to afford the title compound as a yellowish solid (254 mg, 68%): $^1$H NMR (CDCl$_3$, 400 MHz) δ 8.17 (d, 1H, J=8.8 Hz), 7.68 (d, 1H, J=8.8 Hz), 4.08 (s, 3H); $^{13}$C NMR (CDCl$_3$, 100 MHz) δ 159.5, 150.8, 129.8, 128.9, 53.7.

General Procedure L. Methyl 6-chloropyridazine-3-carboxylate (S49, 1 equiv) and Cl$_2$Pd(PPh$_3$)$_2$ (0.1 equiv) were dissolved in 1,4-dioxane (0.4 M). The reaction was evacuated and refilled with argon three times and the corresponding aryl stannane (1.4 equiv) was added neat. The mixture was warmed to 90° C. for 12 h. The reaction mixture was cooled and diluted with EtOAc. The slurry was filtered through a pad of Celite and concentrated to give the crude product which was purified by flash chromatography (SiO$_2$).

General Procedure M. The pyridazine methyl carboxylate (1 equiv) was dissolved in a 2:1 mixture of MeOH:THF and cooled to 0° C. NaBH$_4$ (5 equiv) was added portionwise to the cooled solution due to the evolution of H$_2$ gas. The mixture was allowed to slowly warm to 23° C. and after 3 h the reaction was quenched with the addition of 5% AcOH in EtOH (1 mL) and the resulting mixture was stirred overnight. The solution was diluted with EtOAc and washed with water and saturated aqueous NaCl, and dried over Na$_2$SO$_4$. Evaporation yielded the crude alcohol that was purified by flash chromatography (SiO$_2$). The alcohol (1 equiv) was dissolved in CH$_2$Cl$_2$ (0.03 M) and Dess-Martin periodinane (1.5 equiv) was added. The mixture was stirred at room temperature for 2 h before the reaction mixture was reduced to half volume and this mixture was directly loaded onto silica gel and purified by flash chromatography (SiO$_2$) yielding the desired aldehyde.

General Procedure N.

A solution of 6-bromohexylbenzene (1.5 equiv) in anhydrous THF (0.25 M) was treated dropwise with 1.5 M t-BuLi (3 equiv) at −78° C. After stirring for 15 min, the resulting alkyllithium reagent was added to a cooled solution of the aryl aldehyde (1 equiv) in THF (0.16 M) at −78° C. The reaction mixture was stirred for 1 h before it was quenched with the addition of MeOH at −78° C. The mixture was warmed to 23° C., extracted with EtOAc and washed with water and saturated aqueous NaCl, and dried over Na$_2$SO$_4$. Evaporation yielded the crude alcohol that was purified by flash chromatography (SiO$_2$).

General Procedure O.

A dry vial was charged with freshly activated Mg turnings (5 equiv), 100 μL of anhydrous THF and a drop of 1,2-dibromoethane under Ar. This mixture was treated dropwise with a solution of 6-bromohexylbenzene (1 equiv) in THF (0.2 M) at 23° C. The mixture was warmed and sonicated repeatedly until Grignard formation occurred. The gray solution of the Grignard reagent was added to a solution of the electrophile (0.2 equiv) in THF (1 mL/40 mg of electrophile) at −40° C. Stirring was continued for 1 h before the reaction was quenched with the addition of MeOH at −40° C. The mixture was extracted with EtOAc and washed with water, saturated aqueous NaHCO$_3$ and saturated aqueous NaCl, and then dried over Na$_2$SO$_4$. Evaporation yielded the crude alcohol that was purified by flash chromatography (SiO$_2$). Methyl 6-(Pyridin-2-yl)-pyridazine-3-carboxylate (S50)

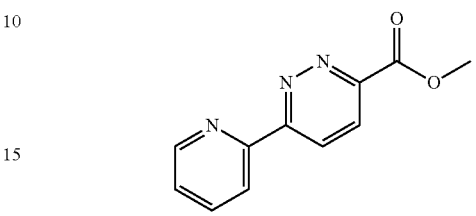

The title compound was prepared from S49 (70 mg, 0.40 mmol) and 2-(tributylstannyl)pyridine (181 μL, 0.57 mmol) following general procedure L. Flash chromatography (SiO$_2$, 1.5×20 cm, 20-50% EtOAc-hexanes) afforded the title compound (30 mg, 35%) as a white solid: $^1$H NMR (CDCl$_3$, 600 MHz) δ 8.77 (d, 1H, J=8.0 Hz), 8.73 (d, 1H, J=4.0 Hz), 8.70 (dd, 1H, J=1.5, 8.8 Hz), 8.29 (dd, 1H, J=1.2, 8.8 Hz), 7.91 (dt, 1H, J=1.7, 7.8 Hz), 7.43 (ddd, 1H, J=1.1, 4.8, 7.5 Hz), 4.09 (s, 3H); $^{13}$C NMR (CDCl$_3$, 150 MHz) δ 164.7, 160.0, 152.6, 151.1, 149.7, 137.4, 128.3, 125.5, 124.9, 122.5, 53.4; HRMS-ESI-TOF m/z 216.0772 ([M+H]$^+$, C$_{11}$H$_9$N$_3$O$_2$ requires 216.0767).

Methyl 6-(Furan-2-yl)-pyridazine-3-carboxylate (S51)

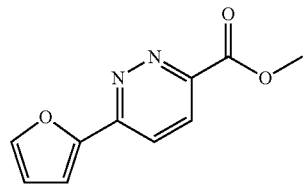

The title compound was prepared from S49 (40 mg, 0.23 mmol) and 2-(tributylstannyl)furan (102 μL, 0.32 mmol) following general procedure L. Flash chromatography (SiO$_2$, 2×15 cm, 5-50% EtOAc-hexanes) afforded the title compound (40 mg, 85%) as a white solid: $^1$H NMR (CDCl$_3$, 400 MHz) δ 8.20 (d, 1H, J=8.9 Hz), 7.93 (d, 1H, J=8.8 Hz), 7.67 (dd, 1H, J=0.7, 1.7 Hz), 7.52 (dd, 1H, J=0.7, 3.5 Hz), 6.65 (dd, 1H, J=1.8, 3.5 Hz), 4.08 (s, 3H); HRMS-ESI-TOF m/z 205.0606 ([M+H]$^+$, C$_{10}$H$_8$N$_2$O$_3$ requires 205.0608).

Methyl 6-(Thiophen-2-yl)-pyridazine-3-carboxylate (S52)

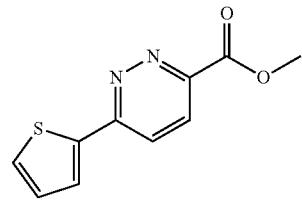

The title compound was prepared from S49 (40 mg, 0.23 mmol) and 2-(tributylstannyl)thiophene (103 µL, 0.33 mmol) following general procedure L. Flash chromatography (SiO$_2$, 2×14 cm, 5-50% EtOAc-hexanes) afforded the title compound (45 mg, 89%) as a white solid: $^1$H NMR (CDCl$_3$, 400 MHz) δ 8.16 (d, 1H, J=8.8 Hz), 7.87 (d, 1H, J=8.9 Hz), 7.79 (dd, 1H, J=1.1, 3.7 Hz), 7.59 (dd, 1H, J=1.0, 5.1 Hz), 7.20 (dd, 1H, J=3.8, 5.0 Hz), 4.07 (s, 3H); HRMS-ESI-TOF m/z 221.0379 ([M+H]$^+$, C$_{10}$H$_8$N$_2$O$_2$S requires 221.0379).

Methyl 6-(6-Cyanopyridin-2-yl)-pyridazine-3-carboxylate (S53)

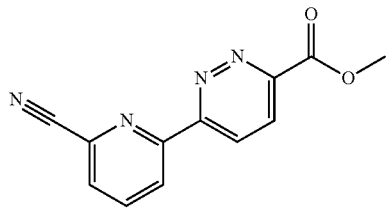 [SMILES: COC(=O)c1ccc(-c2cccc(C#N)n2)nn1]

Methyl 6-chloropyridazine-3-carboxylate (S49, 34 mg, 0.19 mmol), 6-(4,4,5,5-tetramethyl-1,3,2-dioxaborolan-2-yl)picolinonitrile (45 mg, 0.19 mmol), K$_2$CO$_3$ (51 mg, 0.39 mmol), and (Ph$_3$P)$_4$Pd (34 mg, 0.029 mmol) were slurried in DMF (0.3 M). The reaction vessel was evacuated and refilled with argon three times. The mixture was warmed at 85° C. for 16 h. The reaction mixture was cooled and diluted with EtOAc, washed with 9:1 NH$_4$OH:saturated aqueous NH$_4$Cl and saturated aqueous NaCl, and then dried over Na$_2$SO$_4$ Evaporation yielded the crude product that was purified by flash chromatography (SiO$_2$, 1.5×14 cm, 20-100% EtOAc-hexanes) to afford the title compound (25 mg, 53%) as a white solid: $^1$H NMR (CDCl$_3$, 600 MHz) δ 9.03 (d, 1H, J=8.1 Hz), 8.75 (d, 1H, J=8.7 Hz), 8.36 (d, 1H, J=8.7 Hz), 8.09 (t, 1H, J=7.9 Hz), 7.84 (d, 1H, J=7.6 Hz), 4.12 (s, 3H); $^{13}$C NMR (CDCl$_3$, 150 MHz) δ 164.4, 158.2, 154.4, 151.7, 138.7, 133.9, 129.8, 128.7, 125.5, 125.4, 116.9, 53.6; HRMS-ESI-TOF m/z 241.0721 ([M+H]$^+$, C$_{12}$H$_8$N$_4$O$_2$ requires 241.0720).

6-(Pyridin-2-yl)-pyridazine-3-carbaldehyde (S54)

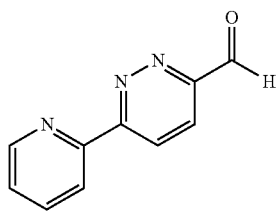 [SMILES: O=Cc1ccc(-c2ccccn2)nn1]

The title compound was prepared from S50 (44 mg, 0.24 mmol) following general procedure M. Flash chromatography (SiO$_2$, 2×14 cm, 20-30% EtOAc-hexanes) afforded the title compound (38 mg, 86%) as a white solid: $^1$H NMR (CDCl$_3$, 500 MHz) δ 10.42 (d, 1H, J=0.7 Hz), 8.76 (td, 1H, J=0.8 Hz, 8.1 Hz), 8.73 (m, 2H), 8.12 (d, 1H, J=8.7 Hz), 7.91 (dt, 1H, J=1.8, 7.8 Hz), 7.43 (ddd, 1H, J=1.1, 4.8, 7.6 Hz); HRMS-ESI-TOF m/z 186.0663 ([M+H]$^+$, C$_{10}$H$_7$N$_3$O requires 186.0662).

6-(Furan-2-yl)-pyridazine-3-carbaldehyde (S55)

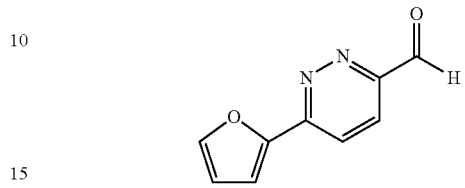

The title compound was prepared from S51 (12 mg, 0.07 mmol) following general procedure M. Flash chromatography (SiO$_2$, 1.5×10 cm, 30% EtOAc-hexanes) afforded the title compound (10 mg, 80%) as a white solid: $^1$H NMR (CDCl$_3$, 400 MHz) δ 10.37 (d, 1H, J=0.8 Hz), 8.05 (d, 1H, J=8.8 Hz), 7.97 (dd, 1H, J=0.8, 8.8 Hz), 7.69 (dd, 1H, J=0.6, 1.6 Hz), 7.56 (dd, 1H, J=0.5, 3.5 Hz), 6.67 (dd, 1H, J=1.8, 3.5 Hz); HRMS-ESI-TOF m/z 175.0501 ([M+H]$^+$, C$_9$H$_6$N$_2$O$_2$ requires 175.0502).

6-(Thiophen-2-yl)-pyridazine-3-carbaldehyde (S56)

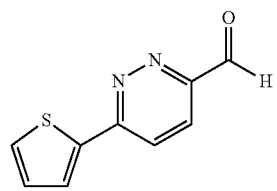 [SMILES: O=Cc1ccc(-c2cccs2)nn1]

The title compound was prepared from S52 (28 mg, 0.15 mmol) following general procedure M. Flash chromatography (SiO$_2$, 2×12 cm, 25% EtOAc-hexanes) afforded the title compound (27 mg, 100%) as a white solid: $^1$H NMR (CDCl$_3$, 500 MHz) δ 10.35 (d, 1H, J=0.8 Hz), 8.02 (d, 1H, J=8.8 Hz), 7.92 (dd, 1H, J=0.7, 8.8 Hz), 7.82 (dd, 1H, J=1.1, 3.7 Hz), 7.64 (dd, 1H, J=1.1, 5.1 Hz), 7.22 (dd, 1H, J=3.8, 5.0 Hz).

6-(6-Formylpyridazin-3-yl)-picolinonitrile (S57)

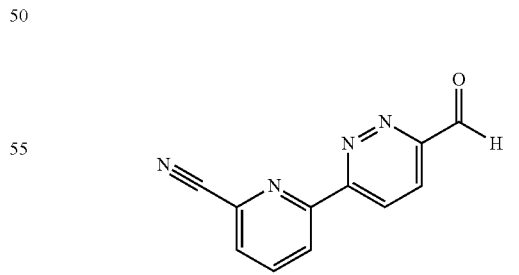

The title compound was prepared from S53 (12 mg, 0.05 mmol) following general procedure M. Flash chromatography (SiO$_2$, 1×12 cm, 25% EtOAc-hexanes) afforded the title compound (7 mg, 59%) as a white solid: $^1$H NMR (CDCl$_3$, 500 MHz) δ 10.48 (d, 1H, J=0.7 Hz), 9.04 (dd, 1H, J=0.9, 8.1 Hz), 8.80 (d, 1H, J=8.7), 8.21 (d, 1H, J=8.7), 8.11 (t, 1H, J=7.9), 7.86 (dd, 1H, J=0.7, 7.7 Hz); HRMS-ESI-TOF m/z 211.0610 ([M+H]$^+$, C$_{11}$H$_6$N$_4$O requires 211.0614).

7-Phenyl-1-(6-(pyridin-2-yl)-pyridazin-3-yl)-heptan-1-ol (S58)

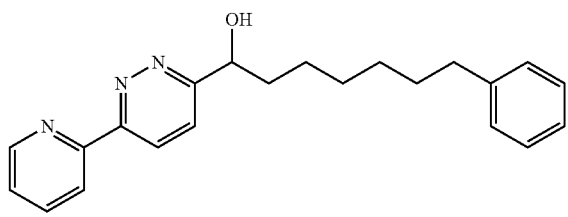 [SMILES: OC(CCCCCCc1ccccc1)c1ccc(-c2ccccn2)nn1]

The title compound was prepared from S54 (15 mg, 0.081 mmol) following general procedure O. Flash chromatography (SiO$_2$, 1.5×20 cm, 20-100% EtOAc-hexanes) afforded the title compound (6.5 mg, 23%) as a white solid: $^1$H NMR (CDCl$_3$, 500 MHz) δ 8.71 (d, 1H, J=4.7 Hz), 8.66 (d, 1H, J=8.0 Hz), 8.56 (d, 1H, J=8.8 Hz), 7.88 (dt, 1H, J=1.8, 7.8 Hz), 7.62 (d, 1H, J=8.8 Hz), 7.40 (ddd, 1H, J=1.1, 4.8, 7.4 Hz), 7.26 (m, 2H), 7.16 (m, 3H), 5.03 (m, 1H), 3.69 (d, 1H(—OH), J=4.5 Hz), 2.58 (t, 2H, J=7.7 Hz), 1.93 (m, 1H), 1.82 (m, 1H), 1.60 (m, 2H), 1.47 (m, 2H), 1.36 (m, 4H); $^{13}$C NMR (CDCl$_3$, 150 MHz) δ 163.9, 158.2, 153.5, 149.6, 142.9, 137.4, 128.5, 128.4, 125.7, 125.3, 125.1, 124.9, 121.6, 72.7, 38.3, 36.0, 31.5, 29.5, 29.3, 25.2; HRMS-ESI-TOF m/z 348.2071 ([M+H]$^+$, C$_{22}$H$_{25}$N$_3$O requires 348.2070).

7-Phenyl-1-(6-(pyridin-2-yl)-pyridazin-3-yl)-heptan-1-one (13b)

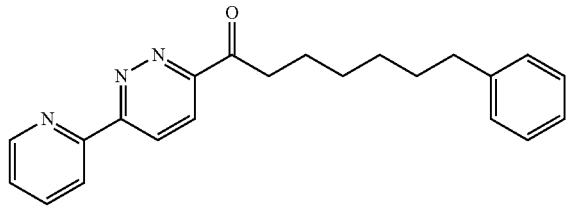 [SMILES: O=C(CCCCCCc1ccccc1)c1ccc(-c2ccccn2)nn1]

The title compound was prepared from S58 (6.5 mg, 0.019 mmol) following general procedure B. Flash chromatography (SiO$_2$, 0.5×6 cm, 20% EtOAc-hexanes) afforded the title compound (6.4 mg, 100%) as a white solid: $^1$H NMR (CDCl$_3$, 600 MHz) δ 8.77 (dd, 1H, J=0.7, 7.9 Hz), 8.75 (dd, 1H, J=0.7, 4.8 Hz), 8.72 (d, 1H, J=8.7 Hz), 8.24 (d, 1H, J=8.7 Hz), 7.93 (dt, 1H, J=1.7, 7.8 Hz), 7.45 (m, 1H), 7.26 (m, 2H), 7.17 (m, 3H), 3.44 (t, 2H, J=7.4 Hz), 2.61 (t, 2H, J=7.8 Hz), 1.82 (m, 2H), 1.65 (m, 2H), 1.45 (m, 4H); $^{13}$C NMR (CDCl$_3$, 150 MHz) δ 200.7, 160.1, 155.4, 152.8, 149.8, 142.9, 137.5, 128.5, 128.4, 125.7 (2C), 125.5, 125.4, 122.4, 38.4, 36.1, 31.5, 29.9, 29.3, 24.1; HRMS-ESI-TOF m/z 346.1914 ([M+H]$^+$, C$_{22}$H$_{23}$N$_3$O requires 346.1914). 112.9, 38.2, 36.1, 31.5, 29.33, 29.26, 24.1; HRMS-ESI-TOF m/z 335.1759 ([M+H]$^+$, C$_{21}$H$_{22}$N$_2$O$_2$ requires 335.1754).

7-Phenyl-1-(6-(thiophen-2-yl)-pyridazin-3-yl)-heptan-1-ol (S60)

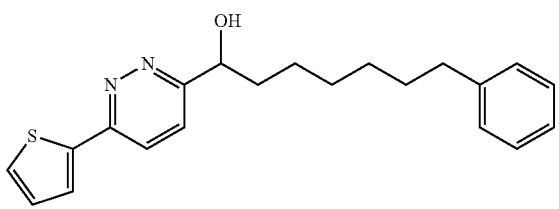

1-(6-(Furan-2-yl)-pyridazin-3-yl)-7-phenylheptan-1-ol (S59)

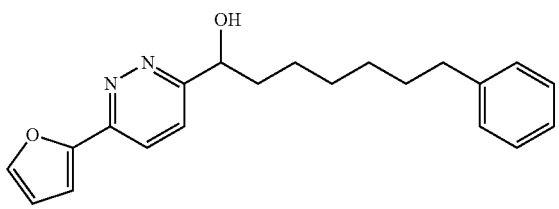 [SMILES: OC(CCCCCCc1ccccc1)c1ccc(-c2ccco2)nn1]

The title compound was prepared from S55 (10 mg, 0.057 mmol) following general procedure N. Flash chromatography (SiO$_2$, 0.5×6 cm, 30% EtOAc-hexanes) afforded the title compound (2.0 mg, 10%) as a white solid: $^1$H NMR (CDCl$_3$, 600 MHz) δ 7.84 (d, 1H, J=8.8 Hz), 7.61 (dd, 1H, J=0.7, 1.7 Hz), 7.51 (d, 1H, J=8.8 Hz), 7.35 (d, 1H, J=3.4 Hz), 7.26 (m, 2H), 7.16 (m, 3H), 6.60 (dd, 1H, J=1.7, 3.4 Hz), 4.97 (td, 1H, J=4.8, 7.6 Hz), 3.58 (d, 1H(—OH), J=5.2 Hz), 2.58 (t, 2H, J=7.7 Hz), 1.89 (m, 1H), 1.79 (m, 1H), 1.61 (m, 2H), 1.44 (m, 2H), 1.34 (m, 4H); $^{13}$C NMR (CDCl$_3$, 150 MHz) δ 162.1, 151.8, 150.8, 144.6, 142.9, 128.5, 128.4, 125.7, 124.7, 122.5, 112.7, 110.5, 72.7, 38.3, 36.1, 31.5, 29.5, 29.3, 25.2.

1-(6-(Furan-2-yl)-pyridazin-3-yl)-7-phenylheptan-1-one (13c)

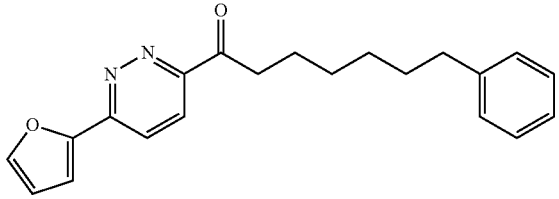

The title compound was prepared from S59 (2 mg, 0.006 mmol) following general procedure B. Flash chromatography (SiO₂, 0.5×6 cm, 10% EtOAc-hexanes) afforded the title compound (1.9 mg, 95%) as a white solid: ¹H NMR (CDCl₃, 600 MHz) δ 8.14 (d, 1H, J=8.8 Hz), 7.95 (d, 1H, J=8.8 Hz), 7.67 (d, 1H, J=1.1 Hz), 7.52 (d, 1H, J=3.5 Hz), 7.27 (m, 2H), 7.17 (m, 3H), 6.66 (dd, 1H, J=1.7, 3.4 Hz), 3.39 (t, 2H, J=7.5 Hz), 2.60 (t, 2H, J=7.8 Hz), 1.79 (m, 2H), 1.63 (m, 2H), 1.43 (m, 4H); ¹³C NMR (CDCl₃, 150 MHz) δ 200.5, 153.7, 153.5, 150.5, 145.7, 142.9, 128.5, 128.4, 125.7, 125.4, 122.1, 113.2, The title compound was prepared from S56 (20 mg, 0.105 mmol) following general procedure N. Flash chromatography (SiO₂, 1.5×15 cm, 10-50% EtOAc-hexanes) afforded the title compound (4.3 mg, 12%) as a white solid: ¹H NMR (CDCl₃, 600 MHz) δ 7.78 (d, 1H, J=8.8 Hz), 7.67 (dd, 1H, J=1.0, 3.7 Hz), 7.49 (m, 2H), 7.26 (m, 2H), 7.16 (m, 4H), 4.96 (dd, 1H, J=4.7, 7.5 Hz), 2.58 (t, 2H, J=7.7 Hz), 1.89 (m, 1H), 1.78 (m, 1H), 1.60 (m, 2H), 1.42 (m, 6H).

7-Phenyl-1-(6-(thiophen-2-yl)-pyridazin-3-yl)-heptan-1-one (13d)

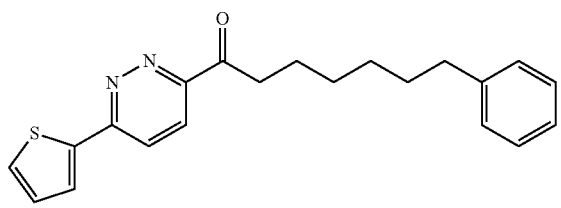 [SMILES: O=C(CCCCCCc1ccccc1)c1ccc(-c2ccco2)nn1]

The title compound was prepared from S60 (1.9 mg, 0.005 mmol) following general procedure B. Flash chromatography (SiO₂, 0.5×6 cm, 10% EtOAc-hexanes) afforded the title compound (1.6 mg, 85%) as a white solid: ¹H NMR (CDCl₃, 600 MHz) δ 8.12 (d, 1H, J=8.8 Hz), 7.90 (d, 1H, J=9.0 Hz), 7.78 (d, 1H, J=3.8 Hz), 7.61 (d, 1H, J=5.0 Hz), 7.27 (m, 2H), 7.21 (m, 1H), 7.17 (m, 3H), 3.38 (t, 2H, J=7.5 Hz), 2.60 (t, 2H, J=7.8 Hz), 1.79 (m, 2H), 1.63 (m, 2H), 1.42 (m, 4H); ¹³C NMR (CDCl₃, 150 MHz) δ 200.5, 156.6, 154.1, 142.9, 140.0, 131.4, 128.6, 128.5, 128.4, 127.9, 125.7, 125.5, 122.7, 38.2, 36.1, 31.5, 29.3, 29.2, 24.1; HRMS-ESI-TOF m/z 351.1523 ([M+H]⁺, C₂₁H₂₂N₂OS requires 351.1526).

6-(6-(1-Hydroxy-7-phenylheptyl)-pyridazin-3-yl)-picolinonitrile (S61)

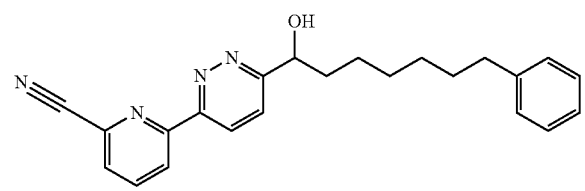 [SMILES: N#Cc1cccc(-c2ccc(C(O)CCCCCCc3ccccc3)nn2)n1]

The title compound was prepared from S57 (17 mg, 0.081 mmol) following general procedure O. Flash chromatography (SiO₂, 2×17 cm, 20-60% EtOAc-hexanes) afforded the title compound (8.0 mg, 27%) as a white solid: ¹H NMR (CDCl₃, 500 MHz) δ 8.92 (dd, 1H, J=0.9, 8.1 Hz), 8.60 (d, 1H, J=8.8 Hz), 8.04 (t, 1H, J=7.9 Hz), 7.80 (dd, 1H, J=0.8, 7.6 Hz), 7.69 (d, 1H, J=8.8 Hz), 7.26 (m, 2H), 7.16 (m, 3H), 5.07 (m, 1H), 3.41 (d, 1H(—OH), J=4.6 Hz), 2.59 (t, 2H, J=7.7 Hz), 1.94 (m, 1H), 1.84 (m, 1H), 1.62 (m, 2H), 1.47 (m, 2H), 1.38 (m, 4H).

Methyl 6-(6-(1-Hydroxy-7-phenylheptyl)-pyridazin-3-yl)-picolinate (S62)

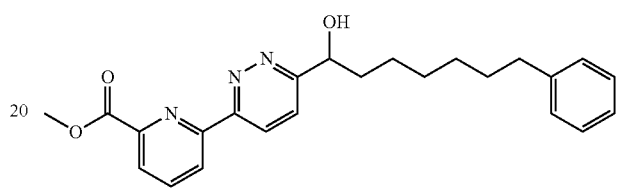

A sample of S61 (2 mg, 0.005 mmol) was dissolved in MeOH (0.01 M) and concentrated HCl (15 μL) was added. The solution was warmed at 80° C. for 6 h. Upon completion, the solution was cooled to 23° C., diluted with EtOAc, washed with saturated aqueous NaHCO₃ and saturated aqueous NaCl, and dried over Na₂SO₄. Evaporation in vacuo yielded the crude ester that was purified by flash chromatography (SiO₂, 0.5×6 cm, 20-100% EtOAc-hexanes) to afford the title compound (1.8 mg, 89%) as a white solid: ¹H NMR (CDCl₃, 400 MHz) δ 8.86 (dd, 1H, J=0.8, 8.0 Hz), 8.70 (d, 1H, J=8.8 Hz), 8.22 (dd, 1H, J=0.9, 7.7 Hz), 8.05 (t, 1H, J=7.8 Hz), 7.65 (d, 1H, J=8.8 Hz), 7.26 (m, 2H), 7.16 (m, 3H), 5.06 (m, 1H), 4.05 (s, 3H), 2.58 (t, 2H, J=7.7 Hz), 1.94 (m, 1H), 1.83 (m, 1H), 1.45 (m, 4H), 1.35 (m, 4H).

6-(6-(7-Phenylheptanoyl)-pyridazin-3-yl)-picolinonitrile (26)

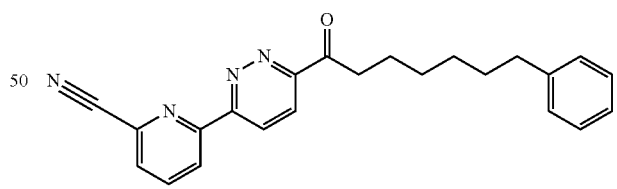

The title compound was prepared from S61 (2 mg, 0.005 mmol) following general procedure B. Flash chromatography (SiO₂, 0.5×6 cm, 20-30% EtOAc-hexanes) afforded the title compound (2.0 mg, 100%) as a white solid: ¹H NMR (CDCl₃, 500 MHz) δ 9.01 (dd, 1H, J=1.0, 8.1 Hz), 8.75 (d, 1H, J=8.7 Hz), 8.28 (d, 1H, J=8.8 Hz), 8.09 (t, 1H, J=7.9 Hz), 7.84 (dd, 1H, J=1.0, 7.7 Hz), 7.27 (m, 2H), 7.16 (m, 3H), 3.44 (t, 2H, J=7.4 Hz), 2.62 (t, 2H, J=7.8 Hz), 1.83 (m, 2H), 1.65 (m, 2H), 1.45 (m, 4H); ¹³C NMR (CDCl₃, 150 MHz) δ 200.3, 158.4, 155.8, 154.5, 142.9, 138.7, 134.0, 129.8, 128.5, 128.4, 126.0, 125.8, 125.7, 125.4, 117.0, 38.5, 36.1, 31.5, 29.3, 29.2, 24.0; HRMS-ESI-TOF m/z 371.1869 ([M+H]$^+$, $C_{23}H_{22}N_4O$ requires 371.1866).

Methyl 6-(6-(7-Phenylheptanoyl)-pyridazin-3-yl)-picolinate (13f)

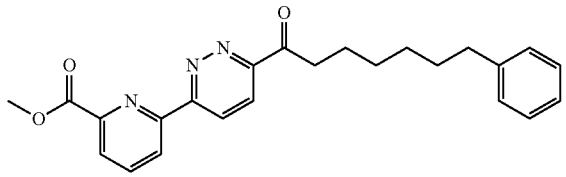 [SMILES: COC(=O)c1cccc(-c2ccc(C(=O)CCCCCCc3ccccc3)nn2)n1]

The title compound was prepared from S62 (3.4 mg, 0.0084 mmol) following general procedure B. Flash chromatography (SiO$_2$, 0.5×6 cm, 20-30% EtOAc-hexanes) afforded the title compound (2.1 mg, 62%) as a white solid: $^1$H NMR (CDCl$_3$, 500 MHz) δ 8.96 (dd, 1H, J=1.0, 8.0 Hz), 8.86 (d, 1H, J=8.7 Hz), 8.26 (m, 2H), 8.09 (t, 1H, J=7.8 Hz), 7.27 (t, 2H, J=7.5 Hz), 7.17 (m, 3H), 4.05 (s, 3H), 3.44 (t, 2H, J=7.4 Hz), 2.62 (t, 2H, J=7.8 Hz), 1.83 (m, 2H), 1.65 (m, 2H), 1.45 (m, 4H); $^{13}$C NMR (CDCl$_3$, 150 MHz) δ 200.5, 165.5, 159.4, 155.6, 153.1, 148.2, 142.9, 138.6, 128.5, 128.4, 126.7, 125.9, 125.8, 125.7, 125.4, 53.3, 38.5, 36.1, 31.5, 29.3 (2C), 24.0; HRMS-ESI-TOF m/z 404.1973 ([M+H]$^+$, $C_{24}H_{25}N_3O_3$ requires 404.1969).

6-(6-(7-Phenylheptanoyl)-pyridazin-3-yl)-picolinic Acid (13g)

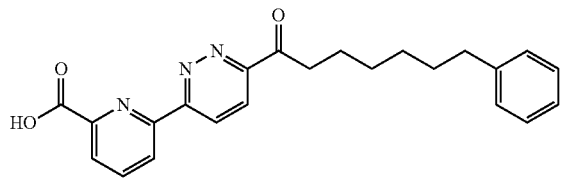 [SMILES: O=C(O)c1cccc(-c2ccc(C(=O)CCCCCCc3ccccc3)nn2)n1]

The title compound was prepared from 13f (1.9 mg, 0.0047 mmol) following general procedure A. Tritration with Et$_2$O afforded the title compound (1.3 mg, 71%) as a white solid: $^1$H NMR (CDCl$_3$, 600 MHz) δ 9.06 (d, 1H, J=7.8 Hz), 8.65 (d, 1H, J=8.7 Hz), 8.42 (d, 1H, J=7.5 Hz), 8.32 (d, 1H, J=8.7 Hz), 8.23 (t, 1H, J=7.8 Hz), 7.27 (m, 2H), 7.17 (m, 3H), 3.45 (t, 2H, J=7.4 Hz), 2.62 (t, 2H, J=7.8 Hz), 1.83 (m, 2H), 1.66 (m, 2H), 1.46 (m, 4H); $^{13}$C NMR (CDCl$_3$, 150 MHz) δ 200.2, 163.5, 158.2, 155.7, 152.2, 146.4, 142.9, 140.2, 128.5, 128.4, 126.7, 126.0, 125.8, 125.7, 125.2, 38.5, 36.1, 31.5, 29.3, 29.2, 24.0; HRMS-ESI-TOF m/z 390.1811 ([M+H]$^+$, $C_{23}H_{23}N_3O_3$ requires 390.1812).

7-Phenyl-1-(pyridazin-3-yl)-heptan-1-ol (S63)

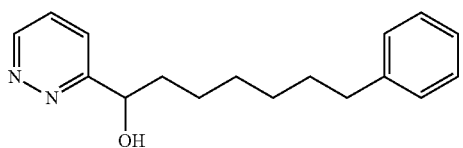 [SMILES: OC(CCCCCCc1ccccc1)c1cccnn1]

2,2,6,6-Tetramethylpiperidine (1.54 mL) was dissolved in anhydrous THF (60 mL) and treated dropwise with 2.0 M n-BuLi (4 equiv) at −40° C. The reaction mixture was stirred at 0° C. for 0.5 h, cooled to −78° C. and treated with a solution of pyridazine (165 μL, 2.26 mmol) in THF (4 mL) immediately followed by a solution of 7-phenylheptanal (435 mg, 2.29 mmol) in THF (2 mL). The reaction mixture was stirred at −78° C. for 1 h before being quenched by the addition of 1 N HCl/EtOH/THF (2/9/9, 40 mL). The reaction mixture was diluted with EtOAc, and washed with H$_2$O, saturated aqueous NaHCO$_3$ and saturated aqueous NaCl. The organic layer was dried over Na$_2$SO$_4$ and the solvent was removed under reduced pressure. Flash chromatography (SiO$_2$, 3×15 cm, 1% MeOH—CH$_2$Cl$_2$) afforded the alcohol (135 mg, 22%) as colorless oil: $^1$H NMR (CDCl$_3$, 500 MHz) δ 9.12 (dd, 1H, J=1.8, 4.7 Hz), 7.49 (m, 2H), 7.26 (m, 2H), 7.17 (m, 3H), 4.97 (td, 1H, J=4.9, 8.0 Hz), 3.60 (d, 1H(—OH), J=5.4 Hz), 2.58 (t, 2H, J=7.7 Hz), 1.88 (m, 1H), 1.77 (m, 1H), 1.43 (m, 2H), 1.34 (m, 6H).

7-Phenyl-1-(pyridazin-3-yl)-heptan-1-one (13a)

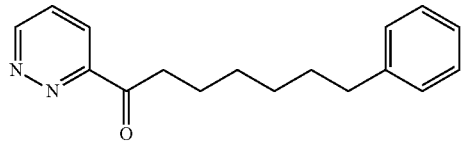 [SMILES: O=C(CCCCCCc1ccccc1)c1cccnn1]

The title compound was prepared from S63 following general procedure B. Flash chromatography afforded the title compound as a white solid: $^1$H NMR (CDCl$_3$, 600 MHz) δ 9.33 (d, 1H, J=4.0 Hz), 8.13 (d, 1H, J=8.3 Hz), 7.64 (dd, 1H, J=5.0, 8.4 Hz), 7.26 (m, 2H), 7.17 (m, 3H), 3.40 (t, 2H, J=7.4 Hz), 2.61 (t, 2H, J=7.7 Hz), 1.79 (m, 2H), 1.64 (m, 2H), 1.43 (m, 4H); $^{13}$C NMR (CDCl$_3$, 150 MHz) δ 200.9, 155.8, 153.4, 142.9, 128.5, 128.4, 127.3, 125.7, 124.8, 38.3, 36.1, 31.5, 29.3, 29.2, 23.9; HRMS-ESI-TOF m/z 269.1647 ([M+H]$^+$, $C_{17}H_{20}N_2O$ requires 269.1648).

Triazoles (14a-14d, 14h, 16, 17, 18):

2-(5-(1-(tert-Butyldimethylsilyloxy)-7-phenylheptyl)-4H-1,2,4-triazol-3-yl)-pyridine (S64)

(General Procedure P)

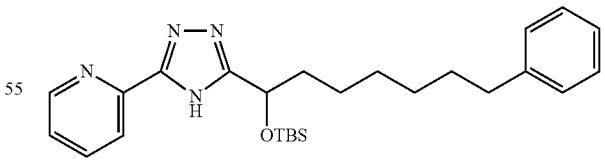

NaH (182 mg, 4.73 mmol) was slurried in anhydrous THF (3.7 mL) and cooled to 0° C. Anhydrous N$_2$H$_4$ (149 μL) was added to the reaction mixture behind a blast shield. After 0.5 h, a solution of 2-(tert-butyldimethylsilyloxy)-8-phenyloctanitrile S19 (520 mg, 1.57 mmol) in THF (7 mL) was added to the slurry over 0.5 h by syringe pump turning the solution a light yellow. Upon formation of the amidrazone (2 h), the reaction mixture was quenched with the addition of ice water (5 mL), diluted with Et₂O, washed with saturated aqueous NaCl, and dried over Na₂SO₄. Evaporation in vacuo yielded the crude amidrazone (468 mg, quant.) which was used without further purification. The amidrazone was dissolved in 1,4-dioxane (0.5 M). 2-Pyridinecarboxaldehyde (123 μL, 1.3 mmol) and piperidine (63 μL, 0.64 mmol) were added to the reaction mixture which was warmed at 110° C. for 16 h. Upon completion of the reaction, the solvent was removed in vacuo and the residue was purified by flash chromatography (SiO₂, 1.5×12 cm, 10-30% EtOAc-hexanes) to afford a mixture of imine (ring opened) and aminal (ring closed) products (470 mg, 82%). The mixture was oxidized with 2,3-dichloro-5,6-dicyano-p-benzoquinone (DDQ, 1.5 equiv) in 1,4-dioxane (0.1 M) to afford the desired compound as a colorless oil: ¹H NMR (CDCl₃, 400 MHz) δ 8.74 (d, 1H, J=4.1 Hz), 8.21 (d, 1H, J=7.8 Hz), 7.82 (dt, 1H, J=1.6, 7.8 Hz), 7.35 (dd, 1H, J=5.0, 6.8 Hz), 7.25 (m, 2H), 7.15 (m, 3H), 5.02 (t, 1H, J=6.0 Hz), 2.57 (t, 2H, J=7.7 Hz), 1.89 (m, 2H), 1.58 (m, 2H), 1.36 (m, 6H), 0.90 (s, 9H), 0.11 (s, 3H), 0.01 (s, 3H).

7-Phenyl-1-(5-(pyridin-2-yl)-4H-1,2,4-triazol-3-yl)heptan-1-ol (S65)

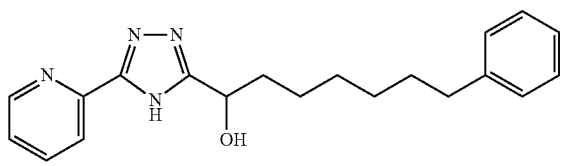 [SMILES: OC(CCCCCCc1ccccc1)c1nnc(-c2ccccn2)[nH]1]

The title compound was prepared from S64 (30 mg, 0.065 mmol) following general procedure G. Flash chromatography (SiO₂, 1.5×15 cm, 50-100% EtOAc-hexanes) afforded the title compound (15 mg, 64%) as a white solid: ¹H NMR (CDCl₃, 400 MHz) δ 8.78 (dd, 1H, J=0.8, 3.4 Hz), 8.30 (d, 1H, J=7.9 Hz), 7.90 (dt, 1H, J=1.7, 7.8 Hz), 7.44 (ddd, 1H, J=1.1, 4.9, 7.6 Hz), 7.26 (m, 2H), 7.15 (m, 3H), 5.12 (t, 1H, J=7.4 Hz), 2.59 (t, 2H, J=7.7 Hz), 2.29 (m, 2H), 1.58 (m, 2H), 1.38 (m, 6H); ¹³C NMR (CDCl₃, 150 MHz) δ 164.8, 155.0, 149.5, 146.0, 142.8, 138.0, 128.4, 128.3, 125.6, 125.4, 122.4, 55.2, 37.1, 36.0, 31.4, 29.1, 28.8, 26.7.

7-Phenyl-1-(5-(pyridin-2-yl)-4H-1,2,4-triazol-3-yl)-heptan-1-one (14b)

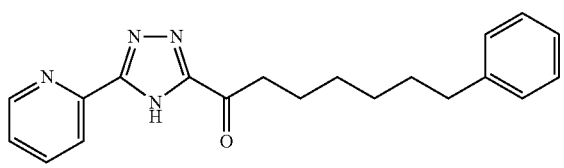 [SMILES: O=C(CCCCCCc1ccccc1)c1nnc(-c2ccccn2)[nH]1]

The title compound was prepared from S65 (10 mg, 0.031 mmol) following general procedure B. Flash chromatography (SiO₂, 0.5×7 cm, 50-75% EtOAc-hexanes) afforded the title compound (9.0 mg, 86%) as a white solid: ¹H NMR (CDCl₃, 400 MHz) δ 8.79 (d, 1H, J=4.4 Hz), 8.38 (d, 1H, J=7.9 Hz), 7.93 (dt, 1H, J=1.3, 7.8 Hz), 7.48 (dd, 1H, J=5.3, 6.9 Hz), 7.26 (m, 2H), 7.17 (m, 3H), 3.17 (t, 2H, J=7.4 Hz), 2.60 (t, 2H, J=7.7 Hz), 1.81 (m, 2H), 1.63 (m, 2H), 1.43 (m, 4H); ¹³C NMR (CDCl₃, 150 MHz) δ 194.2, 160.6, 156.1, 149.6, 145.8, 142.9, 138.2, 128.5, 128.4, 125.8, 125.7, 122.7, 39.7, 36.0, 31.5, 29.8, 29.2, 24.1; HRMS-ESI-TOF m/z 335.1872 ([M+H]⁺, C₂₀H₂₂N₄O requires 335.1866).

3-(1-(tert-Butyldimethylsilyloxy)-7-phenylheptyl)-5-(furan-2-yl)-4H-1,2,4-triazole (S66)

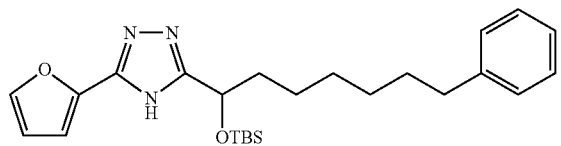 [SMILES: CC(C)(C)[Si](C)(C)OC(CCCCCCc1ccccc1)c1nnc(-c2ccco2)[nH]1]

The title compound was prepared from S19 (89 mg, 0.24 mmol) using general procedure P providing the product (21 mg, 22%) as a colorless oil: ¹H NMR (CDCl₃, 500 MHz) δ 7.52 (d, 1H, J=1.4 Hz), 7.26 (t, 2H, J=7.4 Hz), 7.16 (m, 3H), 6.97 (d, 1H, J=3.3 Hz), 6.51 (dd, 1H, J=1.7, 3.3 Hz), 5.05 (t, 1H, J=5.5 Hz), 2.57 (t, 2H, J=7.7 Hz), 1.84 (m, 2H), 1.58 (m, 2H), 1.32 (m, 6H), 0.93 (s, 9H), 0.12 (s, 3H), 0.03 (s, 3H); ¹³C NMR (CDCl₃, 150 MHz) δ 161.2, 155.4, 146.2, 143.3, 142.8, 128.5, 128.3, 125.7, 111.5, 109.4, 69.1, 37.7, 36.0, 31.5, 29.3, 29.2, 25.9 (3C), 24.3, 18.3, −4.8, −4.9; HRMS-ESI-TOF m/z 440.2717 ([M+H]⁺, C₂₅H₃₇N₃O₂Si requires 440.2718).

1-(5-(Furan-2-yl)-4H-1,2,4-triazol-3-yl)-7-phenyl-heptan-1-ol (S67)

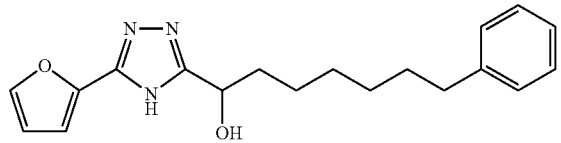 [SMILES: OC(CCCCCCc1ccccc1)c1nnc(-c2ccco2)[nH]1]

The title compound was prepared from S66 (62 mg, 0.14 mmol) following general procedure G. Flash chromatography (SiO₂, 1.5×15 cm, 50-100% EtOAc-hexanes) afforded the title compound (12 mg, 19%) as a white solid: ¹H NMR (CDCl₃, 600 MHz) δ 7.41 (br s, 1H), 7.27 (m, 2H), 7.16 (m, 3H), 6.98 (d, 1H, J=3.1 Hz), 6.45 (m, 1H), 4.97 (dd, 1H, J=5.1, 7.5 Hz), 2.55 (t, 1H, J=7.7 Hz), 1.98 (m, 1H), 1.89 (m, 1H), 1.56 (m, 2H), 1.45 (m, 2H), 1.39 (m, 2H), 1.31 (m, 4H); ¹³C NMR (CDCl₃, 125 MHz) δ 162.5, 152.8, 144.8, 143.7, 142.8, 128.4, 128.3, 125.7, 111.8, 110.4, 67.8, 36.5, 36.0, 31.5, 29.2 (2C), 25.2; HRMS-ESI-TOF m/z 326.1857 ([M+H]⁺, C₁₉H₂₃N₃O₂ requires 326.1863).

1-(5-(Furan-2-yl)-4H-1,2,4-triazol-3-yl)-7-phenyl-heptan-1-one (14c)

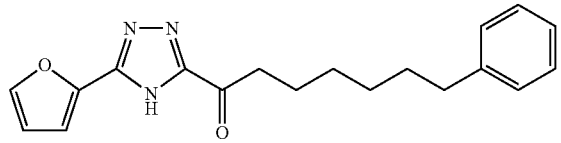 [SMILES: O=C(CCCCCCc1ccccc1)c1nnc(-c2ccco2)[nH]1]

The title compound was prepared from S67 (11 mg, 0.034 mmol) following general procedure B. Flash chromatography (SiO₂, 0.5×7 cm, 50-75% EtOAc-hexanes) afforded the title compound (10 mg, 91%) as a white solid: ¹H NMR (CDCl₃, 600 MHz) δ 7.55 (br s, 1H), 7.26 (dd, 2H, J=6.2, 8.8 Hz), 7.17 (m, 3H), 7.14 (d, 1H, J=3.1 Hz), 6.55 (br s, 1H), 3.16 (t, 2H, J=7.4 Hz), 2.60 (t, 2H, J=7.7 Hz), 1.77 (m, 2H), 1.63 (m, 2H), 1.41 (m, 4H); $^{13}$C NMR (CDCl$_3$, 150 MHz) δ 192.9, 155.9, 152.8, 144.4, 143.8, 142.8, 128.5, 128.4, 125.7, 112.2, 111.7, 39.5, 36.0, 31.4, 29.1 (2C), 23.6; HRMS-ESI-TOF m/z 324.1699 ([M+H]$^+$, C$_{19}$H$_{21}$N$_3$O$_2$ requires 324.1706).

3-(1-(tert-Butyldimethylsilyloxy)-7-phenylheptyl)-5-(thiophen-2-yl)-4H-1,2,4-triazole (S68)

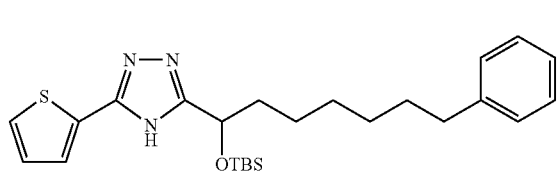 [SMILES: CC(C)(C)[Si](C)(C)OC(CCCCCCc1ccccc1)c1nnc(-c2cccs2)[nH]1]

The title compound was prepared from S19 (127 mg, 0.35 mmol) using general procedure P providing the product (11 mg, 19%) as a colorless oil: $^1$H NMR (CDCl$_3$, 400 MHz) δ 7.68 (d, 1H, J=3.2 Hz), 7.35 (d, 1H, J=4.9 Hz), 7.26 (m, 2H), 7.15 (m, 3H), 7.10 (dd, 1H, J=3.7, 4.8 Hz), 5.06 (t, 1H, J=5.4 Hz), 2.57 (m, 1H), 1.83 (m, 2H), 1.58 (m, 2H), 1.31 (m, 6H), 0.93 (s, 9H), 0.13 (s, 3H), 0.04 (s, 3H).

7-Phenyl-1-(5-(thiophen-2-yl)-4H-1,2,4-triazol-3-yl)-heptan-1-ol (S69)

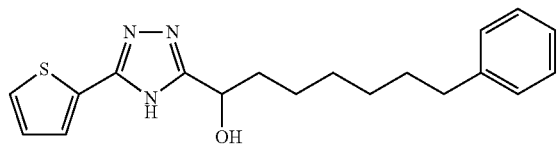

The title compound was prepared from S68 (17 mg, 0.04 mmol) following general procedure G. Flash chromatography (SiO$_2$, 1.0×10 cm, 50-100% EtOAc-hexanes) afforded the title compound (10 mg, 76%) as a white solid: $^1$H NMR (CDCl$_3$, 600 MHz) δ 7.62 (br s, 1H), 7.30 (d, 1H, J=4.6 Hz), 7.25 (m, 2H), 7.14 (m, 3H), 7.01 (m, 1H), 4.96 (m, 1H), 2.54 (t, 1H, J=7.7 Hz), 1.94 (m, 1H), 1.84 (m, 1H), 1.54 (m, 2H), 1.39 (m, 6H).

7-Phenyl-1-(5-(thiophen-2-yl)-4H-1,2,4-triazol-3-yl)-heptan-1-one (14d)

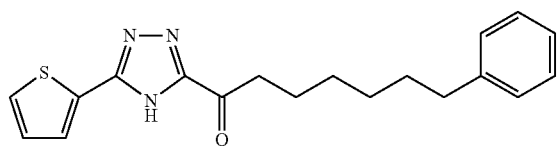 [SMILES: O=C(CCCCCCc1ccccc1)c1nnc(-c2cccs2)[nH]1]

The title compound was prepared from S69 (10 mg, 0.028 mmol) following general procedure B. Flash chromatography (SiO$_2$, 0.5×7 cm, 25% EtOAc-hexanes) afforded the title compound (9.0 mg, 91%) as a white solid: $^1$H NMR (CDCl$_3$, 500 MHz) δ 7.76 (dd, 1H, J=0.8, 3.5 Hz), 7.42 (dd, 1H, J=0.9, 4.9 Hz), 7.27 (m, 2H), 7.16 (m, 3H), 7.13 (dd, 1H, J=3.7, 4.9 Hz), 3.15 (t, 2H, J=7.4 Hz), 2.61 (t, 2H, J=7.7 Hz), 1.78 (m, 2H), 1.64 (m, 2H), 1.42 (m, 4H); $^{13}$C NMR (CDCl$_3$, 125 MHz) δ 192.7, 157.7, 154.3, 142.8, 131.6, 128.5, 128.4, 128.1, 128.0, 127.7, 125.8, 39.4, 36.0, 31.4, 29.1 (2C), 23.6; HRMS-ESI-TOF m/z 340.1485 ([M+H]$^+$, C$_{19}$H$_{21}$N$_3$OS requires 340.1478).

Methyl 5-(1-Hydroxy-7-phenylheptyl)-4H-1,2,4-triazole-3-carboxylate (S70)

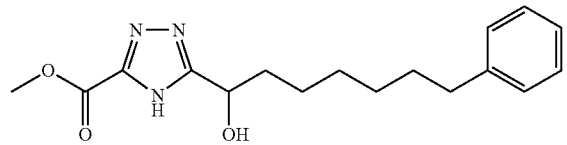 [SMILES: COC(=O)c1nnc(C(O)CCCCCCc2ccccc2)[nH]1]

The amidrazone S19 (200 mg, 0.55 mmol) was dissolved in xylenes (0.7 M) and treated with methyl oxalyl chloride (0.075 mL, 0.83 mmol). The reaction mixture was warmed at 150° C. for 0.75 h. Upon completion, the reaction mixture was diluted with EtOAc, washed with water, saturated aqueous NaHCO$_3$ and saturated aqueous NaCl, and dried over Na$_2$SO$_4$. Evaporation in vacuo yielded the crude deprotected alcohol which was purified by flash chromatography (SiO$_2$, 1.5×10 cm, 10-90% EtOAc-hexanes) to afford the title compound (25 mg, 14%) as a colorless oil: $^1$H NMR (CDCl$_3$, 400 MHz) δ 7.25 (m, 2H), 7.15 (m, 3H), 5.06 (dd, 1H, J=4.6, 8.2 Hz), 3.96 (s, 3H), 2.55 (t, 2H, J=7.7 Hz), 2.00 (m, 1H), 1.87 (m, 1H), 1.58 (m, 2H), 1.43 (m, 2H), 1.31 (m, 4H); $^{13}$C NMR (CDCl$_3$, 125 MHz) δ 162.2, 160.9, 153.8, 142.7, 128.4, 128.3, 125.7, 67.6, 53.2, 36.4, 36.0, 31.5, 29.2 (2C), 25.0.

Methyl 5-(7-Phenylheptanoyl)-4H-1,2,4-triazole-3-carboxylate (14h)

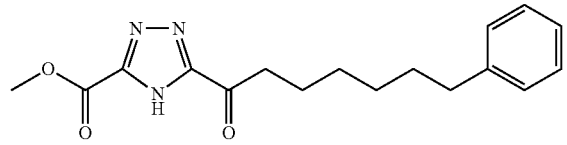 [SMILES: COC(=O)c1nnc(C(=O)CCCCCCc2ccccc2)[nH]1]

The title compound was prepared from S70 (12 mg, 0.038 mmol) following general procedure B. Flash chromatography (SiO$_2$, 0.5×6 cm, 25% EtOAc-hexanes) afforded the title compound (10 mg, 79%) as a colorless oil: $^1$H NMR (CDCl$_3$, 500 MHz) δ 7.26 (t, 2H, J=7.6 Hz), 7.16 (m, 3H), 4.04 (s, 3H), 3.17 (t, 2H, J=7.4 Hz), 2.59 (t, 2H, J=7.7 Hz), 1.75 (m, 2H), 1.62 (m, 2H), 1.38 (m, 4H); $^{13}$C NMR (CDCl$_3$, 125 MHz) δ 192.1, 159.5, 154.2 (2C), 142.7, 128.5, 128.4, 125.8, 53.4, 39.5, 36.0, 31.4, 29.1, 29.0, 23.3; HRMS-ESI-TOF m/z 316.1656 ([M+H]$^+$, C$_{17}$H$_{21}$N$_3$O$_3$ requires 316.1656).

7-Phenyl-1-(4H-1,2,4-triazol-3-yl)-heptan-1-one (14a)

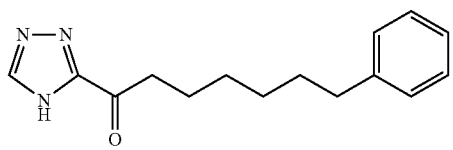 [SMILES: O=C(CCCCCCc1ccccc1)c1nnc[nH]1]

The title compound was prepared by methyl ester hydrolysis and spontaneous decarboxylation from ketone 14h (9.0 mg, 0.03 mmol) following general procedure A. Preparative thin layer chromatography (SiO$_2$, 100% EtOAc) afforded the title compound (4.5 mg, 52%) as a colorless oil: $^1$H NMR (CDCl$_3$, 600 MHz) δ 8.47 (br s, 1H), 7.27 (m, 2H), 7.17 (m, 3H), 3.15 (t, 2H, J=7.4 Hz), 2.61 (t, 2H, J=7.7 Hz), 1.78 (m, 2H), 1.64 (m, 2H), 1.42 (m, 4H); $^{13}$C NMR (CDCl$_3$, 150 MHz) δ 194.3, 157.2, 147.5, 142.8, 128.5, 128.4, 125.8, 39.7, 36.0, 31.4, 29.9, 29.2, 23.7; HRMS-ESI-TOF m/z 258.1599 ([M−H]$^−$, C$_{15}$H$_{19}$N$_3$O requires 258.1606).

1-(1-Methyl-3-(pyridin-2-yl)-1H-1,2,4-triazol-5-yl)-7-phenylheptan-1-ol (S71)

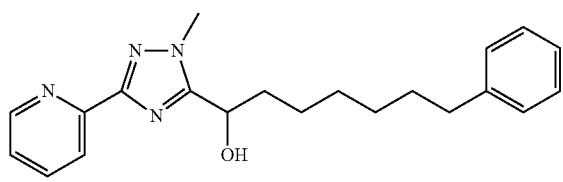 [SMILES: Cn1nc(-c2ccccn2)nc1C(O)CCCCCCc1ccccc1]

A sample of 2-(5-(1-(tert-butyldimethylsilyloxy)-7-phenylheptyl)-4H-1,2,4-triazol-3-yl)-pyridine (S64, 6 mg, 0.01 mmol) was dissolved in MeCN (142 μL) and cooled to 0° C. NaH (60%, 0.4 mg, 0.01 mmol) was added as a solid. After 5 min, MeI (1 μL) was added. Upon completion of the reaction (1.5 h), the solvent was removed in vacuo. The residue was purified by preparative thin layer chromatography (SiO$_2$, 50% EtOAc-hexanes) to afford two separate compounds, the N1 and N2 alkylated triazoles (4.5 mg, 68%) as colorless oils. The individual N2 alkylated TBS ether (15 mg, 0.032 mmol) was dissolved in THF (403 μL), treated with Bu$_4$NF (1 M in THF, 42 μL) and stirred at room temperature for 4.5 h under Ar. The reaction mixture was diluted with EtOAc, washed with saturated aqueous NaCl and dried over Na$_2$SO$_4$. Evaporation in vacuo yielded the crude alcohol that was purified by preparative thin layer chromatography (SiO$_2$, 100% EtOAc) to afford the title compound (7.2 mg, 64%) as a colorless oil (N2 determined by HMBC): $^1$H NMR (CDCl$_3$, 600 MHz) δ 8.71 (d, 1H, J=4.7 Hz), 8.07 (d, 1H, J=7.9 Hz), 7.76 (dt, 1H, J=1.7, 7.8 Hz), 7.29 (dd, 1H, J=5.0, 7.4 Hz), 7.26 (dd, 2H, J=6.5, 8.7 Hz), 7.16 (m, 3H), 4.91 (dd, 1H, J=5.7, 7.9 Hz), 3.97 (s, 3H), 2.58 (t, 2H, J=7.7 Hz), 1.92 (m, 2H), 1.60 (m, 2H), 1.35 (m, 6H); $^{13}$C NMR (CDCl$_3$, 150 MHz) δ 160.1, 158.5, 150.0, 149.7, 142.8, 136.9, 128.5, 128.4, 125.7, 123.9, 121.6, 66.8, 36.4, 36.2, 36.0, 31.5, 29.3, 29.2, 25.4; HRMS-ESI-TOF m/z 351.2181 ([M+H]$^+$, C$_{21}$H$_{26}$N$_4$O requires 351.2179).

1-(1-Methyl-5-(pyridin-2-yl)-1H-1,2,4-triazol-3-yl)-7-phenylheptan-1-ol (S72)

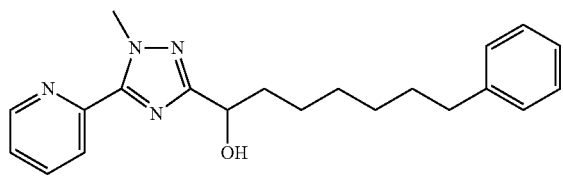 [SMILES: Cn1nc(C(O)CCCCCCc2ccccc2)nc1-c1ccccn1]

A sample of 2-(5-(1-(tert-butyldimethylsilyloxy)-7-phenylheptyl)-4H-1,2,4-triazol-3-yl)-pyridine (S64, 6 mg, 0.01 mmol) was dissolved in MeCN (142 μL) and cooled to 0° C. NaH (60%, 0.4 mg, 0.01 mmol) was added as a solid. After 5 min, MeI (1 μL) was added. Upon completion of the reaction (1.5 h), the solvent was removed in vacuo. The residue was purified by preparative thin layer chromatography (SiO$_2$, 50% EtOAc-hexanes) to afford two separate compounds, the N1 and N2 alkylated triazoles (4.5 mg, 68%) as colorless oils. The individual N1 alkylated TBS ether (6.6 mg, 0.014 mmol) was dissolved in THF (178 μl), treated with Bu$_4$NF (1 M in THF, 18 μL) and stirred at room temperature for 16 h under Ar. The reaction mixture was diluted with EtOAc, washed with saturated aqueous NaCl and dried over Na$_2$SO$_4$. Evaporation in vacuo yielded the crude alcohol that was purified by preparative thin layer chromatography (SiO$_2$, 50% EtOAc-hexanes) to afford the title compound (2.0 mg, 41%) as a colorless oil (N1 isomer determined by HMBC): $^1$H NMR (CDCl$_3$, 600 MHz) δ 8.68 (d, 1H, J=4.7 Hz), 8.19 (d, 1H, J=7.9 Hz). 7.82 (dt, 1H, J=1.8, 7.8 Hz), 7.35 (ddd, 1H, J=1.0, 4.8, 7.5 Hz), 7.26 (m, 2H), 7.15 (m, 3H), 4.82 (br s, 1H), 4.33 (s, 3H), 2.59 (t, 2H, J=7.7 Hz), 1.97 (m, 1H), 1.88 (m, 1H), 1.61 (m, 2H), 1.50 (m, 2H), 1.40 (m, 4H); $^{13}$C NMR (CDCl$_3$, 150 MHz) δ 164.9, 152.3, 149.0, 148.1, 143.0, 137.1, 128.5, 128.4, 125.7, 124.2, 124.1, 68.7, 38.9, 37.1, 36.1, 31.6, 29.5, 29.4, 25.3; HRMS-ESI-TOF m/z 351.2179 ([M+H]$^+$, C$_{21}$H$_{26}$N$_4$O requires 351.2179).

1-(1-Methyl-3-(pyridin-2-yl)-1H-1,2,4-triazol-5-yl)-7-phenylheptan-1-one (16)

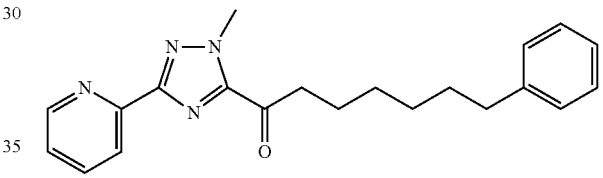

The title compound was prepared from S71 (7.2 mg, 0.021 mmol) following general procedure B. Flash chromatography (SiO$_2$, 0.5×5 cm, 25-50% EtOAc-hexanes) afforded the title compound (6.0 mg, 82%) as a white solid: $^1$H NMR (CDCl$_3$, 600 MHz) δ 8.76 (d, 1H, J=4.7 Hz), 8.16 (d, 1H, J=7.9 Hz), 7.81 (dt, 1H, J=1.7, 7.7 Hz), 7.34 (ddd, 1H, J=1.0, 4.8, 7.6 Hz), 7.26 (m, 2H), 7.17 (m, 3H), 4.28 (s, 3H), 3.26 (t, 2H, J=7.4 Hz), 2.61 (t, 2H, J=7.7 Hz), 1.75 (m, 2H), 1.64 (m, 2H) 1.42 (m, 4H); $^{13}$C NMR (CDCl$_3$, 150 MHz) δ 193.1, 160.1, 150.2, 150.1, 149.3, 142.8, 137.0, 128.5, 128.4, 125.7, 124.3, 121.9, 40.4, 39.2, 36.0, 31.4, 29.2, 29.1, 23.5; HRMS-ESI-TOF m/z 349.2025 ([M+H]$^+$, C$_{21}$H$_{24}$N$_4$O requires 349.2023).

1-(1-Methyl-5-(pyridin-2-yl)-1H-1,2,4-triazol-3-yl)-7-phenylheptan-1-one (17)

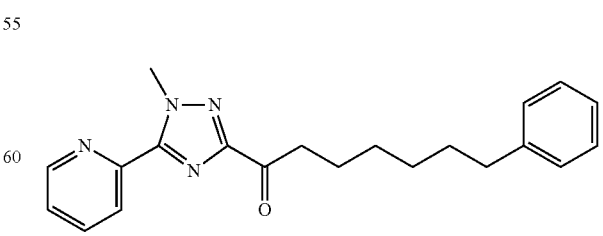

The title compound was prepared from S72 (2.0 mg, 0.006 mmol) following general procedure B. Flash chromatography (SiO$_2$, 0.5×4 cm, 15-35% EtOAc-hexanes) afforded the title compound (2.0 mg, 100%) as a white solid: $^1$H NMR (CDCl$_3$, 600 MHz) δ 8.69 (dd, 1H, J=0.7, 4.8 Hz), 8.33 (dd, 1H, J=0.9, 8.9 Hz), 7.85 (dt, 1H, J=1.7, 7.7 Hz), 7.39 (ddd, 1H, J=0.9, 4.8, 7.6 Hz), 7.26 (m, 2H), 7.16 (m, 3H), 4.44 (s, 3H), 3.10 (t, 2H, J=7.5 Hz), 2.61 (t, 2H, J=7.7 Hz), 1.79 (m, 2H), 1.64 (m, 2H), 1.41 (m, 4H); $^{13}$C NMR (CDCl$_3$, 150 MHz) δ 194.4, 158.5, 153.4, 149.0, 147.6, 142.9, 137.3, 128.5, 128.4, 125.7, 124.7, 124.4, 40.0, 39.7, 36.1, 31.5, 29.2 (2C), 24.2; HRMS-ESI-TOF m/z 349.2020 ([M+H]$^+$, C$_{21}$H$_{24}$N$_4$O requires 349.2023).

1-(4-Methyl-5-(pyridin-2-yl)-4H-1,2,4-triazol-3-yl)-7-phenylheptan-1-one (18)

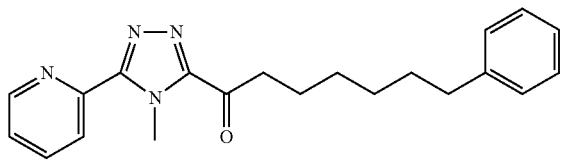 [SMILES: Cn1c(C(=O)CCCCCCc2ccccc2)nnc1-c1ccccn1]

A sample of 14b (3.0 mg, 0.009 mmol) was dissolved in a mixture of MeOH (0.1 mL): CH$_2$Cl$_2$ (0.1 mL). TMSCHN$_2$ (7 μL, 0.013 mmol) was added dropwise causing gas to evolve, and after 0.5 h the reaction mixture was quenched with the dropwise addition of AcOH (50 μL). All volatiles were removed under reduced pressure to afford a residue that was purified by preparative thin layer chromatography (SiO$_2$, 50% EtOAc-hexanes). The title compound (0.735 mg, 23%) was isolated along with the two other regioisomers (16; 1.01 mg, 32%; 17; 0.496 mg, 16%) as a colorless solid: $^1$H NMR (CDCl$_3$, 500 MHz) δ 8.71 (dd, 1H, J=0.9, 4.9 Hz), 8.33 (d, 1H, J=8.0 Hz), 7.88 (dt, 1H, J=1.8, 7.8 Hz), 7.41 (ddd, 1H, J=1.1, 4.9, 7.6 Hz), 7.28 (m, 2H), 7.16 (m, 3H), 4.37 (s, 3H), 3.28 (t, 2H, J=7.4 Hz), 2.61 (t, 2H, J=7.7 Hz), 1.78 (m, 2H), 1.64 (m, 2H), 1.42 (m, 4H); HRMS-ESI-TOF m/z 349.2020 ([M+H]$^+$, C$_{21}$H$_{24}$N$_4$O requires 349.2023).
Tetrazoles (15a-15e, 19a, 19b):

7-Phenyl-1-(2H-tetrazol-5-yl)-heptan-1-ol (S73)

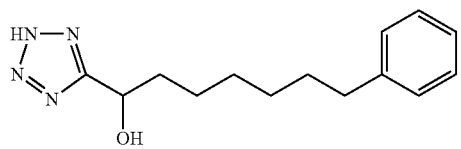 [SMILES: OC(CCCCCCc1ccccc1)c1nn[nH]n1]

A sample of 2-(tert-butyldimethylsilyloxy)-8-phenyloctamide (S19, 335 mg, 1.01 mmol) was dissolved in a mixture of 2-propanol (1.4 mL): water (2.9 mL). NaN$_3$ (197 mg, 3.04 mmol) and ZnBr (250 mg, 1.11 mmol) were added to the reaction mixture as solids, which was subsequently warmed at 100° C. for 90 h. Upon disappearance of starting material, the solution was cooled to room temperature and diluted with EtOAc. 2 N HCl was added to the reaction mixture, which was stirred until all solids dissolved. The organic layer was isolated and the aqueous layer was washed several times with EtOAc. The combine organic phases were dried over Na$_2$SO$_4$ and the solvent was removed under reduced pressure to afford a colorless oil that was used without further purification (270 mg, quant.): $^1$H NMR (CDCl$_3$, 600 MHz) δ 7.25 (m, 2H), 7.15 (m, 3H), 5.26 (m, 1H), 2.57 (t, 2H, J=7.7 Hz), 2.02 (m, 1H), 1.90 (m, 1H), 1.59 (m, 2H), 1.44 (m, 2H), 1.34 (m, 4H); HRMS-ESI-TOF m/z 261.1707 ([M+H]$^+$, C$_{14}$H$_{20}$N$_4$O requires 261.1710).

7-Phenyl-1-(2H-tetrazol-5-yl)-heptan-1-one (15a)

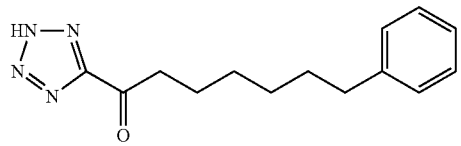 [SMILES: O=C(CCCCCCc1ccccc1)c1nn[nH]n1]

The title compound was prepared from S73 (9.7 mg, 0.037 mmol) following general procedure B. Preparative thin layer chromatography (SiO$_2$, 0-2% AcOH-EtOAc) afforded the title compound (7.0 mg, 73%) as a white solid: $^1$H NMR (CDCl$_3$, 600 MHz) δ 7.23 (m, 2H), 7.15 (d, 2H, J=7.0 Hz), 7.12 (t, 1H, J=7.3 Hz), 3.09 (t, 2H, J=7.4 Hz), 2.60 (t, 2H, J=7.7 Hz), 1.73 (m, 2H), 1.62 (m, 2H), 1.40 (m, 4H); $^{13}$C NMR (CDCl$_3$, 150 MHz) δ 195.7, 162.5, 144.0, 129.4, 129.3, 126.6, 41.5, 36.9, 32.7, 30.2, 30.1, 25.1; HRMS-ESI-TOF m/z 259.1553 ([M+H]$^+$, C$_{14}$H$_{18}$N$_4$O requires 259.1553).

5-(1-(tert-Butyldimethylsilyloxy)-7-phenylheptyl)-2H-tetrazole (S74)

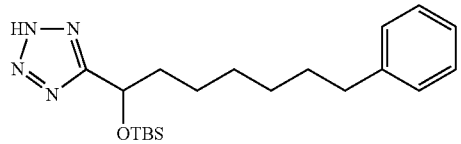 [SMILES: CC(C)(C)[Si](C)(C)OC(CCCCCCc1ccccc1)c1nn[nH]n1]

A solution of S73 (36 mg, 0.14 mmol), TBSCl (63 mg, 0.42 mmol) and imidazole (28 mg, 0.42 mmol) in DMF (0.7 mL) was stirred at room temperature for 72 h before it was diluted with EtOAc, and washed with H$_2$O and saturated aqueous NaCl. The organic layer was dried over Na$_2$SO$_4$ and the solvent was removed under reduced pressure to afford the crude material that was purified by flash chromatography (SiO$_2$, 1.5×15 cm, 10% acetone-hexanes) to afford the title compound (39 mg, 75%) as a colorless oil: $^1$H NMR (CDCl$_3$, 400 MHz) δ 7.26 (dd, 2H, J=6.3, 8.4 Hz), 7.16 (m, 3H), 5.25 (t, 1H, J=5.8 Hz), 2.57 (t, 2H, J=7.7 Hz), 1.85 (m, 2H), 1.58 (m, 2H), 1.31 (m, 6H), 0.90 (s, 9H), 0.13 (s, 3H), 0.01 (s, 3H).

2-(5-(1-(tert-Butyldimethylsilyloxy)-7-phenylheptyl)-2H-tetrazol-2-yl)-pyridine (S75)

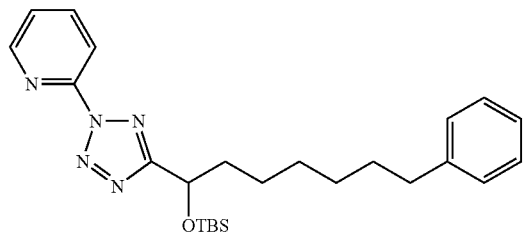 [SMILES: CC(C)(C)[Si](C)(C)OC(CCCCCCc1ccccc1)c1nnn(-c2ccccn2)n1]

In a gas tight vessel, a solution of 5-(1-tert-butyldimethylsilyloxy)-7-phenylheptyl)-2H-tetrazole (S74, 16 mg, 0.043 mmol), 2-iodopyridine (7 μL, 0.064 mmol), CuI (1 mg, 0.004 mmol), K$_2$CO$_3$ (12 mg, 0.085 mmol), and N,N-dimethylethylene diamine (1 μL, 0.006 mmol) in DMF (200 μL) was purged with Ar and sealed. The reaction mixture was warmed at 100° C. for 18 h before it was cooled to room temperature, diluted with EtOAc, and washed with H₂O, 9:1 NH₄OH: saturated aqueous NH₄Cl and saturated aqueous NaCl. The organic layer was dried over Na₂SO₄ and the solvent was removed under reduced pressure to afford the crude material that was purified by flash chromatography (SiO₂, 1.5×15 cm, 5-10% acetone-hexanes) to afford the title compound (4.0 mg, 21%) as a colorless oil: ¹H NMR (CDCl₃, 400 MHz) δ 8.69 (dd, 1H, J=0.9, 4.8 Hz), 8.16 (d, 1H, J=7.5 Hz), 7.98 (dt, 1H, J=1.8, 7.9 Hz), 7.48 (m, 1H), 7.26 (m, 2H), 7.16 (m, 3H), 5.16 (dd, 1H, J=5.9, 7.4 Hz), 2.58 (t, 2H, J=7.7 Hz), 1.99 (m, 2H), 1.60 (m, 2H), 1.34 (m, 6H), 0.88 (s, 9H), 0.10 (s, 3H), −0.02 (s, 3H); ¹³C NMR (CDCl₃, 150 MHz) δ 169.7, 149.6, 149.0, 142.9, 139.5, 128.5, 128.4, 125.7, 125.0, 115.2, 67.4, 37.5, 36.1, 31.5, 29.3, 25.9 (3C), 25.4, 18.4, −4.1, −4.8; HRMS-ESI-TOF m/z 452.2823 ([M+H]⁺, C₂₅H₃₇N₅OSi requires 452.2840).

7-Phenyl-1-(2-(pyridin-2-yl)-2H-tetrazol-5-yl)-heptan-1-ol (S76)

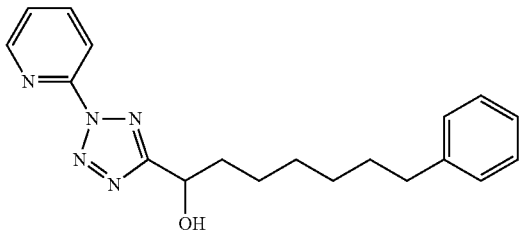

The title compound was prepared from S75 (4.4 mg, 0.009 mmol) following general procedure G. Flash chromatography (SiO₂, 0.5×4 cm, 20-50% EtOAc-hexanes) afforded the title compound (2.7 mg, 79%) as a white solid: ¹H NMR (CDCl₃, 600 MHz) δ 8.69 (dd, 1H, J=1.1, 4.7 Hz), 8.18 (d, 1H, J=8.1 Hz), 8.00 (m, 1H), 7.50 (ddd, 1H, J=0.7, 4.8, 7.4 Hz), 7.26 (m, 2H), 7.16 (m, 3H), 5.16 (m, 1H), 2.59 (t, 2H, J=7.7 Hz), 2.48 (d, 1H(—OH), J=6.1 Hz), 2.07 (m, 2H), 1.61 (m, 2H), 1.52 (m, 2H), 1.40 (m, 4H); ¹³C NMR (CDCl₃, 150 MHz) δ 169.5, 149.6, 148.8, 142.9, 139.6, 128.5, 128.4, 125.7, 125.3, 115.3, 67.0, 36.7, 36.1, 31.5, 29.3 (2C), 25.2; HRMS-ESI-TOF m/z 338.1966 ([M+H]⁺, C₁₉H₂₃N₅O requires 338.1975).

7-Phenyl-1-(2-(pyridin-2-yl)-2H-tetrazol-5-yl)-heptan-1-one (15b)

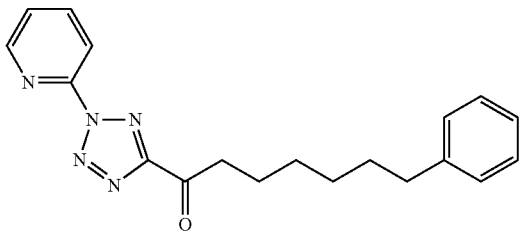 [SMILES: O=C(CCCCCCc1ccccc1)c1nnn(-c2ccccn2)n1]

The title compound was prepared from S76 (2.7 mg, 0.007 mmol) following general procedure B. Flash chromatography (SiO₂, 0.5×4 cm, 10-30% EtOAc-hexanes) afforded the title compound (2.7 mg, 99%) as a white solid: ¹H NMR (CDCl₃, 600 MHz) δ 8.74 (m, 1H), 8.23 (m, 1H), 8.05 (dt, 11-1, J=1.6, 7.9 Hz), 7.57 (dd, 1H, J=4.8, 7.5 Hz), 7.27 (t, 2H, J=7.6 Hz), 7.17 (m, 3H), 3.26 (t, 2H, J=7.4 Hz), 2.61 (t, 2H, J=7.7 Hz), 1.83 (m, 2H), 1.64 (m, 2H), 1.43 (m, 4H); ¹³C NMR (CDCl₃, 150 MHz) δ 191.5, 162.5, 149.9, 148.6, 142.8, 139.8, 128.5, 128.4, 126.0, 125.8, 115.9, 41.0, 36.0, 31.4, 29.1, 29.0, 23.5; HRMS-ESI-TOF m/z 336.1813 ([M+H]⁺, C₁₉H₂₁N₅O requires 336.1819).

5-(1-(tert-Butyldimethylsilyloxy)-7-phenylheptyl)-2-(furan-2-yl)-2H-tetrazole (S77)

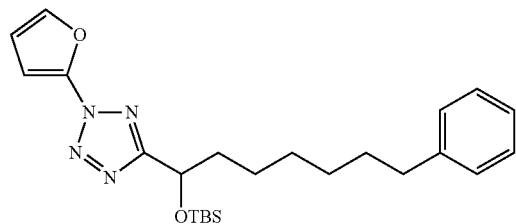 [SMILES: CC(C)(C)[Si](C)(C)OC(CCCCCCc1ccccc1)c1nnn(-c2ccco2)n1]

A solution of 5-(1-(tert-butyldimethylsilyloxy)-7-phenylheptyl)-2H-tetrazole (S74, 12 mg, 0.032 mmol), 2-furanyl(phenyl)iodonium tosylate (see Carroll et al., Tetrahedron Lett. 2000, 41, 5393-5396) (35 mg, 0.08 mmol), Cu(OAc)₂ (6 mg, 0.032 mmol), and Et₃N (5.5 μL, 0.038 mmol) in CH₂Cl₂ (350 μL) was purged with Ar and sealed in a vial. The reaction mixture was stirred at room temperature for 18 h before it was diluted with EtOAc, and washed with H₂O, saturated aqueous NH₄Cl and saturated aqueous NaCl. The organic layer was dried over Na₂SO₄ and the solvent was removed under reduced pressure to afford both the phenyl- and furan-substituted material, which was purified by preparative thin layer chromatography (SiO₂, 5% acetone-hexanes) to afford the title compound (5.8 mg, 41%) as a colorless oil: ¹H NMR (CDCl₃, 500 MHz) δ 7.47 (dd, 1H, J=1.0, 2.0 Hz), 7.26 (m, 2H), 7.16 (m, 3H), 6.78 (dd, 1H, J=1.0, 3.4 Hz), 6.60 (dd, 1H, J=2.0, 3.4 Hz), 5.10 (dd, 1H, J=5.9, 7.4 Hz), 2.59 (t, 2H, J=7.7 Hz), 1.95 (m, 2H), 1.60 (m, 2H), 1.34 (m, 6H), 0.88 (s, 9H), 0.10 (s, 3H), −0.01 (s, 3H).

1-(2-(Furan-2-yl)-2H-tetrazol-5-yl)-7-phenylheptan-1-ol (S78)

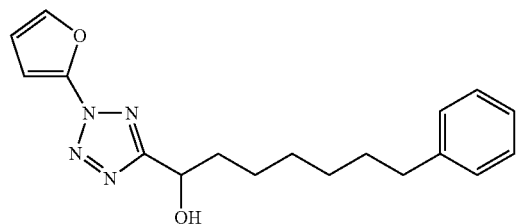 [SMILES: OC(CCCCCCc1ccccc1)c1nnn(-c2ccco2)n1]

The title compound was prepared from S77 (8.0 mg, 0.018 mmol) following general procedure G. Flash chromatography (SiO₂, 0.5×54 cm, 20% EtOAc-hexanes) afforded the title compound (5.9 mg, 100%) as a white solid: ¹H NMR (CDCl₃, 600 MHz) δ 7.48 (dd, 1H, J=1.0, 2.0 Hz), 7.26 (m, 2H), 7.17 (m, 3H), 6.80 (dd, 1H, J=0.8, 3.5 Hz), 6.61 (dd, 1H, J=1.8, 3.5 Hz), 5.11 (dd, 1H, J=5.6, 7.7 Hz), 2.59 (t, 2H, J=7.7 Hz), 2.03 (m, 2H), 1.62 (m, 2H), 1.51 (m, 2H), 1.39 (m, 4H);

$^{13}$C NMR (CDCl$_3$, 150 MHz) δ 169.1, 143.1, 142.9, 141.5, 128.5, 128.4, 125.7, 112.3, 101.7, 66.8, 36.6, 36.1, 31.5, 29.3, 29.2, 25.1; HRMS-ESI-TOF m/z 327.1822 ([M+H]$^+$, C$_{18}$H$_{22}$N$_4$O$_2$ requires 327.1815).

1-(2-(Furan-2-yl)-2H-tetrazol-5-yl)-7-phenylheptan-1-one (15c)

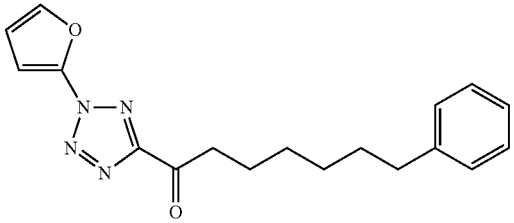 [SMILES: O=C(CCCCCCc1ccccc1)c1nnn(-c2ccco2)n1]

The title compound was prepared from S78 (5.9 mg, 0.018 mmol) following general procedure B. Flash chromatography (SiO$_2$, 0.5×5 cm, 10-20% EtOAc-hexanes) afforded the title compound (5.9 mg, 99%) as a white solid: $^1$H NMR (CDCl$_3$, 500 MHz) δ 7.61 (dd, 1H, J=1.0, 1.9 Hz), 7.35 (td, 2H, J=2.8, 6.6 Hz), 7.25 (m, 3H), 7.01 (dd, 1H, J=0.9, 3.5 Hz), 6.74 (dd, 1H, J=2.0, 3.5 Hz), 3.28 (t, 2H, J=7.4 Hz), 2.69 (t, 2H, J=7.7 Hz), 1.90 (m, 2H), 1.73 (m, 2H), 1.51 (m, 4H); $^{13}$C NMR (CDCl$_3$, 125 MHz) δ 191.2, 162.1, 142.8, 142.7, 142.2, 128.5, 128.4, 125.8, 112.5, 102.8, 40.9, 36.0, 31.4, 29.1 (2C), 23.6; HRMS-ESI-TOF m/z 325.1666 ([M+H]$^+$, C$_{18}$H$_{20}$N$_4$O$_2$ requires 325.1659).

5-(1-(tert-Butyldimethylsilyloxy)-7-phenylheptyl)-2-(thiophen-2-yl)-2H-tetrazole (S79)

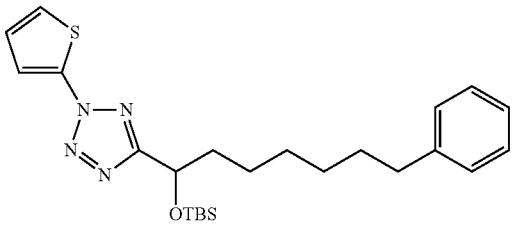

A solution of 5-(1-(tert-butyldimethylsilyloxy)-7-phenylheptyl)-2H-tetrazole (S74, 12 mg, 0.032 mmol), 2-thienyl-(phenyl)iodonium tosylate[4] (35 mg, 0.08 mmol), Cu(OAc)$_2$ (6 mg, 0.032 mmol), and Et$_3$N (5.5 μL, 0.038 mmol) in CH$_2$Cl$_2$ (350 μL) was purged with Ar and sealed in a vial. The reaction mixture was stirred at room temperature for 18 h before it was diluted with EtOAc, and washed with H$_2$O, saturated aqueous NH$_4$Cl and saturated aqueous NaCl. The organic layer was dried over Na$_2$SO$_4$ and the solvent was removed under reduced pressure to afford both the phenyl- and thiophene-substituted material, which was purified by preparative thin layer chromatography (SiO$_2$, 5% acetone-hexanes) to afford the title compound (4.7 mg, 32%) as a colorless oil: $^1$H NMR (CDCl$_3$, 500 MHz) δ 7.62 (dd, 1H, J=1.4, 3.7 Hz), 7.26 (m, 3H), 7.16 (m, 3H), 7.06 (dd, 1H, J=4.0, 5.4 Hz), 5.08 (dd, 1H, J=5.8, 7.4 Hz), 2.59 (t, 2H, J=7.7 Hz), 1.95 (m, 2H), 1.60 (m, 2H), 1.35 (m, 6H), 0.89 (s, 9H), 0.10 (s, 3H), 0.00 (s, 3H).

7-Phenyl-1-(2-(thiophen-2-yl)-2H-tetrazol-5-yl)-heptan-1-ol (S80)

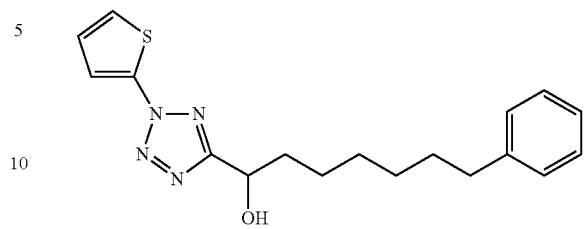

The title compound was prepared from S79 (5.5 mg, 0.012 mmol) following general procedure G. Flash chromatography (SiO$_2$, 0.5×54 cm, 10-20% EtOAc-hexanes) afforded the title compound (3.7 mg, 90%) as a white solid: $^1$H NMR (CDCl$_3$, 500 MHz) δ 7.72 (dd, 1H, J=1.4, 3.8 Hz), 7.36 (m, 1H), 7.34 (d, 2H, J=5.4 Hz), 7.25 (m, 3H), 7.15 (dd, 1H, J=3.9, 5.4 Hz), 5.17 (dd, 1H, J=5.6, 7.6 Hz), 2.68 (t, 2H, J=7.7 Hz), 2.10 (m, 2H), 1.70 (m, 2H), 1.59 (m, 2H), 1.47 (m, 4H); $^{13}$C NMR (CDCl$_3$, 150 MHz) δ 169.0, 142.9, 137.9, 128.5, 128.4, 126.7, 125.7, 124.0, 119.5, 66.8, 36.6, 36.1, 31.5, 29.3 (2C), 25.1; HRMS-ESI-TOF m/z 343.1582 ([M+H]$^+$, C$_{18}$H$_{22}$N$_4$OS requires 343.1587).

7-Phenyl-1-(2-(thiophen-2-yl)-2H-tetrazol-5-yl)-heptan-1-one (15d)

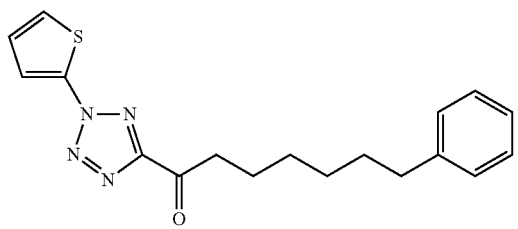

The title compound was prepared from S80 (3.7 mg, 0.011 mmol) following general procedure B. Flash chromatography (SiO$_2$, 0.5×5 cm, 10-20% EtOAc-hexanes) afforded the title compound (2.7 mg, 74%) as a white solid: $^1$H NMR (CDCl$_3$, 600 MHz) δ 7.76 (dd, 1H, J=1.5, 3.9 Hz), 7.36 (dd, 1H, J=1.5, 5.4 Hz), 7.27 (m, 2H), 7.17 (m, 3H), 7.11 (dd, 1H, J=3.9, 5.3 Hz), 3.19 (t, 2H, J=7.4 Hz), 2.61 (t, 2H, J=7.7 Hz), 1.82 (m, 2H), 1.65 (m, 2H), 1.43 (m, 4H); $^{13}$C NMR (CDCl$_3$, 150 MHz) δ 191.4, 162.1, 142.8, 137.3, 128.5, 128.4, 127.0, 125.8, 125.2, 120.7, 40.9, 36.0, 31.4, 29.1 (2C), 23.7; HRMS-ESI-TOF m/z 341.1424 ([M+H]$^+$, C$_{18}$H$_{20}$N$_4$OS requires 341.1431).

5-(1-(tert-Butyldimethylsilyloxy)-7-phenylheptyl)-2-phenyl-2H-tetrazole (S81)

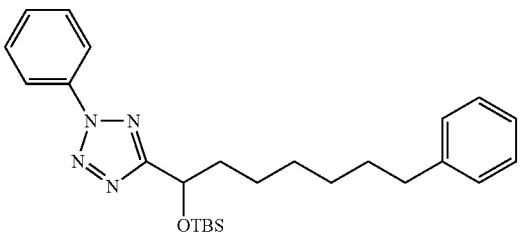

A solution of 5-(1-(tert-butyldimethylsilyloxy)-7-phenylheptyl)-2H-tetrazole (S74, 12 mg, 0.032 mmol), 2-thienyl(phenyl)iodonium tosylate[4] (35 mg, 0.08 mmol), Cu(OAc)$_2$ (6 mg, 0.032 mmol), and Et$_3$N (5.5 µL, 0.038 mmol) in CH$_2$Cl$_2$ (350 µL) was purged with Ar and sealed in a vial. The reaction mixture was stirred at room temperature for 18 h before it was diluted with EtOAc, and washed with H$_2$O, saturated aqueous NH$_4$Cl and saturated aqueous NaCl. The organic layer was dried over Na$_2$SO$_4$ and the solvent was removed under reduced pressure to afford both the phenyl- and thiophene-substituted material, which was purified by preparative thin layer chromatography (SiO$_2$, 5% acetone-hexanes) to afford the title compound (5.0 mg, 35%) as a colorless oil: $^1$H NMR (CDCl$_3$, 500 MHz) δ 8.13 (dd, 2H, J=1.4, 7.7 Hz), 7.55 (m, 2H), 7.48 (m, 1H), 7.26 (m, 2H), 7.16 (m, 3H), 5.11 (dd, 1H, J=5.9, 7.3 Hz), 2.59 (t, 2H, J=7.8 Hz), 1.98 (m, 2H), 1.60 (m, 2H), 1.36 (m, 6H), 0.89 (s, 9H), 0.11 (s, 3H), 0.00 (s, 3H).

7-Phenyl-1-(2-phenyl-2H-tetrazol-5-yl)-heptan-1-ol (S82)

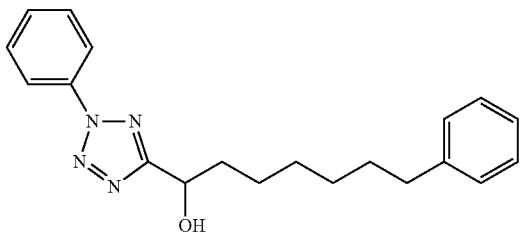 [SMILES: OC(CCCCCCc1ccccc1)c1nnn(-c2ccccc2)n1]

The title compound was prepared from S81 (11 mg, 0.024 mmol) following general procedure G. Flash chromatography (SiO$_2$, 0.5×54 cm, 20% EtOAc-hexanes) afforded the title compound (7.7 mg, 95%) as a white solid: $^1$H NMR (CDCl$_3$, 600 MHz) δ 8.13 (m, 2H), 7.56 (t, 2H, J=7.7 Hz), 7.50 (t, 1H, J=7.3 Hz), 7.26 (dd, 2H, J=6.6, 8.5 Hz), 7.16 (m, 3H), 5.12 (br t, 1H, J=6.5 Hz), 2.60 (t, 2H, J=7.8 Hz), 2.03 (m, 2H), 1.62 (m, 2H), 1.53 (m, 2H), 1.39 (m, 4H); $^{13}$C NMR (CDCl$_3$, 150 MHz) δ 169.8, 142.9, 137.0, 129.9, 129.8, 128.5, 128.4, 125.7, 120.1, 66.9, 36.7, 36.1, 31.5, 29.3 (2C), 25.2; HRMS-ESI-TOF m/z 337.2019 ([M+H]$^+$, C$_{20}$H$_{24}$N$_4$O requires 337.2023).

7-Phenyl-1-(2-phenyl-2H-tetrazol-5-yl)-heptan-1-one (15e)

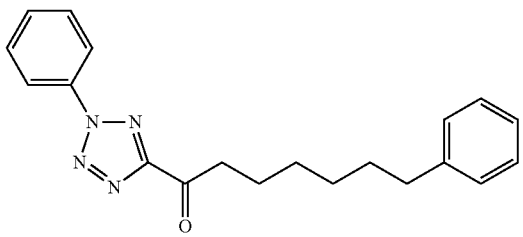

The title compound was prepared from S82 (7.7 mg, 0.023 mmol) following general procedure B. Flash chromatography (SiO$_2$, 0.5×5 cm, 10-20% EtOAc-hexanes) afforded the title compound (7.7 mg, 99%) as a white solid: $^1$H NMR (CDCl$_3$, 500 MHz) δ 8.20 (m, 2H), 7.57 (m, 3H), 7.27 (m, 2H), 7.17 (m, 3H), 3.22 (t, 2H, J=7.4 Hz), 2.62 (t, 2H, J=7.7 Hz), 1.84 (m, 2H), 1.65 (m, 2H), 1.44 (m, 4H); $^{13}$C NMR (CDCl$_3$, 125 MHz) δ 191.8, 162.5, 142.8, 136.6, 130.7, 130.0, 128.5, 128.4, 125.8, 120.5, 40.9, 36.0, 31.4, 29.9, 29.1, 23.7; HRMS-ESI-TOF m/z 335.1871 ([M+H]$^+$, C$_{20}$H$_{22}$N$_4$O requires 335.1866).

1-(2-Methyl-2H-tetrazol-5-yl)-7-phenylheptan-1-ol (S83)

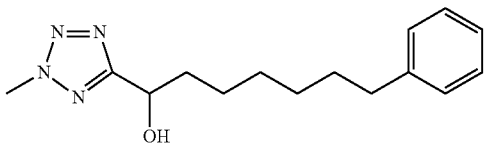 [SMILES: Cn1nnc(C(O)CCCCCCc2ccccc2)n1]

The title compound was prepared as two separable compounds, the N1 and N2 alkylated products (4.0 mg, 28%). The N2 isomer (2.0 mg, 0.005 mmol) was dissolved in THF (64 µL), treated with Bu$_4$NF (1 M in THF, 7 µL) and stirred at room temperature for 2 h under Ar. The reaction mixture was diluted with EtOAc, washed with saturated aqueous NaCl and dried over Na$_2$SO$_4$. Evaporation in vacuo yielded the crude alcohol that was purified by flash chromatography (SiO$_2$, 0.5×5 cm, 10-40% EtOAc-hexanes) to afford the title compound (1.4 mg, 99%) as a colorless oil (N2 determined by HMBC): $^1$H NMR (CDCl$_3$, 400 MHz) δ 7.27 (m, 2H), 7.17 (m, 3H), 5.01 (m, 1H), 4.34 (s, 3H), 2.59 (t, 2H, J=7.7 Hz), 2.33 (d, 1H(—OH), J=5.7 Hz), 1.95 (m, 2H), 1.62 (m, 2H), 1.38 (m, 6H); $^{13}$C NMR (CDCl$_3$, 150 MHz) δ 169.0, 142.9, 128.5, 128.4, 125.7, 66.9, 39.6, 36.7, 36.1, 31.5, 29.3 (2C), 25.1; HRMS-ESI-TOF m/z 275.1875 ([M+H]$^+$, C$_{15}$H$_{22}$N$_4$O requires 275.1866).

1-(1-Methyl-1H-tetrazol-5-yl)-7-phenylheptan-1-ol (S84)

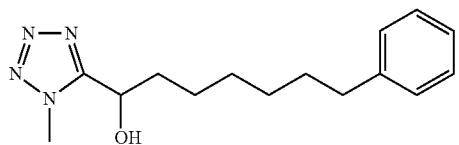 [SMILES: Cn1nnnc1C(O)CCCCCCc1ccccc1]

The title compound was prepared as two separable compounds, the N1 and N2 alkylated products, (4.0 mg, 28%). The N1 isomer (2.0 mg, 0.005 mmol) was dissolved in THF (64 µL), treated with Bu$_4$NF (1 M in THF, 7 µL) and stirred at room temperature for 2 h under Ar. The reaction mixture was diluted with EtOAc, washed with saturated aqueous NaCl and dried over Na$_2$SO$_4$. Evaporation in vacuo yielded the crude alcohol that was purified by flash chromatography (SiO$_2$, 0.5×5 cm, 10-40% EtOAc-hexanes) to afford the title compound (1.2 mg, 85%) as a colorless oil (N1 determined by HMBC): $^1$H NMR (CDCl$_3$, 600 MHz) δ 7.28 (d, 2H, J=7.8 Hz), 7.17 (m, 3H), 5.08 (m, 1H), 4.14 (s, 3H), 2.60 (t, 2H, J=7.7 Hz), 2.25 (d, 1H(—OH), J=6.6 Hz), 1.99 (t, 2H, J=7.7 Hz), 1.62 (m, 2H), 1.37 (m, 6H); $^{13}$C NMR (CDCl$_3$, 150 MHz) δ 156.1, 142.7, 128.5, 128.4, 125.8, 65.6, 36.0, 35.8, 34.6, 31.4, 29.9, 29.2, 25.2; HRMS-ESI-TOF m/z 275.1875 ([M+H]+, C15H22N4O requires 275.1866).

1-(2-Methyl-2H-tetrazol-5-yl)-7-phenylheptan-1-one (19a)

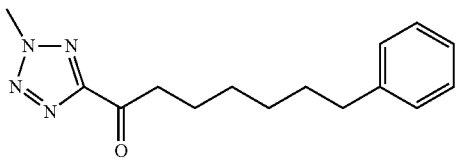 [SMILES: Cn1nnc(C(=O)CCCCCCc2ccccc2)n1]

The title compound was prepared from S83 (1.4 mg, 0.005 mmol) following general procedure B. Flash chromatography (SiO2, 0.5×4 cm, 10-30% EtOAc-hexanes) afforded the title compound (1.3 mg, 94%) as a white solid: $^1$H NMR (CDCl3, 400 MHz) δ 7.27 (m, 2H), 7.17 (m, 3H), 4.44 (s, 3H), 3.14 (t, 2H, J=7.4 Hz), 2.60 (t, 2H, J=7.7 Hz), 1.79 (m, 2H), 1.63 (m, 2H), 1.41 (m, 4H); $^{13}$C NMR (CDCl3, 150 MHz) δ 191.8, 162.8, 142.8, 128.5, 128.4, 125.8, 40.7, 40.1, 36.0, 31.4, 29.9, 29.1, 23.6; HRMS-ESI-TOF m/z 273.1719 ([M+H]+, C15H20N4O requires 273.171).

1-(1-Methyl-1H-tetrazol-5-yl)-7-phenylheptan-1-one (19b)

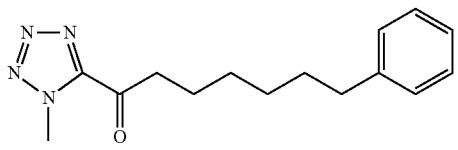 [SMILES: Cn1nnnc1C(=O)CCCCCCc1ccccc1]

The title compound was prepared from S84 (1.2 mg, 0.004 mmol) following general procedure B. Flash chromatography (SiO2, 0.5×4 cm, 10-30% EtOAc-hexanes) afforded the title compound (0.8 mg, 73%) as a white solid: $^1$H NMR (CDCl3, 600 MHz) δ 7.27 (m, 2H), 7.16 (m, 3H), 4.32 (s, 3H), 3.23 (t, 2H, J=7.3 Hz), 2.60 (t, 2H, J=7.7 Hz), 1.76 (m, 2H), 1.63 (m, 2H), 1.40 (m, 4H); $^{13}$C NMR (CDCl3, 150 MHz) δ 191.4, 149.4, 142.7, 128.5, 128.4, 125.8, 41.3, 36.7, 36.0, 31.4, 29.9, 29.1, 29.0; HRMS-ESI-TOF m/z 273.1719 ([M+H]+, C15H20N4O requires 273.171).

Des-keto-1,3,4-Oxadiazoles (33, 34): 4-(Biphenyl-4-yl)but-3-yn-1-ol (S85)

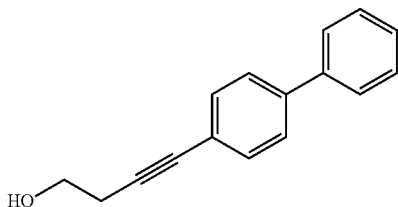 [SMILES: OCCC#Cc1ccc(-c2ccccc2)cc1]

A sample of 4-iodobiphenyl (400 mg, 1.40 mmol) and (PPh3)4Pd (32 mg, 0.02 mmol) were dissolved in Et3N (6 mL) and stirred at 23° C. for 15 min before CuI (13.5 mg, 0.071 mmol) and but-3-yn-1-ol (0.129 mL, 1.71 mmol) were added. The reaction mixture was stirred at 23° C. for 3 h and then diluted with CH2Cl2, washed with saturated aqueous NH4Cl and saturated aqueous NaCl, and dried over Na2SO4. Evaporation in vacuo yielded the crude product. Flash chromatography (SiO2, 20% EtOAc-hexanes) afforded the title compound (270 mg, 85%) as a white solid: $^1$H NMR (CDCl3, 500 MHz) δ 7.59 (dd, 2H, J=8.5 Hz), 7.54 (dd, 4H, J=8.5 Hz), 7.44 (t, 2H, J=7.5 Hz), 7.36 (t, 1H, J=7.5 Hz), 3.84 (t, 2H, J=6.5 Hz), 2.73 (t, 2H, J=6.0 Hz); $^{13}$C NMR (CDCl3, 125 MHz) δ 140.6, 140.2, 132.0, 128.7, 127.5, 126.9, 126.8, 122.2, 87.0, 82.2, 61.1, 23.9.

4-(Biphenyl-4-yl)-butan-1-ol (S86)

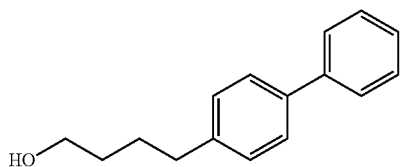 [SMILES: OCCCCc1ccc(-c2ccccc2)cc1]

A sample of S85 (100 mg, 0.449 mmol) and 10% Pd/C (10 mg) were slurried in EtOH (3 mL). The mixture was flushed with H2 and kept under an atmosphere of H2 (50 psi) for 17 h. Upon completion, the reaction mixture was filtered through a pad of Celite and washed with EtOH. Evaporation in vacuo yielded the title compound (101 mg, 98%) as a white solid that required no further purification: $^1$H NMR (CDCl3, 500 MHz) δ 7.61 (dd, 2H, J=8.0 Hz), 7.53 (d, 2H, J=6.0 Hz), 7.43 (t, 2H, J=7.0 Hz), 7.34 (t, 1H, J=7.5 Hz), 7.27 (d, 2H, J=6.5 Hz), 3.68 (t, 2H, J=6.5 Hz), 2.70 (t, 2H, J=7.5 Hz), 1.78-1.72 (m, 2H), 1.67-1.62 (m, 2H), 1.40 (s, 1H); $^{13}$C NMR (CDCl3, 125 MHz) δ 141.3, 141.0, 138.6, 128.7, 128.6, 126.9 (2C), 126.8, 62.6, 35.1, 32.2, 27.4.

4-(Biphenyl-4-yl)-butanoic Acid (S87)

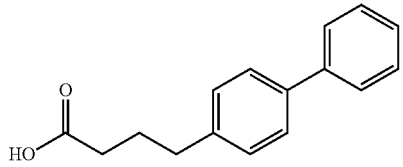 [SMILES: O=C(O)CCCc1ccc(-c2ccccc2)cc1]

A sample of S86 (400 mg, 1.76 mmol) was dissolved in a mixture of CCl4/CH3CN/H2O (5/5/6 mL) and RuCl3·3H2O (7.3 mg, 0.035 mmol) and H5IO6 (1.64 g, 7.21 mmol) were added as solids. The reaction mixture was stirred at 23° C. for 1.5 h and then diluted with EtOAc, washed with saturated aqueous NaCl, and dried over Na2SO4. Evaporation in vacuo yielded the crude product. Flash chromatography (SiO2, 50% EtOAc-hexanes) afforded the title compound (294 mg, 70%) as a white solid: $^1$H NMR (CDCl3, 500 MHz) δ 7.58 (m, 2H), 7.53 (d, 2H, J=6.0 Hz), 7.43 (t, 2H, J=7.0 Hz), 7.33 (t, 1H, J=7.5 Hz), 7.27 (d, 2H, J=7.0 Hz), 2.76 (t, 2H, J=7.5 Hz), 2.45

(t, 2H, J=7.5 Hz), 2.08-2.02 (m, 2H); $^{13}$C NMR (CDCl$_3$, 125 MHz) δ 180.0, 140.9, 138.9, 128.8, 128.6, 127.1, 126.9, 34.5, 33.3, 26.1.

N-(4-(Biphenyl-4-yl)-butanoyl)-6-bromopicolinohydrazide (S88)

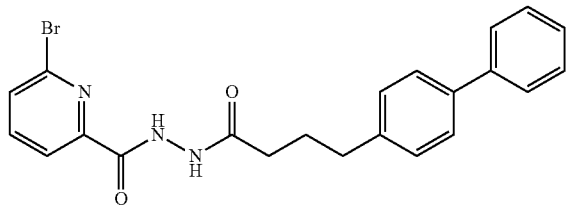 [SMILES: O=C(CCCc1ccc(-c2ccccc2)cc1)NNC(=O)c1cccc(Br)n1]

A sample of S87 (150 mg, 0.625 mmol) and S3 (134 mg, 0.618 mmol) were dissolved in CH$_2$Cl$_2$ (10 mL) and EDCI (177 mg, 0.927 mmol) was added. The reaction mixture was stirred at 23° C. for 16 h and then evaporated in vacuo. The residue was dissolved in EtOAc, washed with 1 N aqueous HCl, 5% aqueous NaHCO$_3$ and saturated aqueous NaCl before the organic phase was dried over Na$_2$SO$_4$. Evaporation in vacuo yielded the crude product that was purified by flash chromatography (SiO$_2$, 50% CH$_2$Cl$_2$—[CH$_2$Cl$_2$/MeOH/NH$_4$OH-89/10/1]) to afford the title compound (180 mg, 66%) as a white solid: $^1$H NMR (CDCl$_3$, 500 MHz) δ 10.23 (s, 1H), 9.62 (s, 1H), 8.00 (dd, 1H, J=7.0 Hz), 7.61-7.54 (m, 3H), 7.48 (d, 2H, J=8.0 Hz), 7.41 (t, 2H, J=7.5 Hz), 7.32 (t, 1H, J=7.0 Hz), 7.24 (d, 2H, J=8.5 Hz), 2.70 (t, 2H, J=7.5 Hz), 2.41 (t, 2H, J=7.5 Hz), 2.10-2.03 (m, 2H); $^{13}$C NMR (CDCl$_3$, 125 MHz) δ 170.1, 159.4, 148.9, 140.8, 140.7, 140.2, 139.4, 138.6, 131.3, 128.8, 128.6, 126.9, 126.7, 121.3, 34.5, 33.1, 26.7.

2-(3-(Biphenyl-4-yl)-propyl)-5-(6-bromopyridin-2-yl)-1,3,4-oxadiazole (S89)

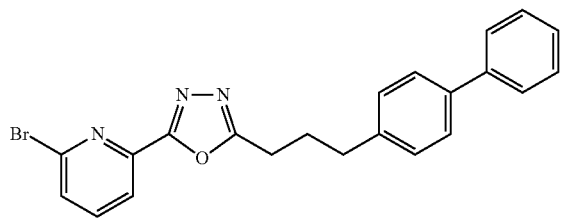 [SMILES: Brc1cccc(-c2nnc(CCCc3ccc(-c4ccccc4)cc3)o2)n1]

A sample of S88 (100 mg, 0.22 mmol) was dissolved in CH$_2$Cl$_2$ (5 mL). TsCl (130 mg, 0.68 mmol) and Et$_3$N (0.096 mL, 0.68 mmol) were added. The reaction mixture was stirred at 23° C. for 16 h and then evaporated in vacuo. The residue was dissolved in EtOAc, washed with saturated aqueous NaCl and dried over Na$_2$SO$_4$. The solvent was removed under reduced pressure. Flash chromatography (SiO$_2$, 95% CH$_2$Cl$_2$—[CH$_2$Cl$_2$/MeOH/NH$_4$OH-89/10/1]) afforded the title compound (85.7 mg, 92%) as a white solid: $^1$H NMR (CDCl$_3$, 500 MHz) δ 8.18 (d, 1H, J=7.5 Hz), 7.70 (t, 1H, J=7.5 Hz), 7.62 (d, 1H, J=8.0 Hz), 7.58 (d, 2H, J=8.5 Hz), 7.52 (d, 2H, J=6.5 Hz), 7.43 (t, 2H, J=7.5 Hz), 7.33 (t, 1H, J=7.5 Hz), 7.28 (d, 2H, J=7.5 Hz), 3.01 (t, 2H, J=7.5 Hz), 2.81 (t, 2H, J=7.5 Hz), 2.26 (q, 2H, J=8.0 Hz); $^{13}$C NMR (CDCl$_3$, 125 MHz) δ 168.0, 162.8, 144.1, 142.3, 140.8, 139.6, 139.2, 139.0, 130.2, 128.8, 128.6, 127.1, 127.0, 126.8, 121.7, 34.5, 27.8, 24.8.

Methyl 6-(5-(3-(Biphenyl-4-yl)-propyl)-1,3,4-oxadiazol-2-yl)-picolinate (33)

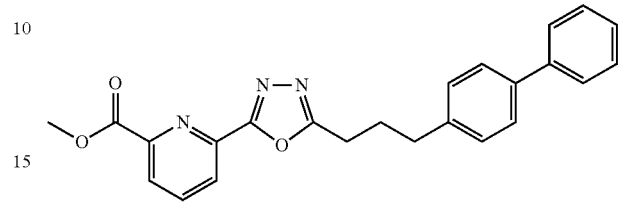

In a gas tight vessel, compound S89 (85.7 mg, 0.203 mmol) was dissolved in 8:2 toluene/MeOH (2.8 mL), then Cl$_2$Pd(PPh$_3$)$_2$ (28 mg, 0.04 mmol) and Et$_3$N (0.085 mL, 0.61 mmol) were added. CO(g) was bubbled through the reaction mixture for 30 min before the reaction vessel was sealed and warmed at 90° C. for 36 h. The reaction mixture was dissolved in EtOAc, washed with water and saturated aqueous NaCl, and dried over Na$_2$SO$_4$. Evaporation in vacuo yielded the crude ester which was purified by flash chromatography (SiO$_2$, 50% EtOAc-[CH$_2$Cl$_2$-hexanes]) to yield the title compound (21.1 mg, 32%) as a white solid: $^1$H NMR (CDCl$_3$, 600 MHz) δ 8.42 (d, 1H, J=8.4 Hz), 8.26 (d, 1H, J=8.4 Hz), 8.03 (t, 1H, J=7.8 Hz), 7.56 (d, 2H, J=8.4 Hz), 7.52 (d, 2H, J=8.4 Hz), 7.42 (t, 2H, J=7.8 Hz), 7.32 (t, 1H, J=7.8 Hz), 7.28 (d, 2H, J=8.4 Hz), 4.04 (s, 3H), 3.03 (t, 2H, J=7.8 Hz), 2.83 (t, 2H, J=7.8 Hz), 2.28 (q, 2H, J=7.8 Hz); $^{13}$C NMR (CDCl$_3$, 150 MHz) δ 168.2, 164.8, 163.3, 148.4, 143.9, 140.9, 139.7, 139.1, 138.4, 128.9, 128.6, 127.2, 127.0, 126.9, 126.8, 126.0, 53.2, 34.5, 27.8, 24.9; HRMS-ESI-TOF m/z 400.1658 ([M+H]$^+$, C$_{24}$H$_{21}$N$_3$O$_3$ requires 400.1656).

6-(5-(3-(Biphenyl-4-yl)-propyl)-1,3,4-oxadiazol-2-yl)-picolinic Acid (34)

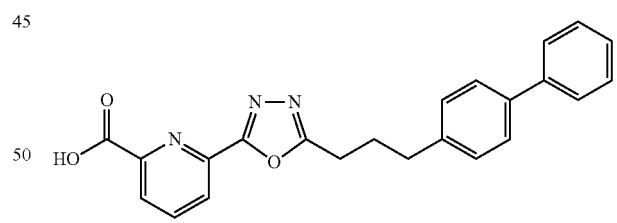

The title compound was prepared from 33 (14.3 mg, 0.035 mmol) following general procedure A. Flash chromatography (SiO$_2$, 95% CH$_2$Cl$_2$—[CH$_2$Cl$_2$/MeOH/NH$_4$OH-89/10/1]) yielded the title compound (11.6 mg, 89%) as a white solid: $^1$H NMR (DMSO-d$_6$+0.1% TFA, 600 MHz) δ 8.29 (d, 1H, J=8.4 Hz), 8.17 (d, 1H, J=8.4 Hz), 8.12 (t, 1H, J=7.8 Hz), 7.57 (d, 2H, J=8.4 Hz), 7.53 (d, 2H, J=8.4 Hz), 7.38 (t, 2H, J=7.8 Hz), 7.30 (t, 1H, J=7.8 Hz), 7.28 (d, 2H, J=8.4 Hz), 2.99 (t, 2H, J=7.8 Hz), 2.75 (t, 2H, J=7.8 Hz), 2.13 (q, 2H, J=7.8 Hz); $^{13}$C NMR (DMSO-d$_6$+0.1% TFA, 150 MHz) δ 168.1, 165.8, 163.6, 149.4, 143.6, 140.7, 140.6, 139.4, 138.5, 129.4, 129.1, 127.5, 127.1, 126.9, 125.9, 34.2, 28.0, 24.6; HRMS-ESI-TOF m/z 386.1505 ([M+H]$^+$, C$_{23}$H$_{19}$N$_3$O$_3$ requires 386.1499).

β-keto-1,3,4-Oxadiazoles (35-38): 2-(Biphenyl-4-yl)-acetaldehyde (S90)

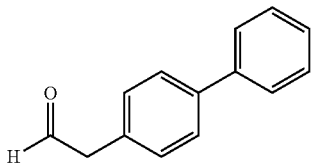 [SMILES: O=CCc1ccc(-c2ccccc2)cc1]

The title compound was prepared from 4-biphenylethanol[1] (150 mg, 0.75 mmol) following general procedure B. Flash chromatography (SiO$_2$, 10% EtOAc-hexanes) yielded the title compound (79.6 mg, 54%) as a white solid: $^1$H NMR (CDCl$_3$, 400 MHz) δ 9.80 (t, 1H, J=1.6 Hz), 7.62 (m, 4H), 7.47 (t, 2H, J=7.8 Hz), 7.38 (t, 1H, J=7.8 Hz), 7.30 (d, 2H, J=7.8 Hz), 3.76 (d, 2H, J=2.0 Hz); $^{13}$C NMR (CDCl$_3$, 100 MHz) δ 199.2, 140.5, 140.3, 130.7, 130.0, 128.7, 127.6, 127.3, 127.0, 50.1.

Methyl 4-(Biphenyl-4-yl)-3-hydroxybutanoate (S91)

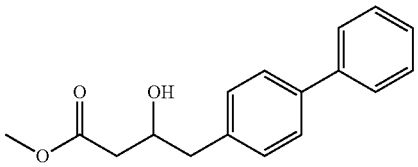 [SMILES: COC(=O)CC(O)Cc1ccc(-c2ccccc2)cc1]

A solution of diisopropylamine (0.241 mL, 1.72 mmol) in anhydrous THF (1.5 mL) was treated with n-BuLi (1.6 M in hexane, 0.7 mL, 1.72 mmol) at −78° C. The mixture was kept at this temperature for 1 h, and then a solution of methyl acetate (0.137 mL, 1.72 mmol) in anhydrous THF (1 mL) was added at −78° C. The reaction mixture was stirred for 1 h at −78° C., and a solution of 2-(biphenyl-4-yl)acetaldehyde (S90, 282 mg, 1.43 mmol) in anhydrous THF (2 mL) was added. The reaction mixture was stirred for another hour, then quenched by the addition of saturated aqueous NH$_4$Cl, which was extracted with EtOAc. The combined extracts were dried over Na$_2$SO$_4$ and the solvent was removed under reduced pressure. Flash chromatography (SiO$_2$, 50% Et$_2$O-hexanes) yielded the title compound (226 mg, 58%) as a white solid: $^1$H NMR (CDCl$_3$, 400 MHz) δ 7.64 (dd, 2H, J=7.2 Hz), 7.58 (dd, 2H, J=8.0 Hz), 7.49 (t, 2H, J=7.6 Hz), 7.38 (t, 1H, J=7.0 Hz), 7.34 (d, 2H, J=8.0 Hz), 4.38-4.34 (m, 1H), 3.71 (s, 3H), 3.35 (s, 1H(—OH)), 2.97-2.82 (m, 2H), 2.61-2.43 (m, 2H); $^{13}$C NMR (CDCl$_3$, 75 MHz) δ 172.7, 140.5, 139.1, 136.6, 129.6, 128.5, 126.9, 126.7, 68.7, 51.4, 42.3, 40.3.

Methyl 4-(Biphenyl-4-yl)-3-(tert-butyldimethylsilyloxy)-butanoate (S92)

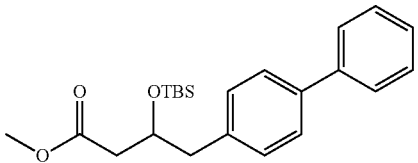 [SMILES: COC(=O)CC(Cc1ccc(-c2ccccc2)cc1)O[Si](C)(C)C(C)(C)C]

A sample of S91 (200 mg, 0.73 mmol) was dissolved in DMF (2 mL). Imidazole (126 mg, 1.84 mmol) and TBSCl (134 mg, 0.88 mmol) were added as solids. The reaction mixture was stirred at 23° C. for 16 h. The mixture was evaporated in vacuo, dissolved in EtOAc, washed with saturated aqueous NaCl and dried over Na$_2$SO$_4$. The solvent was removed under reduced pressure. Flash chromatography (SiO$_2$, 5% Et$_2$O-hexanes) yielded the title compound (211 mg, 80%) as a colorless oil: $^1$H NMR (CDCl$_3$, 500 MHz) δ 7.63 (dd, 2H, J=8.5 Hz), 7.56 (dd, 2H, J=8.0 Hz), 7.46 (t, 2H, J=7.5 Hz), 7.36 (t, 1H, J=8.5 Hz), 7.30 (d, 2H, J=7.0 Hz), 4.42 (q, 1H, J=6.5 Hz), 3.69 (s, 3H), 2.94-2.86 (m, 2H), 2.52 (d, 2H, J=6.5 Hz), 0.92 (s, 9H), 0.07 (s, 3H), −0.02 (s, 3H); $^{13}$C NMR (CDCl$_3$, 125 MHz) δ 171.9, 140.9, 139.2, 137.1, 130.1, 128.6, 127.0, 126.9, 70.6, 51.3, 43.7, 42.0, 25.7, 17.9 (3C), −4.8, −5.1.

4-(Biphenyl-4-yl)-3-(tert-butyldimethylsilyloxy)-butanoic Acid (S93)

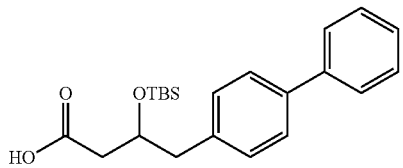 [SMILES: CC(C)(C)[Si](C)(C)OC(CC(=O)O)Cc1ccc(-c2ccccc2)cc1]

The title compound was prepared from S92 (211.3 mg, 0.54 mmol) following general procedure A. Evaporation in vacuo yielded the crude acid. Flash chromatography (SiO$_2$, 5% Et$_2$O-hexanes) afforded the title compound (185 mg, 92%) as a colorless oil: $^1$H NMR (CDCl$_3$, 600 MHz) δ 7.57 (dd, 2H, J=8.4 Hz), 7.53 (d, 2H, J=8.4 Hz), 7.44 (t, 2H, J=7.0 Hz), 7.32 (t, 1H, J=7.0 Hz), 7.24 (d, 2H, J=7.5 Hz), 4.34-4.30 (q, 1H, J=6.5 Hz), 2.92-2.83 (m, 2H), 2.56-2.49 (m, 2H), 0.87 (s, 9H), 0.04 (s, 3H), −0.06 (s, 3H); $^{13}$C NMR (CDCl$_3$, 150 MHz) δ 174.6, 140.8, 139.5, 136.6, 130.1, 128.7, 127.1, 126.9, 70.7, 43.3, 41.1, 25.7, 17.9 (3C), −4.9, 5.0.

Methyl 6-(2-(4-(Biphenyl-4-yl)-3-(tert-butyldimethylsilyloxy)-butanoyl)-hydrazinecarbonyl)-picolinate (S94)

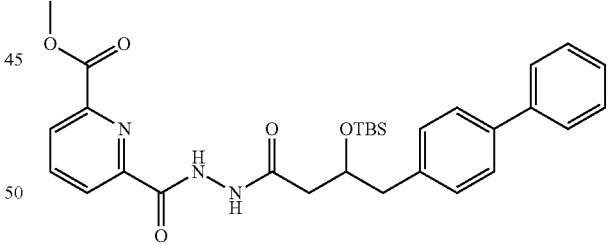

A sample of S93 (100 mg, 0.27 mmol) and methyl 6-(hydrazinecarbonyl)-picolinate (see Zhiqiang et al., *J. Chem. Soc., Dalton Trans.* 2002, 12, 2462-2466) (52.7 mg, 0.27 mmol) were dissolved in CH$_2$Cl$_2$ (4 mL). EDCI (52 mg, 0.27 mmol) was then added as a solid. The reaction mixture was stirred at 23° C. for 16 h. The solvent was evaporated in vacuo and the residue dissolved in EtOAc, washed with 1 N aqueous HCl, 5% aqueous NaHCO$_3$ and saturated aqueous NaCl, and dried over Na$_2$SO$_4$. The solvent was removed under reduced pressure and flash chromatography (SiO$_2$, 20% MeOH—CH$_2$Cl$_2$) afforded the title compound (127 mg, 86%) as a colorless oil: $^1$H NMR (CDCl$_3$, 500 MHz) δ 10.30 (d, 1H, J=5.0 Hz), 9.28 (d, 1H, J=5.0 Hz), 8.32 (dd, 1H, J=8.0 Hz), 8.22 (d, 1H, J=8.0 Hz), 7.98 (t, 1H, J=7.5 Hz), 7.56 (d, 2H, J=7.5 Hz), 7.50 (d, 2H, J=7.5 Hz), 7.40 (t, 2H, J=7.5 Hz), 7.30 (t, 1H, J=7.0 Hz), 7.27 (d, 2H, J=7.5 Hz), 4.33 (q, 1H, J=6.5 Hz), 3.99 (s, 3H), 2.99 (d, 2H, J=6.5 Hz), 2.65-2.49 (m, 2H), 0.89 (s, 9H), 0.05 (s, 3H), −0.07 (s, 3H); $^{13}$C NMR (CDCl$_3$, 125 MHz) δ 168.2, 164.7, 160.1, 148.5, 146.8, 140.8, 139.3, 138.4, 136.9, 130.2, 128.6, 127.9, 127.6, 127.0, 126.9, 126.8, 125.5, 70.7, 53.1, 42.6, 41.4, 25.7, 17.9 (3C), −5.0, −5.1.

Methyl 6-(5-(3-(Biphenyl-4-yl)-2-(tert-butyldimethylsilyloxy)propyl)-1,3,4-oxadiazol-2-yl)-picolinate (S95)

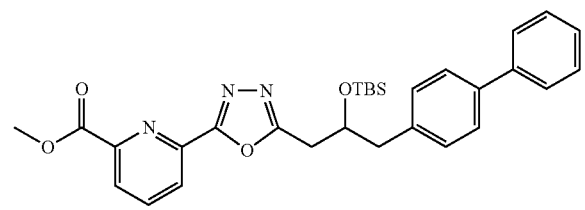 [SMILES: COC(=O)c1cccc(-c2nnc(CC(Cc3ccc(-c4ccccc4)cc3)O[Si](C)(C)C(C)(C)C)o2)n1]

A sample of S94 (127.1 mg, 0.23 mmol) was dissolved in CH$_2$Cl$_2$ (4 mL). TsCl (132.7 mg, 0.69 mmol) and Et$_3$N (0.097 mL, 0.69 mmol) were added. The reaction mixture was stirred at 23° C. for 16 h. The solvent was evaporated in vacuo and the residue was dissolved in EtOAc, washed with saturated aqueous NaCl and dried over Na$_2$SO$_4$. The solvent was removed under reduced pressure, Purification by flash chromatography (SiO$_2$, 1% MeOH—CH$_2$Cl$_2$) afforded the title compound (91.7 mg, 75%) as a yellow oil: $^1$H NMR (CDCl$_3$, 500 MHz) δ 8.37 (dd, 1H, J=7.0 Hz), 8.24 (dd, 1H, J=7.0 Hz), 8.00 (d, 1H, J=8.0 Hz), 7.56 (d, 2H, J=7.5 Hz), 7.51 (d, 2H, J=7.5 Hz), 7.41 (t, 2H, J=7.2 Hz), 7.32-7.30 (m, 3H), 4.49 (q, 1H, J=6.5 Hz), 4.02 (s, 3H), 3.12 (d, 2H, J=6.5 Hz), 2.96-2.94 (m, 2H), 0.80 (s, 9H), −0.09 (s, 3H), −0.11 (s, 3H); $^{13}$C NMR (CDCl$_3$, 125 MHz) δ 166.2, 164.8, 163.3, 148.4, 143.7, 140.8, 139.4, 138.3, 136.5, 130.1, 128.6, 127.9, 127.0, 126.9, 126.8, 126.6, 125.8, 71.1, 43.6, 33.1, 25.6, 17.8 (3C), −5.0, −5.2.

Methyl 6-(5-(3-(Biphenyl-4-yl)-2-hydroxypropyl)-1,3,4-oxadiazol-2-yl)-picolinate (36)

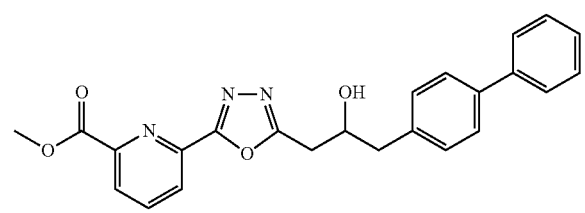 [SMILES: COC(=O)c1cccc(-c2nnc(CC(O)Cc3ccc(-c4ccccc4)cc3)o2)n1]

The title compound was prepared from S95 (11 mg, 0.025 mmol) following general procedure G. Flash chromatography (SiO$_2$, 80% EtOAc-hexanes) afforded the title compound (5.4 mg, 65%) as a colorless oil: $^1$H NMR (CDCl$_3$, 600 MHz) δ 8.41 (d, 1H, J=7.8 Hz), 8.26 (d, 1H, J=7.8 Hz), 8.03 (t, 1H, J=7.8 Hz), 7.57-7.54 (m, 4H), 7.43 (t, 2H, J=7.2 Hz), 7.34-7.33 (m, 3H), 4.56-4.52 (m, 1H), 4.03 (s, 3H), 3.22-3.12 (m, 2H), 3.04-2.99 (m, 2H); $^{13}$C NMR (CDCl$_3$, 150 MHz) δ 166.5, 164.7, 163.4, 148.4, 143.6, 140.7, 139.8, 138.5, 136.2, 129.8, 128.7, 127.4, 127.2, 127.0, 126.9, 126.1, 69.5, 53.2, 42.7, 32.8; HRMS-ESI-TOF m/z 416.1606 ([M+H]$^+$, C$_{24}$H$_{21}$N$_3$O$_4$ requires 416.1605).

6-(5-(3-(Biphenyl-4-yl)-2-hydroxypropyl)-1,3,4-oxadiazol-2-yl)-picolinic Acid (38)

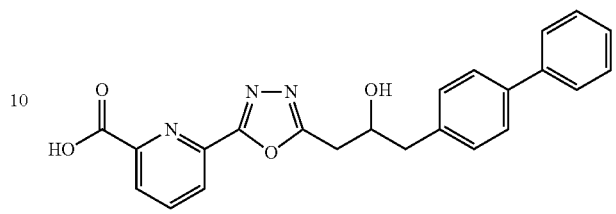

The title compound was prepared from 36 (7.5 mg, 0.017 mmol) following general procedure A. Flash chromatography (SiO$_2$, 5% MeOH—CH$_2$Cl$_2$) afforded the title compound (6.5 mg, 95%) as a white solid: $^1$H NMR (DMSO-d$_6$, 600 MHz) δ 8.26 (dd, 1H, J=8.4 Hz), 8.16 (dd, 1H, J=8.4 Hz), 8.06 (t, 1H, J=7.8 Hz), 7.55-7.51 (m, 4H), 7.36-7.33 (m, 3H), 7.24 (t, 1H, J=7.2 Hz), 4.26-4.22 (m, 1H), 3.13-2.99 (m, 2H), 2.86-2.84 (m, 2H); $^{13}$C NMR (DMSO-d$_6$, 150 MHz) δ 167.2, 166.2, 164.2, 149.9, 144.1, 141.1, 139.6, 139.2, 138.7, 130.9, 129.5, 127.9, 127.5, 127.3, 126.3, 70.2, 43.4, 33.7; HRMS-ESI-TOF m/z 402.1443 ([M+H]$^+$, C$_{23}$H$_{19}$N$_3$O$_4$ requires 402.1448).

Methyl 6-(5-(3-(Biphenyl-4-yl)-2-oxopropyl)-1,3,4-oxadiazol-2-yl)-picolinate (35)

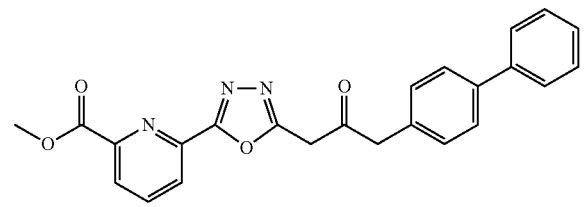 [SMILES: COC(=O)c1cccc(-c2nnc(CC(=O)Cc3ccc(-c4ccccc4)cc3)o2)n1]

The title compound was prepared from 36 (22 mg, 0.052 mmol) following general procedure B. Flash chromatography (SiO$_2$, 5% MeOH—CH$_2$Cl$_2$) afforded the title compound (10.2 mg, 47%) as a white solid: $^1$H NMR (CDCl$_3$, 600 MHz) δ 8.39 (d, 1H, J=7.8 Hz), 8.25 (d, 1H, J=7.8 Hz), 8.02 (t, 1H, J=7.8 Hz), 7.59-7.54 (m, 4H), 7.44 (t, 2H, J=7.8 Hz), 7.36-7.30 (m, 2H), 4.19 (s, 2H), 4.02 (s, 3H), 3.93 (s, 2H); $^{13}$C NMR (CDCl$_3$, 150 MHz) δ 199.1, 164.7, 164.1, 162.1, 148.5, 143.5, 140.5, 140.4, 138.4, 131.4, 129.9, 128.7, 127.7, 127.4 (2C), 127.1, 127.0 (2C), 126.1, 53.2, 49.4, 38.9; HRMS-ESI-TOF m/z 414.1460 ([M+H]$^+$, C$_{24}$H$_{19}$N$_3$O$_4$ requires 414.1448).

6-(5-(3-(Biphenyl-4-yl)-2-oxopropyl)-1,3,4-oxadiazol-2-yl)-picolinic Acid (37)

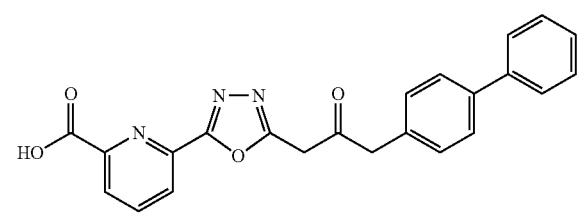 [SMILES: O=C(Cc1ccc(-c2ccccc2)cc1)Cc1nnc(-c2cccc(C(=O)O)n2)o1]

The title compound was prepared from 35 (4.5 mg, 0.010 mmol) following general procedure A. Flash chromatography (SiO$_2$, 10% MeOH—CH$_2$Cl$_2$) afforded the title compound (3.4 mg, 85%) as a yellow solid: $^1$H NMR (DMSO-d$_6$+0.1% TFA, 600 MHz) δ 8.29 (d, 1H, J=7.8 Hz), 8.17 (d, 1H, J=7.8 Hz), 8.08 (t, 1H, J=7.8 Hz), 7.57-7.55 (m, 4H), 7.36 (t, 2H, J=7.8 Hz), 7.29-7.25 (m, 2H), 4.02 (s, 4H); $^{13}$C NMR (DMSO-d$_6$+0.1% TFA, 150 MHz) δ 202.1, 166.2, 164.7, 163.3, 150.0, 143.1, 142.2, 141.0, 139.9, 133.9, 131.1, 128.9, 128.0, 127.7, 127.5, 127.3, 126.7, 48.0, 39.8; HRMS-ESI-TOF m/z 400.1299 ([M+H]$^+$, C$_{23}$H$_{17}$N$_3$O$_4$ requires 400.1292).

| Purity Analysis[a] | |
|---|---|
| Compd | Purity |
| 4c | 95 |
| 4d | 95 |
| 5c | 98 |
| 6 | 98 |
| 8a | 96 |
| 8d | >99 |
| 8f | 99 |
| 8g | 97 |
| 8h | 95 |
| 9a | 96 |
| 9b | 96 |
| 9c | 95 |
| 9d | 97 |
| 9f | 97 |
| 9g | 95 |
| 10a | 96 |
| 10b | 96 |
| 10c | 95 |
| 10d | 97 |
| 10f | 97 |
| 10g | 95 |
| 10h | 97 |
| 11a | 98 |
| 11b | >99 |
| 11c | 99 |
| 11d | 96 |
| 11f | 96 |
| 11g | >99 |
| 12a | 95 |
| 12b | >99 |
| 12c | >99 |
| 12d | 95 |
| 12f | 99 |
| 12g | >99 |
| 12h | 96 |
| 13a | >99 |
| 13b | >99 |
| 13c | >99 |
| 13d | >99 |
| 13f | 97 |
| 13g | 98 |
| 14a | 99 |
| 14b | >99 |
| 14c | 99 |
| 14d | 98 |
| 14h | 98 |
| 15a | 97 |
| 15b | 99 |
| 15c | >99 |
| 15d | 98 |
| 15e | >99 |
| 16 | 98 |
| 17 | 96 |
| 18 | 96 |
| 19a | 97 |
| 19b | 96 |
| 20 | >99 |
| 21 | 95 |
| 22 | 95 |
| 23 | 99 |
| 24 | 95 |

| Purity Analysis[a] | |
|---|---|
| Compd | Purity |
| 25 | 96 |
| 26 | 95 |
| 27 | 96 |
| 28 | 98 |
| 29 | 98 |
| 30 | 98 |
| 33 | 98 |
| 34 | 98 |
| 35 | 96 |
| 36 | 97 |
| 37 | 96 |
| 38 | 98 |

[a]Purity of each compound was determined on an Agilent 1100 LC/MS instrument on a ZORBAX® SB-C18, 3.5 mm, 4.6×50, a flow rate of 0.75 mL/min, detection at 220 and 254 nm, with a 10-98% acetonitrile/water/0.1% formic acid gradient and a 50-98% acetonitrile/water/0.1% formic acid gradient.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

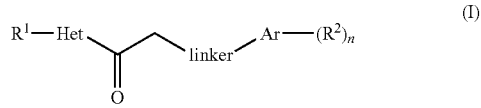

wherein
R$^1$ is one of the following:
(a) furanyl, thiophenyl, or pyridinyl,
(b) —CO$_2$(C$_1$-C$_8$)alkyl or —CO$_2$H, or
(c) furanyl, thiophenyl, or pyridinyl, each of which substituted with one or more substituents selected from the group consisting of alkyl, halo, alkoxycarbonyl, carboxy, and cyano;
Het is thiazole;
linker is a (C$_1$-C$_{20}$)alkyl chain;
Ar is phenyl;
n is 1;
R$^2$ is H,
or a pharmaceutically acceptable salt thereof.

2. The compound of claim 1 wherein R$^1$ is 2-pyridyl, 2-furyl, or 2-thiophenyl.

3. The compound of claim 1 wherein R$^1$ is —CO$_2$H or —CO$_2$Me.

4. The compound of claim 1 wherein the linker is a (C$_1$-C$_8$)alkyl.

5. A composition comprising a compound of claim 1 and a diluent or carrier.

6. A compound of formula (I) of claim 1 selected from
7-Phenyl-1-(5-(pyridin-2-yl)-thiazol-2-yl)-heptan-1-one;
1-(5-(Furan-2-yl)-thiazol-2-yl)-7-phenylheptan-1-one;
7-Phenyl-1-(5-(thiophen-2-yl)-thiazol-2-yl)-heptan-1-one;
Methyl 6-(2-(7-Phenylheptanoyl)-thiazol-5-yl)-picolinate;
6-(2-(7-Phenylheptanoyl)thiazol-5-yl)-picolinic acid;

7-Phenyl-1-(5-(pyridin-2-yl)-1,3,4-thiadiazol-2-yl)-heptan-1-one;

1-(5-(Furan-2-yl)-1,3,4-thiadiazol-2-yl)-7-phenylheptan-1-one;

7-Phenyl-1-(5-(thiophen-2-yl)-1,3,4-thiadiazol-2-yl)-heptan-1-one;

1-(5-(6-Bromopyridin-2-yl)-1,3,4-thiadiazol-2-yl)-7-phenylheptan-1-one;

Methyl 6-(5-(7-Phenylheptanoyl)-1,3,4-thiadiazol-2-yl)-picolinate;

6-(5-(7-Phenylheptanoyl)-1,3,4-thiadiazol-2-yl)-picolinic acid;

Methyl 5-(7-Phenylheptanoyl)-1,3,4-thiadiazole-2-carboxylate;

or a salt thereof.

* * * * *

UNITED STATES PATENT AND TRADEMARK OFFICE
CERTIFICATE OF CORRECTION

PATENT NO. : 8,987,312 B2
APPLICATION NO. : 13/002905
DATED : March 24, 2015
INVENTOR(S) : Dale L. Boger It is certified that error appears in the above-identified patent and that said Letters Patent is hereby corrected as shown below:

ON THE TITLE PAGE

Item (57), in "Abstract", in column 2, line 1, delete "-αketoheterocyclic" and insert --α-ketoheterocyclic--, therefor On page 2, in column 1, under "Other Publications", line 4-5, delete "Opt imiza t ion of the cent r a l heterocycle of alpha-ketoheterocyc l e" and insert --Optimization of the central heterocycle of alpha-ketoheterocycle--, therefor

IN THE SPECIFICATION

In column 4, line 11, after "formula", insert --I:--, therefor

In column 7, line 17, delete "Spiro" and insert --spiro--, therefor

In column 10, line 45, delete "with" (1st occurrence) and insert --with $^{14}C$),--, therefor In column 14, line 21, delete "of" and insert --of,--, therefor In column 16, line 66, delete "R$_2$" and insert --R$^2$--, therefor In column 36, line 3-9, delete " 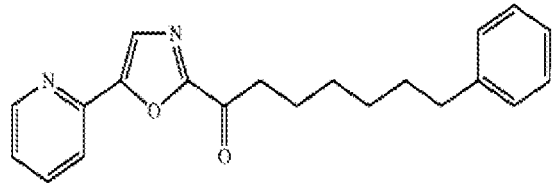 " and Signed and Sealed this
Twentieth Day of October, 2015

Michelle K. Lee
*Director of the United States Patent and Trademark Office* insert -- 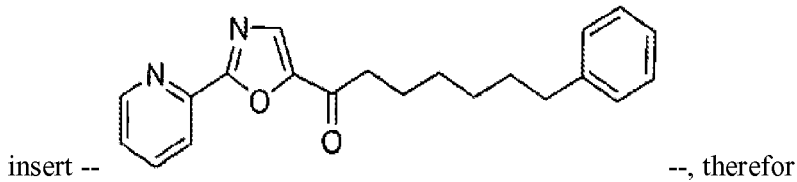 --, therefor

In column 43, line 12 (Approx.), delete "(300pM)" and insert --(300 pM)--, therefor In column 54, line 5, delete "0° C." and insert --0 °C.--, therefor In column 56, line 2, delete "0° C." and insert --0 °C.--, therefor In column 62, line 55, delete "0° C." and insert --0 °C.--, therefor In column 65, line 10-18, delete " 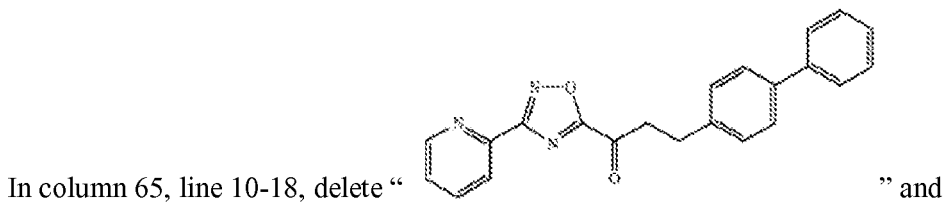 " and insert -- 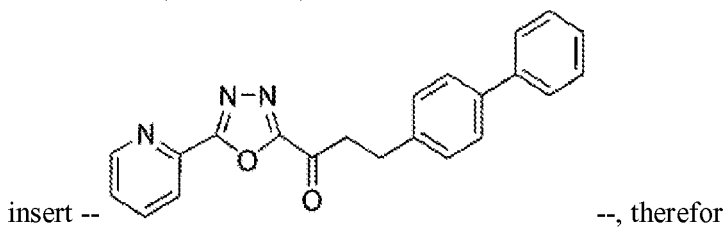 --, therefor In column 67, line 1, delete "Z)" and insert --(Z)--, therefor In column 67, line 2, delete "(4b" and insert --(4b)--, therefor In column 69, line 48, delete "0° C." and insert --0 °C.--, therefor In column 71, line 57, delete "0° C." and insert --0 °C.--, therefor In column 72, line 40, delete "0° C." and insert --0 °C.--, therefor In column 73, line 32, delete "(175 L)" and insert --(175 μL)--, therefor In column 73, line 33, delete "0° C." and insert --0 °C.--, therefor In column 78, line 20 (Approx.), delete "8:3-7" and insert --8.3-7--, therefor In column 78, line 43, before "NMR", insert --[1]H--, therefor In column 79, line 27, "0° C." and insert --0 °C.--, therefor In column 85, line 51, delete "0° C." and insert --0 °C.--, therefor In column 86, line 63, delete "I=0.6," and insert --J=0.6,--, therefor In column 87, line 12, delete "(31 pt," and insert --(31 μL,--, therefor In column 88, line 4 (Approx.), delete "Z)" and insert --(Z)--, therefor In column 88, line 4 (Approx.), delete "(5a" and insert --(5a)--, therefor In column 88, line 30 (Approx.), delete "Z)" and insert --(Z)--, therefor In column 88, line 30 (Approx.), delete "(5b" and insert --(5b)--, therefor In column 88, line 57 (Approx.), delete "Z)" and insert --(Z)--, therefor In column 88, line 57 (Approx.), delete "(5c" and insert --(5c)--, therefor In column 91, line 15, delete "0° C." and insert --0 °C.--, therefor In column 93, line 35, delete "0° C." and insert --0 °C.--, therefor In column 102, line 61, delete "0° C." and insert --0 °C.--, therefor In column 107, line 27, delete "0° C." and insert --0 °C.--, therefor In column 107, line 67, delete "0° C." and insert --0 °C.--, therefor In column 112, line 1, delete "11-1," and insert --1H,--, therefor